United States Patent
Strömberg et al.

(10) Patent No.: US 10,023,610 B2
(45) Date of Patent: Jul. 17, 2018

(54) LIGANDS FOR PREVENTION OF NEUROTOXICITY OF THE ALZHEIMER'S DISEASE RELATED AMYLOID-BETA PEPTIDE

(71) Applicant: AlphaBeta AB, Djursholm (SE)

(72) Inventors: Roger Strömberg, Stockholm (SE); Dmytro Honcharenko, Stockholm (SE); Jyotirmoy Maity, Stockholm (SE); Alok Juneja, Stockholm (SE); Firoz Roshan Kurudenkandy, Stockholm (SE); Jenny Presto, Stockholm (SE); Lisa Dolfe, Stockholm (SE); André Fisahn, Stockholm (SE); Jan Johansson, Stockholm (SE); Lennart Nilsson, Stockholm (SE)

(73) Assignee: AlphaBeta AB, Djursholm (SE)

( * ) Notice: Subject to any disclaimer, the term of this patent is extended or adjusted under 35 U.S.C. 154(b) by 2 days.

(21) Appl. No.: 15/111,248

(22) PCT Filed: Jan. 16, 2015

(86) PCT No.: PCT/EP2015/050816
§ 371 (c)(1),
(2) Date: Jul. 13, 2016

(87) PCT Pub. No.: WO2015/107170
PCT Pub. Date: Jul. 23, 2015

(65) Prior Publication Data
US 2016/0340387 A1 Nov. 24, 2016

(30) Foreign Application Priority Data

Jan. 17, 2014 (EP) .................................. 14151655

(51) Int. Cl.
C07K 5/02 (2006.01)
C07K 5/078 (2006.01)
(Continued)

(52) U.S. Cl.
CPC ........ C07K 5/06156 (2013.01); C07K 5/0215 (2013.01); C07K 5/06078 (2013.01);
(Continued)

(58) Field of Classification Search
None
See application file for complete search history.

(56) References Cited

U.S. PATENT DOCUMENTS

| 4,522,811 A | 6/1985 | Eppstein et al. | |
| 2011/0250653 A1* | 10/2011 | Toda | C12N 9/80 435/106 |

FOREIGN PATENT DOCUMENTS

| WO | 2006090289 A2 | 8/2006 |
| WO | WO2007068474 * | 6/2007 |
| WO | WO 2014026143 * | 2/2014 |

OTHER PUBLICATIONS

Sigma "Wang Resins" accessed from sigmaaldrich.com on Oct. 19, 2017 (Year: 2017).*

(Continued)

Primary Examiner — Adam Weidner
(74) Attorney, Agent, or Firm — Dilworth IP, LLC

(57) ABSTRACT

The present invention relates to the field of molecular biochemistry and medicine, and in particular to ligands comprising modified amino acid residues, targeting the amyloid-β peptide associated with Alzheimer's disease for prevention of aggregation, neurotoxicity and use thereof as drugs for treatment of Alzheimer's disease.

8 Claims, 11 Drawing Sheets

Figure 1:
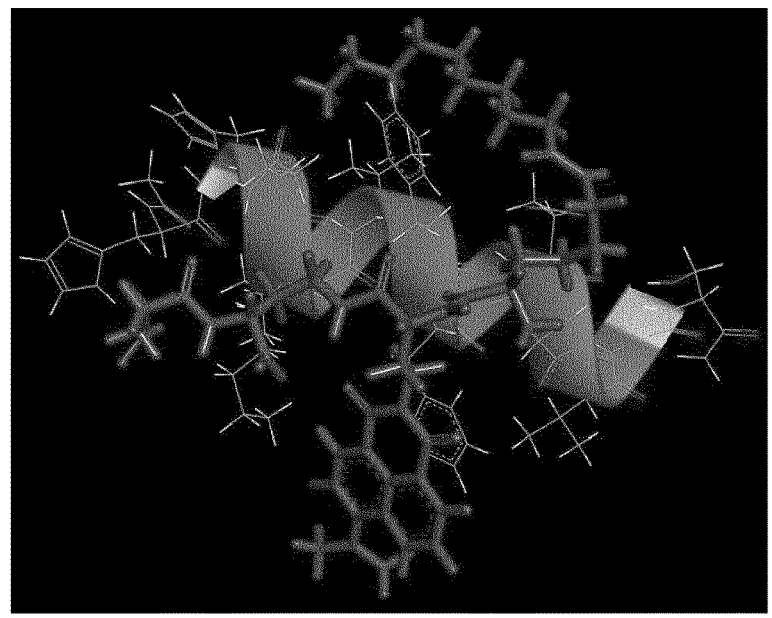
Figure 1:
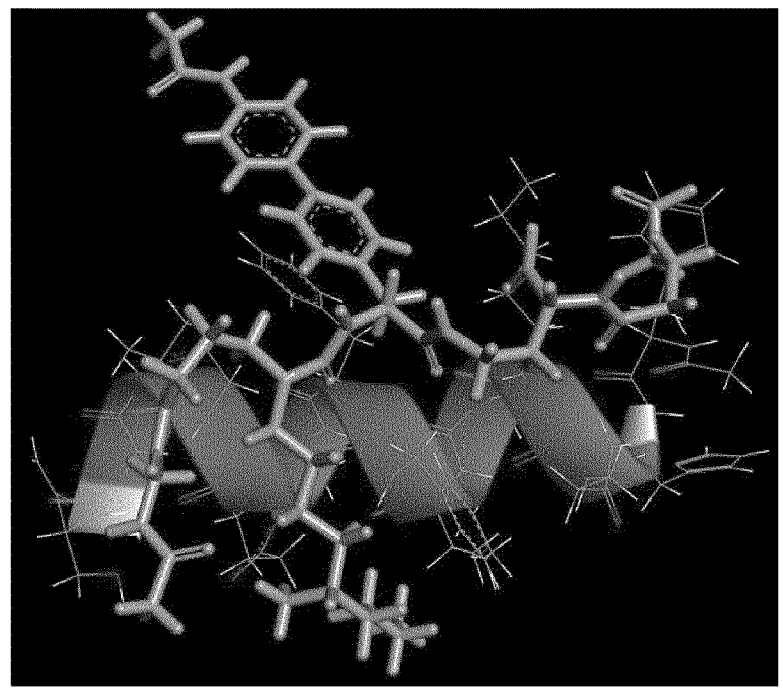

(51) Int. Cl.
    *C07K 5/097*     (2006.01)
    *A61K 38/00*     (2006.01)
    *C07K 5/068*     (2006.01)
    *C07K 5/065*     (2006.01)
    *G01N 33/68*     (2006.01)

(52) U.S. Cl.
    CPC ...... *C07K 5/06086* (2013.01); *C07K 5/06139* (2013.01); *C07K 5/0821* (2013.01); *G01N 33/6896* (2013.01); *A61K 38/00* (2013.01); *G01N 2500/04* (2013.01); *G01N 2800/2821* (2013.01)

(56) References Cited

OTHER PUBLICATIONS

Stanford "Alzheimer's prevention, treatment and research—a Q and A with dr frank longo" accessed from stanfordhealthcare.org on May 3, 2016 (Year: 2016).*
Dictionary "Functional Group" accessed from google.com on Oct. 23, 2017 (Year: 2017).*
Sitcar "synthesis and sar of N-Benzoyl-L-Biphenylalanine Derivatives: Discovery of TR-14035, a Dual 47/41 Integrin Antagonisty" bioorg med chem 10:2051-2066 (Year: 2002).*
Ito, M. et al.: "Effects of Ligands on Unfolding of the Amyloid [beta]-Peptide Central Helix: Mechanistic Insights from Molecular Dynamics Simulations", PLOS One, vol. 7, No. 1, Jan. 23, 2012, p. e30510.
Honcharenko, D. et al.: "Synthesis and evaluation of anti neurotoxicity properties of an amyloid-[beta] peptide targeting ligand containing a triamino acid", Organic & Biomolecular Chemistry, vol . 12, No. 34, Jun. 30, 2014, pp. 6684-6693.
PCT International Search Report dated Mar. 31, 2015 from corresponding Application No. PCT/EP2015/050816, 13 pages.
Benson, M. D. et al. Kidney Int. 2008, 74, 218-222.
Fratiglioni, L. et al. Neurology 2000, 54, S10-15.
Mattson, M. P. Physiol. Rev. 1997, 77, 1081-1132.
Goedert, M.; Spillantini, M. G. Science 2006, 314, 777-781.
Kallberg, Y. et al. J. Biol. Chem. 2001, 276, 12945-12950.
Dahlgren, K. N. et al. J Biol Chem 2002, 277, 32046-32053.
Walsh, D. M. et al. Nature 2002, 416, 535-539.
Petkova, A. T. et al., Proc. Natl. Acad. Sci. U.S. A. 2002, 99, 16742-16747.
Janek, K. et al. Biochemistry 2001, 40, 5457-5463.
Roberson, E. D.; Mucke, L. Science 2006, 314, 781-784.
Soto, C. et al. Nat Med 1998, 4, 822-826.
Riek, R. et al. Eur. J. Biochem. 2001, 268, 5930-5936.
Yan, Y.; Wang, C. J. Mo/. Biol. 2006, 364, 853-862.
Jarvet, J. et al. J. Biomol. NMR 2007, 39, 63-72.
Crescenzi, 0. et al. Eur J Biochem 2002, 269, 5642-5648.
Subramanian Vivekanandan et al. Biochemical and Biophysical Research Communications 2011, 411, 312-316.
Hardy, J. A.; Higgins, G. A. Science 1992, 256, 184-185.
Hardy, J.; Selkoe, D. J. Science 2002, 297, 353-356.
Liu, R. et al. J. Neurosci. Res. 2004, 75, 162-17t.
Nerelius, C. et al. Proc. Natl. Acad. Sci. U.S.A. 2009, 106, 9191-9196.
Crowther, D. C. et al. Neuroscience 2005, 132, 123-135.
Ito, M. et al. PLoS One 2011, 6, e17587.
Selkoe, 2000, JAMA 283:1615-1617.
Permanne et al., 2002, FASEB J. 16:860-862.
Sturchler-Pierrat et al., 1999, Rev. Neurosci. 10:15-24.
Seabrook et al., 1999, Neuropharmacol. 38:1-17.
DeArmond et al., 1995, Brain Pathology 5:77-89.
Telling, 2000, Neuropathol. Appl. Neurobiol. 26:209-220.
Price et al., 1998, Science 282:1079-1083.
Chhabra, S. R. et al. Tetrahedron Lett. 1999, 40, 4905-4908.
Chhabra, S. R. et al. J. Org. Chem. 2002, 67, 4017-4029.
Loving, G.; Imperiali, B., Journal of the American Chemical Society 2008, 130, 13630-13638.
Juneja, A. et al. J. Chem. Theory Comput. 2013, 9, 834-846.
Loncharich, R. J. et al. Biopolymers 1992, 32, 523-535.
Brooks, B. R. et al. Journal of Computational Chemistry 1983, 4, 187-217.
Brooks, B. R. et al. Journal of Computational Chemistry 2009, 30, 1545-1614.
MacKerell, A. D. et al. Journal of Physical Chemistry B 1998, 102, 3586-3616.
MacKerell, A. D. et al. Journal of the American Chemical Society 2004, 126, 698-699.
Lee, M. S. et al. J Comput Chem 2003, 24, 1348-1356.
Ryckaert, J. P. et al. Journal of Computational Physics 1977, 23, 327-341.
Feller, S. et al. The Journal of Chemical Physics 1995, 103, 4613-4621.
Deloof, H. et al. Journal of the American Chemical Society 1992, 114, 4028-4035.
Kabsch, W.; Sander, C. Biopolymers 1983, 22, 2577-2637.
Hovmoller, S. et al. Acta Crystallographica Section D 2002, 58, 768-776.
Fisahn, A. J Physiol 2005, 562, 65-72.
Fisahn, A. et al. Nature 1998, 394, 186-189.
Matsumori, N. et al. Chem. Biodiversity 2004, 1, 346-352.
Ting, R. et al. Journal of the American Chemical Society 2005, 127, 13094-13095.
Ribary, U. et al. Proc Natl Acad Sci US A 1991, 88, 11037-11041.

* cited by examiner

A

B

LIGANDS FOR PREVENTION OF NEUROTOXICITY OF THE ALZHEIMER'S DISEASE RELATED AMYLOID-BETA PEPTIDE

FIELD OF INVENTION

The present invention relates to the field of molecular biochemistry and medicine, and in particular to ligands comprising modified amino acid residues, targeting the amyloid-β peptide associated with Alzheimer's disease for prevention of aggregation, neurotoxicity and use thereof as drugs for treatment of Alzheimer's disease.

BACKGROUND OF THE INVENTION

A number of diseases are associated with the misfolding and aggregation of proteins and peptides into structures known as amyloid fibrils. This group of misfolding diseases includes for example the neurodegenerative Alzheimer's, Parkinson's and Creutzfeldt-Jacob's diseases (Benson, M. D. et al. *Kidney Int.* 2008, 74, 218-222). Amyloid fibrils are highly stable, β-sheet structures with similar morphology regardless of what protein they are formed from.

Alzheimer's disease (AD) is the most common cause of dementia, accounting for about 60% of all cases (Fratiglioni, L. et al. *Neurology* 2000, 54, S10-15). It is a progressive neurodegenerative disorder for which there is no cure. One of the hallmarks of AD is cerebral extracellular deposits, called plaques. These plaques are mainly composed of amyloid fibrils formed from the amyloid β-peptide (Aβ). Aβ is an amphipathic peptide of mainly 40- or 42-residues produced by enzymatic cleavages from an integral membrane protein, the amyloid β precursor protein (AβPP) (Mattson, M. P. *Physiol. Rev.* 1997, 77, 1081-1132), a protein with no known function. The 40-42 residues long Aβ is invariably present in amyloid plaques found in association with Alzheimer's disease, and formation of Aβ fibrils, through aggregation of peptides in β-strand conformation, is thought to be a major part of the cause of this devastating disease (Goedert, M.; Spillantini, M. G. *Science* 2006, 314, 777-781). When generated from AβPP, initially Aβ harbours α-helices which are strongly predicted to form β-strands (discordant helices) (Kallberg, Y. et al. *J. Biol. Chem.* 2001, 276, 12945-12950). It is not settled what intermediate(s) in the pathway leading to fibril formation is the dominant toxic species (Dahlgren, K. N. et al. *J Biol Chem* 2002, 277, 32046-32053). Evidence is accumulating that prefibrillar soluble aggregates, including species referred to as protofibrils, are more toxic than the mature fibrils (Walsh, D. M. et al. *Nature* 2002, 416, 535-539).

The structure of amyloid fibrils was recently established (Petkova, A. T. et al. *Proc. Natl. Acad. Sci. U.S.A* 2002, 99, 16742-16747) and support the indication that a region around positions 17-20 is essential for Aβ fibril formation (Janek, K. et al. *Biochemistry* 2001, 40, 5457-5463). Obstruction of fibril and/or oligomer/protofibril formation could prevent the occurrence or progression of Alzheimer's disease and several ways are being explored to accomplish this (Roberson, E. D.; Mucke, L. *Science* 2006, 314, 781-784). Major attempts to prevent fibril toxicity involve active or passive immunisation. These attempts have given promising results in animal models, but also given serious side-effects in clinical trials. An alternative approach involves targeting Aβ fibril formation with low molecular weight compounds. Compounds which can abrogate fibril formation by interfering with peptide-peptide contacts in fibrils have been identified (Soto, C. et al. *Nat Med* 1998, 4, 822-826). A potential drawback with such compounds is that they not only reduce fibril formation, but may also increase the amounts of oligomers/protofibrils (that could be toxic).

In aqueous solution, Aβ is found to be mainly disordered but shows non-random conformations in some regions. Hydrophobic interactions have been indicated between side chains of residues 16-24 and a turn-like structure has been mapped to residue 8-12 (Riek, R. et al. *Eur. J. Biochem.* 2001, 268, 5930-5936). Despite their different aggregation behavior monomeric $A\beta_{1-40}$ and $A\beta_{1-42}$ have very similar secondary structures with the exception that the longer variant is more rigid in its C-terminal (Yan, Y.; Wang, C. *J. Mol. Biol.* 2006, 364, 853-862). In SDS-micelles, $A\beta_{1-40}$ has been shown to form two helices, covering residues 15-24 and 30-35 respectively (Jarvet, J. et al. *J. Biomol. NMR* 2007, 39, 63-72). In the micelles, the first helix is superficially located and the second helix is buried in the hydrophobic interior. Helix formation, in similar locations of the peptide, has also been observed in both $A\beta_{1-40}$ and $A\beta_{1-42}$ using structure-inducing solvents such as trifluorethanol and hexafluoro-isopropanol (Crescenzi, O. et al. *Eur J Biochem* 2002, 269, 5642-5648) and at physiological salt concentrations (Subramanian Vivekanandan et al. *Biochemical and Biophysical Research Communications* 2011, 411, 312-316).

Finding ways of inhibiting Aβ misfolding and amyloid formation is important but challenging and several strategies have been proposed. The aggregation process of Aβ is not fully understood and it is unclear which forms of Aβ that are toxic. Earlier it was believed that the mature fibrils were the main cause of the disease (Hardy, J. A.; Higgins, G. A. *Science* 1992, 256, 184-185) and a number of inhibitors of fibril formation have been reported. However, more and more findings point to the toxic nature of soluble oligomers produced early in the aggregation pathway (Hardy, J.; Selkoe, D. J. *Science* 2002, 297, 353-356). These early aggregates are not structurally defined making inhibitor design a difficult task and it is also possible that targeting species on the fibrillation pathway may result in accumulation of toxic oligomers. A more appealing idea would be to target and stabilize an Aβ-monomer, thereby preventing misfolding and subsequent amyloid formation.

Aβ contains a discordant helix (residue 16-23) i.e. a helix composed of amino acids with a high propensity for β-strand conformation (Kallberg, Y. et al. *J. Biol. Chem.* 2001, 276, 12945-12950). Peptides derived from this region form fibrils and, in Aβ, this region has been found essential for fibril formation (Liu, R. et al. *J. Neurosci. Res.* 2004, 75, 162-171). It has previously been shown that by using small designed ligands, directed towards the discordant region of Aβ (residues 13-23), it is possible to stabilize a helical structure and reduce aggregation in vitro (Nerelius, C. et al. *Proc. Natl. Acad. Sci. U.S.A* 2009, 106, 9191-9196). These ligands also reduced cell toxicity of Aβ and prevented Aβ-induced reduction of γ oscillations of hippocampal slices. Oral administration of two of these compounds in a *Drosophila* model of Alzheimer's disease (Crowther, D. C. et al. *Neuroscience* 2005, 132, 123-135) increases longevity, decreases locomotor dysfunction and reduces neuronal damage (Nerelius, C. et al. *Proc. Natl. Acad. Sci. U.S.A* 2009, 106, 9191-9196). These results indicate that this approach holds promise for the development of orally available compounds against Alzheimer's disease. Additional support for the concept comes from recent molecular dynamics simulations that also uncover details of the mechanism of unfolding of the Aβ central helix (Ito, M. et al. *PLoS One* 2011, 6, e17587) as well as retardation of the folding in presence of ligands designed to interact with the native helical conformation (Ito, M. et al. *PLoS One* 2012, 7, e30510).

The inventors have developed a number of new ligands designed to have more extended interaction with Aβ, through interaction with several both hydrophobic and polar regions across the central part of the peptide. In particular, the new ligands are designed to have higher affinity to helical Aβ in order to reduce the Aβ associated neurotoxicity. The synthesis strategy also involves a number of novel amino acids which allows for substantial variation of substituents and hence makes it possible to fine-tune the structures further.

DESCRIPTION OF THE INVENTION

The present invention relates to compounds of formula I

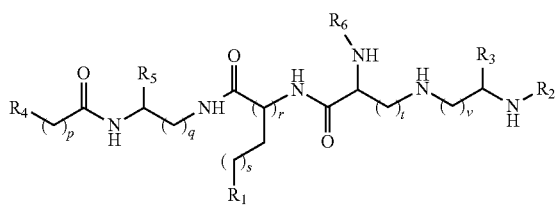

I wherein

R1 is a substituted or non-substituted, aromatic or heteroaromatic moiety;

R2 is H or a substituted or non-substituted, saturated or unsaturated alkyl or acyl group;

R3 is H or a substituted or non-substituted, saturated or unsaturated alkyl, alkyl group containing an aromatic moiety or a substituted or non-substituted, saturated or unsaturated acyl group;

R4 is a carboxylate, phosphonate or phosphate group;

R5 is a carboxylate, sulphonate or phosphonate group;

R6 is H or a substituted alkyl or acyl group;

p and q represent an integer of 1, 2, 3 or 4;

r and v represent an integer of 1 or 2;

s represents an integer of 0, 1 or 2; and t represents an integer of 1, 2, 3 or 4; or a pharmaceutically acceptable salt or hydrate thereof and for for use in therapy, in particular for in treatment of an Aβ peptide-related disorder, such as Alzheimer's disease.

An "Aβ peptide" is generally an Aβ peptide that includes the discordant helix of an amyloid precursor protein (APP). In general, an Aβ peptide can be between Aβ I-39 and Aβ I-43 (e.g., Aβ I-40 or Aβ I-42), Aβ (12-24), Aβ 12-28, or Aβ (14-23). In general, an Aβ peptide used in an in vitro assay is an Aβ peptide that forms β form and subsequently forms fibrils, e.g., Aβ (I-42) (e.g., Selkoe, 2000, *JAMA* 283:1615-1617).

An "Aβ peptide in α-helical form" is generally an Aβ peptide that at least partially forms an α-helical structure, in particular in the region consisting of amino acids 13-26. Aβ Aβ peptide in β-form is generally an Aβ peptide that at least partially forms a β-structure.

A "discordant helix" is an amino acid sequence that is able to form an α-helix and is also predicted to be able to form a beta-strand. A discordant helix can be identified using structure analysis programs that predict secondary structure of polypeptides, specifically by analyzing an amino acid sequence for experimentally determined (for example, by NMR or crystallography) α-helix and also analyzing the amino acid sequence for predicted beta-strand. A sequence that is experimentally determined to form α-helix and is predicted to form a beta-strand is a discordant helix. A discordant helix amino acid sequence can be an isolated peptide, or form part of a polypeptide. A discordant helix can be naturally occurring in a wild type or mutant polypeptide. A discordant helix can also be in a synthetic amino acid sequence. In general, the discordant helix amino acid sequence is at least about 6 amino acids in length. Such sequences can be longer, e.g., 7, 8, 9, 10, 11, 12, 14, 16, 18, 22, 24, or 26 amino acids in length. A discordant helix can also be determined using other methods that can identify a sequence that is both predicted to form or is experimentally shown to form α-helix and is predicted to form or is experimentally shown to form beta-strand.

A "polypeptide" means a chain of amino acids regardless of length or post-translational modifications.

Depending upon the substituents present in compounds of the formula I, the compounds may form esters, amides, and/or salts which are within the scope of the present invention. Salts and solvates of compounds of formula I which are suitable for use in medicine are those wherein a counter ion or an associated solvent is pharmaceutically acceptable. However, salts and solvates having non-pharmaceutically acceptable counter ions or associated solvents are within the scope of the present invention, for example, for use as intermediates in the preparation of the compounds of formula I and their pharmaceutically acceptable salts, solvates, and physiologically functional derivatives. By the term "physiologically functional derivative" is meant a chemical derivative of a compound of formula I having the same physiological function as the free compound of formula I, for example, by being convertible in the body thereto. Esters and amides are examples of physiologically functional derivatives.

A compound which, upon administration to the recipient, is capable of being converted into a compound of formula I as described above, or an active metabolite or residue thereof, is known as a "prodrug". A prodrug may, for example, be converted within the body, e.g. by hydrolysis in the blood, into its active form that has medical effects. Pharmaceutical acceptable prodrugs are described in T. Higuchi and V. Stella, Prodrugs as Novel Delivery Systems, Vol. 14 of the A. C. S. Symposium Series (1976); "Design of Prodrugs" ed. H. Bundgaard, Elsevier, 1985; and in Edward B. Roche, ed., Bioreversible Carriers in Drug Design, American Pharmaceutical Association and Pergamon Press, 1987, which are incorporated herein by reference.

Suitable salts according to the invention include those formed with organic or inorganic acids or bases. In particular, suitable salts formed with acids according to the invention include those formed with mineral acids, strong organic carboxylic acids, such as alkanecarboxylic acids of 1 to 4 carbon atoms which are unsubstituted or substituted, for example, by halogen, such as saturated or unsaturated dicarboxylic acids, such as hydroxycarboxylic acids, such as amino acids, or with organic sulfonic acids, such as ($C_1$-$C_4$)alkyl- or aryl-sulfonic acids which are unsubstituted or substituted, for example by halogen. Pharmaceutically acceptable acid addition salts include, but are not limited to, those formed from hydrochloric, hydrobromic, sulphuric, nitric, citric, tartaric, acetic, phosphoric, lactic, pyruvic, acetic, trifluoroacetic, succinic, perchloric, fumaric, maleic, glycolic, lactic, salicylic, oxaloacetic, methanesulfonic, ethanesulfonic, p-toluenesulfonic, formic, benzoic, malonic, naphthalene-2-sulfonic, benzenesulfonic, isethionic, ascorbic, malic, phthalic, aspartic, and glutamic acids, lysine, and arginine. Other acids such as oxalic, while not in themselves pharmaceutically acceptable, may be useful as intermediates in obtaining the compounds of the invention and their pharmaceutical acceptable acid addition salts.

Pharmaceutically acceptable base salts include, but are not limited to, ammonium salts, alkali metal salts, for example those of potassium and sodium, alkaline earth metal salts, for example those of calcium and magnesium, and salts with organic bases, for example dicyclohexylamine, N-methyl-D-glucamine, morpholine, thiomorpholine, piperidine, pyrrolidine, a mono-, di- or tri-lower alkylamine, for example ethyl-, tert-butyl-, diethyl-, diisopropyl-, triethyl-, tributyl- or dimethyl-propylamine, or a mono-, di- or trihydroxy lower alkylamine, for example mono-, di- or triethanolamine. Corresponding internal salts may furthermore be formed.

Those skilled in the art of organic chemistry will appreciate that many organic compounds can form complexes with solvents in which they are reacted or from which they are precipitated or crystallized. These complexes are known as "solvates". For example, a complex with water is known as a "hydrate".

As used herein, the term "substituted or non-substituted, saturated or unsaturated alkyl group" means both straight and branched chain saturated and unsaturated hydrocarbon groups, that also can include substitution by heteroatom containing functional groups. Examples of alkyl groups include, but are not limited to, methyl, ethyl, n-propyl, iso-propyl, n-butyl, t-butyl, iso-butyl, and sec-butyl, pentyl hexyl, heptyl octyl, nonyl, decyl, undecyl, dodecyl, tetradecyl, hexadecyl, octadecyl, benzyl, methylbenzyl, phenyl ethyl and methyl phenylethyl groups. Among unbranched alkyl groups, there are preferred n-butyl, n-hexyl, n-octyl. N-decyl and n-dodecyl groups. Among branched alkyl groups, there may be mentioned iso-propyl, t-butyl, iso-butyl, sec-butyl, neopentyl and methyl and etyl butyl, pentyl hexyl, octyl, nonyl, decyl and dodecyl groups.

As used herein, the term "substituted or non-substituted, saturated or unsaturated acyl group" means the group R—C(O)—, where R is an alkyl which can include substitution by aromatic groups as well as heteroatom containing functional groups. Examples of acyl groups include, but are not limited to, acetyl and propanoyl, butanoyl, pentanoyl, hexanoyl, heptanoyl, octanoyl, nonanoyl, decanoyl, undecanoyl, dodecanoyl, myristoyl, palmitoyl, stearoyl, 9-carboxynonanoyl, 11-carboxyundecanoyl, 13-carboxyltridecanoyl, 9-carbamoylnonanoyl, 11-carbamoylundecanoyl, 13-carbamoyltridecanoyl groups. Other examples include benzoyl, alkyllbenzoyl, phenylacetyl, alkylphenylacetyl, phenylpropanoyl, phenylbutanoyl, such as ethyl phenylacetyl or ethyl phenyl propanoyl groups.

As used herein, the term "carboxylate group" means a group comprising —COO$^-$, —COOH or protected forms of these, i.e. precursors that will generate the —COO$^-$ group, in vivo.

As used herein, the term "sulphonate group" means a group comprising of —SO$_3$ or its protected form, i.e. precursors that will generate the —SO$_3$ group, in vivo.

As used herein, the term "phosphonate group" means a group comprising —P(O)O$_2^{2-}$, —P(O)O$_2$H$^-$, —P(O)(OH)$_2$ or protected forms of these, i.e. precursors that will generate the —P(O)O$_2^{2-}$ or —P(O)O$_2$H$^-$ group, in vivo.

As used herein, the term "phosphate group" means a group comprising of —OP(O)O$_2^{2-}$, —OP(O)O$_2$H$^-$, —OP(O)(OH)$_2$ or alkylated or otherwise protected form of these that will generate the —OP(O)O$_2^{2-}$, —OP(O)O$_2$H, or $^-$—OP(O)O$_2$R$^-$ group, in vivo.

As used herein, the term "aromatic moiety" means a monocyclic, bicyclic or tricyclic aromatic carbocyclic group. Examples of aryl groups include, but are not limited to, phenyl, biphenyl, naphthyl and phenanthryl. The phenyl group may be optionally substituted with one or several substituents in the 2, 3, 4, 5 or 6-position. A biphenyl group may be attached in the para or meta position with respect to the second phenyl ring. Both phenyl groups in a biphenyl group may be substituted at the 2, 3, 4, 5 or 6- or 2', 3', 4', 5' or 6' positions. A naphthyl group may be attached through the 1 or the 2 position. In a bicyclic or tricyclic aromatic moiety, one of the rings may, for example, be partially saturated. Examples of such groups include, but are not limited to, indanyl and tetrahydronaphthyl.

As used herein, the term "heteroaromatic moiety" means an aromatic cyclic group of carbon atoms wherein from one to three of the carbon atoms is/are replaced by one or more heteroatoms independently selected from nitrogen, oxygen or sulfur. A heteroaryl group may, for example, be monocyclic, bicyclic or tricyclic. Examples of monocyclic heteroaryl groups include, but are not limited to, furanyl, thienyl, pyrrolyl, oxazolyl, thiazolyl, imidazolyl, oxadiazolyl, thiadiazolyl, pyridyl, triazolyl, triazinyl, pyridazyl, isothiazolyl, isoxazolyl, pyrazinyl, pyrazolyl, and pyrimidinyl. Examples of bicyclic heteroaryl groups include, but are not limited to, quinoxalinyl, quinazolinyl, pyridopyrazinyl, benzoxazolyl, benzothiophenyl, benzimidazolyl, naphthyridinyl, quinolinyl, benzofuranyl, indolyl, indazolyl, benzothiazolyl, pyridopyrimidinyl, and isoquinolinyl, indol-3-yl, indol-2-yl, quinolin-4-yl, coumarin-3-yl, coumarin-4-yl, including substituted derivatives of these. Examples of tricyclic heteroaryl groups include, but are not limited to, carbazole, dibenzofuran, xanthene, and acridine, benzo[de]isoquinoline-1,3(2H)-dion-1-yl, including substituted derivatives of these.

A "non-amyloidogenic form" of a polypeptide containing a predicted discordant helix is the form of the protein in which α-helix is the predominant conformation of the discordant amino acid sequence. Compounds that promote the α-helix conformation of a discordant helix are useful for preventing the formation of amyloid. A non-amyloidogenic form can be a form of a discordant sequence that is predicted to be in an α-helical conformation with higher frequency than a corresponding sequence (e.g., an allele).

A disorder related to Alzheimer's disease is a disorder in which peptides derived from the APP protein have been demonstrated to be present or are suspected of being present. Such disorders include dementia pugilistica, Down syndrome, and severe head trauma.

Unless otherwise defined, all technical and scientific terms used herein have the same meaning as commonly understood by one of ordinary skill in the art to which this invention belongs. Although methods and materials suitable for practicing the invention are described below, methods and materials similar or equivalent to those described herein can be used in the practice or testing of the present invention. AU publications, patent applications, patents, and other references mentioned herein are incorporated by reference. The materials, methods, and examples are illustrative only and not intended to be limiting.

SHORT DESCRIPTION OF DRAWINGS

FIG. 1 provides molecular models of examples of ligands that are designed to "straddle" or "clamp" the central helix of the Aβ-peptide (the helix with side groups being rendered as line representations). The ligands are rendered as stick presentations. A), Aβ with the DH18_Dmn (left panel) which has hydrophobic contacts in two regions and polar contacts in two regions. B), Aβ with the ligand Ac4NdiAEDabpBp (right panel) which has hydrophobic contacts in two regions and polar contacts in three regions.

Figure 2:
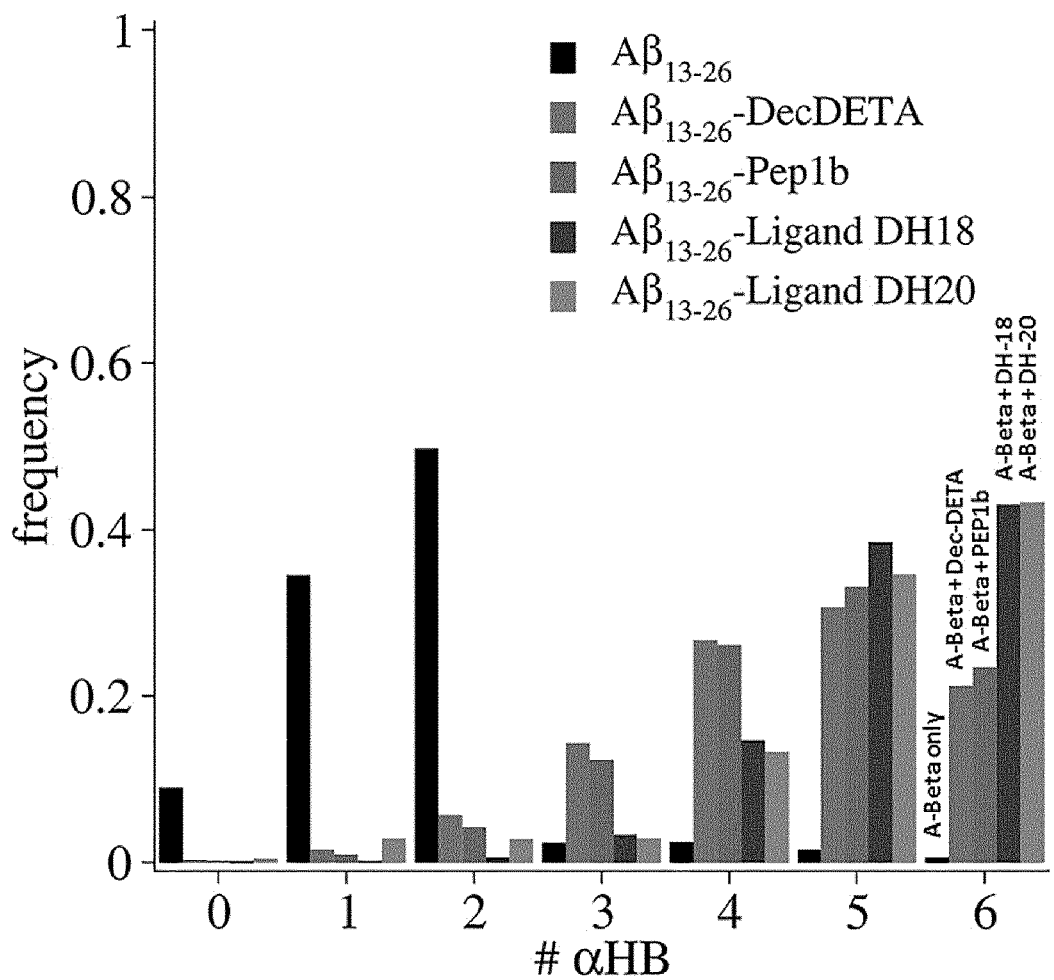

FIG. 2. Histogram of the number of alfa-hydrogen bonds (aHBs) of the Aβ model in the absence or presence of selected ligands. The histograms of the Aβ in the absence and presence of first generation ligands as well as ligand DH-18 or DH-20 are shown, from left to right: $Aβ_{13-26}$ alone; $Aβ_{13-26}$-DecDETA; $Aβ_{13-26}$-Pep1b; $Aβ_{13-26}$-Ligand DH18; $Aβ_{13-26}$-Ligand DH20. The histograms were obtained using the data of the whole simulations. The relative frequencies of the appearance of the Aβ structures sorted out by the number of n aHBs (n=0-6) of the Aβ middle region are indicated.

Figure 3A:
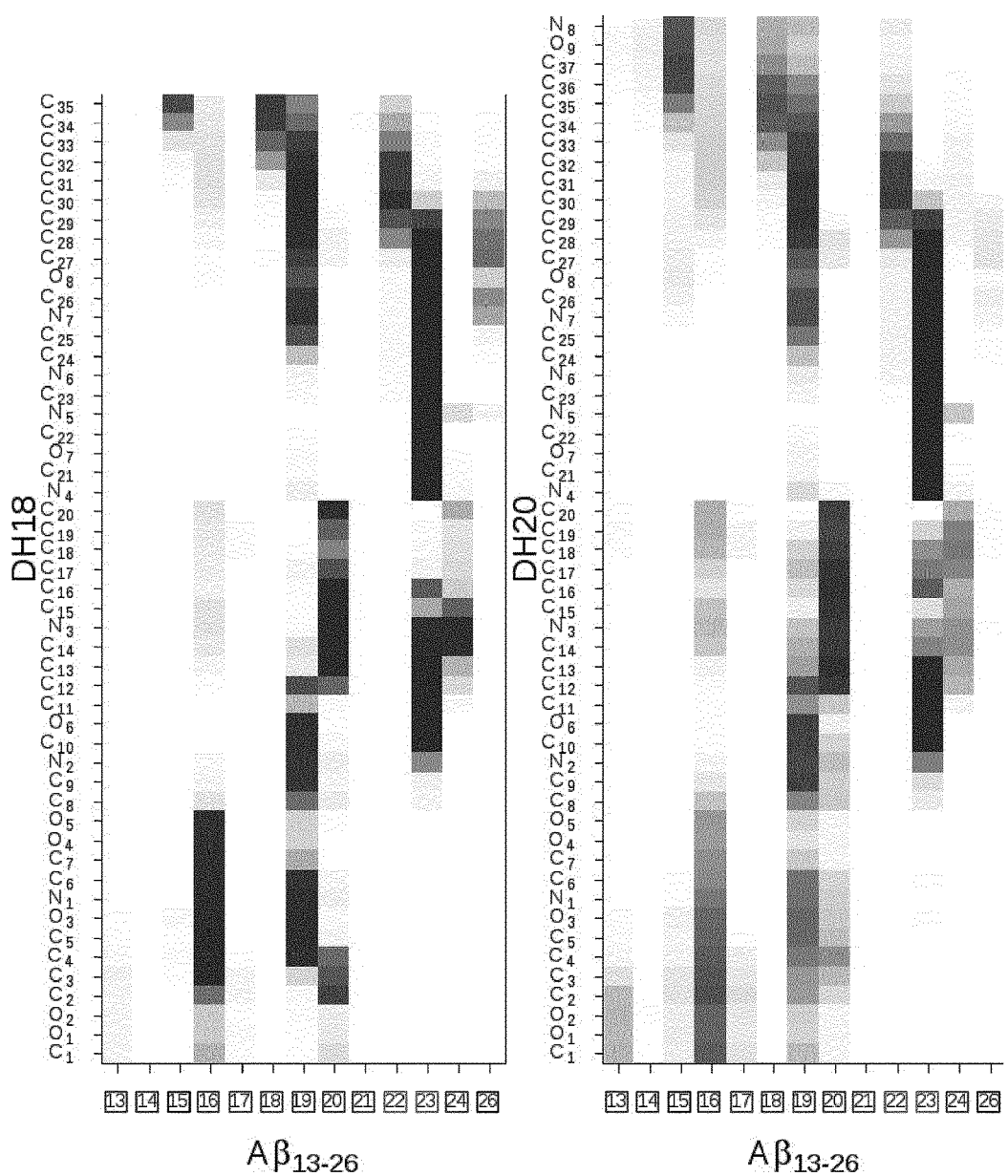
Figure 3B:
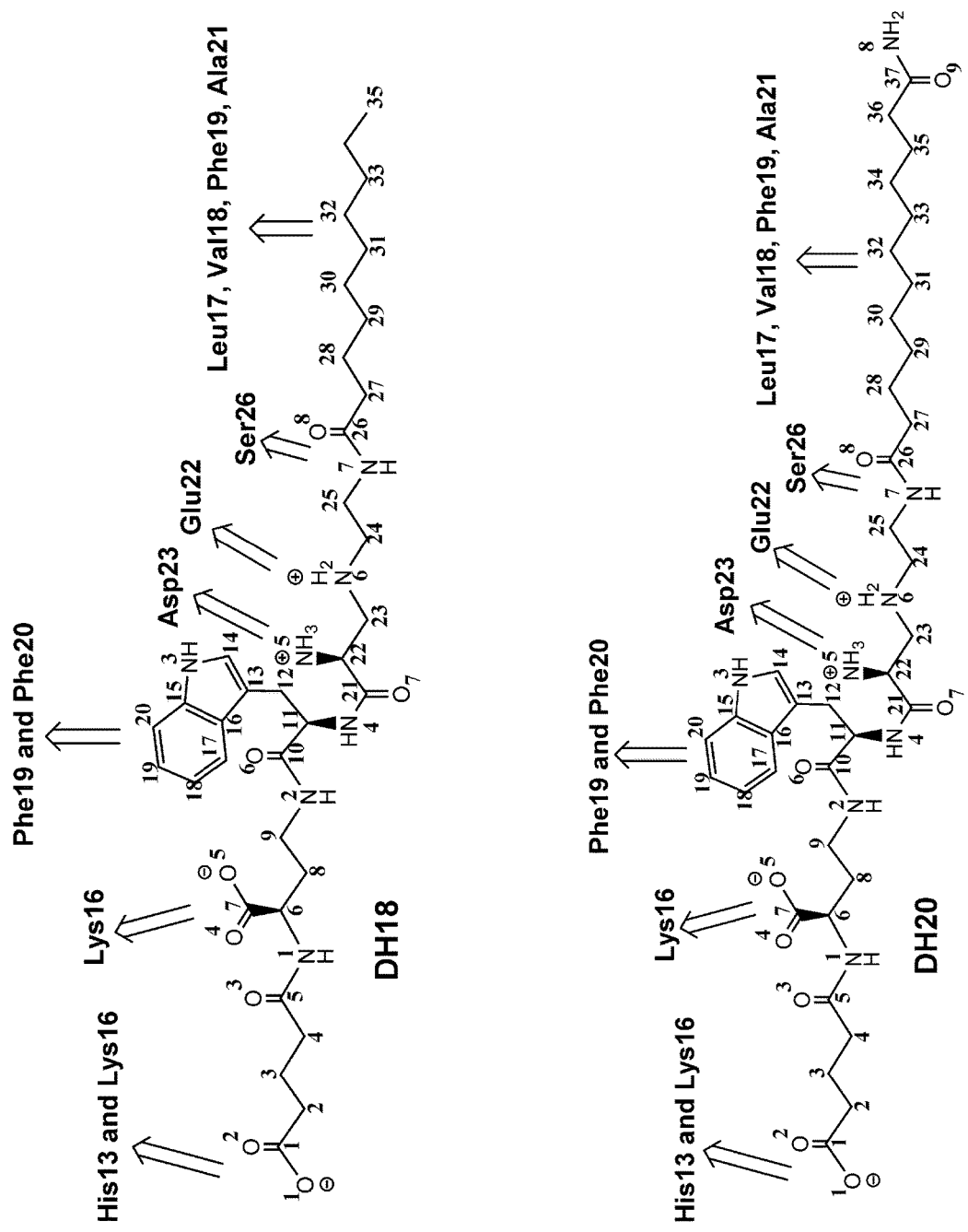

FIG. 3. Contact maps of the Aβ/DH-18 (left panel) and Aβ/DH-20 (right panel) complexes (FIG. 3A). The probability of the contact between the center of geometry of sidechain heavy atoms of each Aβ residue and each ligand heavy atom is shaded (white to black grids). The probability was calculated using the data obtained from the whole simulations. The Aβ residues and ligand atoms corresponding to the X and Y-axis numbers, respectively, are listed in FIG. 3B.

Figure 4:
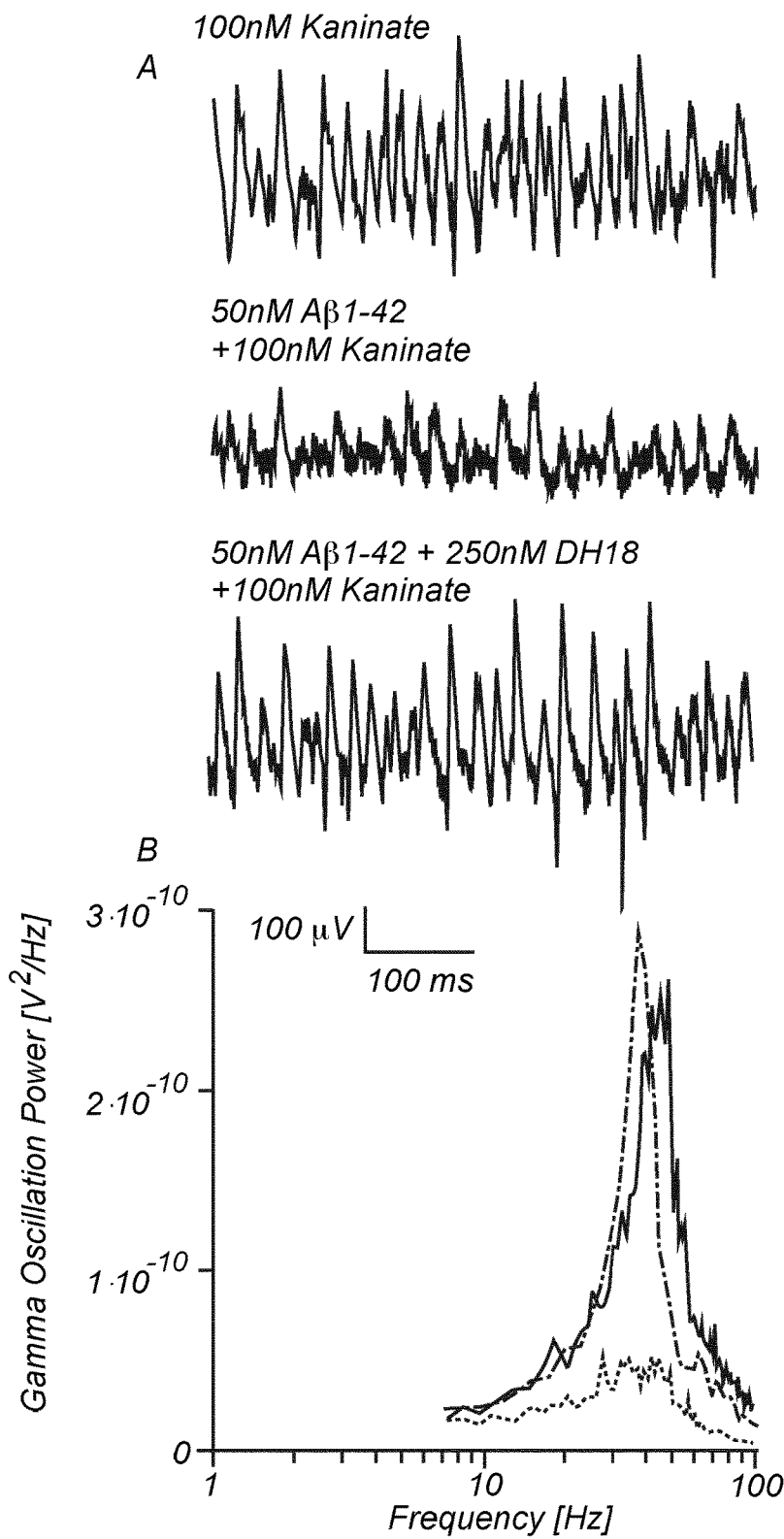

FIG. 4 provides that ligand DH18 reverses Aβ-induced reduction of gamma oscillation in hippocampal slices. (A) Traces of kainate-induced gamma oscillations in area CA3 of naïve slices, after incubation with 50 nM Aβ1-42 alone, and in the presence of 250 nM ligand DH18. (B) Power spectra of gamma oscillations in a naïve slices (solid trace), after incubation with $Aβ_{1-42}$ alone (lower dotted trace) and in the presence of ligand DH18 (upper dashed-dotted trace).

Figure 5:
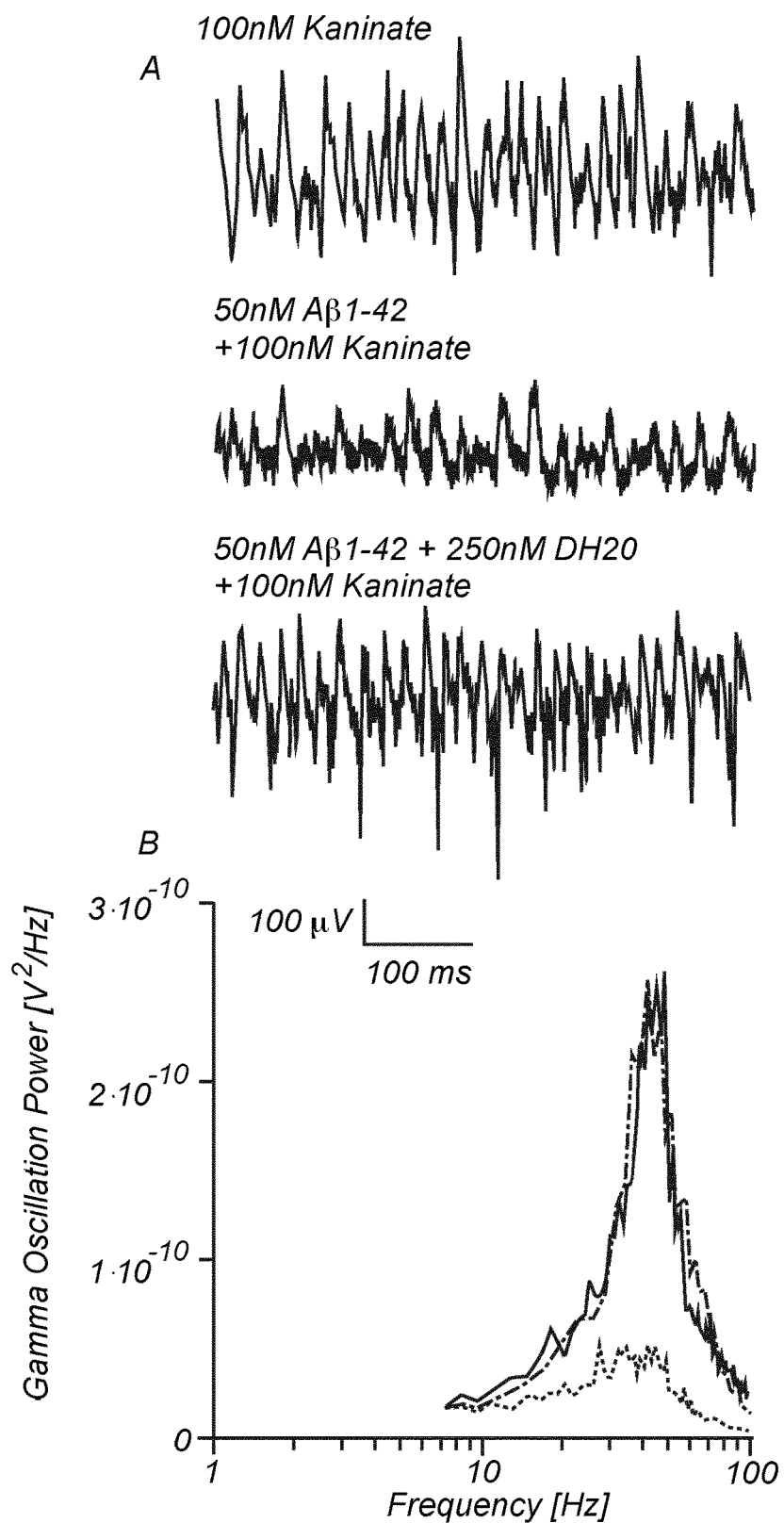

FIG. 5 provides that ligand DH20 reverses Aβ-induced reduction of gamma oscillation in hippocampal slices. (A) Traces of kainate-induced gamma oscillations in area CA3 of naïve slices, after incubation with 50 nM Aβ1-42 alone, and in the presence of 250 nM ligand DH20. (B) Power spectra of gamma oscillations in a naïve slices (solid trace), after incubation with $Aβ_{1-42}$ alone (lower dotted trace) and in the presence of ligand DH20 (upper dashed-dotted trace).

Figure 6:
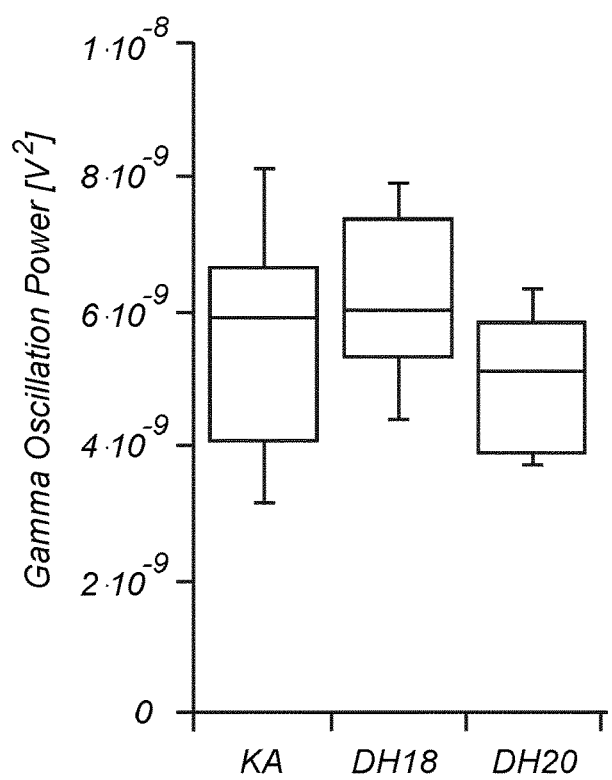

FIG. 6 provides control experiment showing no effect of only ligands DH18 and DH20 on kainate-induced gamma oscillations. Summary histogram of gamma oscillation power in naïve slices (KA), slices incubated in the presence of DH18, and slices incubated in the presence of DH20.

Figure 7:
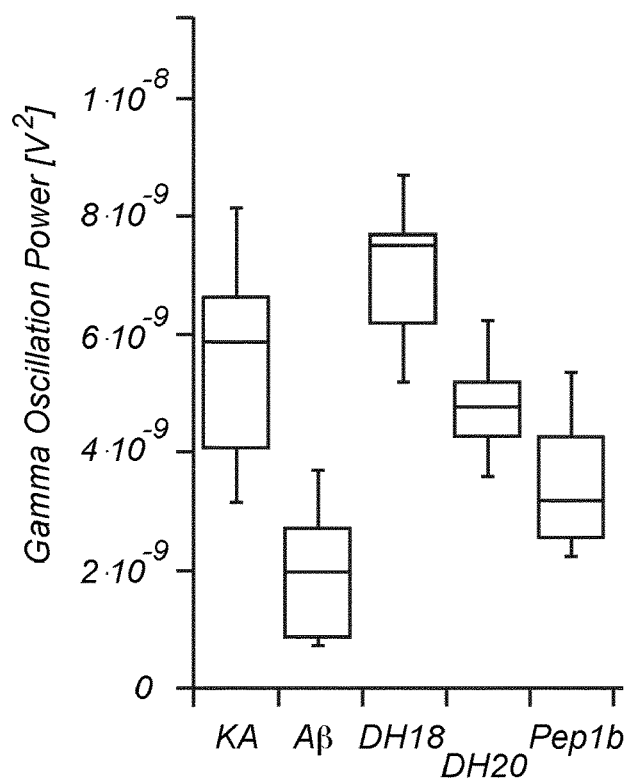

FIG. 7 provides illustration of prevention of Aβ-induced degradation of network gamma oscillations by second-generation ligands (DH18 and DH20) compared to a first-generation ligand (Pep1b). Summary histogram of gamma oscillation power in naïve slices (KA), $Aβ_{1-42}$ incubated slices (Aβ), $Aβ_{1-42}$ incubated slices in the presence of DH18, $Aβ_{1-42}$ incubated slices in the presence of DH20, and $Aβ_{1-42}$ incubated slices in the presence of Pep1 b.

Figure 8A:
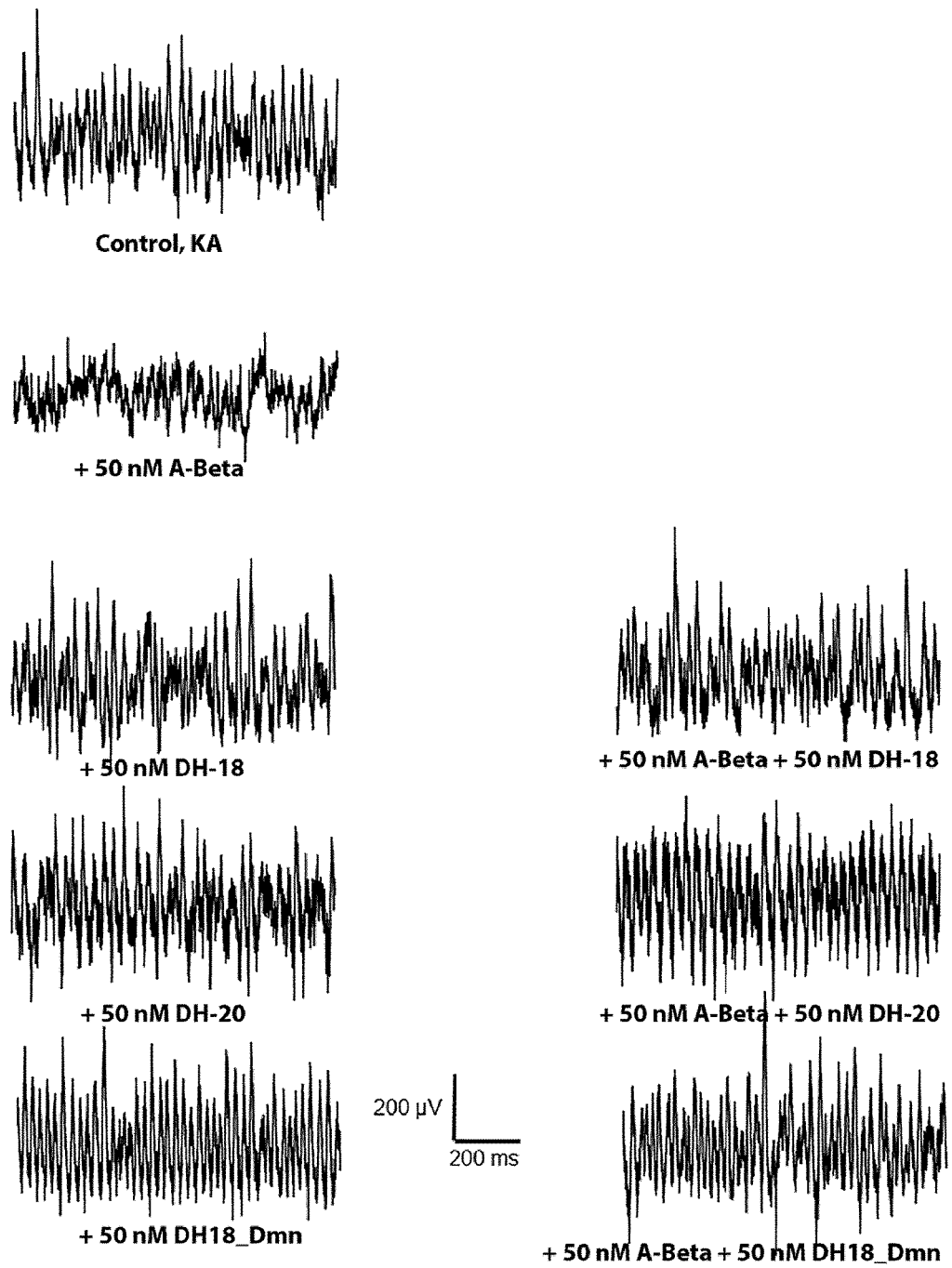
Figure 8B:
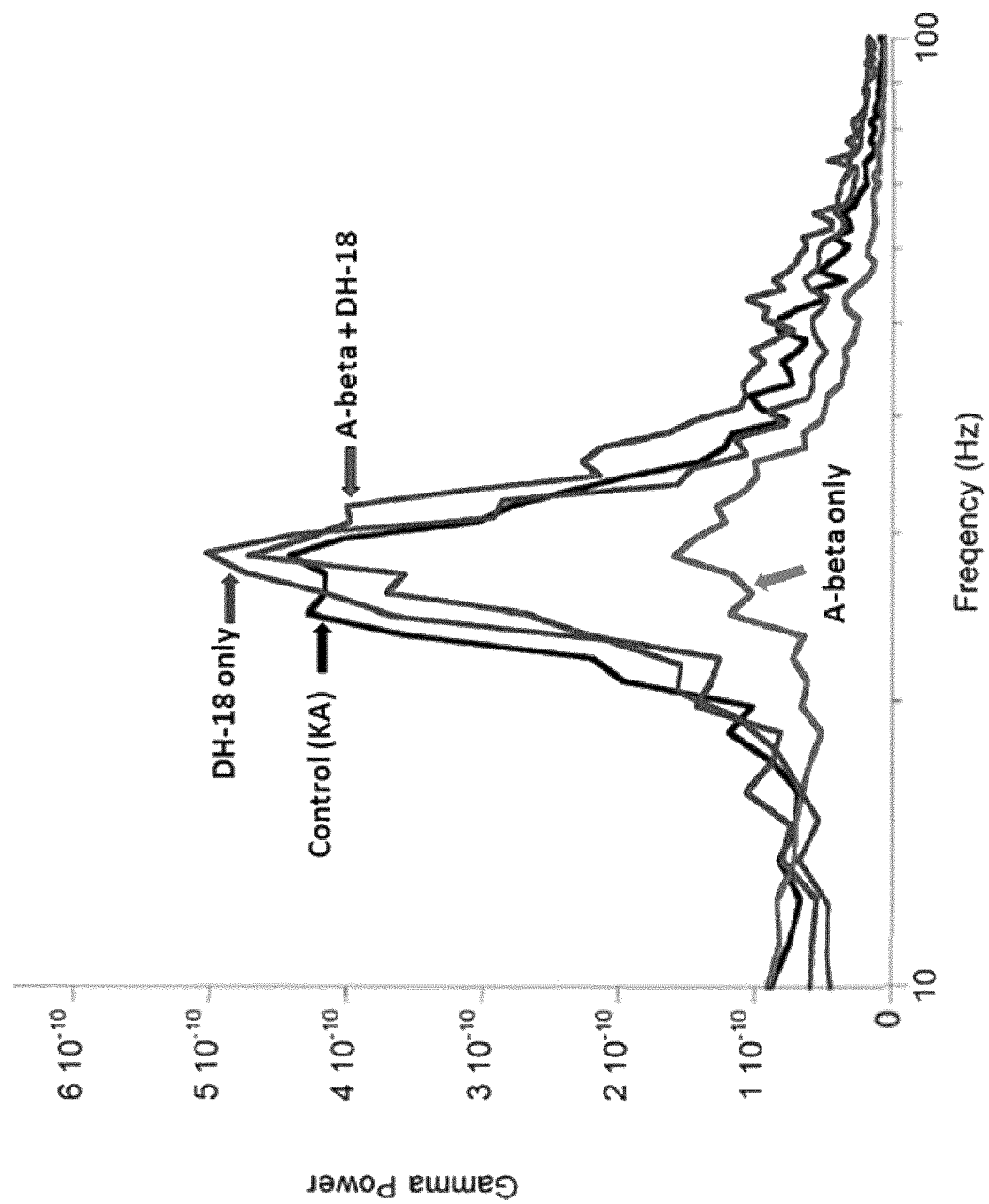

FIG. 8 provides that ligands DH-18, DH-20 and DH18_Dmn reverse Aβ-induced reduction of gamma oscillation in hippocampal slices also at only 1:1 ratio to Aβ1-42. FIG. 8A shows traces of kainate-induced gamma oscillations of naïve slices: Left panel; after incubation with 50 nM Aβ1-42 alone or with 50 nM DH-18, DH-20 or DH18_Dmn alone. Right Panel: after incubation with 50 nM Aβ1-42 in the presence of 50 nM of ligands DH-18, DH-20 and DH18_Dmn. FIG. 8B: Power spectra of gamma oscillations in naïve slices (one of the the three upper traces, see indication in graph), after incubation with 50 nM $Aβ_{1-42}$ alone (lower trace), after incubation with DH-18 alone (one of the the three upper traces, see indication in graph) and after incubation with 50 nM $Aβ_{1-42}$ in the presence of 50 nM of ligand DH18 (one of the the three upper traces, see indication in graph).

Figure 9A:
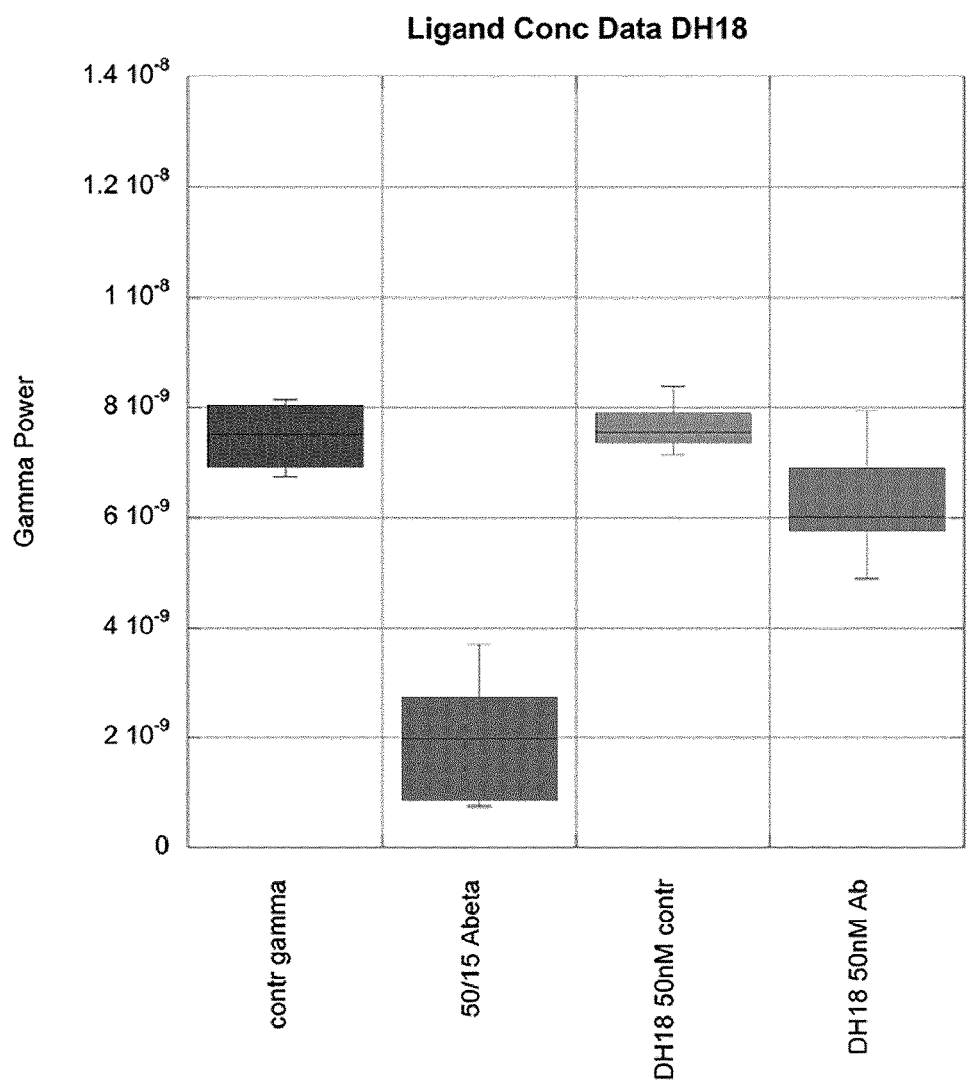
Figure 9B:
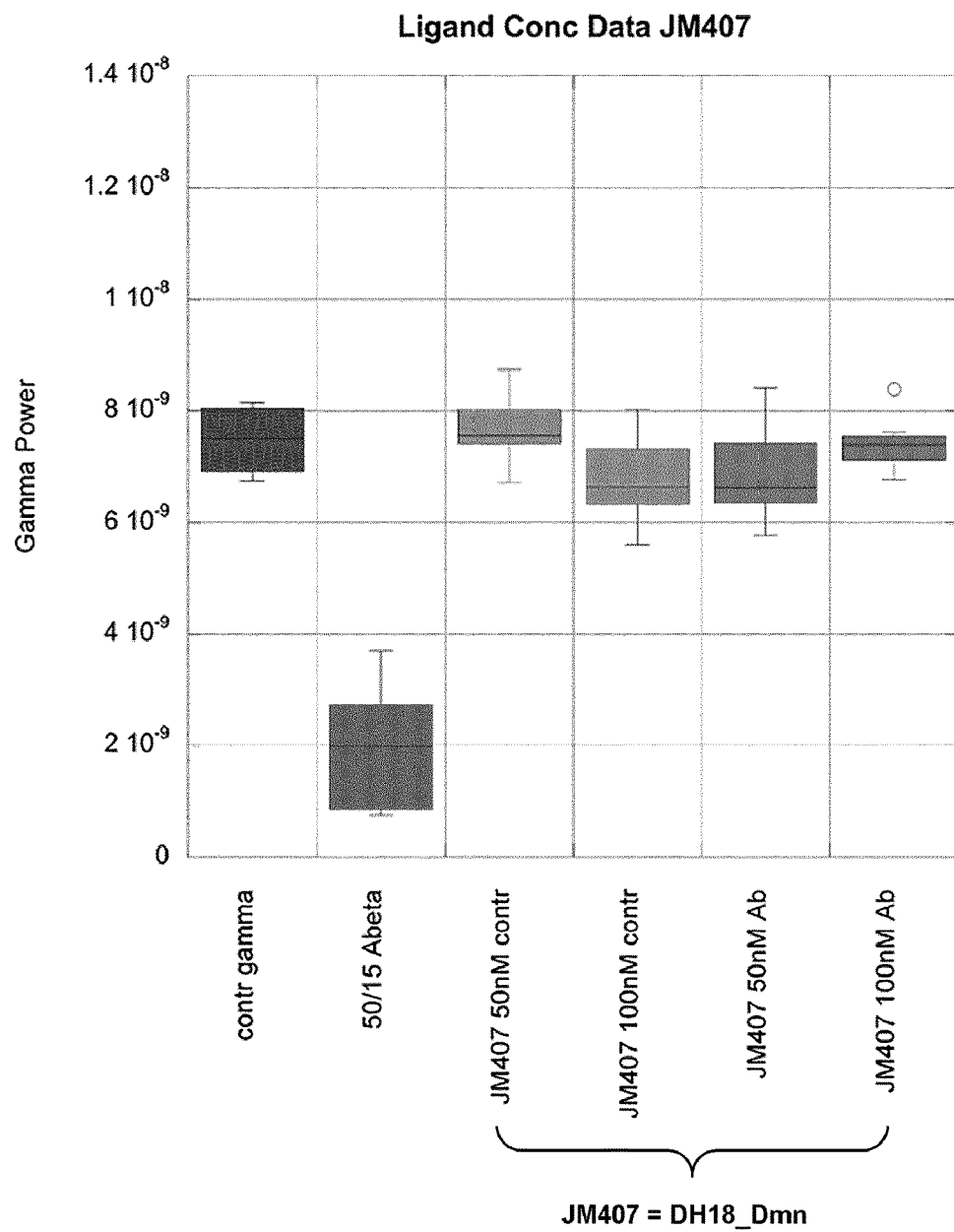

FIG. 9 provides illustration of prevention of Aβ-induced degradation of network gamma oscillations by DH18 and DH18_Dmn at only equimolar amounts to $Aβ_{1-42}$. (A) Summary histogram of gamma oscillation power in naïve hippocampus slices (contr gamma), slices incubated with 50 nM $Aβ_{1-42}$ (Abeta), slices incubated with 50 mM DH18 (DH18 contr), $Aβ_{1-42}$ incubated slices in the presence 50 mM DH18 (DH18 Ab). (B) Summary histogram of gamma oscillation power in naïve hippocampus slices (contr gamma), slices incubated with 50 nM $Aβ_{1-42}$ (Abeta), slices incubated with 50 or 100 mM DH18_Dmn (JM407 contr), $Aβ_{1-42}$ incubated slices in the presence of two different concentration of DH18_Dmn (JM407 Ab).

In a first aspect of the present invention, there is provided a compound of formula I

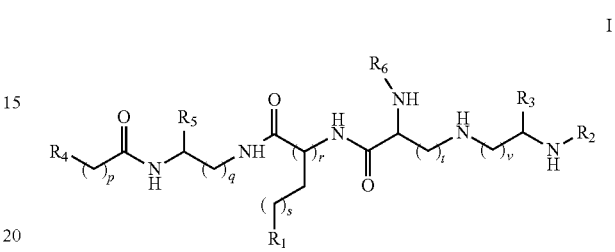

wherein
R1 is a substituted or non-substituted, aromatic or heteroaromatic moiety;
R2 is H or a substituted or non-substituted, saturated or unsaturated alkyl or acyl group;
R3 is H or a substituted or non-substituted, saturated or unsaturated alkyl group optionally containing an aromatic moiety or a substituted or non-substituted, saturated or unsaturated acyl group;
R4 is a carboxylate, phosphonate or phosphate group;
R5 is a carboxylate, sulphonate or phosphonate group;
R6 is H or a substituted alkyl or acyl group;
p and q independently represent an integer of 1, 2, 3 or 4;
r and v independently represent an integer of 1 or 2;
s represents an integer of 0, 1 or 2; and
t represents an integer of 1, 2, 3 or 4;
or a pharmaceutically acceptable salt or hydrate thereof.

In certain embodiments, R1 is an aromatic or heteroaromatic moiety.

In some embodiments, R2 is H or a saturated or unsaturated alkyl or acyl group.

In specific embodiments, R3 is H or a saturated or unsaturated alkyl group optionally containing an aromatic moiety or a saturated or unsaturated acyl group.

In one embodiment of this aspect, R2 is a saturated or unsaturated acyl group, preferably substituted or non-substituted, and R3 is H.

In another embodiment of this aspect, R2 is H and R3 is a saturated or unsaturated alkyl or acyl group, preferably substituted or non-substituted, containing an aromatic moiety.

In yet another embodiment of this aspect, R2 is H, R3 is H and R6 is a substituted alkyl or acyl group.

In other embodiments of this aspect, R2, R3 and R6 are not all H.

In further embodiments of this aspect, R2 and R3 are not both H.

In another embodiment of this aspect, said alkyl group containing an aromatic moiety in R3 represents an arylalkyl.

In another embodiment of this aspect, R1 is selected from

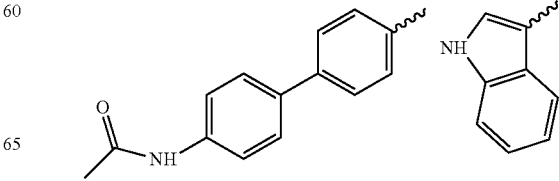

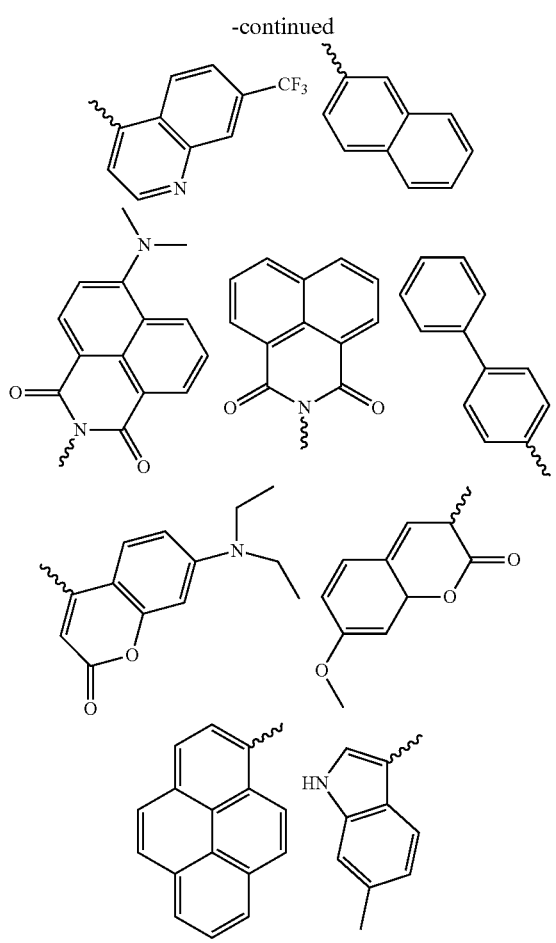

In another embodiment of this aspect, p and q independently represent an integer of 2 or 3; r represents an integer of 1; t represents an integer of 1 or 2 or 3, such as 2 or 3; and s represents an integer of 0 or 1 or 2, such as 0 or 1.

In another embodiment of this aspect, R2, when being a saturated or unsaturated alkyl or acyl group, preferably substituted or non-substituted, comprises from 6 to 16 carbon atoms.

In another embodiment of this aspect, R3, when being a saturated or unsaturated alkyl or acyl group, preferably substituted or non-substituted, comprises from 4 to 16 carbon atoms.

In another embodiment of this aspect, R4 is a carboxylate group.

In another embodiment of this aspect, R5 is a carboxylate group.

In another embodiment of this aspect, R6 is a substituted alkyl or acyl group selected from 2-acetamidoacetamido)eth-1-yl, 2-(2-benzylamino)eth-1-yl, 2-(2-acetamido-3-hydroxypropanamido)eth-1-yl, 2-(2-acetamido-4-amino-4-oxobutanamido)eth-1-yl, 2-(2-(2-acetamido-3-hydroxypropanamido)acetamido)eth-1-yl and 2-(2-(2-acetamido-4-amino-4-oxobutanamido)acetamido)eth-1-yl.

In another embodiment of this aspect, there is provided a compound according to formula I, said compound being selected from the following structures which have been shown to stabilize the helical conformation of the Aβ model more than with Pep 1b and Dec-DETA as evidenced by the higher values of retained aAHBs found in molecular dynamics experiments (Tables 1 and 2):

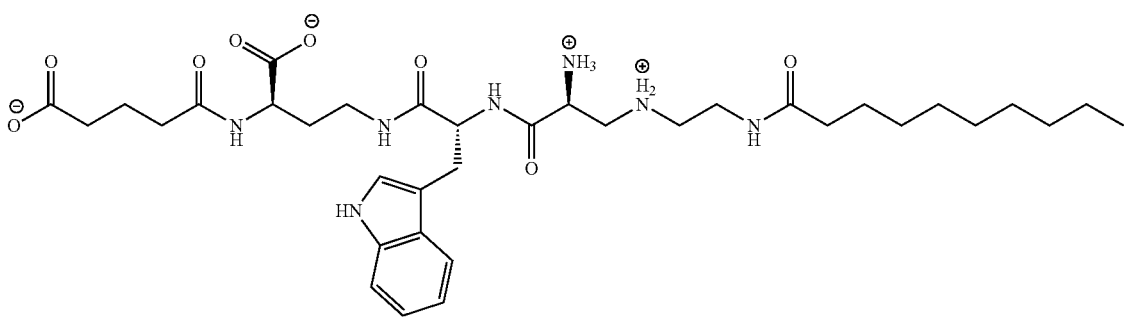

DH18

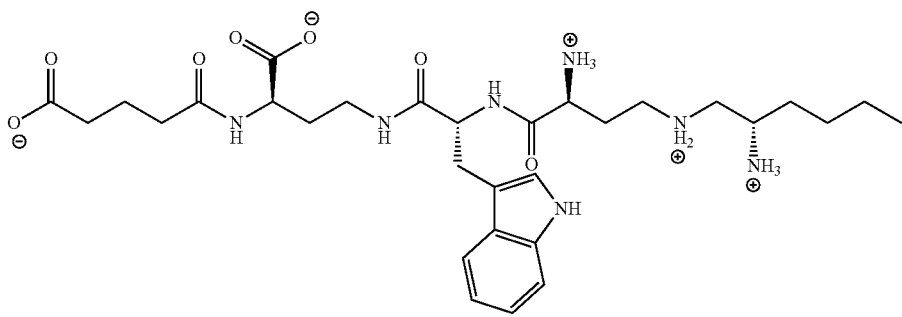

4NAEDab

-continued
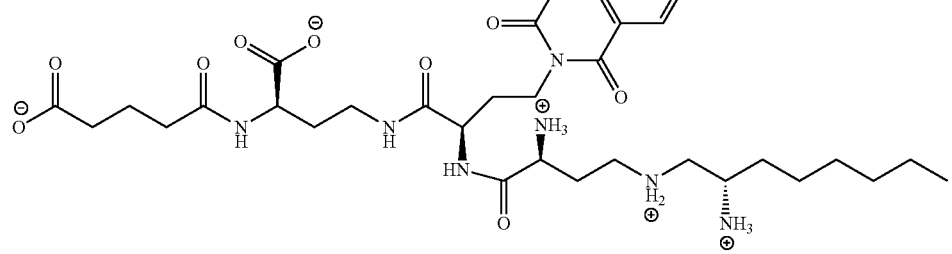
8AEDabDmnDabGla
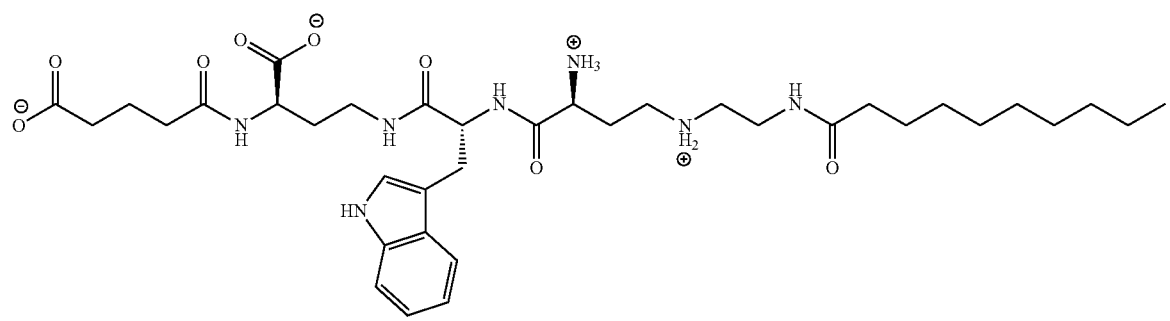
DecAEDab
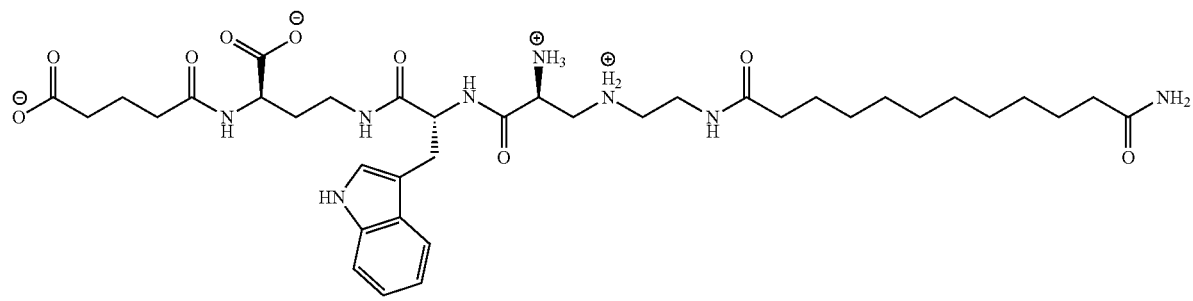
DH20
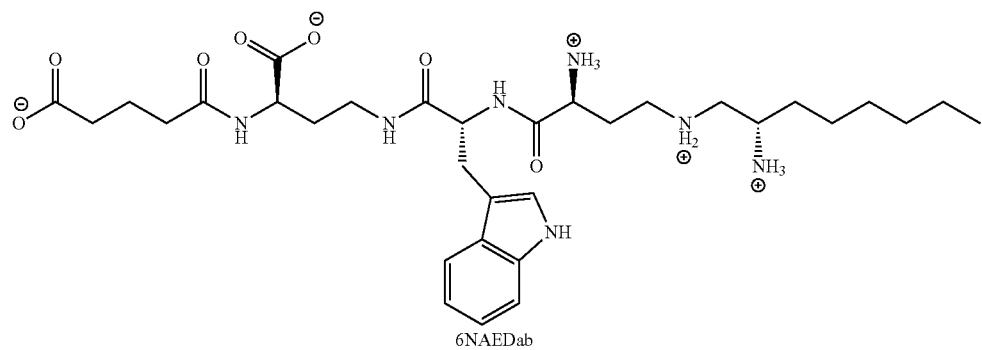
6NAEDab

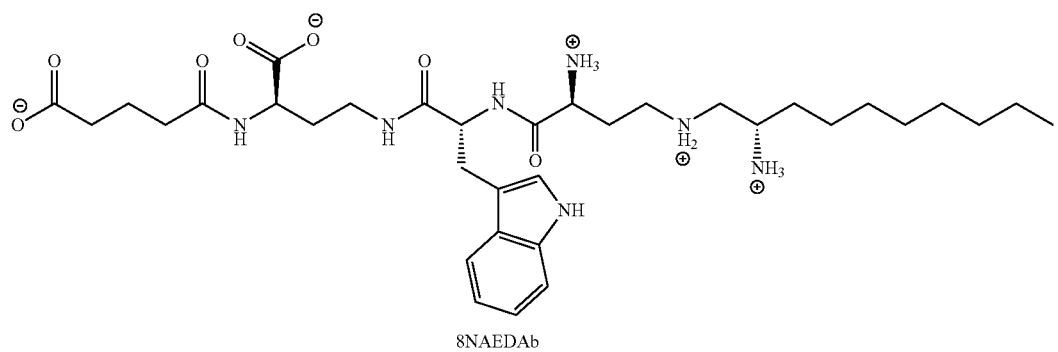
8NAEDAb
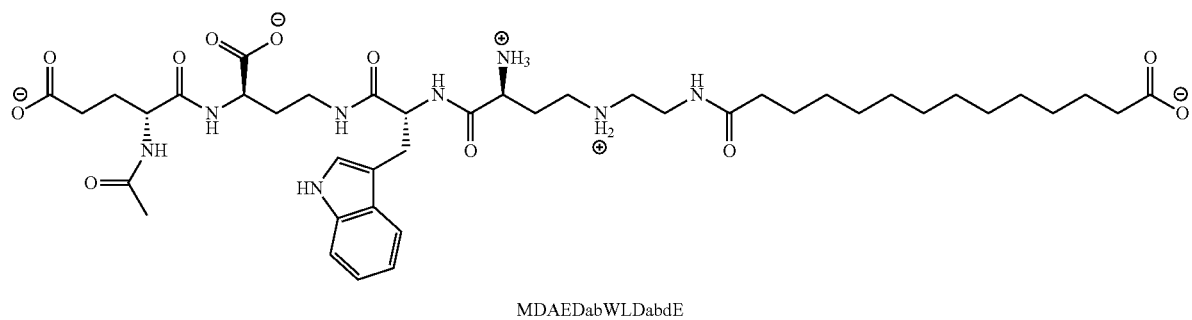
MDAEDabWLDabdE
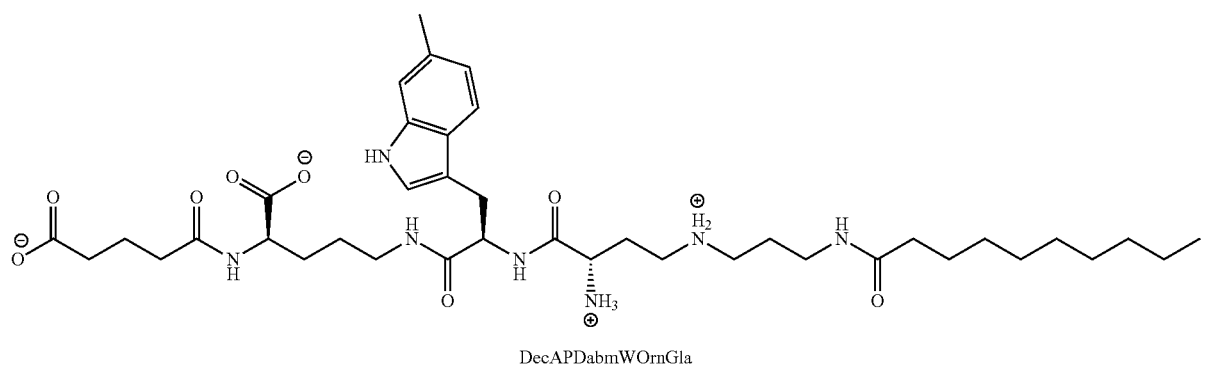
DecAPDabmWOrnGla
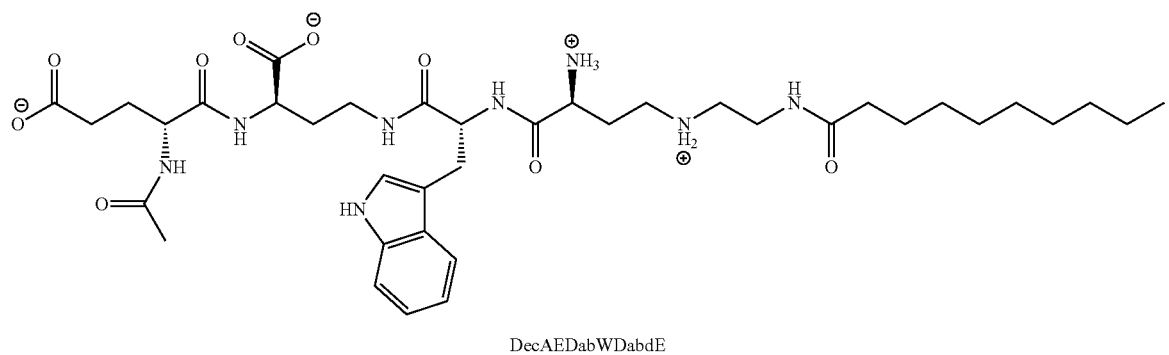
DecAEDabWDabdE -continued
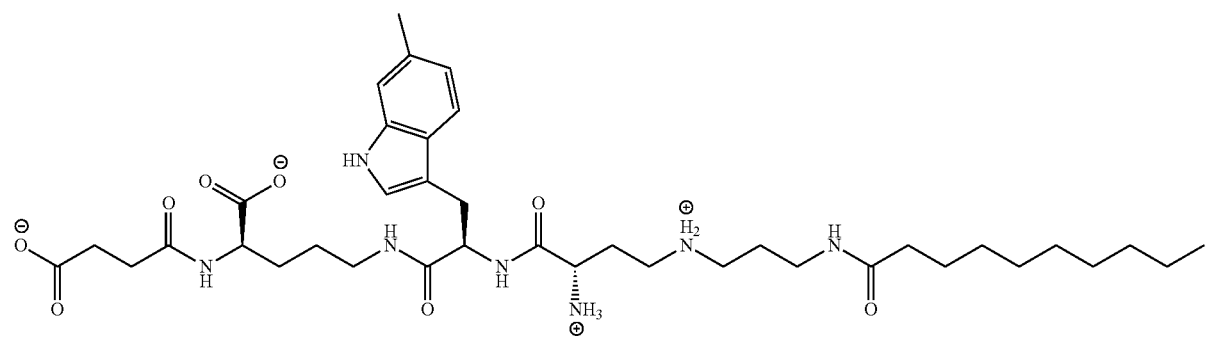
DecAPDabmWOrnSu
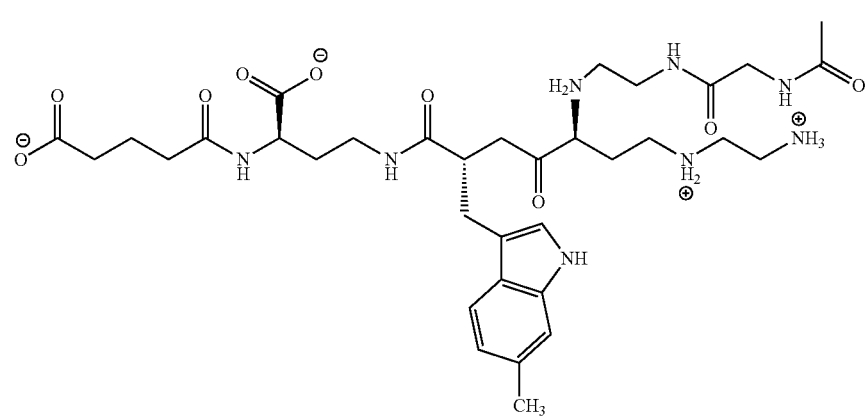
AcGdiAEDab
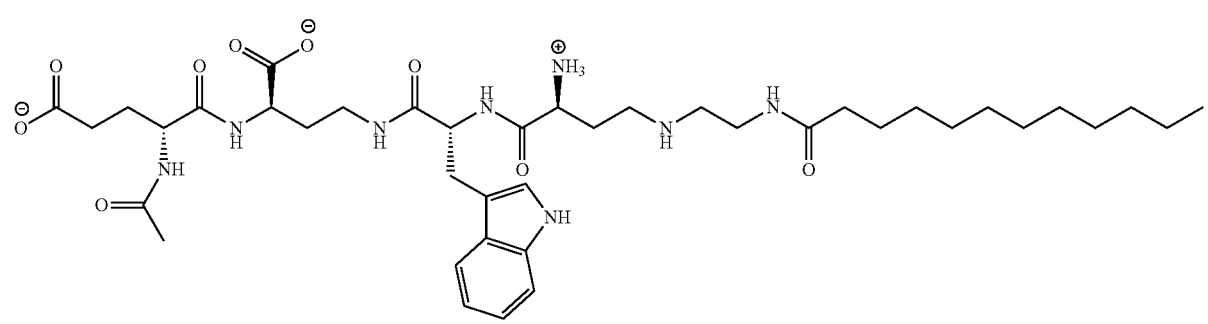
DodecAEDabWDabdE
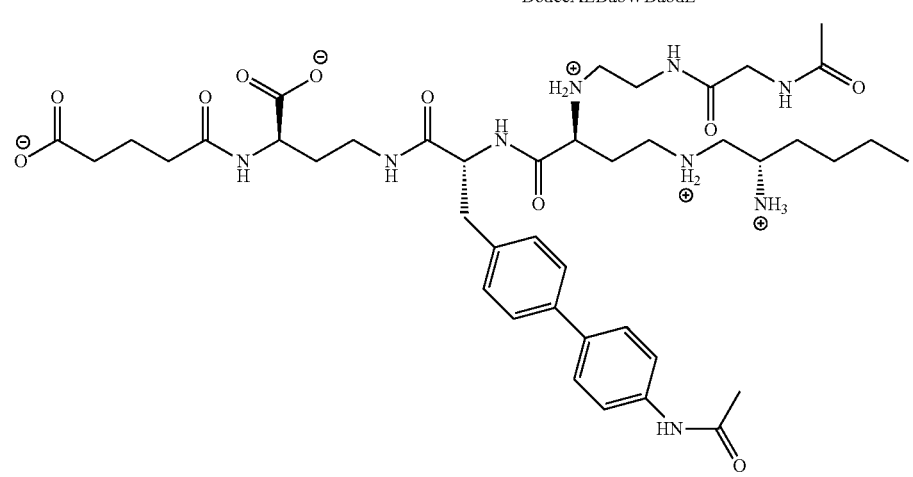
Ac4NdiAEDabpBp -continued
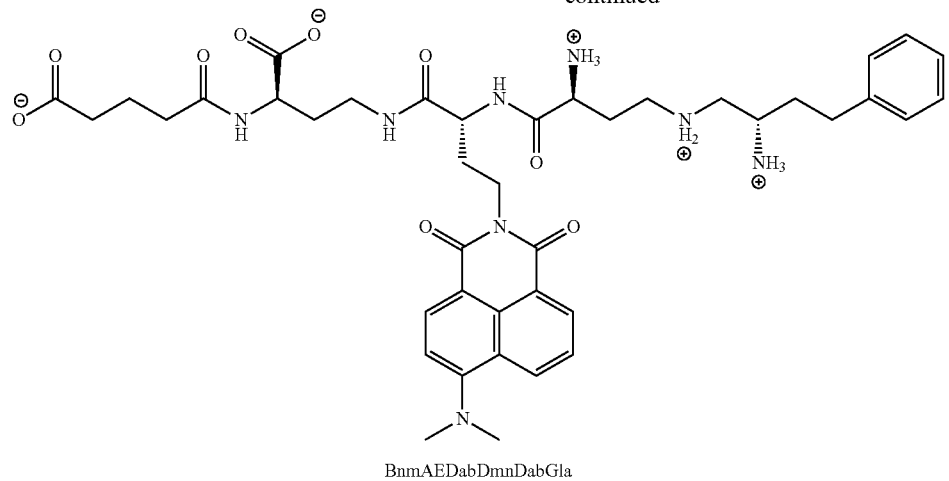
BnmAEDabDmnDabGla
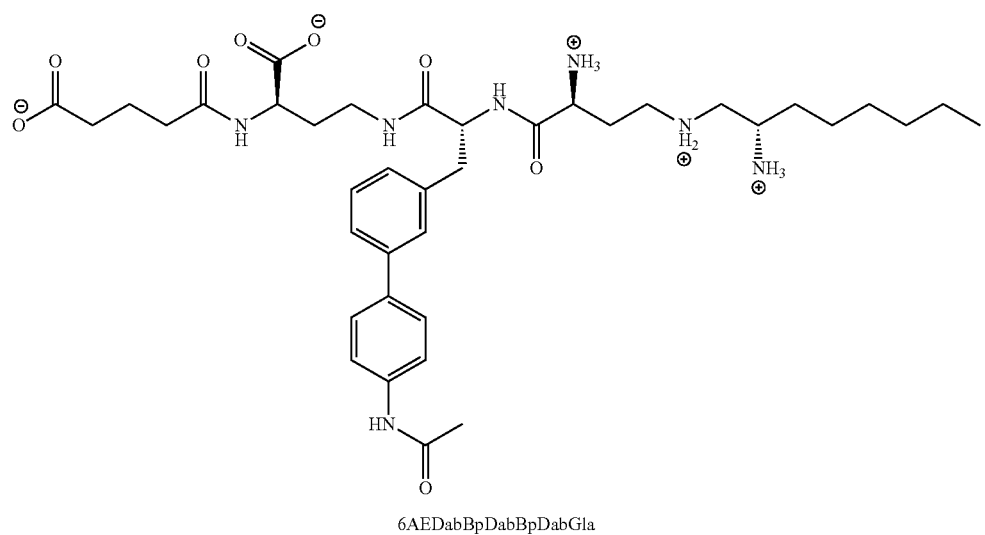
6AEDabBpDabBpDabGla
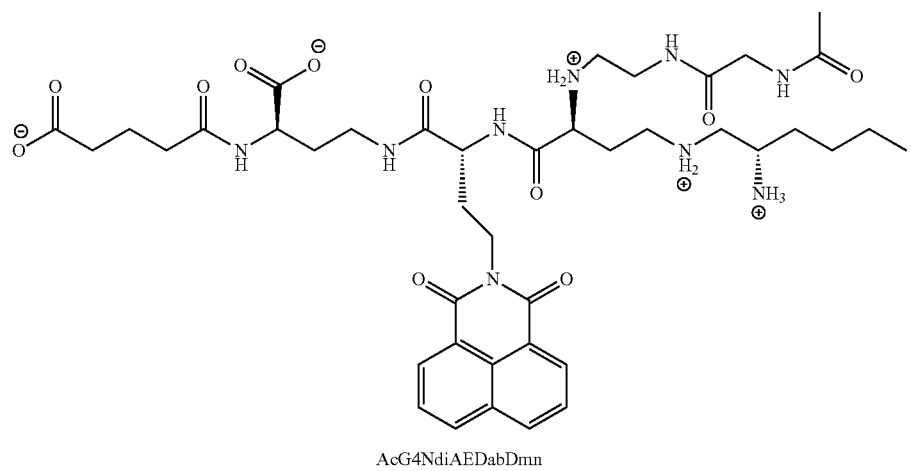
AcG4NdiAEDabDmn -continued
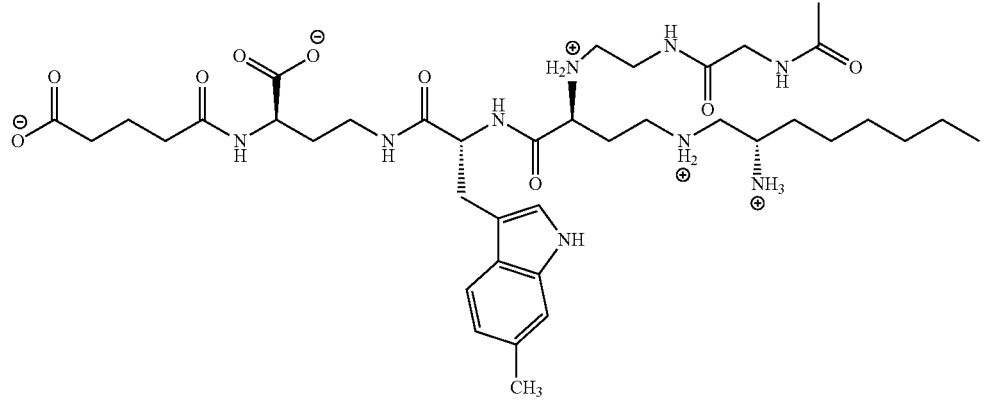
AcG6NdiAEDabmW
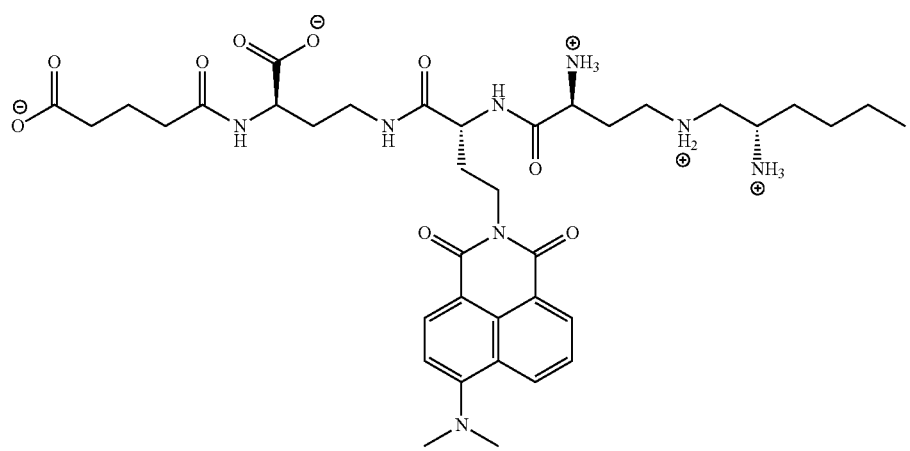
6AEDabDmnDabGla
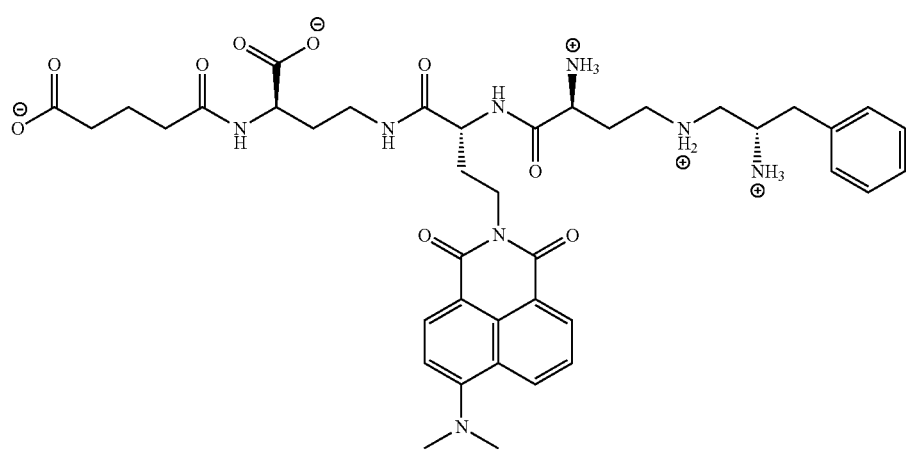
BnAEDabDmnDabGla

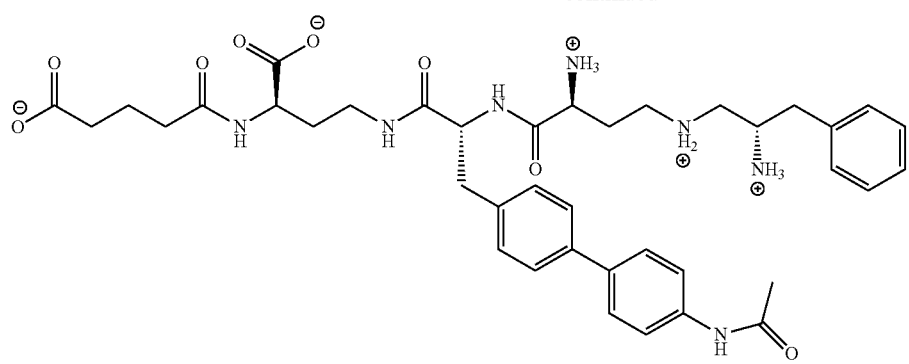
BnAEDabpBp
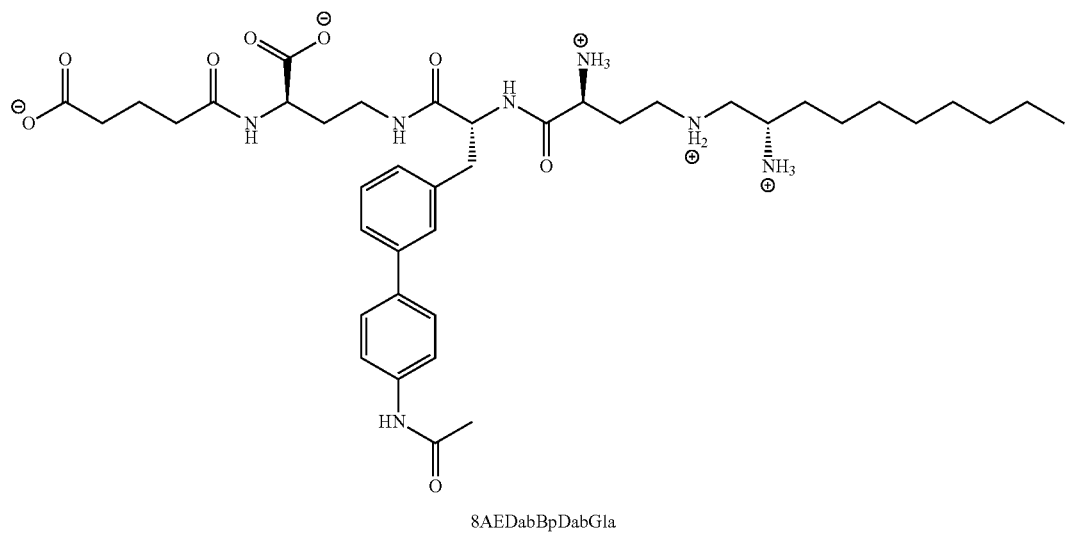
8AEDabBpDabGla
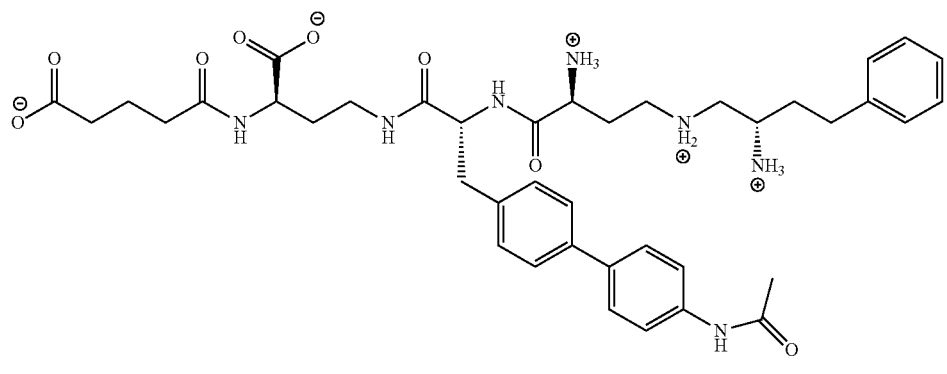
BnmAEDabpBp

-continued
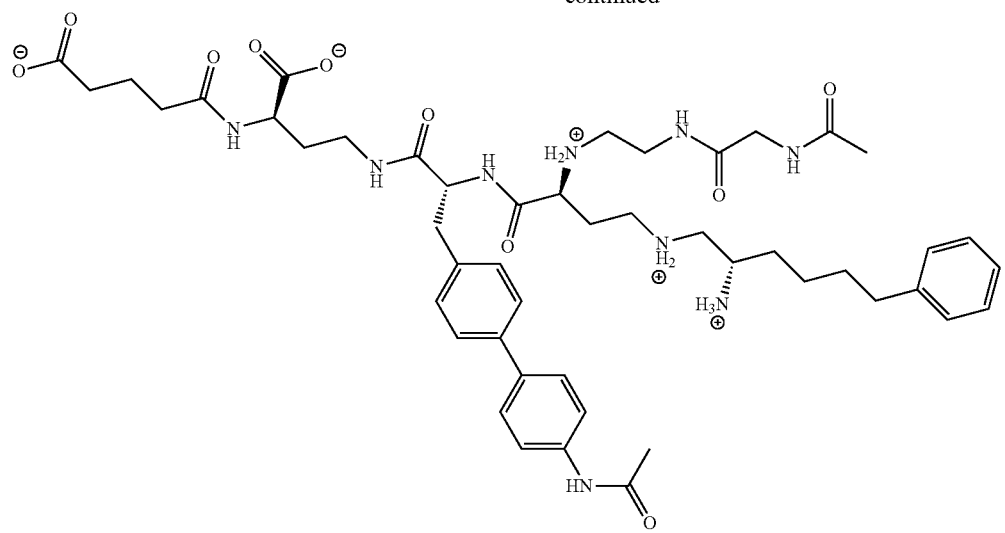
BnmAEXDabpBp
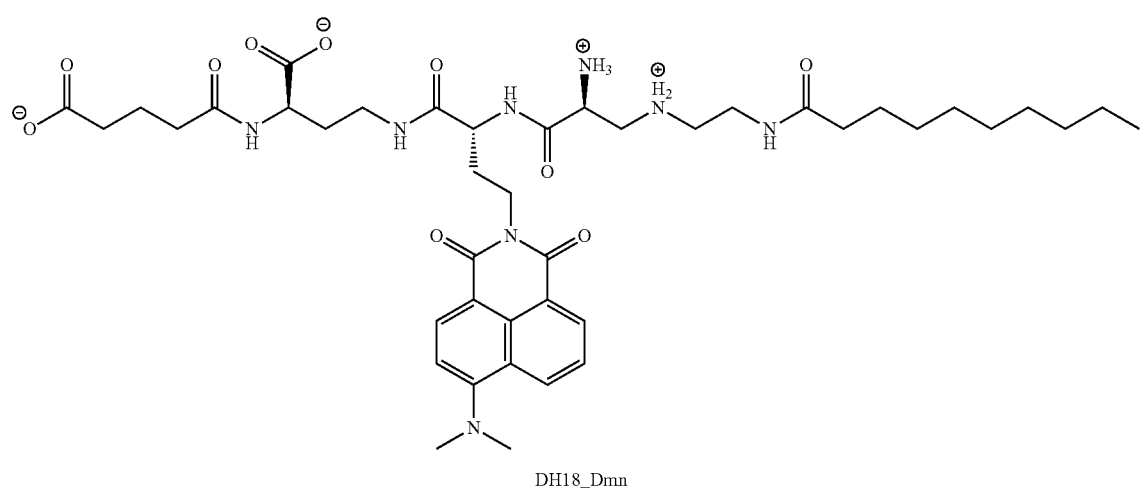
DH18_Dmn
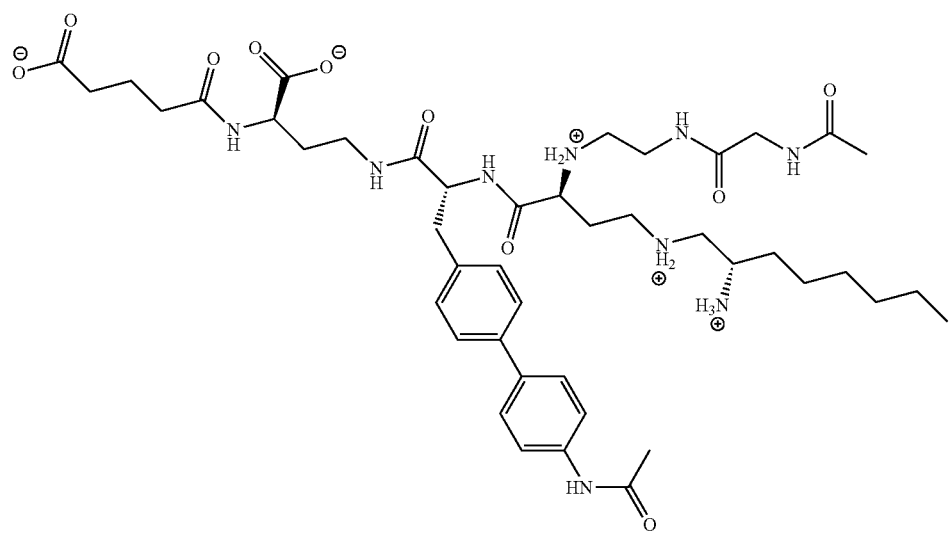
15_Hexyl

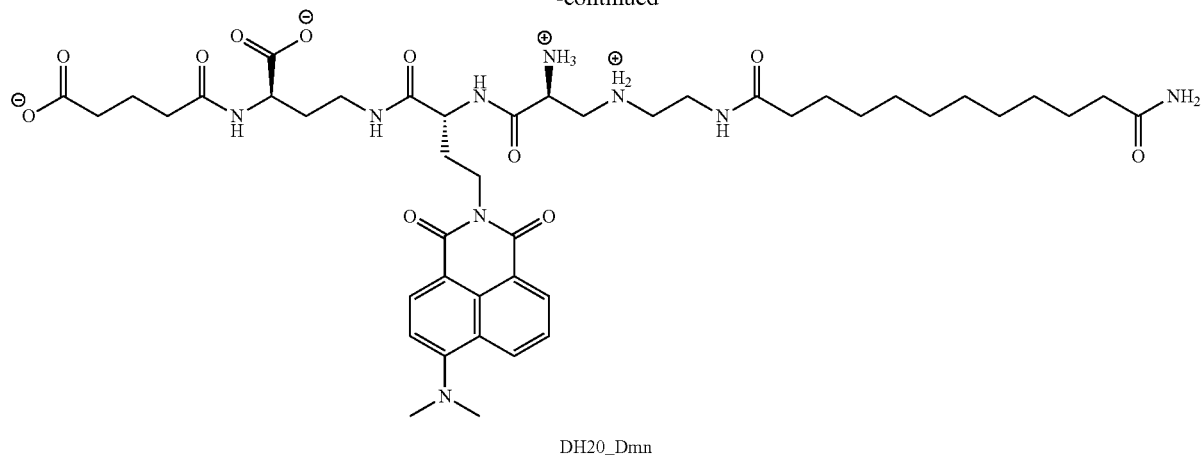

DH20_Dmn

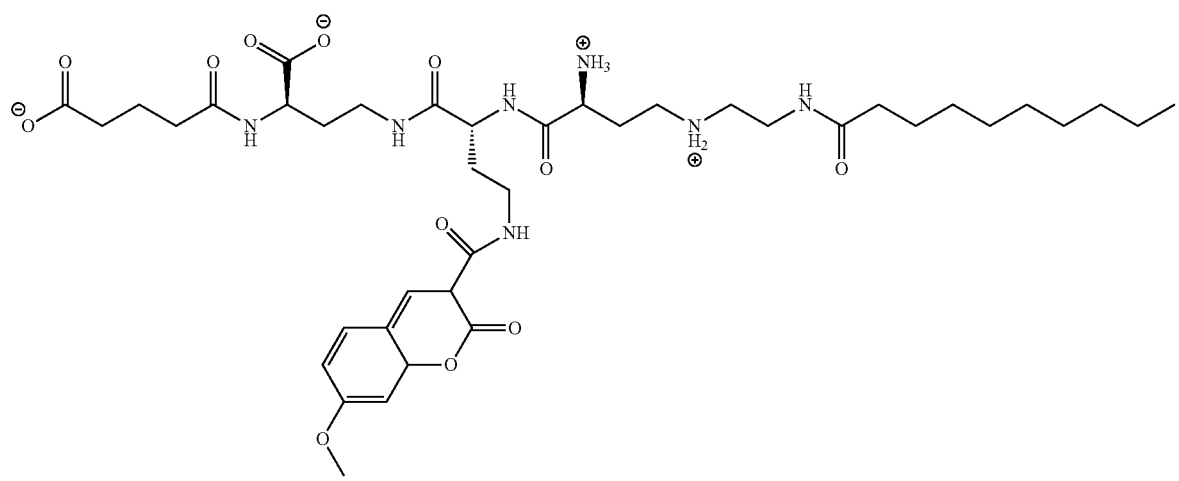 [SMILES: CCCCCCCCCC(=O)NCC[NH2+]CC[C@H]([NH3+])C(=O)N[C@H](CCNC(=O)C1C=C2C=CC(OC)=CC2OC1=O)C(=O)NCC[C@@H](NC(=O)CCCC(=O)[O-])C(=O)[O-]]

In another embodiment of this aspect, there is provided a compound according to formula I, said compound being selected from the following structures which have been shown to stabilize the helical conformation of the Aβ model more than with Pep 1b and Dec-DETA as evidenced by the higher values of retained aAHBs found in molecular dynamics experiments (Tables 1 and 2):

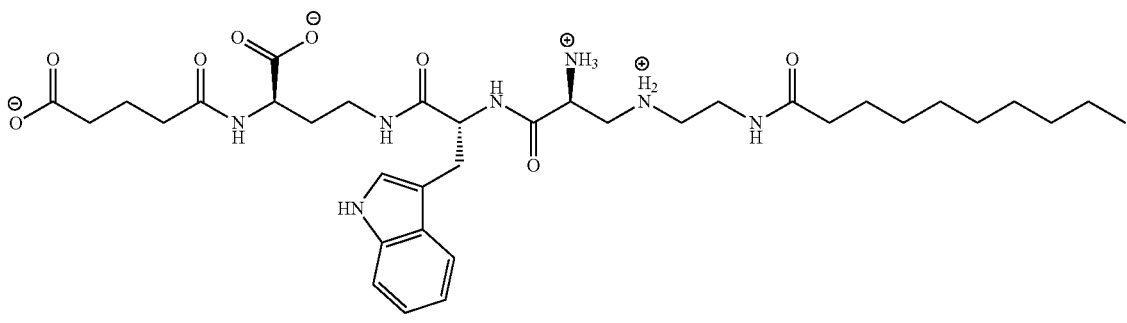

DH18

-continued
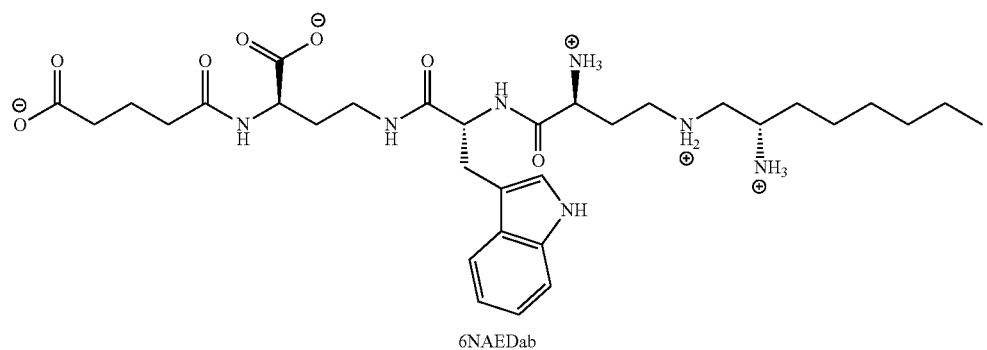
6NAEDab
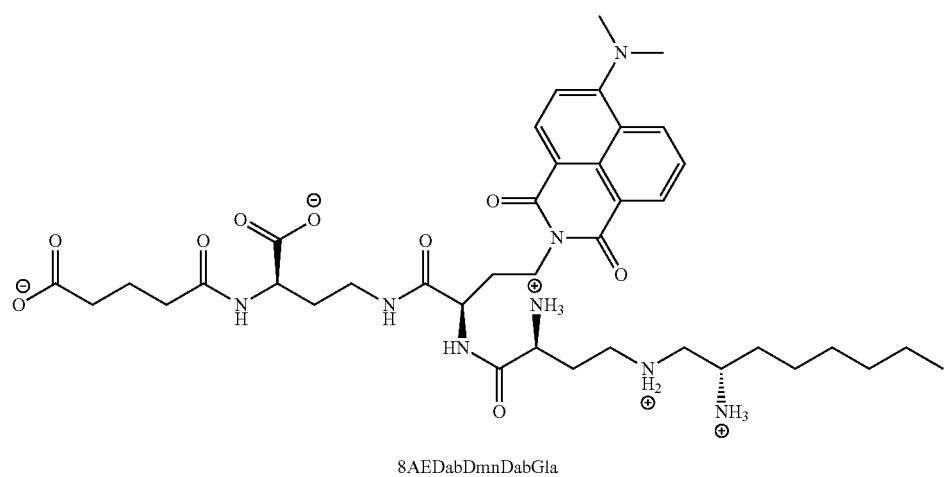
8AEDabDmnDabGla
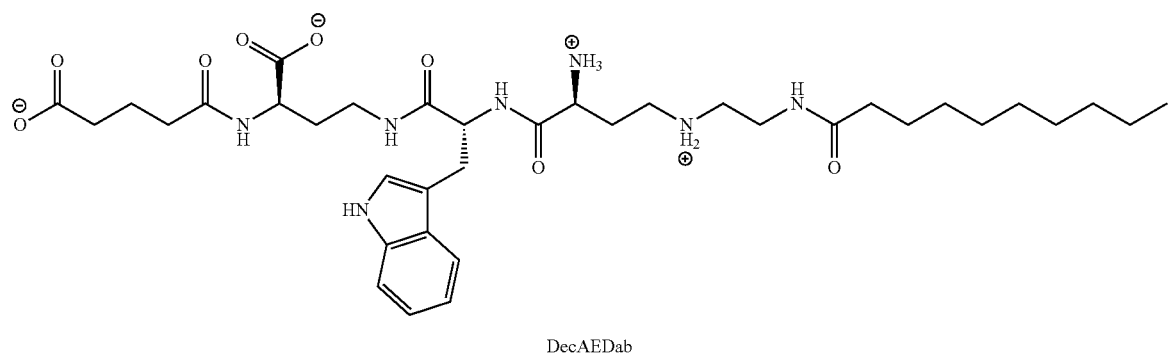
DecAEDab
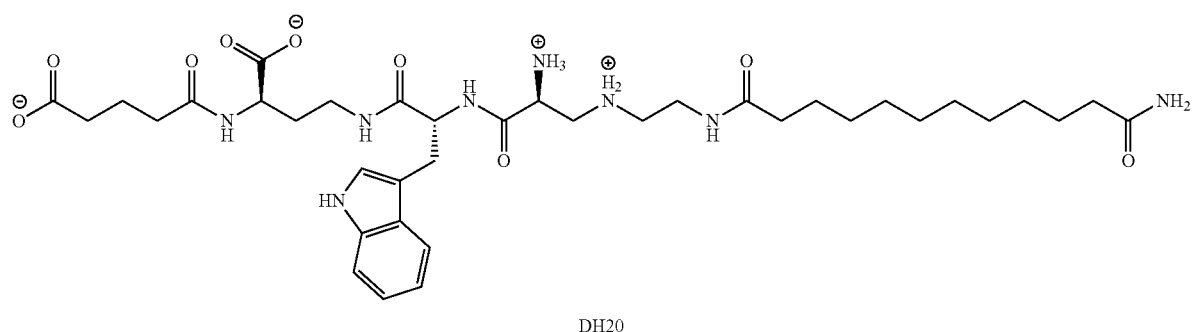
DH20

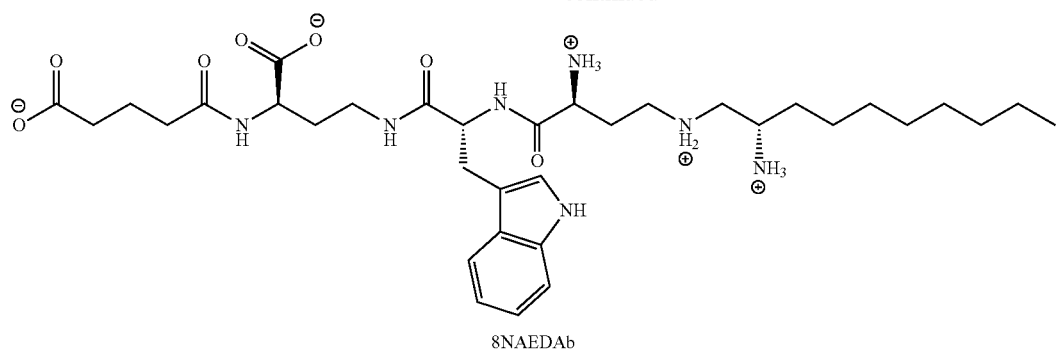
8NAEDAb
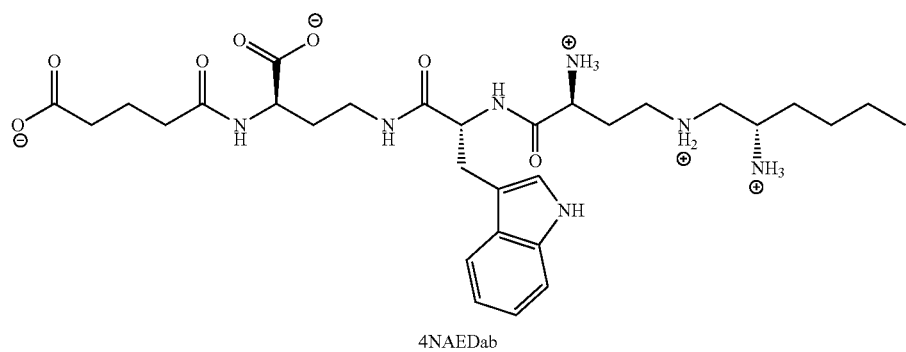
4NAEDab
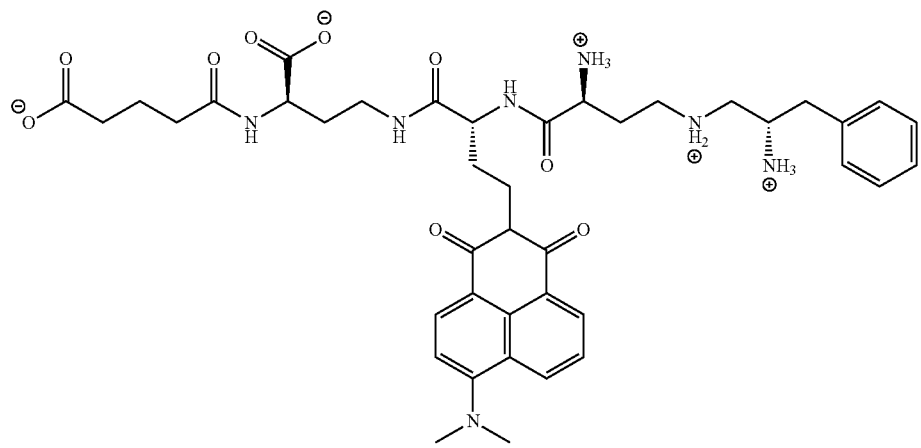
BnAEDabDmnDabGla
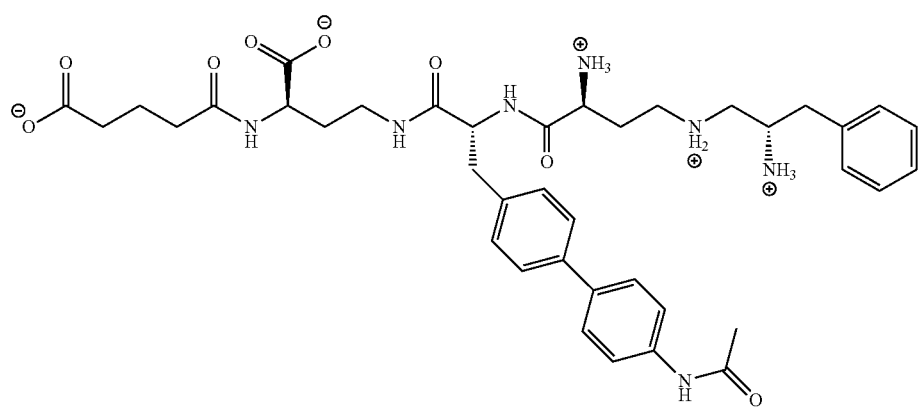
BnAEDabpBp

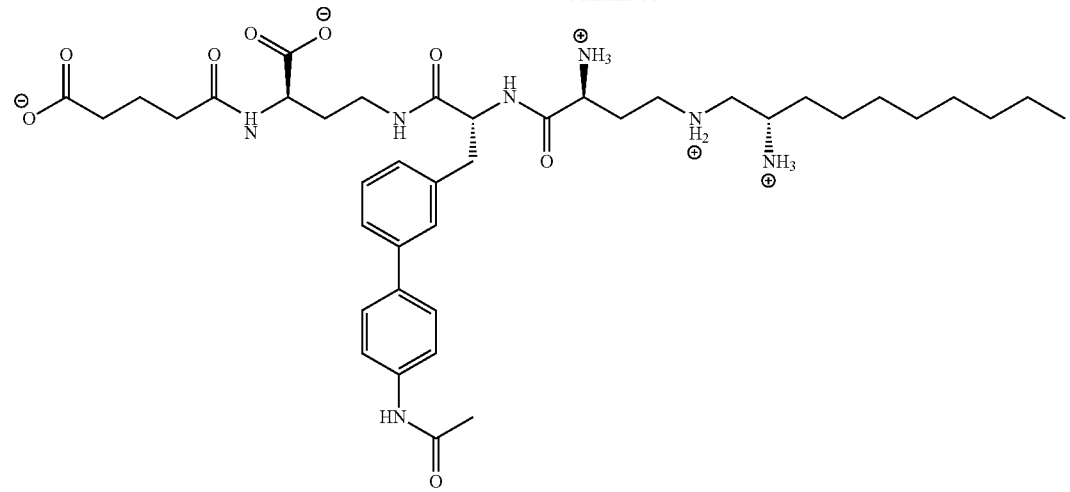
8AEDabBpDabGla
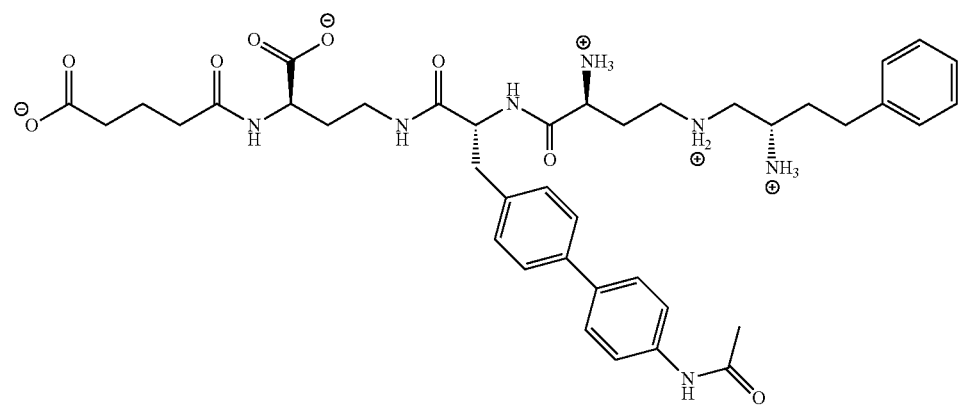
BnmAEDabpBp
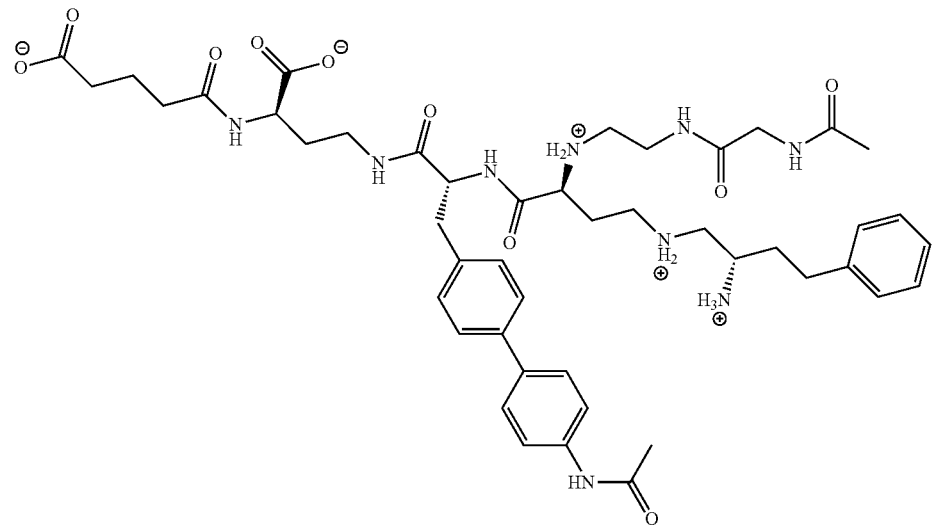
BnmAEXDabpBp

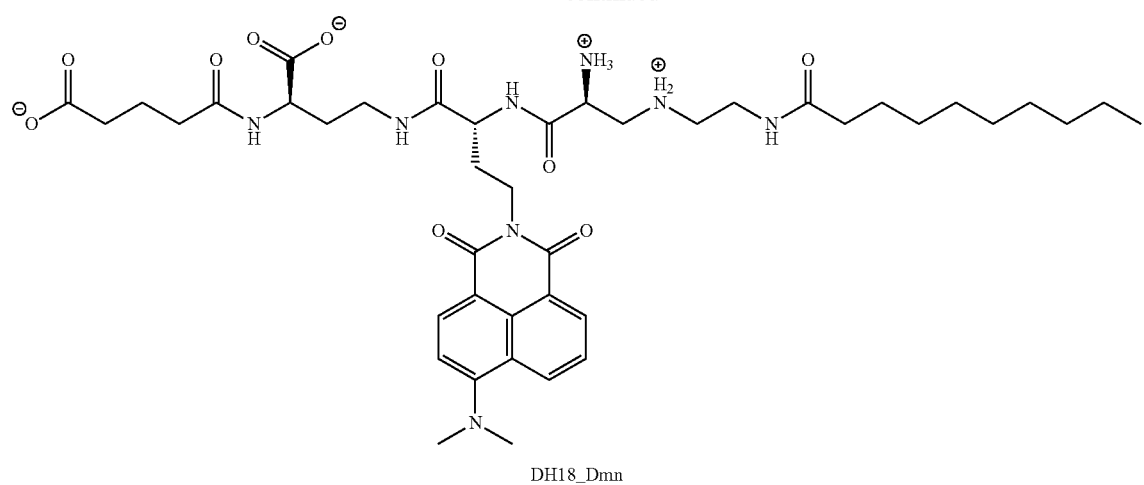
DH18_Dmn
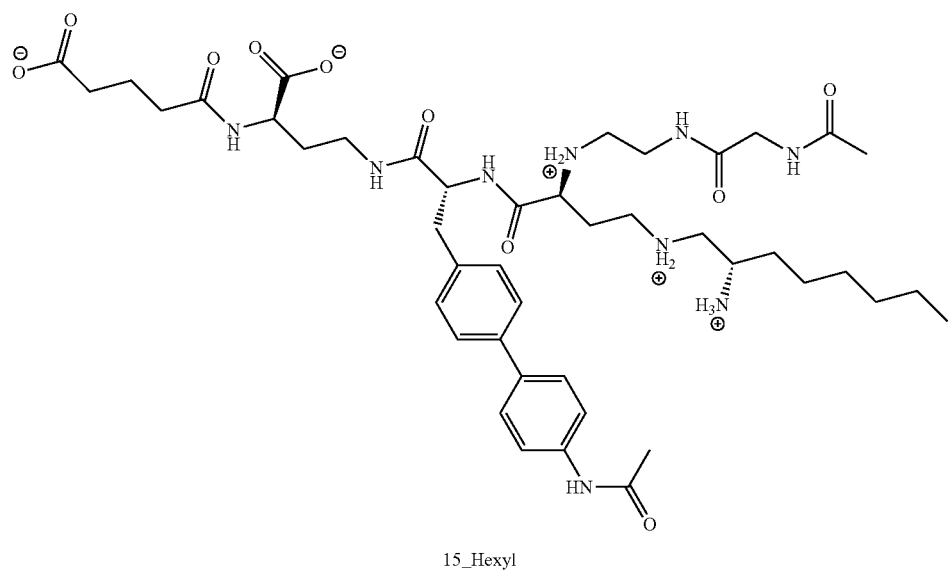
15_Hexyl
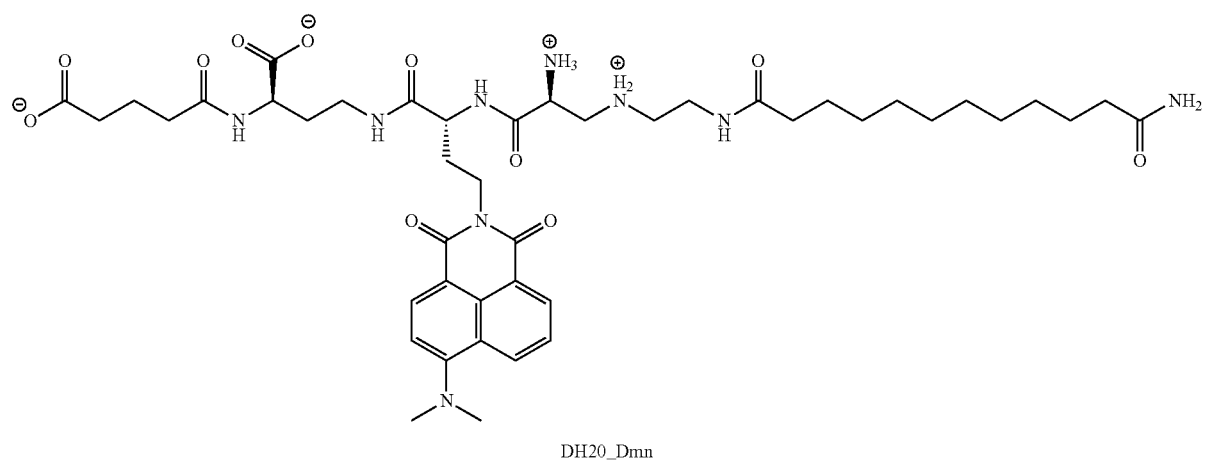
DH20_Dmn

-continued
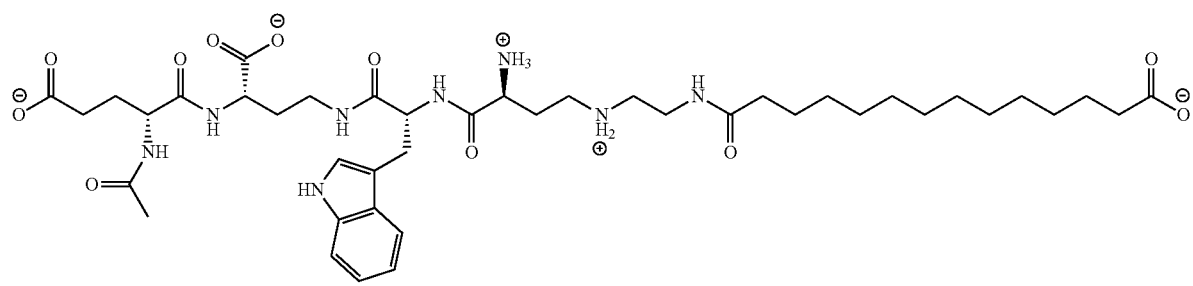
MDAEDabWLDabdE
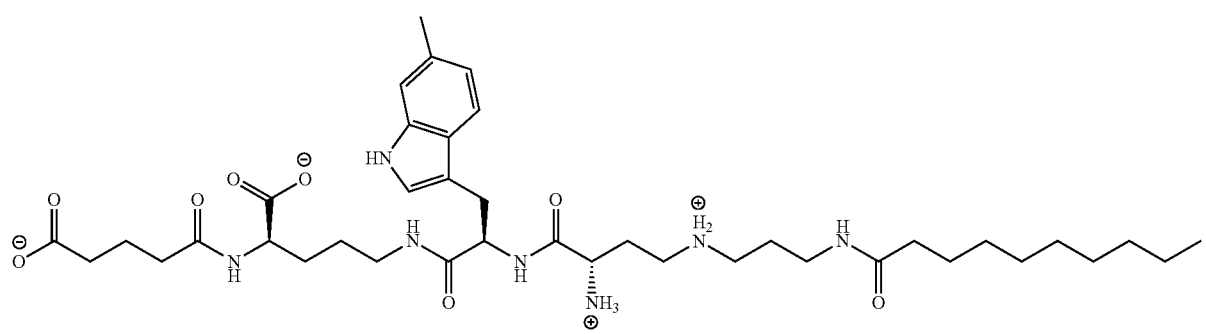
DecAPDabmWOrnGla
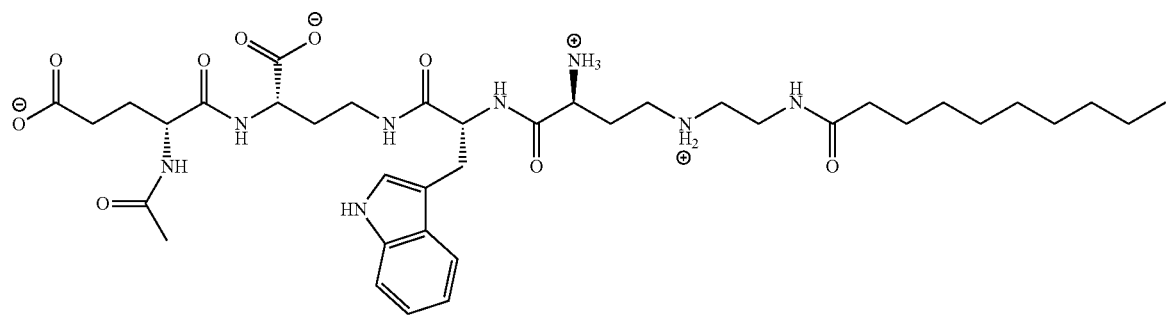
DecAEDabWDabdE
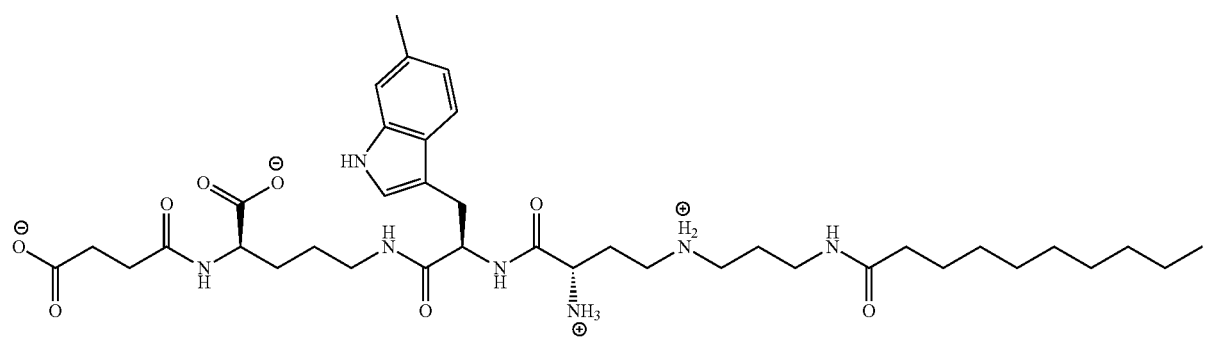
DecAPDabmWOrnSu -continued
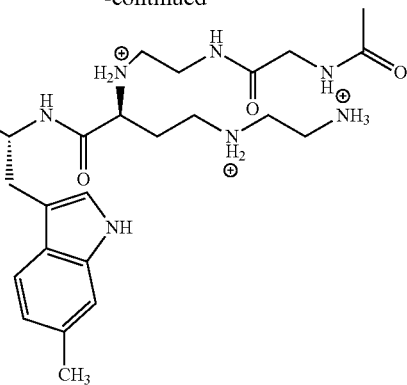
AcGdiAEDab
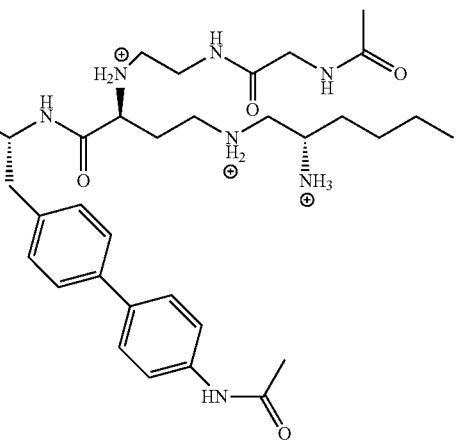
DodecAEDabWDabdE
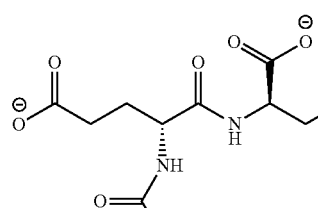
Ac4NdiAEDabpBp
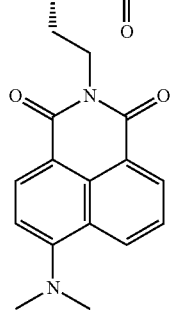
BnmAEDabDmnDabGla -continued
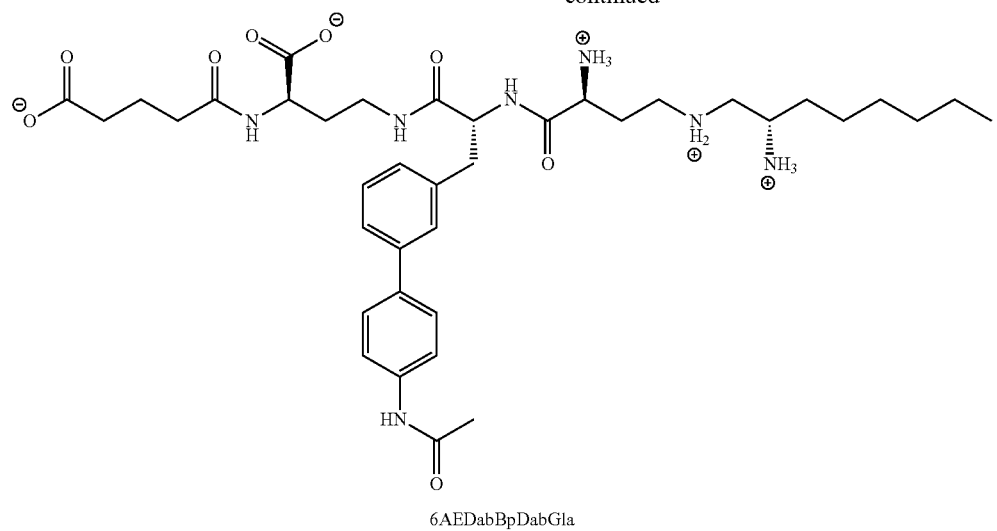
6AEDabBpDabGla
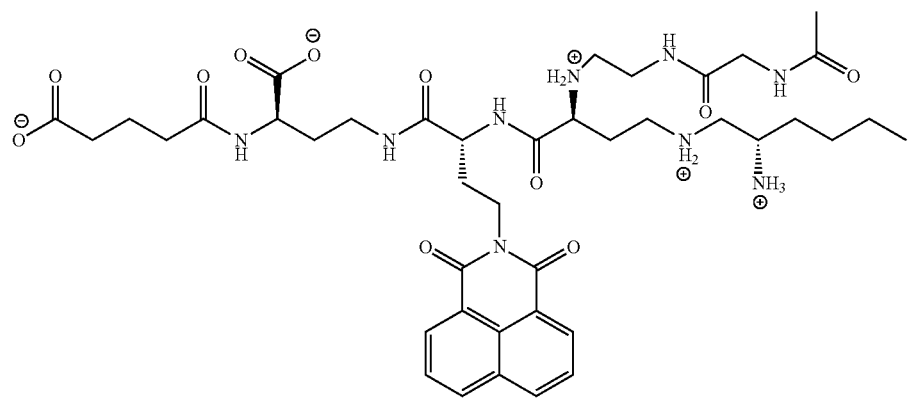
AcG4NdiAEDabDmn
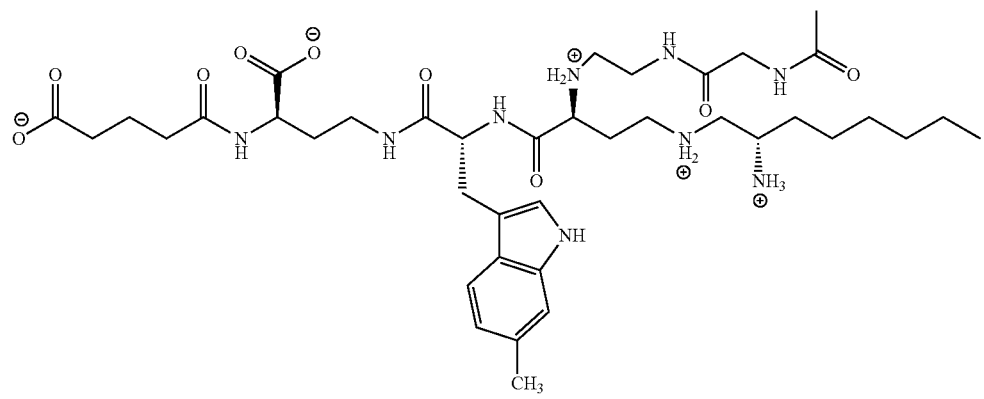
AcG6NdiAEDabmW

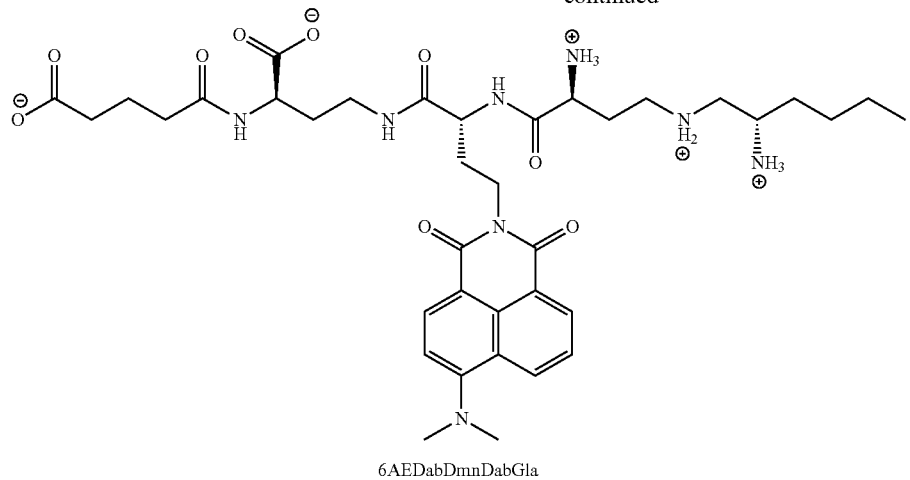
6AEDabDmnDabGla
In another embodiment of this aspect, there is provided a compound according to formula I, said compound being selected from
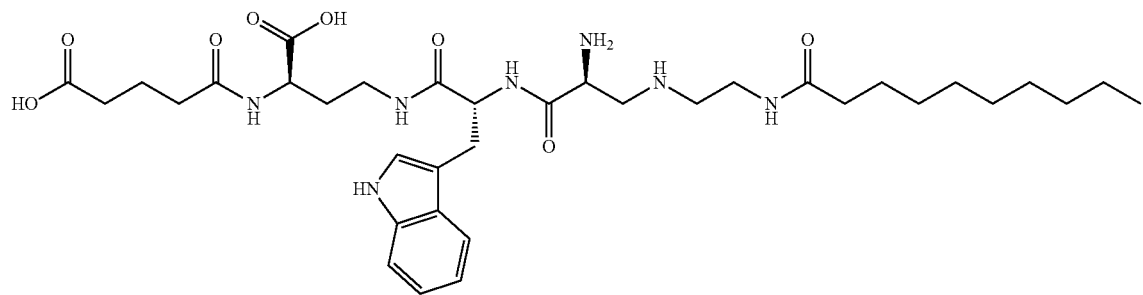 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]
(R)—N⁴—[N²—(N³—(N-decanoyl-2-aminoethyl)-(S)-2,3-diaminopropionyl)-D-tryptophanyl]-N²-glutanoyl-2,4-di-aminobutanoic acid;
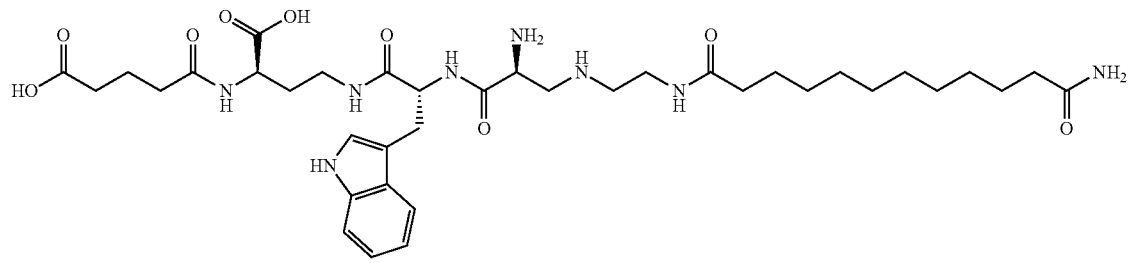 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid;
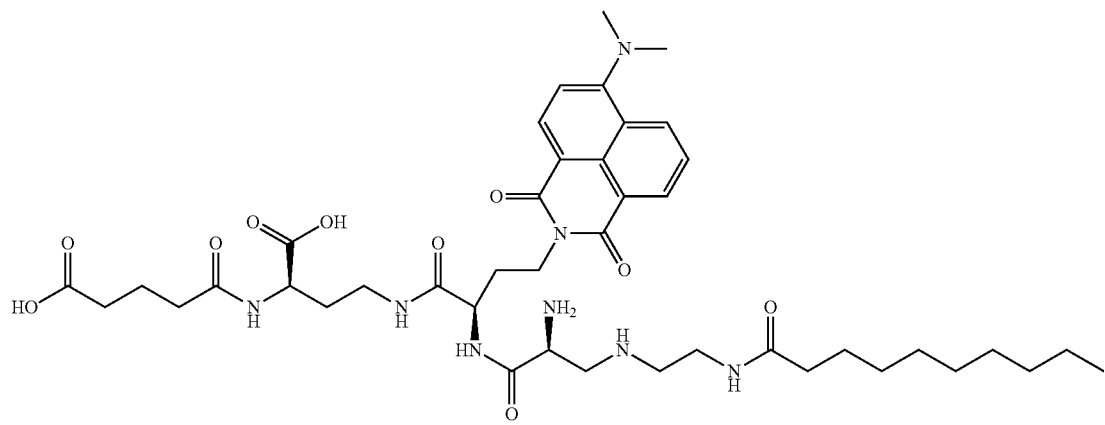 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)-AE-decanoyl;
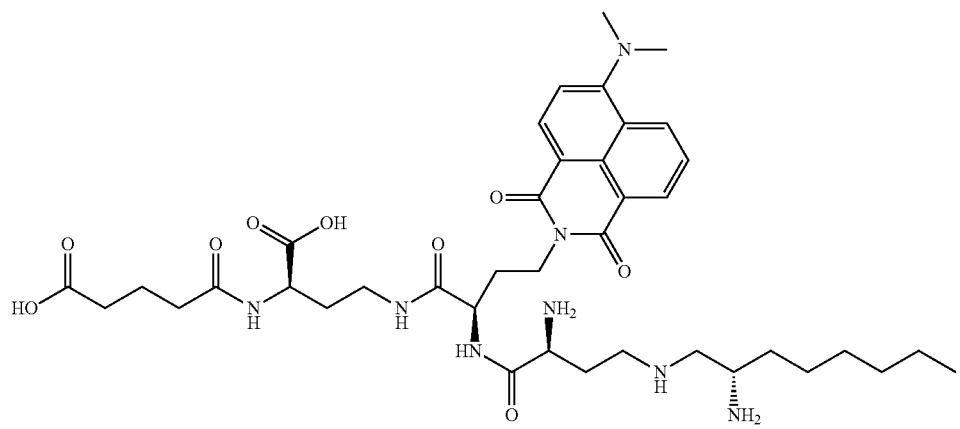 [SMILES: CCCCCC[C@H](N)CNCC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)—CH₂CH(NH₂)—C6; and
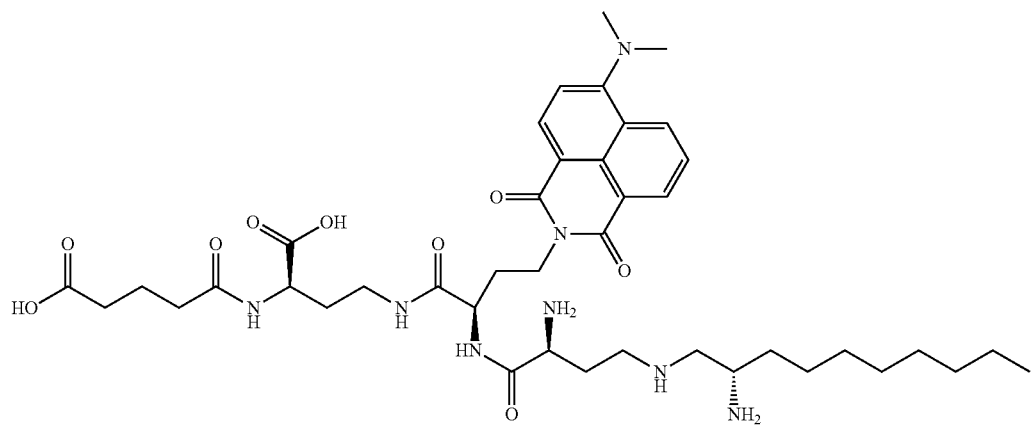 [SMILES: CCCCCCCC[C@H](N)CNCC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]

HO-Gla-D-Dab-(COOH)-D-DMNA-L-Dap-(NH₂)—CH₂CH(NH₂)—C8.

In a specific embodiment of this aspect, there is provided a compound according to formula I, said compound being selected from

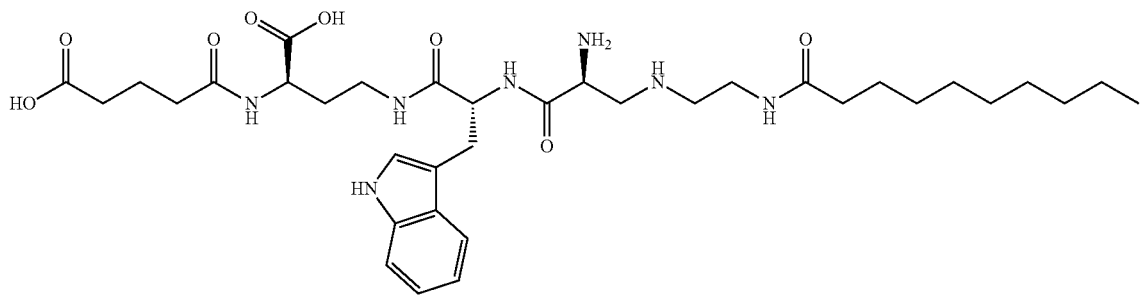 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-decanoyl-2-aminoethyl)-(S)-2,3-diaminopropionyl)-D-tryptophanyl]-N²-glutanoyl-2,4-diaminobutanoic acid;

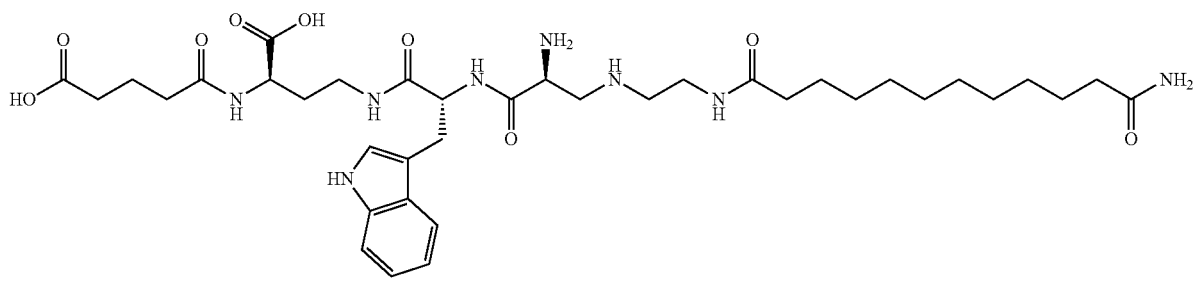 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid. and

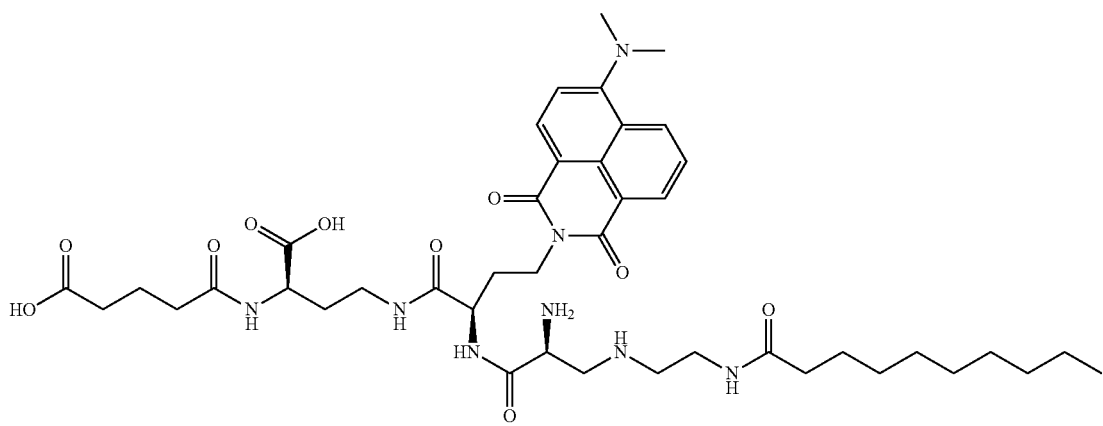 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]

HO-Gla-D-Dab-(COOH)-D-DMNA-L-Dap-(NH₂)-AE-decanoyl;

A preferred compound according to formula I is

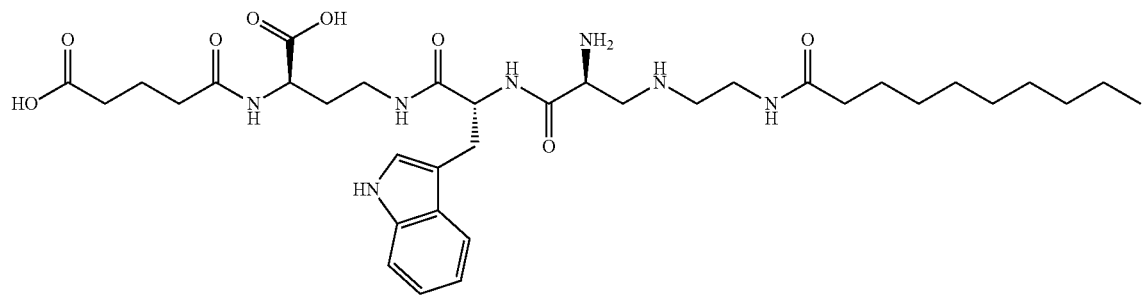 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-decanoyl-2-aminoethyl)-(S)-2,3-diaminopropionyl)-D-tryptophanyl]-N²-glutanoyl-2,4-diaminobutanoic acid.

Another preferred compound according to formula I is

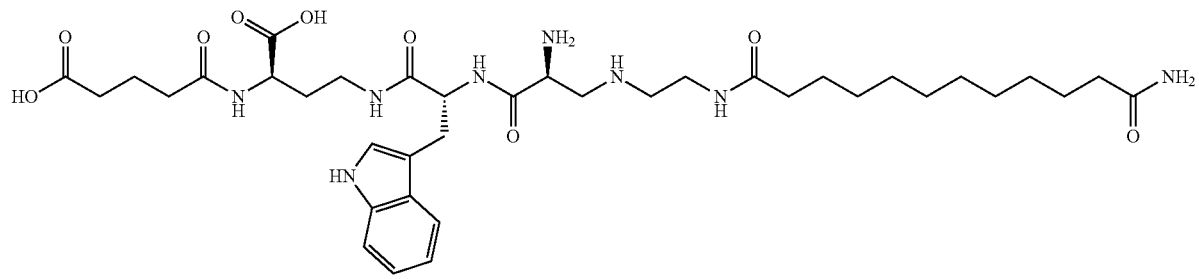 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid.

Another preferred compound according to formula I is

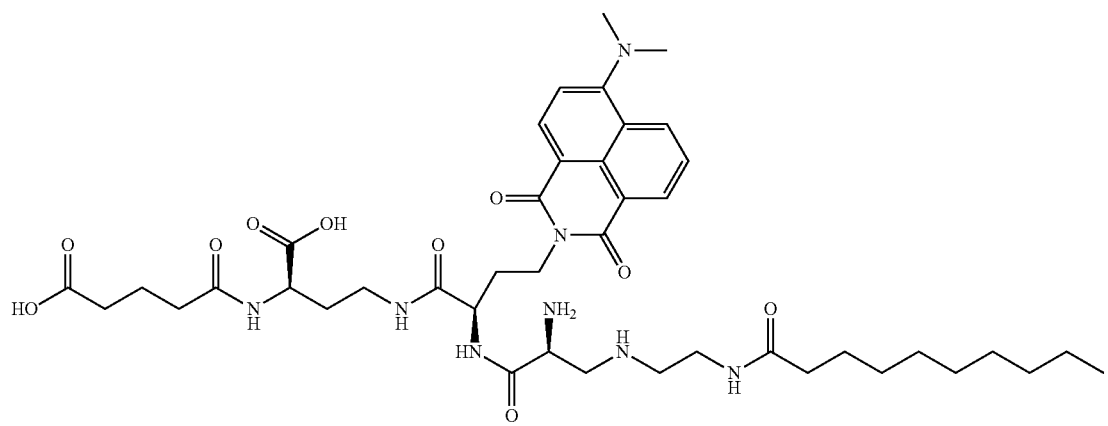 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]

HO-Gla-D-Dab-(COOH)-D-DMNA-L-Dap-(NH₂)-AE-decanoyl.

In another embodiment of this aspect, said compound of formula I is able to interact with at least two of
 the side chain of Lys16 of an Aβ peptide;
 the side chain of His 13 of an Aβ peptide;
 the side-chain of Glu23 of an Aβ peptide;
 the side chain of Phe19 of an Aβ peptide;
 the side chain of Phe20 or an Aβ peptide;
 the side-chain of Asp22 of an Aβ peptide; and
 the side-chain of Val18 of an Aβ peptide.

In another embodiment of this aspect, said compound of formula I is able to interact with at least three of
 the side chain of Lys16 of an Aβ peptide;
 the side chain of His 13 of an Aβ peptide;
 the side-chain of Glu23 of an Aβ peptide;
 the side chain of Phe19 of an Aβ peptide;
 the side chain of Phe20 or an Aβ peptide;
 the side-chain of Asp22 of an Aβ peptide; and
 the side-chain of Val18 of an Aβ peptide.

In another embodiment of this aspect, said compound of formula I is able to interact with at least four of the side chain of Lys16 of an Aβ peptide;
the side chain of His 13 of an Aβ peptide;
the side-chain of Glu23 of an Aβ peptide;
the side chain of Phe19 of an Aβ peptide;
the side chain of Phe20 or an Aβ peptide;
the side-chain of Asp22 of an Aβ peptide; and
the side-chain of Val18 of an Aβ peptide.

In another embodiment of this aspect, said compound of formula I is able to interact with at least five of
the side chain of Lys16 of an Aβ peptide;
the side chain of His 13 of an Aβ peptide;
the side-chain of Glu23 of an Aβ peptide;
the side chain of Phe19 of an Aβ peptide;
the side chain of Phe20 or an Aβ peptide;
the side-chain of Asp22 of an Aβ peptide; and
the side-chain of Val18 of an Aβ peptide.

In another embodiment of this aspect, said compound of formula I is able to interact with at least two, three, four or five of
the side chain of Lys16 of an Aβ peptide;
the side chain of His 13 of an Aβ peptide;
the side-chain of Glu23 of an Aβ peptide;
the side chain of Phe19 of an Aβ peptide;
the side chain of Phe20 or an Aβ peptide;
the side-chain of Asp22 of an Aβ peptide; or
the side-chain of Val18 of an Aβ peptide.

In another embodiment of this aspect, said compound of formula I is able to decrease the loss of an α-helix in an Aβ peptide.

In another aspect of the invention, there is provided a compound of formula I for use in therapy.

In another aspect of the invention, there is provided a compound of formula I for use in treatment of an Aβ peptide-related disorder.

In another aspect of the invention, there is provided a compound of formula I for use in treatment of Alzheimer's disease.

In another aspect of the invention, there is provided use of a compound of formula I for use in the manufacture of a medicament useful in the treatment of an Aβ peptide-related disorder.

In another aspect of the invention, there is provided use of a compound of formula I for use in the manufacture of a medicament useful in the treatment of Alzheimer's disease.

In another aspect of the invention, there is provided a method of treating a subject at risk for or having an Aβ peptide-related disorder, the method comprising administering a therapeutically effective amount of a compound of formula I to said subject. Preferably, said Aβ peptide-related disorder is Alzheimer's disease.

In another aspect of the invention, there is provided a method of treating a subject at risk for or having an Aβ peptide-related disorder, the method comprising
identifying a subject at risk for or having an Aβ peptide-related disorder; and
administering a therapeutically effective amount of a compound of formula I to the subject.

Preferably, the Aβ peptide-related disorder is Alzheimer's disease, the subject is a mammal such as a a human.

In another aspect of the invention, there is provided a method of identifying a compound that is a candidate compound for treating an Aβ peptide-related disorder, the method comprising;
providing a compound of formula I to the subject;
contacting an Aβ peptide with the compound, thereby providing a sample;
determining the amount of Aβ peptide in α-helical form or β form in the sample;
comparing the amount of Aβ peptide in α-helical form or β form compared to a reference, wherein a compound that increases the amount of Aβ peptide in α-helical form or decreases the amount of Aβ peptide in β form in the sample compared to the reference is a candidate compound.

Preferably, said Aβ peptide is provided in vitro or provided in an animal, such as in an animal model.

In another aspect of the invention, there is provided a precursor for use in a process of synthesizing a compound of formula I. The compounds are useful as precursors in the synthesis of a compound of formula I.

There is also provided a process of synthesizing a compound of formula I, comprising the following steps:
a) providing one or more precursors compounds as set out herein; and
b) synthesizing the compound of formula I from said one or more precursors. In one embodiment, step b) involves amide bond formation between specific precursors and other modular building blocks.

In one embodiment, said precursor is a compound selected from

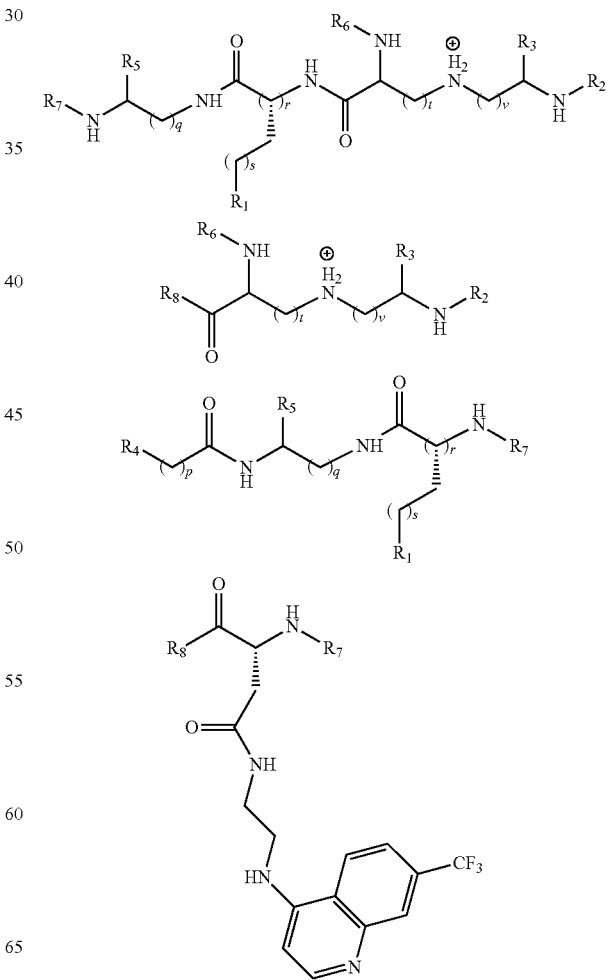

-continued

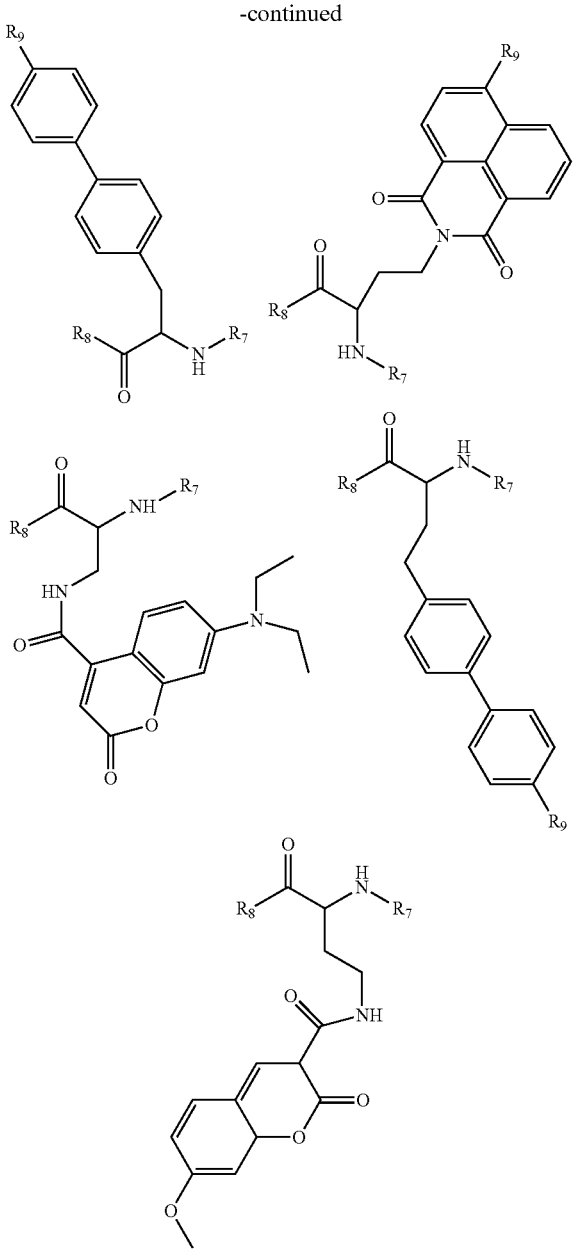

wherein
R1, R3, R4 and R5 p, q, r, s, t, v are as defined for formula I;

R2 is as defined for formula I or H or an amino protecting group (as typically used is peptide chemistry), for example tert-butoxycarbonyl, 9-fluorenylmethoxycarbonyl, allyloxycarbonyl or benzyloxycarbonyl;

R7 is H or an amino protecting group (as typically used is peptide chemistry), for example tert-butoxycarbonyl, 9-fluorenylmethoxycarbonyl, allyloxycarbonyl or benzyloxycarbonyl;

R8 is OH, O—, or a substituted or non-substituted O-alkyl group, i.e., to provide a protected carboxyl acid (as typically used is peptide chemistry), for example methyl, benzyl, t-butyl, 9-fluorenylmethyl esters or attachment to a solid support (e.g. Wang resin); and R9 is H, N-dimethylamino, N-acetamido or O-alkyl.

In another embodiment, said precursor is an organic compound selected from $N^3$—(N-tert-butoxycarbonyl-2-aminoethyl)-$N^2$,$N^3$-dibenzyloxycarbonyl-(S)-2,3-diaminopropionic acid;
$N^4$—(N-tert-butoxycarbonyl-2-aminoethyl)-$N^2$,$N^4$-dibenzyloxycarbonyl-(S)-2,4-diaminobutanoic acid;
$N^2$,$N^4$-dibenzyloxycarbonyl-$N^4$—[N-(9-fluorenylmethoxycarbonyl)-2-aminoethyl]-(S)-2,4-diaminobutanoic acid;
$N^2$,$N^3$-bis-tert-butoxycarbonyl-$N^3$—[N-(9-fluorenylmethoxycarbonyl)-2-aminoethyl]-(S)-2,3-diaminopropionic acid;
$N^2$,$N^4$-bis-tert-butoxycarbonyl-$N^4$—[N-(9-fluorenylmethoxycarbonyl)-2-aminoethyl]-(S)-2,4-diaminobutanoic acid;
$N^2$,$N^5$-bis-tert-butoxycarbonyl-$N^5$—[N-(9-fluorenylmethoxycarbonyl)-2-aminoethyl]-(S)-2,5-diaminopentanoic acid;
(2S,7S)—$N^2$-(tert-butoxycarbonyl)-$N^7$-(9-fluorenylmethoxycarbonyl)-5-tert-butoxycarbonyl-5-aza-2,7-diaminoundecanoic acid;
(2S,7S)—$N^2$-(tert-butoxycarbonyl)-$N^7$-(9-fluorenylmethoxycarbonyl)-5-(tert-butoxycarbonyl)-5-aza-2,7-diaminotridecanoic acid;
(2S,7S)—$N^2$-(tert-butoxycarbonyl)-$N^7$-(9-fluorenylmethoxycarbonyl)-5-(tert-butoxycarbonyl)-5-aza-2,7-diaminopentdecanoic acid;
(R)-methyl-$N^4$-(9-fluorenylmethoxycarbonyl)-2,4-diaminobutanoate;
4-(4'-acetamidophenyl)-$N^2$-(9-fluorenylmethoxycarbonyl)-D-phenylalanine;
(R)-2-(9-fluorenylmethoxycarbonyl)amino-3-(4'-acetamido-[1,1'-biphenyl]-4-yl)propanoic acid;
(R)-4-(4'-N,N-dimethylamino-1,8-naphthalimido)-$N^2$-(9-fluorenylmethoxycarbonyl)-2-aminobutanoic acid;
$N^3$—(N-tert-butoxycarbonyl-2-aminoethyl)-$N^2$,$N^3$-dibenzyloxycarbonyl-(S)-2,3-diaminopropionic acid pentafluorophenyl ester;
$N^3$—(N-tert-butoxycarbonyl-2-aminoethyl)-$N^2$,$N^3$-dibenzyloxycarbonyl-(S)-2,3-diaminopropionic acid p-nitrophenyl ester; and
12-amino-12-oxododecanoic acid p-nitrophenyl ester.

Drug Administration

A compound as described herein can be administered using different methods. In some cases, different methods of administration are evaluated for their efficacy and/or the half-life of the compound in the animal, e.g., in peripheral blood or cerebrospinal fluid (CSF). In mice, oral administration, intraperitoneal injection, intracerebral injection (e.g., into the hippocampus), and intra-cerebroventricular infusion can be used. The total doses and dosing schemes can be varied to identify an effective dose. In such testing, compounds are generally administered in doses in milligram amounts, e.g., total doses of about 1-100 mg, 1-50 mg, or 50-100 mg are administered three to four days per week for several weeks to achieve the total dose, (e.g. Permanne et al., 2002, FASEB J. 16:860-862). For Drosophila, as described above, oral administration is generally used (i.e., the compound is mixed with the food), however, injection and transcutaneous administration can be used. In general, compounds described herein are administered in doses from about 1-500 mg, 1-300 mg, 100-500 mg, 100-300 mg, 1-100 mg, 1-50 mg, 1-30 mg, 10-50 mg, or 10-20 mg. For example, oral administration of ligand 3 is generally between about 1-100 mg or 1-25 mg. Ligands containing fatty acyl chains are generally administered at doses from about 1-500 mg, 100-500 mg, or 100-300 mg. Compounds (ligands) as described herein can be used for the preparation of a medicament for use in any of the methods of treatment described herein.

Pharmaceutical Compositions

The compounds described herein, can be incorporated into pharmaceutical compositions. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Examples of routes of administration include, without limitation, parenteral (e.g., intravenous, intradermal, subcutaneous), oral, intranasal (e.g., inhalation), transdermal, transmucosal, intrathecal, intracerebral ventricular (e.g., using an Omaya reservoir-shunt with in-line filter that is surgically placed into the cisternal space), and rectal administration. Potentially useful parenteral delivery systems for a composition include, without limitation, slow-dissolving polymer particles, implantable infusion systems, and liposomes. Solutions or suspensions used for parenteral application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. Other appropriate solutions or suspensions can be used. pH can be adjusted with acids or bases, such as hydrochloric acid or sodium hydroxide. The parenteral preparation can be, for example, enclosed in ampoules, disposable syringes or multiple dose vials made of glass or plastic. Treatment of a disorder related to an A beta peptide, e.g., the undesirable production of an A beta peptide or the production of fibrils comprising such peptides may also be effected by direct delivery of a compound described herein to the central nervous system, e.g., to the brain. Pharmaceutical compositions suitable for injectable use include, without limitation, sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating on particles of the active substance (e.g., lecithin), by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it is preferable to include isotonic agents in the composition. Examples of such agents include sugars, polyalcohols (e.g., mannitol and sorbitol), and sodium chloride. Prolonged absorption of the injectable compositions can be effected by including in the composition an agent that delays absorption, for example, aluminum monostearate or gelatin. In general, methods for making such pharmaceutical compositions are known in the art. Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation are generally vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used for example, in the form of tablets, troches, or capsules, e.g., gelatin capsules. Pharmaceutically compatible binding agents, and/or adjuvant materials can be included as part of the composition. The tablets, pills, capsules, troches, and the like can contain other ingredients that are known in the art, e.g., the following ingredients, or ingredients of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. For administration by inhalation, the compounds can be delivered in the form of an aerosol spray from pressured container or dispenser that contains a suitable propellant, e.g., a gas such as carbon dioxide, or a nebulizer. Systemic administration can also be by transmucosal or transdermal means. For transmucosal or transdermal administration, penetrants appropriate to the barrier to be permeated are generally used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art. The compounds can also be prepared in the form of suppositories (e.g., with conventional suppository bases such as cocoa butter and other glycerides) or retention enemas for rectal delivery.

In one embodiment, the compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art and materials are commercially available, e.g., Alza Corporation and Nova Pharmaceuticals, Inc. Liposomal suspensions (including liposomes targeted to cells specifically affected by A beta peptides such as neurons or glia with monoclonal antibodies or fragments thereof) can also be used as pharmaceutically acceptable carriers. These compositions can be prepared according to methods known to those skilled in the art, for example, as described in U.S. Pat. No. 4,522,811.

It is advantageous to formulate oral or parenteral compositions in dosage unit form for ease of administration and uniformity of dosage. Dosage unit form as used herein refers to physically discrete units suited as unitary dosages for the subject to be treated, each unit containing a predetermined quantity of active compound calculated to produce the desired therapeutic effect in association with the required pharmaceutical carrier. Toxicity and therapeutic efficacy of compounds can be determined by known pharmaceutical procedures in cell cultures or experimental animals, e.g., for determining the LD50 (the dose lethal to 50 percent of the population) and the ED50 (the dose therapeutically effective in 50 percent of the population). Suitable animal models can be used such as those described for A beta-associated conditions including animal models generated using genetic engineering (such as rodents engineered to express a human A beta peptide) or naturally occurring conditions. Examples of animal models are described supra and also include Sturchler-Pierrat et al. (1999, Rev. Neurosci. 10:15-24), Seabrook et al. (1999, Neuropharmacol. 38:1-17), DeArmond et al. (1995, Brain Pathology 5:77-89), Telling (2000, Neuropathol. Appl. Neurobiol. 26:209-220), and Price et al. (1998, Science 282:1079-1083). The dose ratio between toxic and therapeutic effects is the therapeutic index and it can be expressed as the ratio LD5O/ED5O. Compounds that exhibit high therapeutic indices are preferred. While compounds that exhibit toxic side effects may be used, care should be taken to design a delivery system that targets such compounds to the site of affected tissue in order to minimize potential damage to unaffected cells and thereby reduce side effects. Data obtained from the cell culture assays and animal studies can be used in formulating a range of dosage for use in humans. The dosage of a compound generally lies within a range of circulating concentrations that include the ED50 with little or no toxicity. The dosage may vary within this range depending upon the dosage form employed and the route of administration utilized. For any compound used in a method described herein, the therapeutically effective dose can be estimated initially from cell culture assays in which, e.g., the rate of fibril formation or the rate of cell death is observed. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. As defined herein, a therapeutically effective amount of a compound described herein (i.e., an effective dosage) ranges from about 0.001 to 100 mg/kg body weight, for example, about 0.01 to 25 mg/kg body weight, about 0.05 to 20 mg/kg body weight, about 0.1 to 10 mg/kg body weight, or about 20-100 mg/kg body weight. The compound can be administered over an extended period of time to the subject, e.g., over the subject's lifetime. In some cases the compound can be administered one time per week for between about 1 to 10 weeks, for example, between 2 to 8 weeks, between about 3 to 7 weeks, or for about 4, 5, or 6 weeks, The compound can also be administered chronically. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a compound can include a single treatment or, more generally, can include a series of treatments.

When one or more of these molecules is to be administered to an animal (e.g., a mammal such as a human) to treat a disease associated with an A beta peptide is involved (e.g., Alzheimer's disease), a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated. The pharmaceutical compositions can be included in a container, pack, or dispenser together with instructions for administration. For example, the instructions can include directions to use the composition to treat an individual having or at risk for an amyloidosis.

Methods of Treatment

The present invention provides for both prophylactic and therapeutic methods of treating a subject at risk for (or susceptible to) a disorder or having a disorder associated with an A beta peptide, e.g., Alzheimer's disease, Dementia pugilistica, severe head trauma, and certain pathologies and symptoms of Down syndrome. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes the compounds described herein. Provided herein are methods for preventing a disease or condition (i.e., decreasing the risk of contracting, or decreasing the rate at which symptoms appear that are associated with a disease or condition) associated with the presence of an A beta peptide. Subjects at risk for a disease that is caused or exacerbated by such peptides can be identified by, for example, any or a combination of appropriate diagnostic or prognostic assays known in the art. Administration of a compound described herein as a prophylactic agent that can slow or prevent the pathology or other stigmata of an A beta-associated disease can occur prior to the manifestation of symptoms characteristic of the disease, such that the disease is prevented or, alternatively, delayed in its progression.

The compounds described herein that are useful for treating or preventing an A beta-related disease can be administered to a patient at therapeutically effective doses to prevent, treat, or ameliorate disorders involving an A beta peptide. A therapeutically effective dose refers to that amount of the compound sufficient to result in amelioration of symptoms of the disorders or to slow or prevent the appearance of such symptoms. Toxicity and therapeutic efficacy of such compounds can be determined by pharmaceutical procedures as described above and that are known in the art.

The invention is further illustrated by the following examples. The examples are provided for illustrative purposes only. They are not to be construed as limiting the scope or content of the invention in any way.

EXAMPLES

A) Building Blocks for Ligand Synthesis

Example 1

Synthesis of the $N^3$—(N-tert-butoxycarbonyl-2-aminoethyl)-$N^2,N^3$-dibenzyloxycarbonyl-(S)-2,3-diaminopropionic acid (2) being a precursor for the amyloid-β peptide targeting ligands of the invention

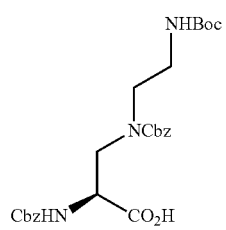

Synthesis of $N^3$—(N-tert-butoxycarbonyl-2-aminoethyl)-$N^2,N^3$-dibenzyloxycarbonyl-(S)-2,3-diaminopropionic acid (2)

The derivative 1, Scheme 1, was prepared using Cbz-L-Dap-OMe and N-Boc-glycinal in 1% AcOH in MeOH in the presence of $NaBH_3CN$ (Chhabra, S. R. et al. Tetrahedron Lett. 1999, 40, 4905-4908 and Chhabra, S. R. et al. J. Org. Chem. 2002, 67, 4017-4029). Compound 1 (1.6 g, 4.05 mmol) was dissolved in 1,4-dioxane/water (1:1) mixture (40 mL) and cooled in an ice-water bath. To the resulting solution $NaHCO_3$ (1.02 g, 12.15 mmol) was added followed by the addition of N-(benzyloxycarbonyloxy)succinimide (1.51 g, 6.07 mmol). The reaction mixture was allowed to warm to ambient temperature and was stirred for 20 h. The solvents were removed in vacuo and the residue was re-dissolved in ethyl acetate and washed with water. The organic phase was dried over $Na_2SO_4$, filtered and concentrated under reduced pressure. The crude product was dissolved in a methanol/water (9:1) mixture and treated with LiOH (0.175 g, 7.3 mmol) at room temperature for 17 h. Volatiles were evaporated in vacuo, the residue was dissolved in water, acidified with 1 M aqueous $KHSO_4$ and extracted with ethyl acetate. The organic phase was dried over $Na_2SO_4$, filtered and concentrated under reduced pressure. The residue was subjected to column chromatography using 10 to 40% ethyl acetate (EtOAc) in toluene containing 10% acetic acid (AcOH) as eluent. The collected fractions were combined, solvents were evaporated in vacuo and traces of AcOH were removed by co-evaporation with toluene/methanol mixture to give compound 2 (1.31 g, 63%). $R_f$=0.62 ($CH_2Cl_2/CH_3OH/AcOH$, 9:1:0.1 v/v). $^1H$ NMR (400 MHz, DMSO-$d_6$): δ=7.69-7.51 (m, 1H), 7.44-7.21 (m, 10H), 6.93-6.76 (m, 1H), 5.14-4.94 (m, 4H), 4.39-4.24 (m, 1H), 3.80-3.64 (m, 1H), 3.46-2.96 (m, 5H), 1.36 (s, 9H) ppm. $^{13}C$ NMR (100.6 MHz, DMSO-$d_6$): δ=172.1, 172.0, 156.1, 155.6, 155.5, 155.3, 137.0, 136.8, 128.3, 127.8, 127.8, 127.6, 127.1, 77.6, 66.2, 65.5, 53.0, 52.4, 48.6, 48.0, 47.7, 47.4, 38.4, 37.9, 28.2 ppm. HRMS (ESI-TOF): calcd. for $C_{26}H_{32}N_3O_8$ [M−H]$^−$ 514.2195. found 514.2175.

Scheme 1. Synthesis of the triamino acid building block 2.

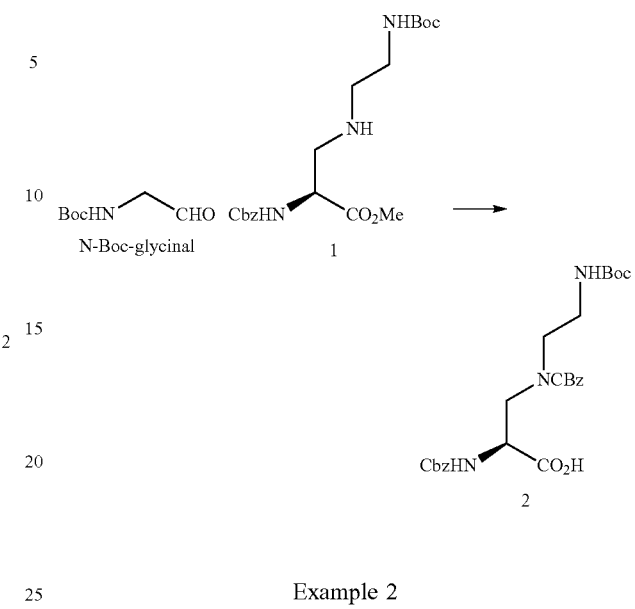

Example 2

Synthesis of the $N^4$—(N-tert-butoxycarbonyl-2-aminoethyl)-$N^2,N^4$-dibenzyloxycarbonyl-(S)-2,4-diaminobutanoic acid (4) being a precursor for the amyloid-β peptide targeting ligands of the invention

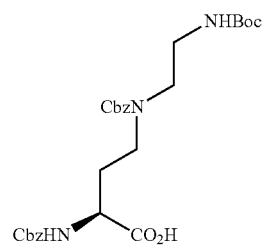

Synthesis of $N^2$-benzyloxycarbonyl-$N^4$—(N-tert-butoxycarbonyl-2-aminoethyl)-(S)-2,4-diaminobutanoic acid (3)

Method A $N^2$-Benzyloxycarbonyl-L-2,4-diaminobutanoic acid (Cbz-L-Dab-OH, 0.5 g, 2.0 mmol) was dissolved in water (20 ml) and tetrabutylammonium hydrogensulphate (0.68 g, 2.0 mmol) was added at room temperature followed by the addition of 1.26 mL of a solution of N-tert-butoxycarbonyl-glycinal (0.35 g, 2.2 mmol) in methanol. After 30 min sodium cyanoborohydride (0.38 g, 6.0 mmol) was added portionwise over 30 min and the reaction mixture was stirred for 18 h. The solvents were removed in vacuo and the residue was re-dissolved in water and lyophilized. Methanol was added and the insoluble material was filtered off. The filtrate was concentrated and the product was purified by flash column chromatography using first EtOAc/MeOH/AcOH (20:2:1 v/v) and then EtOAc/MeOH/AcOH/$H_2O$ (10:2:1:1 v/v) as eluent. The collected fractions were combined, concentrated in vacuo and traces of AcOH were removed by co-evaporation with a toluene/methanol mixture to afford 3 (0.23 g, 29%).

Method B

To a suspension of Cbz-L-Dab-OH (0.5 g, 2.0 mmol) in anhydrous methanol (40 mL) containing 2.5% of AcOH N-tert-butoxycarbonylglycinal (0.35 g, 2.2 mmol) was added and the reaction mixture was stirred for 45 min at room temperature under a nitrogen atmosphere. Sodium cyanoborohydride (0.38 g, 6.0 mmol) was added portionwise over 30 min and the reaction mixture was kept stirring overnight. Additional portions of N-tert-butoxycarbonylglycinal (0.16 g, 1.0 mmol) and sodium cyanoborohydride (0.38 g, 6.0 mmol) were added and the reaction was stirred for additional 4 h. The solvents were removed in vacuo and the residue was dissolved in water, acidified with 1 M aqueous $KHSO_4$ and extracted with ethyl acetate. The organic phase was washed with brine, water, dried over $Na_2SO_4$, filtered and concentrated under reduced pressure. The residue was subjected to flash column chromatography using first EtOAc/MeOH/AcOH (20:2:1 v/v) and then EtOAc/MeOH/AcOH/$H_2O$ (10:2:1:1 v/v) as eluent. The collected fractions were combined, concentrated in vacuo and traces of AcOH were removed by co-evaporation with a toluene/methanol mixture. The product was re-dissolved in small volume of water/acetonitrile (9:1) and lyophilized to give 3 (0.34 g, 43%). $R_f$=0.50 (EtOAc/MeOH/AcOH/$H_2O$, 10:2:1:1 v/v). $^1$H NMR (400 MHz, DMSO-$d_6$): δ=7.37-7.25 (m, 5H), 6.88 (br. t, 1H), 6.63 (br. d, 1H), 4.99 (s, 2H), 3.75-3.68 (m, 1H), 3.10-3.00 (m, 2H), 2.75-2.59 (m, 4H), 1.85-1.72 (m, 2H), 1.36 (s, 9H) ppm. $^{13}$C NMR (100.6 MHz, DMSO-$d_6$): δ=173.8, 173.3, 155.6, 155.3, 137.3, 128.3, 127.7, 127.6, 77.7, 65.1, 54.4, 47.4, 45.5, 38.4, 31.0, 28.2 ppm. HRMS (ESI-TOF): calcd. for $C_{19}H_{28}N_3O_6$ [M–H]$^-$ 394.1984. found 394.1978.

Synthesis of $N^4$—(N-tert-Butoxycarbonyl-2-aminoethyl)-$N^2$,$N^4$-dibenzyloxycarbonyl-(S)-2,4-diaminobutanoic acid (4)

To an ice-water bath chilled solution of compound 3 (0.179 g, 0.45 mmol) in 1,4-dioxane/water (1:1, 5 mL) $NaHCO_3$ (0.076 g, 0.91 mmol) was added. To the resulting solution N-(benzyloxycarbonyloxy)succinimide (0.169 g, 0.68 mmol) was added whereupon the reaction mixture was allowed to warm to ambient temperature and was stirred for 21 h. The solvents were evaporated in vacuo and the residue was re-dissolved in water, acidified with 1 M aqueous $KHSO_4$ and extracted with ethyl acetate. The organic layer was dried over $Na_2SO_4$, filtered and concentrated under reduced pressure. The residue was subjected to flash column chromatography using 0 to 6% MeOH in dichloromethane containing 0.1% AcOH as eluent. The collected fractions with product were reduced in vacuo and traces of AcOH were removed by co-evaporation with toluene to give compound 4 (0.18 g, 75%). $R_f$=0.66 ($CH_2Cl_2$/$CH_3OH$/AcOH, 9:1:0.1 v/v). $^1$H NMR (400 MHz, DMSO-$d_6$): δ=7.68-7.54 (m, 1H), 7.47-7.21 (m, 10H), 6.87 (br. d, 1H), 5.17-4.92 (m, 4H), 3.98-3.85 (m, 1H), 3.61-2.94 (m, 6H), 2.07-1.87 (m, 1H), 1.86-1.67 (m, 1H), 1.35 (s, 9H) ppm. $^{13}$C NMR (100.6 MHz, DMSO-$d_6$): δ=173.5, 156.1, 155.6, 155.3, 137.0, 136.9, 128.3, 127.8, 127.7, 127.6, 127.2, 77.6, 66.1, 65.5, 51.8, 46.9, 46.4, 44.8, 44.3, 38.6, 38.1, 29.8, 29.1, 28.2 ppm. HRMS (ESI-TOF): calcd. for $C_{27}H_{34}N_3O_8$ [M–H]$^-$ 528.2351. found 528.2341.

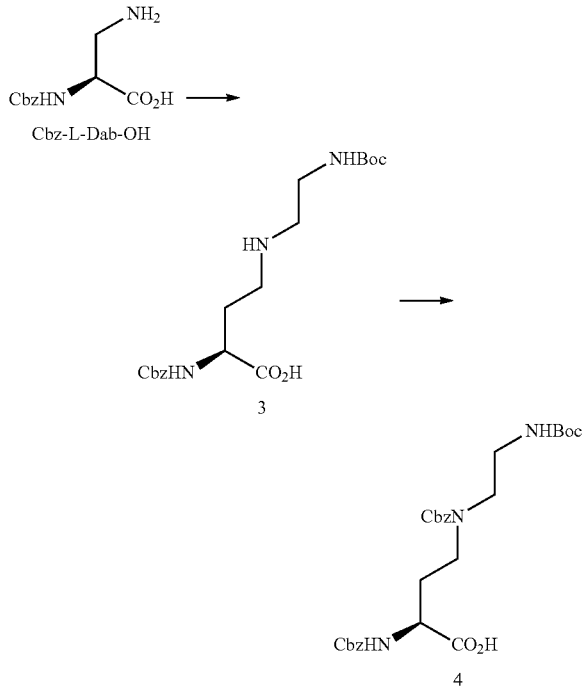

Scheme 2. Synthesis of the triamino acid building block 4.

Example 3

Synthesis of the $N^2$,$N^4$-dibenzyloxycarbonyl-$N^4$—[N-(9-fluorenylmethoxycarbonyl)-2-aminoethyl]-(S)-2,4-diaminobutanoic acid (6) being a precursor for the amyloid-β peptide targeting ligands of the invention

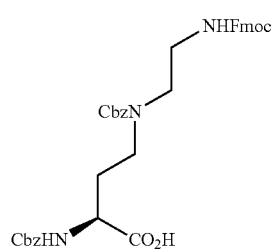

Synthesis of $N^2$-benzyloxycarbonyl-$N^4$—[N-(9-fluorenylmethoxycarbonyl)-2-aminoethyl]-(S)-2,4-diaminobutanoic acid (5)

$N^2$-Benzyloxycarbonyl-L-2,4-diaminobutanoic acid (0.4 g, 1.59 mmol) was suspended in anhydrous methanol (30 mL) containing 5% of AcOH. After stirring for 10 min an N-(9-fluorenylmethoxycarbonyl)glycinal (Matsumori, N. et al. *Chem. Biodiversity* 2004, 1, 346-352) (0.53 g, 1.9 mmol) was added and the reaction mixture was stirred for 30 min at room temperature under a nitrogen atmosphere. Sodium cyanoborohydride (0.4 g, 6.34 mmol) was added portionwise over 30 min and the reaction mixture was kept stirring for 17 h. Additional portions of N-(9-fluorenylmethoxycarbonyl)glycinal (0.27 g, 0.95 mmol) and sodium cyanoborohydride (0.2 g, 3.17 mmol) were added and the reaction was stirred for 24 h more. The solvents were evaporated in vacuo, and the residue was dissolved in ethyl acetate, washed with water and brine. The organic layer was dried over $Na_2SO_4$, filtered and concentrated under reduced pressure. The residue was purified by flash column chromatography using first EtOAc/MeOH/AcOH (20:2:1 v/v) and then EtOAc/MeOH/AcOH/$H_2O$ (10:2:1:1 v/v) as eluent. The collected fractions were combined, solvents were evaporated in vacuo and the residue was dried by evaporation of an added toluene/methanol mixture. The product was dissolved in small volume of water/acetonitrile (9:1) mixture and lyophilized to give compound 5 (0.35 g, 42%). $R_f$=0.56 (EtOAc/MeOH/AcOH/$H_2O$, 10:2:1:1 v/v). $^1H$ NMR (400 MHz, $CD_3OD$): δ=7.79 (d, J=7.5 Hz, 2H), 7.64 (d, J=7.4 Hz, 2H), 7.44-7.25 (m, 9H), 5.11-4.98 (m, 2H), 4.45-4.34 (m, 2H), 4.21 (br. t, 1H), 4.13 (br. t, 1H), 3.46-3.37 (m, 2H), 3.17-2.99 (m, 4H), 2.27-2.12 (m, 1H), 2.05-1.95 (m, 1H) ppm. $^{13}C$ NMR (100.6 MHz, DMSO-$d_6$): δ=173.6, 155.2, 142.6, 139.4, 137.4, 137.3, 128.9, 128.3, 127.65, 127.61, 127.3, 127.1, 121.4, 120.0, 65.05, 64.98, 63.5, 54.3, 46.7, 29.0, 28.7 ppm. HRMS (ESI-TOF): calcd. for $C_{29}H_{30}N_3O_6$ [M−H]$^−$ 516.2140. found 516.2149.

Synthesis of $N^2,N^4$-dibenzyloxycarbonyl-$N^4$—[N-(9-fluorenylmethoxycarbonyl)-2-aminoethyl]-(S)-2,4-diaminobutanoic acid (6)

Compound 5 (0.24 g, 0.46 mmol) was dissolved in 1,4-dioxane/water (3:1, 12 mL) and chilled in an ice-water bath. To the resulting mixture $NaHCO_3$ (0.078 g, 0.93 mmol) was added followed by the addition of N-(benzyloxycarbonyloxy)succinimide (0.173 g, 0.69 mmol). The reaction mixture was allowed to warm to ambient temperature and was stirred for 22 h. The solvents were reduced in vacuo, the residue was acidified with 1 M aqueous $KHSO_4$ and extracted with ethyl acetate. The organic phase was dried over $Na_2SO_4$, filtered and concentrated under reduced pressure. The product was purified by flash column chromatography using 0 to 15% MeOH in dichloromethane as eluent (silica gel column was prepared with addition of 1% AcOH in dichloromethane) to afford 6 (0.215 g, 71%). $R_f$=0.36 ($CH_2Cl_2/CH_3OH$, 9:1 v/v). $^1H$ NMR (400 MHz, DMSO-$d_6$): δ=7.88 (d, J=7.5 Hz, 2H), 7.70-7.61 (m, 2H), 7.42-7.27 (m, 15H), 7.15-7.03 (m, 1H), 5.10-4.91 (m, 4H), 4.31-4.12 (m, 3H), 3.87-3.75 (m, 1H), 3.56-2.99 (m, 6H), 2.07-1.89 (m, 1H), 1.85-1.67 (m, 1H) ppm. $^{13}C$ NMR (100.6 MHz, DMSO-$d_6$): δ=174.3, 156.2, 155.8, 155.4, 155.2, 143.9, 140.7, 137.1, 137.0, 128.9, 128.31, 128.30, 127.71, 127.66, 127.60, 127.3, 127.2, 127.0, 125.2, 120.1, 120.0, 66.0, 65.4, 65.2, 52.9, 46.7, 46.0, 44.8, 44.3, 38.4, 30.9, 30.2 ppm. HRMS (ESI-TOF): calcd. for $C_{37}H_{36}N_3O_8$ [M−H]$^−$ 650.2508. found 650.2506.

Scheme 3. Synthesis of the triamino acid building block 6.

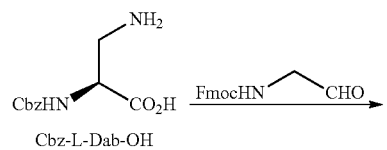

Cbz-L-Dab-OH

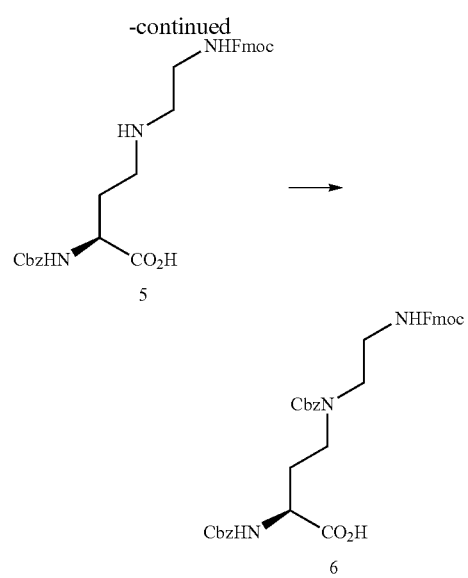

Example 4

Synthesis of $N^2,N^3$-bis-tert-butoxycarbonyl-$N^3$—[N-(9-fluorenylmethoxycarbonyl)-2-aminoethyl]-(S)-2,3-diaminopropionic acid (8) being a precursor for the amyloid-β peptide targeting ligands of the invention

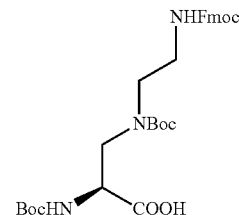

Synthesis of $N^2$-tert-butoxycarbonyl-$N^3$—[N-(9-fluorenylmethoxycarbonyl)-2-aminoethyl]-(S)-2,3-diaminopropionic acid (7)

$N^2$-tert-Butoxycarbonyl-L-2,3-diaminopropionic acid (0.102 g, 0.5 mmol) was dissolved under stirring in anhydrous methanol (10 mL) containing 1% of AcOH. N-(9-fluorenylmethoxycarbonyl)glycinal (Matsumori, N. et al. *Chem. Biodiversity* 2004, 1, 346-352) (0.129 g, 0.46 mmol) was added to the reaction mixture under a nitrogen atmosphere followed by the addition of sodium cyanoborohydride (0.072 g, 1.14 mmol). The reaction mixture was stirred at room temperature for 18 h. The solvents were evaporated in vacuo, and the residue was dissolved in ethyl acetate. The organic layer was washed with water and brine, dried over $Na_2SO_4$, filtered and concentrated under reduced pressure. The residue was purified by flash column chromatography using 0 to 15% MeOH in dichloromethane containing 1% AcOH as eluent to give compound 7 (0.1 g, 43%). $R_f$=0.14 ($CH_2Cl_2/CH_3OH/AcOH$, 9:1:0.1 v/v). $^1H$ NMR (400 MHz, $CD_3OD$): δ=7.68 (d, J=7.2 Hz, 2H), 7.53 (d, J=7.2 Hz, 2H), 7.28 (d, J=7.2 Hz, 2H), 7.19 (d, J=7.2 Hz, 2H), 4.28 (d, J=6.8 Hz, 2H), 4.09 (t, J=6.8 Hz, 1H), 4.03 (t, J=6.0 Hz, 1H), 3.35-3.32 (m, 2H), 3.15-3.14 (m, 2H), 3.08-3.05 (m, 2H), 1.32 (s, 9H) ppm. $^{13}$C NMR (100.6 MHz, CD$_3$OD): δ=177.4, 159.3, 158.0, 145.2, 142.6, 128.8, 128.1, 126.1, 120.9, 81.0, 68.1, 52.8, 51.0, 49.1, 48.5, 38.6, 28.7 ppm. HRMS (ESI-TOF): calcd. for $C_{25}H_{30}N_3O_6$ [M–H]$^-$ 468.2140. found 468.2147.

Synthesis of $N^2,N^3$-bis-tert-butoxycarbonyl-$N^3$—[N-(9-fluorenylmethoxycarbonyl)-2-aminoethyl]-(S)-2,3-diaminopropionic acid (8)

Compound 7 (0.103 g, 0.22 mmol) was dissolved in 1,4-dioxane/water (1:1) mixture (10 mL) under stirring and cooled in an ice-water bath. To the resulted solution Na$_2$CO$_3$ (0.048 g, 0.45 mmol) was added followed by the addition of di-tert-butyl dicarbonate (0.092 g, 0.42 mmol). Ice-water bath was removed after 1 h and the reaction mixture was stirred at room temperature overnight. After disappearance of starting material the reaction mixture was cooled in an ice-water bath, water was added and the pH of solution was adjusted to pH 3 using 1 M HCl. The product was extracted with ethyl acetate. Organic phase was washed with water and brine, dried over Na$_2$SO$_4$, filtered and concentrated to dryness under reduced pressure. Crude product was purified by flash column chromatography using 0 to 90% EtOAc in hexane containing 1% AcOH as eluent to afford 8 (0.084 g, 67%). $R_f$=0.20 EtOAc/hexane/AcOH (8:2:0.1 v/v). $^1$H NMR (400 MHz, CDCl$_3$): δ=7.67 (d, J=7.2 Hz, 2H), 7.51 (d, J=7.2 Hz, 2H), 7.31 (t, J=7.2 Hz, 2H), 7.21 (t, J=7.2 Hz, 2H), 4.45-4.30 (m, 3H), 4.17-4.09 (m, 1H), 3.50 (br. s, 2H), 3.37-3.14 (m, 4H), 1.36 (s, 18H) ppm. $^{13}$C NMR (100.6 MHz, CDCl$_3$): δ=173.8, 173.3, 157.1, 156.7, 156.3, 155.7, 144.0, 141.4, 127.8, 127.2, 125.2, 120.1, 81.7, 81.4, 80.5, 67.1, 66.9, 54.1, 53.0, 50.1, 49.5, 48.6, 47.6, 47.3, 40.7, 40.0, 28.4 ppm. HRMS (ESI-TOF): calcd. for $C_{30}H_{38}N_3O_8$ [M–H]$^-$ 568.2664. found 568.2670.

Scheme 4. Synthesis of $N^2,N^3$-bis-tert-butoxycarbonyl-$N^3$-[N-(9-fluorenylmethoxycarbonyl)-2-aminoethyl]-(S)-2,3-diaminopropionic acid (8).

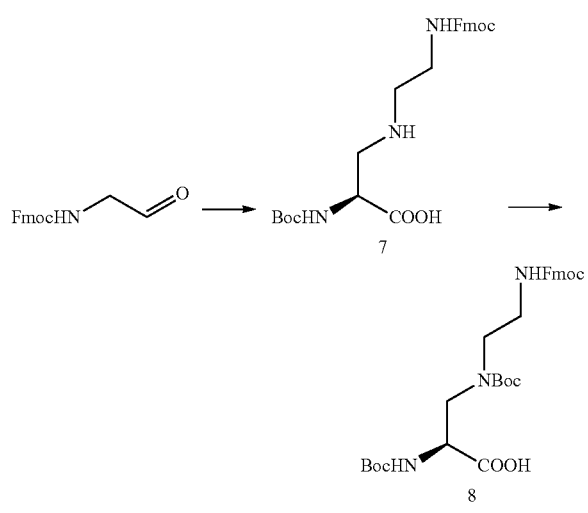

Example 5

Synthesis of $N^2,N^4$-bis-tert-butoxycarbonyl-$N^4$—[N-(9-fluorenylmethoxycarbonyl)-2-aminoethyl]-(S)-2,4-diaminobutanoic acid (10) being a precursor for the amyloid-β peptide targeting ligands of the invention

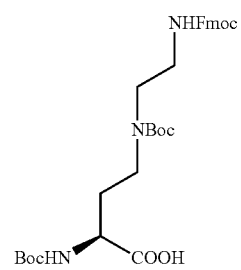

Synthesis of $N^2$-tert-butoxycarbonyl-$N^4$—[N-(9-fluorenylmethoxycarbonyl)-2-aminoethyl]-(S)-2,4-diaminobutanoic acid (9)

$N^2$-tert-Butoxycarbonyl-L-2,4-diaminobutanoic acid (0.109 g, 0.5 mmol) and N-(9-fluorenylmethoxycarbonyl) glycinal (0.129 g, 0.46 mmol) in the presence of sodium cyanoborohydride (0.072 g, 1.14 mmol), and using the procedure described for 7 gave compound 9 (0.101 g, 42%). $R_f$=0.20 (CH$_2$Cl$_2$/CH$_3$OH/AcOH, 9:1:0.1 v/v). $^1$H NMR (400 MHz, CD$_3$OD): δ=7.67 (d, J=7.6 Hz, 2H), 7.52 (d, J=7.6 Hz, 2H), 7.27 (d, J=7.6 Hz, 2H), 7.19 (d, J=7.6 Hz, 2H), 4.27 (d, J=6.8 Hz, 2H), 4.08 (t, J=6.8 Hz, 1H), 3.90 (t, J=6.0 Hz, 1H), 3.34-3.32 (m, 2H), 2.98-2.97 (m, 4H), 2.06-1.99 (m, 1H), 1.90-1.80 (m, 1H), 1.32 (s, 9H) ppm. $^{13}$C NMR (100.6 MHz, CD$_3$OD): δ=179.9, 159.2, 159.0, 145.2, 142.6, 128.8, 128.1, 126.1, 120.9, 80.7, 68.1, 54.9, 48.9, 48.3, 46.5, 38.5, 31.2, 28.7 ppm. HRMS (ESI-TOF): calcd. for $C_{26}H_{32}N_3O_6$ [M–H]$^-$ 482.2297. found 482.2286.

Synthesis of $N^2,N^4$-bis-tert-butoxycarbonyl-$N^4$—[N-(9-fluorenylmethoxycarbonyl)-2-aminoethyl]-(S)-2,4-diaminobutanoic acid (10)

Reaction of compound 9 (0.106 g, 0.22 mmol), Na$_2$CO$_3$ (0.048 g, 0.45 mmol), and (Boc)$_2$O (0.092 g, 0.42 mmol) in the same procedure described for synthesis of compound 8 afforded compound 10 (0.085 g, 66%). $R_f$=0.28 EtOAc/hexane/AcOH (8:2:0.1 v/v). $^1$H NMR (400 MHz, CDCl$_3$): δ=7.69-7.67 (m, 2H), 7.53 (d, J=7.2 Hz, 2H), 7.34-7.30 (m, 2H), 7.24-7.20 (m, 2H), 4.45-4.44 (m, 1H), 4.24-4.19 (m, 1H), 4.13-4.10 (m, 2H), 3.77-3.70 (m, 1H), 3.30-3.25 (m, 3H), 2.98-2.94 (m, 1H), 2.87-2.83 (m, 1H), 2.04-1.94 (m, 1H), 1.76-1.71 (m, 1H), 1.39 (s, 9H), 1.35 (s, 9H) ppm. $^{13}$C NMR (100.6 MHz, CDCl$_3$): δ=173.0, 158.4, 156.9, 155.6, 144.1, 141.4, 127.8, 127.2, 125.3, 120.1, 82.8, 80.5, 66.7, 51.2, 50.3, 47.4, 46.3, 40.7, 34.4, 28.5, 28.4 ppm. HRMS (ESI-TOF): calcd. for $C_{31}H_{40}N_3O_8$ [M–H]$^-$ 582.2821. found 582.2816.

Scheme 5. Synthesis of $N^2,N^4$-bis-tert-butoxycarbonyl-$N^4$-[N-(9-fluorenylmethoxycarbonyl)-2-aminoethyl]-(S)-2,4-diaminobutanoic acid (10).

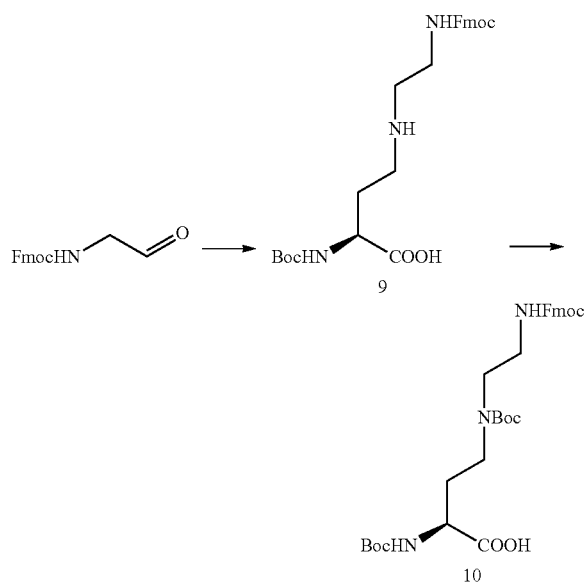

Example 6

Synthesis of $N^2,N^5$-bis-tert-butoxycarbonyl-$N^5$—[N-(9-fluorenylmethoxycarbonyl)-2-aminoethyl]-(S)-2,5-diaminopentanoic acid or $N^2,N^5$-bis-tert-butoxycarbonyl-$N^5$—[N-(9-fluorenylmethoxycarbonyl)-2-aminoethyl]-L-ornithine (12) being a precursor for the amyloid-β peptide targeting ligands of the invention

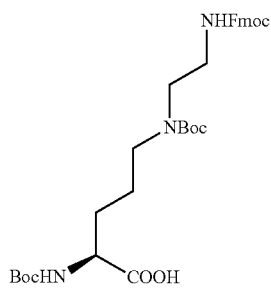

Synthesis of $N^2$-tert-butoxycarbonyl-$N^5$—[N-(9-fluorenylmethoxycarbonyl)-2-aminoethyl]-(S)-2,5-diaminopentanoic acid (11)

The reaction between $N^2$-tert-butoxycarbonyl-L-2,5-diaminopentanoic acid ($N^2$—Boc-L-Orn, 0.116 g, 0.5 mmol) and N-(9-fluorenylmethoxycarbonyl)glycinal (0.129 g, 0.46 mmol) in the presence of sodium cyanoborohydride (0.072 g, 1.14 mmol) under same reaction conditions described for synthesis of compound 7 gave compound 11 (0.104 g, 42%). $R_f$=0.17 ($CH_2Cl_2/CH_3OH/AcOH$, 9:1:0.1 v/v). $^1H$ NMR (400 MHz, $CD_3OD$): δ=7.70 (d, J=7.6 Hz, 2H), 7.55 (d, J=7.6 Hz, 2H), 7.29 (d, J=7.6 Hz, 2H), 7.21 (d, J=7.6 Hz, 2H), 4.32 (d, J=6.8 Hz, 2H), 4.11 (t, J=6.8 Hz, 1H), 3.86 (br. s, 1H), 3.31 (t, J=5.6 Hz, 2H), 2.98 (t, J=5.6 Hz, 2H), 2.90 (t, J=5.6 Hz, 2H), 1.74-1.61 (m, 4H), 1.32 (s, 9H) ppm. $^{13}C$ NMR (100.6 MHz, $CD_3OD$): δ=179.5, 159.2, 157.6, 145.2, 142.6, 128.8, 128.1, 126.1, 120.9, 80.2, 68.0, 56.2, 48.9, 48.8, 48.6, 48.4, 38.5, 31.3, 28.8, 23.5 ppm. HRMS (ESI-TOF): calcd. for $C_{27}H_{34}N_3O_6$ $[M-H]^-$ 496.2453. found 496.2463.

Synthesis of $N^2,N^5$-bis-tert-butoxycarbonyl-$N^5$—[N-(9-fluorenylmethoxycarbonyl)-2-aminoethyl]-(S)-2,5-diaminopentanoic acid or $N^2,N^5$-bis-tert-butoxycarbonyl-$N^5$—[N-(9-fluorenylmethoxycarbonyl)-2-aminoethyl]-L-ornithine (12)

Compound 11 (0.109 g, 0.22 mmol) was treated with $Na_2CO_3$ (0.048 g, 0.45 mmol) and $(Boc)_2O$ (0.092 g, 0.42 mmol) with the same reaction conditions described for the synthesis of compound 8, which afforded compound 12 (0.097 g, 74%). $R_f$=0.17 EtOAc/hexane/AcOH (8:2:0.1 v/v). $^1H$ NMR (400 MHz, $CDCl_3$): δ=7.67 (d, J=7.6 Hz, 2H), 7.45 (d, J=7.6 Hz, 2H), 7.30 (t, J=7.6 Hz, 2H), 7.21 (t, J=7.6 Hz, 2H), 4.43-4.27 (m, 3H), 4.11 (t, J=6.8 Hz, 1H), 3.26-3.02 (m, 6H), 1.74-1.71 (m, 1H), 1.56-1.51 (m, 3H), 1.36 (s, 18H) ppm. $^{13}C$ NMR (100.6 MHz, $CDCl_3$): δ=175.3, 157.0, 156.8, 155.8, 144.0, 141.4, 127.8, 127.1, 125.2, 120.1, 80.7, 80.5, 80.2, 67.0, 66.8, 54.4, 53.0, 47.3, 46.8, 46.4, 40.5, 40.1, 29.9, 28.5, 27.0, 24.6, 24.2 ppm. HRMS (ESI-TOF): calcd. for $C_{32}H_{42}N_3O_8$ $[M-H]^-$ 596.2977. found 596.2984.

Scheme 6. Synthesis of $N^2,N^5$-bis-tert-butoxycarbonyl-$N^5$-[N-(9-fluorenylmethoxycarbonyl)-2-aminoethyl]-(S)-2,5-diaminopentanoic acid or $N^2,N^5$-bis-tert-butoxycarbonyl-$N^5$-[N-(9-fluorenylmethoxycarbonyl)-2-aminoethyl]-L-ornithine (12).

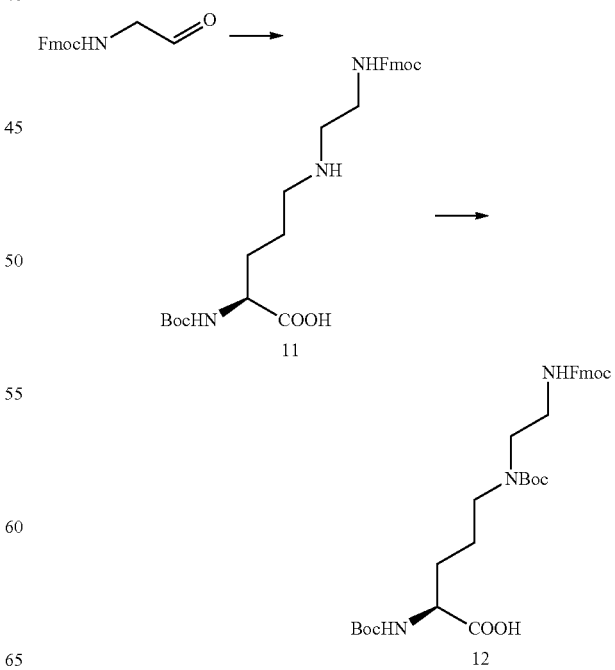

Example 7

Synthesis of (2S,7S)—N²-(tert-butoxycarbonyl)-N⁷-(9-fluorenylmethoxycarbonyl)-5-tert-butoxycarbonyl-5-aza-2,7-diaminoundecanoic acid (17) being a precursor for the amyloid-β peptide targeting ligands of the invention

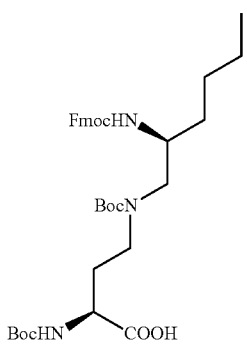

17

Synthesis of (S)—S-ethyl-2-[(9-fluorenylmethoxycarbonyl)amino]hexanthioate (14)

Fmoc-amino acid 13 (0.45 g, 1.3 mmol) was dissolved in anhydrous DCM (20 mL) at rt. Ethanethiol (0.37 mL, 5 mmol) was added into the reaction mixture, followed by addition of solid N,N'-dicyclohexylcarbodiimide (DCC, 0.33 g, 1.6 mmol) and 4-dimethylaminopyridine (0.04 g, 0.25 mmol) under inert atmosphere and stirred for 2 h at room temperature. Progress of the reaction was monitored by TLC. Upon complete conversion of the starting material into product, water (20 mL) was added into the reaction mixture and layers were separated. Organic layer was collected and washed with brine (2×10 mL), dried over $Na_2SO_4$ and evaporated to dryness under reduced pressure to get the crude product. Pure compound 14 was obtained by purifying the compound using column chromatography (71% yield). $R_f$ value=0.54 (20% EtOAc-hexane), ¹H NMR (400 MHz, $CDCl_3$): δ=7.69 (d, J=7.6 Hz, 2H), 7.54 (d, J=7.2 Hz, 2H), 7.33 (d, J=7.6 Hz, 2H), 7.24 (d, J=7.6 Hz, 2H), 5.13 (d, J=8.0 Hz, 1H), 4.44-4.40 (m, 1H), 4.36-4.30 (m, 2H), 4.17 (t, J=6.8 Hz, 1H), 2.81 (q, J=7.2 Hz, 2H), 1.85-1.80 (m, 1H), 1.57-1.51 (m, 1H), 1.30-1.23 (m, 4H), 1.18 (t, J=7.2 Hz, 3H), 0.83 (t, J=6.8 Hz, 3H) ppm. ¹³C NMR (100.6 MHz, $CDCl_3$): δ=201.1, 156.0, 144.1, 143.9, 141.5, 127.9, 127.2, 125.2, 120.1, 67.2, 61.1, 47.4, 32.8, 27.5, 23.4, 22.4, 14.6, 14.0 ppm. ESI-TOF MS (m/z): calcd. for $C_{23}H_{26}NNaO_3S$ [M+Na]⁺ 421.2. found 420.6.

Synthesis of (S)-2-[(9-fluorenylmethoxycarbonyl)amino]hexanaldehyde (15)

Compound 14 (0.36 g, 0.8 mmol) were dissolved in dry acetone (6 mL) at rt. 10% Pd/C was added into the reaction mixture followed by addition of triethylsilane (0.217 mL, 1.28 mmol) under inert atmosphere and stirred at rt. Progress of the reaction was monitored on TLC. The reaction mixture was stirred for 2 h and then it was passed through a short pad of celite and washed with acetone (3×6 mL). Combined organic layer was evaporated to dryness under reduced pressure and dissolved in ethylacetate (15 mL), which was washed with brine (2×8 mL), dried over $Na_2SO_4$ and evaporated under reduced pressure to get the crude product. Pure compound 15 (84%) was obtained by purifying the crude material by using column chromatography. $R_f$ value=0.22 (20% EtOAc-hexane), ¹H NMR (400 MHz, $CDCl_3$): δ=9.58 (s, 1H), 7.76 (d, J=7.6 Hz, 2H), 7.60 (d, J=7.2 Hz, 2H), 7.40 (d, J=7.2 Hz, 2H), 7.32 (d, J=7.6 Hz, 2H), 5.31 (d, J=6.8 Hz, 1H), 4.43 (d, J=6.8 Hz, 1H), 4.23 (t, J=6.8 Hz, 2H), 1.93-1.89 (m, 1H), 1.63-1.58 (m, 1H), 1.33-1.24 (m, 4H), 0.93-0.87 (m, 3H) ppm. ¹³C NMR (100.6 MHz, $CDCl_3$): δ=199.4, 156.2, 144.0, 143.9, 141.5, 127.9, 127.2, 125.2, 120.1, 67.1, 60.4, 47.4, 29.0, 27.3, 22.6, 14.0 ppm. ESI-TOF MS (m/z): calcd. for $C_{22}H_{23}NNaO_3$ [M+Na]⁺ 360.2. found 360.7.

Synthesis of (2S,7S)—N²-(tert-butoxycarbonyl)-N⁷-(9-fluorenylmethoxycarbonyl)-5-aza-2,7-diaminoundecanoic acid (16)

Boc-L-Dab-OH (0.11 g, 0.5 mmol) was dissolved in 1% AcOH-MeOH solvent mixture (10 mL) at rt under stirring. Compound 15 (0.154 g, 0.46 mmol) was added into the reaction mixture slowly followed by addition of $NaCNBH_3$ (0.072 g, 1.14 mmol). The reaction mixture was stopped and stirred at room temperature for 18 h. TLC was checked to monitor the progress of the reaction. After 18 h, the reaction mixture was evaporated to dryness and then it was dissolved in ethylacetate. Organic layer was washed with water (10 mL) and brine (10 mL×2), dried over $Na_2SO_4$ and evaporated to dryness under reduced pressure to get crude compound. Pure compound 16 (50%) was obtained by purification of the crude using column chromatography. $R_f$ value=0.34 (7.5% MeOH-1% AcOH-DCM), ¹H NMR (400 MHz, $CDCl_3$): δ=7.72 (d, J=7.2 Hz, 2H), 7.59 (d, J=7.2 Hz, 2H), 7.36 (t, J=7.2 Hz, 2H), 7.27 (d, J=7.6 Hz, 2H), 5.79-5.59 (m, 1H), 4.40-4.34 (m, 1H), 4.25-4.17 (m, 2H), 4.02-3.96 (m, 1H), 3.88-3.85 (m, 1H), 3.26-3.13 (m, 2H), 3.03-2.93 (m, 1H), 2.12-2.01 (m, 3H), 1.75-1.68 (m, 1H), 1.43-1.32 (m, 13H), 0.90-0.86 (m, 3H), 0.67-0.60 (m, 1H) ppm. ¹³C NMR (100.6 MHz, $CDCl_3$): δ=177.6, 156.7, 155.7, 144.1, 141.3, 127.7, 127.1, 125.5, 125.4, 120.0, 79.7, 67.1, 51.4, 50.8, 49.6, 48.7, 47.3, 32.2, 31.7, 31.0, 28.5, 22.4, 14.1 ppm. ESI-TOF MS (m/z): calcd. for $C_{30}H_{42}N_3O_6$ [M+H]⁺ 540.3. found 540.7.

Synthesis of (2S,7S)—N²-(tert-butoxycarbonyl)-N⁷-(9-fluorenylmethoxycarbonyl)-5-tert-butoxycarbonyl-5-aza-2,7-diaminoundecanoic acid (17)

Compound 16 (0.224 g, 0.416 mmol) was treated with $Na_2CO_3$ (0.168 g, 2.0 mmol) and $(Boc)_2O$ (0.28 g, 1.28 mmol) with the same reaction conditions described for the synthesis of compound 5, which afforded compound 17 (88%). $R_f$ value=0.47 (75% EtOAc-1% AcOH-hexane), ¹H NMR (400 MHz, $CDCl_3$): δ=7.75 (d, J=7.6 Hz, 2H), 7.57 (d, J=6.8 Hz, 2H), 7.38 (d, J=7.6 Hz, 2H), 7.29 (d, J=6.8 Hz, 2H), 4.50-4.32 (m, 2H), 4.25-4.15 (m, 2H), 3.86-3.54 (m, 2H), 3.50-3.29 (m, 2H), 3.22-2.89 (m, 2H), 2.12-2.00 (m, 1H), 1.44 (s, 18H), 1.36-1.26 (m, 5H), 0.92-0.86 (m, 4H) ppm. ¹³C NMR (100.6 MHz, $CDCl_3$): δ=173.8, 156.8, 156.7, 156.2, 143.9, 141.3, 127.7, 127.1, 125.2, 125.0, 120.0, 82.0, 80.9, 80.8, 80.2, 66.8, 66.4, 66.3, 66.2, 51.2, 50.6, 49.6, 47.3, 44.0, 43.9, 43.5, 43.0, 33.1, 32.8, 32.0, 31.1, 30.5, 29.7, 28.4, 27.9, 22.6, 14.0 ppm. HRMS (ESI-TOF) (m/z): calcd. for $C_{35}H_{48}N_3O_8$ [M−H]⁻ 638.3447. found 638.3454.

69

Scheme 7. Synthesis of (2S,7S)-N²-(tert-butoxycarbonyl)-N⁷-(9-fluorenylmethoxycarbonyl)-5-tert-butoxycarbonyl-5-aza-2,7-diaminoundecanoic acid (17).

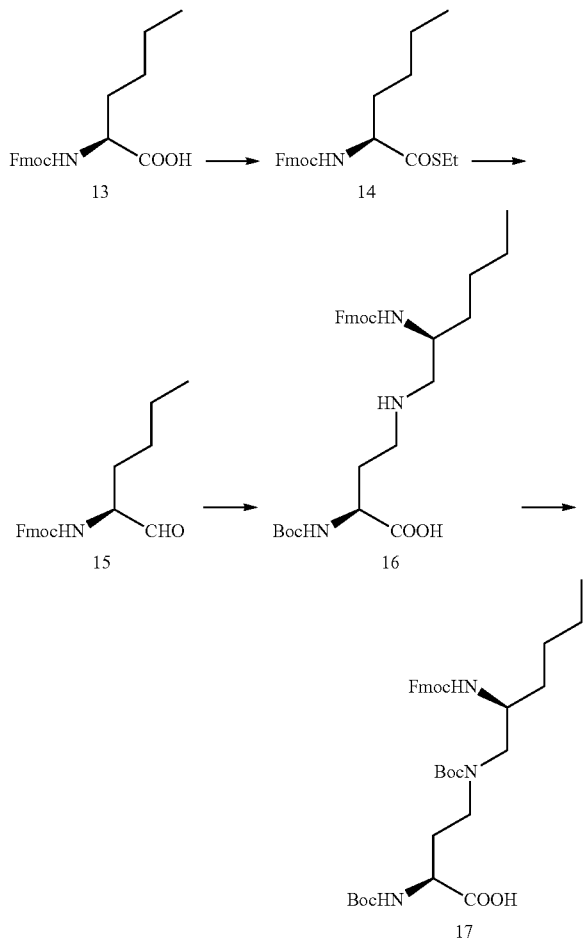

Example 8

Synthesis of (2S,7S)—N²-(tert-butoxycarbonyl)-N⁷-(9-fluorenylmethoxycarbonyl)-5-(tert-butoxycarbonyl)-5-aza-2,7-diaminotridecanoic acid (22) being a precursor for the amyloid-β peptide targeting ligands of the invention

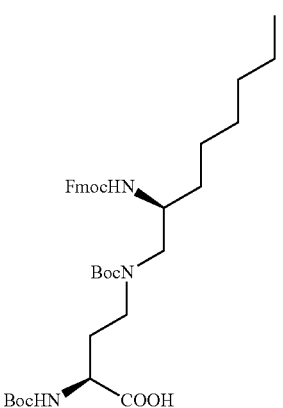

22

70

Synthesis of (S)—S-ethyl-2-[(9-fluorenylmethoxycarbonyl)amino]octanthioate (19)

Fmoc amino acid 18 (0.342 g, 0.9 mmol) was treated with ethanethiol (0.25 mL, 3.5 mmol), DCC (0.231 g, 1.12 mmol) and DMAP (0.222 g, 1.8 mmol) in DCM (12 mL) by the same reaction conditions as for the synthesis of compound 14 from Fmoc amino acid 13 to obtain compound 19 (0.336 g, 88%) after purification by column chromatography. $R_f$ value=0.56 (20% EtOAc-hexane), $^1$H NMR (400 MHz, CDCl$_3$): δ=7.70 (d, J=7.6 Hz, 2H), 7.55 (d, J=7.2 Hz, 2H), 7.33 (d, J=7.6 Hz, 2H), 7.25 (d, J=7.6 Hz, 2H), 5.11 (d, J=8.4 Hz, 1H), 4.44-4.40 (m, 1H), 4.36-4.30 (m, 2H), 4.17 (t, J=6.8 Hz, 1H), 2.82 (q, J=7.2 Hz, 2H), 1.84-1.78 (m, 1H), 1.57-1.49 (m, 1H), 1.26-1.16 (m, 11H), 0.81 (t, J=6.8 Hz, 3H) ppm. $^{13}$C NMR (100.6 MHz, CDCl$_3$): δ=201.1, 156.0, 144.1, 143.9, 141.5, 127.9, 127.2, 125.2, 120.1, 67.2, 61.1, 47.4, 33.1, 31.7, 29.0, 25.3, 23.4, 22.7, 14.7, 14.2 ppm. ESI-TOF MS (m/z): calcd. for $C_{25}H_{31}NNaO_3S$ [M+Na]⁺ 448.2. found 448.7.

Synthesis of (S)-2-[(9-fluorenylmethoxycarbonyl)amino]octanaldehyde (20)

Compound 19 (0.322 g, 0.756 mmol) was treated with 10% Pd/C (0.161 g) and triethylsilane (0.193 g, 1.66 mmol) in acetone (12 mL) in the same reaction conditions applied for the synthesis of compound 15 from compound 14. The reaction yielded aldehyde 20 (0.255 g, 92%) after purification by column chromatography. $R_f$ value=0.28 (20% EtOAc-hexane), $^1$H NMR (400 MHz, CDCl$_3$): δ=9.59 (s, 1H), 7.77 (d, J=7.6 Hz, 2H), 7.60 (d, J=7.2 Hz, 2H), 7.40 (d, J=7.2 Hz, 2H), 7.32 (d, J=7.6 Hz, 2H), 5.30 (d, J=6.4 Hz, 1H), 4.43 (d, J=6.8 Hz, 2H), 4.34-4.29 (m, 1H), 1.94-1.89 (m, 1H), 1.66-1.58 (m, 1H), 1.33-1.26 (m, 9H), 0.87 (t, J=7.2 Hz, 3H) ppm. $^{13}$C NMR (100.6 MHz, CDCl$_3$): δ=199.3, 156.3, 143.8, 141.4, 127.7, 127.1, 125.0, 120.0, 67.0, 60.3, 47.2, 31.5, 29.2, 29.0, 25.0, 22.5, 14.0 ppm.

Synthesis of (2S,7S)—N²-(tert-butoxycarbonyl)-N⁷-(9-fluorenylmethoxycarbonyl)-5-aza-2,7-diaminotridecanoic acid (21)

Compound 20 (0.194 g, 0.53 mmol) and Boc-L-Dab-OH (0.127 g, 0.582 mmol) were dissolved in a solvent mixture of 1% AcOH-MeOH (15 mL) and treated with NaBH$_3$CN (0.085 g, 1.35 mmol) in the same reaction conditions for the synthesis of compound 16 from compound 15 by reductive amination process. The crude product obtained in the reaction was purified by column chromatography to obtain compound 21 (0.253 g, 57%) in pure form. $R_f$ value=0.46 (7.5% MeOH-1% AcOH-DCM), $^1$H NMR (400 MHz, CDCl$_3$): δ=7.73 (d, J=6.8 Hz, 2H), 7.62-7.58 (m, 2H), 7.36 (d, J=6.4 Hz, 2H), 7.26-7.23 (m, 2H), 4.39-4.34 (m, 1H), 4.22-4.15 (m, 2H), 4.03-3.86 (m, 2H), 3.29-3.06 (m, 2H), 3.00-2.91 (m, 2H), 2.15-1.96 (m, 2H), 1.38 (s, 9H), 1.31-1.09 (m, 7H), 0.91-0.78 (m, 6H). $^{13}$C NMR (100.6 MHz, CDCl$_3$): δ=177.7, 156.7, 155.7, 144.2, 141.4, 127.7, 127.2, 125.5, 125.4, 120.0, 79.7, 79.5, 67.1, 53.6, 51.4, 50.7, 48.7, 47.2, 32.5, 32.0, 31.8, 31.0, 29.1, 29.0, 28.5, 26.3, 26.2, 22.7, 14.2 ppm. ESI-TOF MS (m/z): calcd. for $C_{32}H_{46}N_3O_6$ [M+H]⁺ 568.3. found 568.7.

Synthesis of (2S,7S)—N²-(tert-butoxycarbonyl)-N⁷-(9-fluorenylmethoxycarbonyl)-5-(tert-butoxycarbonyl)-5-aza-2,4-diaminotridecanoic acid (22)

Compound 21 (0.165 g, 0.29 mmol) was treated with (Boc)$_2$O (0.102 g, 0.47 mmol) in presence of Na$_2$CO$_3$ (0.05 g, 0.60 mmol) in a solvent mixture of dioxane and water (12 mL, 1:1) following the same reaction conditions used for synthesis of compound 17 from compound 16. The reaction yielded the crude product, which was purified by column chromatography to obtain the final monomer 22 (0.232 g, 88%) in pure form. $R_f$ value=0.53 (75% EtOAc-1% AcOH-hexane), $^1$H NMR (400 MHz, CDCl$_3$): δ=7.75 (d, J=7.6 Hz, 2H), 7.58 (d, J=6.8 Hz, 2H), 7.38 (d, J=7.2 Hz, 2H), 7.29 (t, J=7.2 Hz, 2H), 4.50-4.35 (m, 2H), 4.22-4.11 (m, 2H), 3.88-3.69 (m, 2H), 3.66-3.60 (m, 1H), 3.49-3.44 (m, 1H), 3.22-2.88 (m, 2H), 2.09-2.02 (m, 1H), 1.44 (s, 18H), 1.33-1.24 (m, 9H), 0.92-0.84 (m, 4H) ppm. $^{13}$C NMR (100.6 MHz, CDCl$_3$): δ=173.7, 157.0, 156.24, 156.18, 155.6, 144.1, 141.3, 127.8, 127.2, 125.3, 125.1, 120.1, 82.0, 80.9, 80.8, 80.2, 67.0, 66.5, 66.3, 66.1, 51.4, 50.7, 47.4, 44.0, 43.0, 33.5, 32.4, 31.8, 31.6, 30.5, 29.8, 29.4, 28.5, 22.7, 14.2 ppm. HRMS(ESI-TOF) (m/z): calcd. for $C_{37}H_{52}N_3O_8$ [M–H]$^-$ 666.3760. found 666.3755.

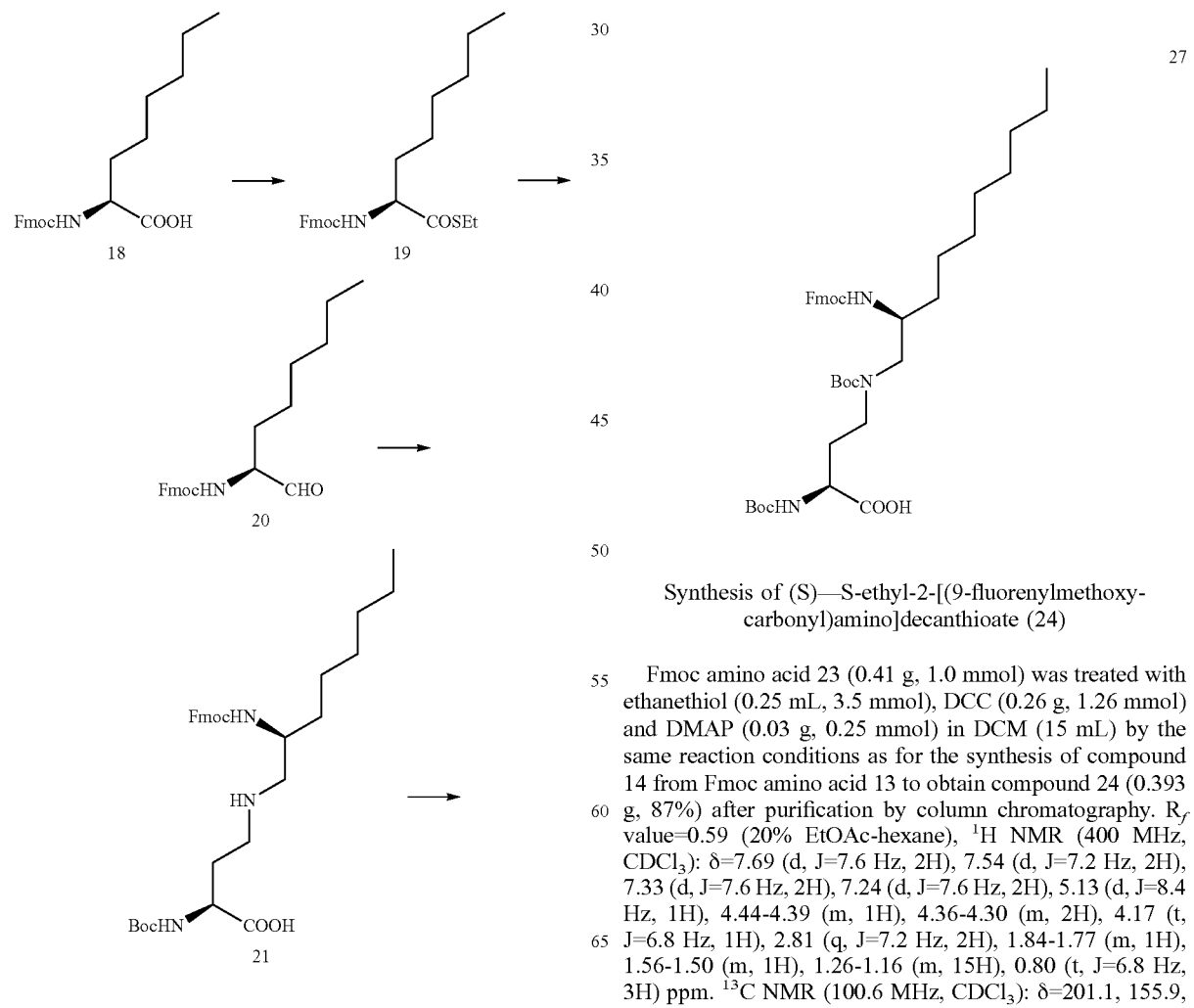

Scheme 8. Synthesis of (2S, 7S)-N$^2$-(tert-butoxycarbonyl)-N$^7$-(9-fluorenylmethoxycarbonyl)-5-(tert-butoxycarbonyl)-5-aza-2,7-diaminotridecanoic acid (22).

Example 9

Synthesis of (2S,7S)—N$^2$-(tert-butoxycarbonyl)-N$^7$-(9-fluorenylmethoxycarbonyl)-5-(tert-butoxycarbonyl)-5-aza-2,7-diaminopentdecanoic acid (24) being a precursor for the amyloid-β peptide targeting ligands of the invention Synthesis of (S)—S-ethyl-2-[(9-fluorenylmethoxycarbonyl)amino]decanthioate (24)

Fmoc amino acid 23 (0.41 g, 1.0 mmol) was treated with ethanethiol (0.25 mL, 3.5 mmol), DCC (0.26 g, 1.26 mmol) and DMAP (0.03 g, 0.25 mmol) in DCM (15 mL) by the same reaction conditions as for the synthesis of compound 14 from Fmoc amino acid 13 to obtain compound 24 (0.393 g, 87%) after purification by column chromatography. $R_f$ value=0.59 (20% EtOAc-hexane), $^1$H NMR (400 MHz, CDCl$_3$): δ=7.69 (d, J=7.6 Hz, 2H), 7.54 (d, J=7.2 Hz, 2H), 7.33 (d, J=7.6 Hz, 2H), 7.24 (d, J=7.6 Hz, 2H), 5.13 (d, J=8.4 Hz, 1H), 4.44-4.39 (m, 1H), 4.36-4.30 (m, 2H), 4.17 (t, J=6.8 Hz, 1H), 2.81 (q, J=7.2 Hz, 2H), 1.84-1.77 (m, 1H), 1.56-1.50 (m, 1H), 1.26-1.16 (m, 15H), 0.80 (t, J=6.8 Hz, 3H) ppm. $^{13}$C NMR (100.6 MHz, CDCl$_3$): δ=201.1, 155.9, 144.0, 143.9, 141.5, 127.9, 127.2, 125.2, 120.1, 67.2, 61.1, 47.4, 33.1, 32.0, 29.5, 29.3, 25.4, 23.4, 22.8, 14.6, 14.2 ppm. ESI-TOF MS (m/z): calcd. for $C_{27}H_{35}NNaO_3S$ $[M+Na]^+$ 476.2. found 476.7.

Synthesis of (S)-2-[(9-fluorenylmethoxycarbonyl)amino]decanaldehyde (25)

Compound 24 (0.493 g, 1.09 mmol) was treated with 10% Pd/C (0.247 g) and triethylsilane (0.277 mL, 1.74 mmol) in acetone (16 mL) in the same reaction conditions applied for the synthesis of compound 15 from compound 14. The reaction yielded aldehyde 25 (0.360 g, 84%) after purification by column chromatography. $R_f$ value=0.35 (20% EtOAc-hexane), $^1$H NMR (400 MHz, CDCl$_3$): δ=9.58 (s, 1H), 7.77 (d, J=7.6 Hz, 2H), 7.60 (d, J=7.6 Hz, 2H), 7.40 (t, J=7.6 Hz, 2H), 7.32 (d, J=7.6 Hz, 2H), 5.31 (d, J=6.8 Hz, 1H), 4.43 (d, J=6.8 Hz, 2H), 4.34-4.29 (m, 1H), 4.23 (t, J=6.8 Hz, 1H), 1.93-1.89 (m, 1H), 1.65-1.58 (m, 1H), 1.33-1.26 (m, 12H), 0.88 (t, J=7.2 Hz, 3H) ppm. $^{13}$C NMR (100.6 MHz, CDCl$_3$): δ=199.3, 156.0, 143.8, 143.7, 141.3, 127.7, 127.1, 125.0, 120.0, 67.0, 60.3, 47.2, 31.8, 29.3, 29.2, 25.0, 22.6, 14.1 ppm. ESI-TOF MS (m/z): calcd. for $C_{25}H_{31}NNaO_3$ $[M+Na]^+$ 416.2. found 416.8.

Synthesis of (2S,7S)—$N^2$-(tert-butoxycarbonyl)-$N^7$-(9-fluorenylmethoxycarbonyl)-5-aza-2,7-diaminopentdecanoic acid (26)

Compound 25 (0.26 g, 0.66 mmol) and Boc-L-Dab-OH (0.167 g, 0.743 mmol) were dissolved in a solvent mixture of 1% AcOH-MeOH (20 mL) and treated with NaBH$_3$CN (0.106 g, 1.69 mmol) in the same reaction conditions for the synthesis of compound 16 from compound 15 by reductive amination process. The crude product obtained in the reaction was purified by column chromatography to obtain compound 26 (0.325 g, 60%) in pure form. $R_f$ value=0.29 (7.5% MeOH-1% AcOH-DCM), $^1$H NMR (400 MHz, CDCl$_3$): δ=7.73 (d, J=7.6 Hz, 2H), 7.60 (t, J=6.8 Hz, 2H), 7.36 (t, J=7.6 Hz, 2H), 7.29-7.25 (m, 2H), 4.35-4.31 (m, 1H), 4.27-4.16 (m, 2H), 4.04-3.86 (m, 2H), 3.27-3.14 (m, 2H), 3.02-2.92 (m, 2H), 2.10-2.04 (m, 1H), 1.77-1.57 (m, 2H), 1.38 (s, 9H), 1.36-1.31 (m, 2H), 1.28-1.19 (m, 10H), 0.90-0.86 (m, 4H) ppm. $^{13}$C NMR (100.6 MHz, CDCl$_3$): δ=177.6, 156.7, 156.0, 144.2, 144.1, 141.4, 127.9, 127.8, 127.2, 125.4, 120.0, 79.9, 67.2, 55.3, 54.6, 51.5, 49.6, 48.8, 47.3, 47.2, 32.0, 31.0, 30.8, 29.6, 29.4, 28.5, 26.3, 22.8, 21.0, 14.2 ppm. ESI-TOF MS (m/z): calcd. for $C_{34}H_{50}N_3O_6$ $[M+H]^+$ 596.4. found 596.7.

Synthesis of (2S,7S)—$N^2$-(tert-butoxycarbonyl)-$N^7$-(9-fluorenylmethoxycarbonyl)-5-(tert-butoxycarbonyl)-5-aza-2,7-diaminopentdecanoic acid (27)

Compound 26 (0.275 g, 0.46 mmol) was treated with (Boc)$_2$O (0.160 g, 0.73 mmol) in presence of Na$_2$CO$_3$ (0.08 g, 0.95 mmol) in a solvent mixture of dioxane and water (25 mL, 1:1) following the same reaction conditions used for synthesis of compound 22 from compound 21. The reaction yielded the crude product, which was purified by column chromatography to obtain the final monomer 27 (0.365 g, 79%) in pure form. $R_f$ value=0.58 (75% EtOAc-1% AcOH-hexane), $^1$H NMR (400 MHz, CDCl$_3$): δ=7.75 (d, J=7.6 Hz, 2H), 7.57 (d, J=6.8 Hz, 2H), 7.38 (t, J=7.6 Hz, 2H), 7.29 (t, J=6.8 Hz, 2H), 4.46-4.38 (m, 2H), 4.19-4.16 (m, 2H), 3.82-3.71 (m, 2H), 3.60-3.32 (m, 2H), 3.22-2.88 (m, 2H), 2.10-2.00 (m, 1H), 1.44 (s, 20H), 1.26 (m, 12H), 0.87 (t, J=6.8 Hz, 3H) ppm. $^{13}$C NMR (100.6 MHz, CDCl$_3$): δ=174.0, 156.8, 156.7, 156.1, 155.7, 144.0, 141.3, 127.7, 127.1, 125.2, 125.0, 120.0, 90.8, 81.9, 81.0, 80.2, 66.8, 66.4, 66.1, 62.3, 51.3, 50.6, 49.6, 47.4, 43.9, 42.9, 33.4, 31.9, 30.4, 29.5, 29.3, 28.4, 25.8, 22.7, 14.1 ppm. HRMS(ESI-TOF) (m/z): calcd. for $C_{39}H_{56}N_3O_8$ $[M-H]^-$ 694.4073. found 694.4063.

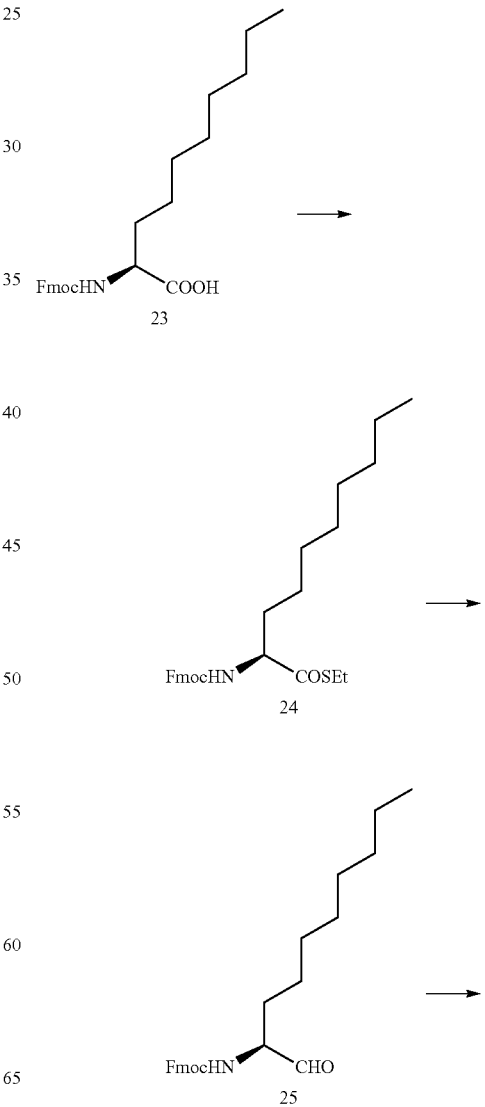

Scheme 9. Synthesis of (2S,7S)-$N^2$-(tert-butoxycarbonyl)-$N^7$-(9-fluorenylmethoxycarbonyl)-5-(tert-butoxycarbonyl)-5-aza-2,7-diaminopentdecanoic acid (27).

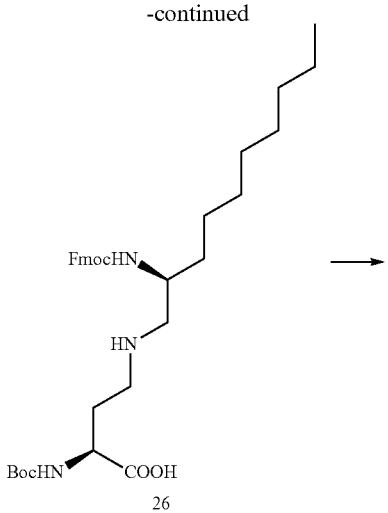

Example 10

Synthesis of (R)-methyl-N⁴-(9-fluorenylmethoxy-carbonyl)-2,4-diaminobutanoate (30) being a precursor for the amyloid-β peptide targeting ligands of the invention

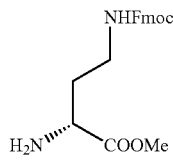

Synthesis of (R)—N⁴-(9-fluorenylmethoxycarbonyl)-2,4-diaminobutanoic acid (29)

Compound 28 (D-Dab.2HCl, 0.573 g, 3 mmol) and copper (II) acetate (0.3 g, 1.5 mmol) were dissolved in 10 mL of 10% sodium carbonate solution and the solution was stirred vigorously for 1 h. Solution dioxane-water (250 mL, 2:3) was added into it followed by addition of solid Fmoc succinimidyl carbonate (1.011 g, 3 mmol) into the reaction mixture. After stirring this reaction mixture for 1 h, the reaction mixture was acidified with 5 M HCl and extracted with diethylether (100 mL×2) and ethylacetate (100 mL×2). The desired compound came in the ethylacetate layer which was dried with Na₂SO₄ and evaporated to dryness under reduced pressure. Next, the crude product was suspended in water (12 mL) and Na₂S (0.068 g, 0.87 mmol) was added into it. After stirring for 0.5 h, the solution was filtered. The solid compound on the filter paper was dissolved in methanol (100 mL) and collected in a round bottomed flask. Evaporation of the solvent afforded us desired compound 29 (0.558 g, 55%).

Synthesis of (R)-methyl-N⁴-(9-fluorenylmethoxy-carbonyl)-2,4-diaminobutanoate (30)

Compound 29 (0.34 g, 1.0 mmol) was suspended over methanol (20 mL) and inert atmosphere was created inside the round bottomed flask. The reaction mixture was cooled to 0° C. using an icebath and SOCl₂ was added into it dropwise and stirred for 18 h, when TLC showed consumption of the starting material. Solvent from the reaction mixture was evaporated under reduced pressure till few drops of solvent remains. Next, 50 mL water was added into it and the compound was extracted with ethylacetate (60 mL×3). Combined organic layer was washed with half saturated brine (30 mL×2), dried over Na₂SO₄ and evaporated to dryness to get crude compound, which was purified by column chromatography to afford compound 30 (0.295 g, 84%) as a white solid. $^1$H NMR (400 MHz, CD₃OD): δ 7.81 (d, J=7.6 Hz, 2H), 7.66 (d, J=7.6 Hz, 2H), 7.40 (t, J=7.6 Hz, 2H), 7.32 (t, J=7.6 Hz, 2H), 4.39 (d, J=6.6 Hz, 2H), 4.21 (t, J=6.8 Hz, 2H), 3.71 (s, 3H), 3.48-3.44 (m, 1H), 3.24 (t, J=6.8 Hz, 1H), 1.97-1.89 (m, 1H), 1.79-1.70 (m, 1H) ppm; $^{13}$C NMR (100.6 MHz, CD₃OD): δ 0180.8, 145.0, 142.7, 141.5, 139.4, 129.9, 128.7, 128.2, 126.2, 122.1, 121.0, 120.7, 108.3, 67.6, 53.1, 40.0, 38.2, 35.5, 31.2, 29.2 ppm. ESI-TOF MS (m/z): calcd. for $C_{20}H_{23}N_2O_4$ [M+H]⁺ 355.2. found 355.7.

Scheme 10. Synthesis of (R)-methyl-N⁴-(9-fluorenylmethoxycarbonyl)-2,4-diaminobutanoate (30).

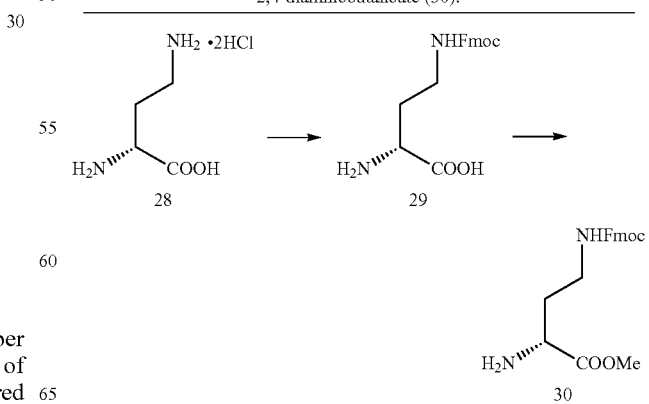

Example 11

Synthesis of 4-(4'-acetamidophenyl)-$N^2$-(9-fluorenylmethoxycarbonyl)-D-phenylalanine or (R)-2-(9-fluorenylmethoxycarbonyl)amino-3-(4'-acetamido-[1,1'-biphenyl]-4-yl)propanoic acid (33) being a precursor for the amyloid-β peptide targeting ligands of the invention

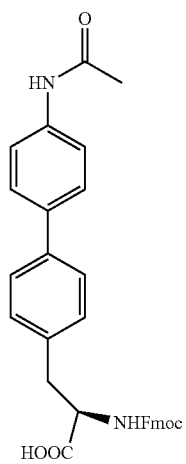

33

Synthesis of pinacol diester of N-acetylphenylboronic acid or N-(4-(4,4,5,5-tetramethyl-1,3,2-dioxaborolan-2-yl)phenyl)acetamide (Ting, R. et al. *Journal of the American Chemical Society* 2005, 127, 13094-13095) (32)

Compound 31 (0.2 g, 0.92 mmol) was dissolved in acetic anhydride (10 mL) and reaction mixture was stirred for 1 h. Next, the reaction mixture was evaporated to dryness under reduced pressure, followed by coevaporation by diethylether (10 mL×3) to get compound 32 (0.22 g, 93%) as white solid. $^1$H NMR (400 MHz, CDCl$_3$): δ=7.76 (d, J=8.4 Hz, 2H), 7.51 (d, J=8.4 Hz, 2H), 7.30 (brs, 1H), 2.17 (s, 3H), 1.34 (s, 12H) ppm. $^{13}$C NMR (100.6 MHz, CDCl$_3$): δ=168.2, 140.5, 135.8, 118.5, 83.7, 24.9, 24.8 ppm.

Synthesis of 4-(4'-acetamidophenyl)-$N^2$-(9-fluorenylmethoxycarbonyl)-D-phenylalanine or (R)-2-(9-fluorenylmethoxycarbonyl)amino-3-(4'-acetamido-[1,1'-biphenyl]-4-yl)propanoic acid (33)

Compound 32 (24 mg, 0.05 mmol) was dissolved in a solvent mixture of ethylene glycol and THF (6 mL, 1:2) at room temperature. N-(9-Fluorenylmethoxycarbonyl)-4-bromo-D-phenylalanine (9 mg, 0.05 mmol) was added into it and stirred. Catalyst PdCl$_2$ (5 mol %, 1 mg) was added into the reaction mixture and nitrogen was bubbled through the reaction mixture for 15 minutes. Next, base K$_2$CO$_3$ (0.021 g, 0.15 mmol) was added into the reaction mixture and round bottomed flask was degassed with nitrogen, followed by heating at 60° C. for 3 h, when the TLC showed completion of the reaction. Water (8 mL) was added into the reaction mixture and was extracted with ethylacetate (10 mL×3). Combined organic layer was washed with half saturate brine (15 mL×2), dried over Na$_2$SO$_4$ and evaporated to dryness under reduced pressure. Crude was purified by column chromatography to afford compound 33 (38 mg, 80%) in pure form. R$_f$ value=0.25 (5% MeOH-DCM, 1% AcOH), $^1$H NMR (400 MHz, CD$_3$OD): δ=7.67 (d, J=6.8 Hz, 2H), 7.52-7.44 (m, 6H), 7.37 (d, J=7.6 Hz, 3H), 7.28-7.12 (m, 5H), 4.36 (dd, J=7.6, 4.8 Hz, 1H), 4.23-4.19 (m, 1H), 4.12-4.08 (m, 1H), 4.05-4.01 (m, 1H), 3.16 (dd, J=14.0, 4.8 Hz, 1H), 2.82 (dd, J=14.0, 9.6 Hz, 1H), 2.04 (s, 3H) ppm. $^{13}$C NMR (100.6 MHz, CD$_3$OD): δ=171.7, 158.4, 145.3, 142.6, 140.3, 139.2, 137.9, 137.7, 130.9, 128.8, 128.2, 128.0, 127.7, 126.4, 126.3, 121.5, 120.9, 68.0, 64.4, 48.4, 38.4, 23.9 ppm. HRMS(ESI-TOF) (m/z): calcd. for C$_{32}$H$_{27}$N$_2$O$_5$ [M−H]$^-$ 519.1925. found 519.1924.

Scheme 11. Synthesis of 4-(4'-acetamidophenyl)-$N^2$-(9-fluorenylmethoxycarbonyl)-D-phenylalanine or (R)-2-(9-fluorenylmethoxycarbonyl)amino-3-(4'-acetamido-[1,1'-biphenyl]-4-yl)propanoic acid (33).

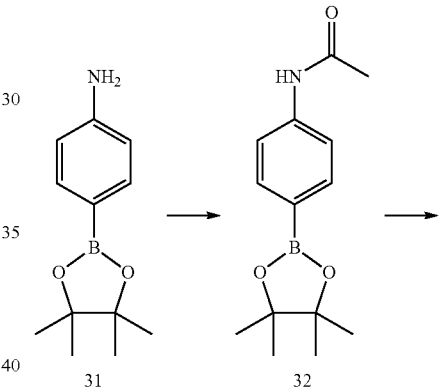

31         32

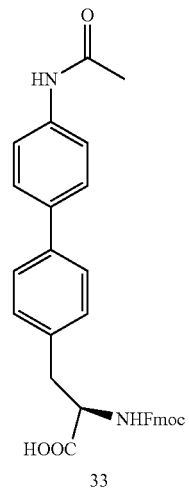

33

Example 12

Synthesis of (R)-4-(4'-N,N-dimethylamino-1,8-naphthalimido)-$N^2$-(9-fluorenylmethoxycarbonyl)-2-aminobutanoic acid (37) being a precursor for the amyloid-β peptide targeting ligands of the invention

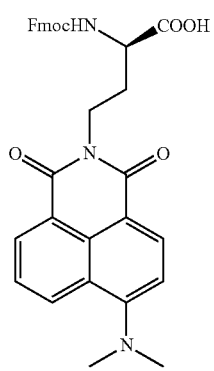

37

Synthesis of 4-(N,N-dimethylamino)-1,8-naphthalic anhydride (Loving, G.; Imperiali, B. *Journal of the American Chemical Society* 2008, 130, 13630-13638) (35)

4-Bromo-1,8-naphthalic anhydride (34, 0.555 g, 2 mmol) was suspended over isoamylalcohol (20 mL) and 3-dimethylamino propionate (0.79 g, 8 mmol) was added into it. The flask was fitted with water condenser and the reaction mixture was stirred at 132° C. The reaction mixture was stirred for 16 h when TLC showed consumption of the starting material. Precipitation occurred when the reaction mixture was cooled down. Orange precipitate was filtered through Whatman filterpaper, washed with water and hexane. Crude product was coevaporated with dichloromethane and dried under reduced pressure for overnight to afford compound 35 (0.352 g, 88%). $R_f$ value=0.6 (DCM), $^1$H NMR (400 MHz, CDCl$_3$): δ =8.56 (d, J=7.2 Hz, 1H), 8.49 (d, J=8.5 Hz, 1H), 8.45 (d, J=8.5 Hz, 1H), 7.68 (t, J=7.8 Hz, 1H), 7.10 (d, J=8.3 Hz, 1H), 3.18 (s, 6H) ppm. $^{13}$C NMR (100.6 MHz, CDCl$_3$): δ=161.7, 160.7, 157.9, 135.0, 133.0, 132.9, 132.8, 125.0, 124.9, 119.3, 113.2, 109.5, 44.6 ppm. ESI-TOF MS (m/z): calcd. for $C_{14}H_{12}NO_3$ [M+H]$^+$ 242.1. found 242.7.

Synthesis of (R)-4-(4'-N,N-dimethylamino-1,8-naphthalimido)-$N^2$-(tert-butoxycarbonyl)-2-aminobutanoic acid (36)

Compound 35 (0.266 g, 1.1 mmol) was taken in a three neck round bottom flask fitted with water condenser and nitrogen atmosphere was created inside. Dioxane (25 mL) was added into the reaction mixture through septum. Temperature was raised to the boiling temperature of dioxane and the suspension was stirred vigorously. Boc-D-Dab-OH (0.218 g, 1.0 mmol) was dissolved in aqueous solution (5 mL) containing NaHCO$_3$ (0.42 g, 5 mmol) and added into the reaction mixture. The reaction mixture was refluxed for 1 h, when TLC showed complete consumption of the amino acid. Then it was concentrated under reduced pressure to remove dioxane and then 60 mL water was added into it, followed by washing with diethylether (60 mL×2). Aqueous layer was acidified with 5 N HCl when yellow precipitation of the product appeared. It was extracted with DCM (80 mL×3), combined organic layers dried over Na$_2$SO$_4$, filtered and concentrated under reduced pressure. Crude compound was purified by column chromatography to afford compound 36 (0.27 g, 66%) in pure form. $R_f$ value=0.2 (50% ethylacetate-hexane, 1% AcOH), $^1$H NMR (400 MHz, CDCl$_3$): δ 8.49 (d, J=7.2 Hz, 1H), 8.39 (d, J=7.6 Hz, 1H), 8.36 (d, J=8.4 Hz, 1H), 7.58 (t, J=8.0 Hz, 1H), 7.02 (d, J=8.4 Hz, 1H), 5.52 (d, J=7.6 Hz, 1H), 4.27-4.16 (m, 3H), 3.04 (s, 6H), 2.21-2.11 (m, 2H), 1.35 (s, 9H) ppm. $^{13}$C NMR (100.6 MHz, CDCl$_3$): δ=174.6, 165.1, 164.6, 157.5, 156.0, 133.4, 131.9, 131.7, 130.5, 125.2, 125.0, 122.7, 114.2, 113.4, 80.4, 52.0, 44.9, 36.8, 30.8, 28.5 ppm. HRMS (ESI-TOF) (m/z): calcd. for $C_{23}H_{26}N_3O_6$ [M−H]$^−$ 440.1827. found 440.1827.

Synthesis of (R)-4-(4'-N,N-dimethylamino-1,8-naphthalimido)-$N^2$-(9-fluorenylmethoxycarbonyl)-2-aminobutanoic acid (37)

Compound 36 (0.12 g, 0.27 mmol) was dissolved in DCM (3 mL) and stirred Cold trifluoroacetic acid (3 mL) was added into the reaction mixture over 5 min and it was stirred for 2 h. Next, the reaction mixture was evaporated to dryness under reduced pressure and coevaporated with chloroform (10 mL×3). Crude was dried under vacuum overnight and was redissolved in water (4 mL) containing NaHCO$_3$ (0.114 g, 1.35 mmol). Dioxane (10 mL) was added into it, followed by addition of Fmoc-OSu (0.101 g, 0.3 mmol). Reaction mixture was stirred at 0° C. for 2 h, when TLC showed consumption of the starting material. The reaction mixture was diluted with water (20 mL) and aqueous layer was washed with diethylether (20 mL×2). Then it was acidified with 6 N HCl to adjust the pH at 6, followed by extraction of the compound with DCM (25 mL×3). Combined organic layers dried over Na$_2$SO$_4$, filtered and concentrated under reduced pressure. Crude compound was purified by column chromatography to afford compound 37 (0.116 g, 71%) in pure form. $R_f$ value=0.6 (2.5% MeOH-DCM, 1% AcOH), $^1$H NMR (400 MHz, CDCl$_3$): δ □8.51 (d, J=6.8 Hz, 1H), 8.41 (d, J=8.4 Hz, 1H), 8.35 (d, J=8.4 Hz, 1H), 7.67 (d, J=7.2 Hz, 2H), 7.59-7.52 (m, 3H), 7.31 (t, J=7.2 Hz, 2H), 7.23 (t, J=7.2 Hz, 2H), 7.00 (d, J=8.0 Hz, 1H), 5.96 (d, J=8.0 Hz, 1H), 4.35-4.31 (m, 1H), 4.29-4.19 (m, 4H), 4.13 (t, J=7.2 Hz, 1H), 3.03 (s, 6H), 2.34-2.25 (m, 1H), 2.19-2.11 (m, 1H), 0.83-0.76 (m, 2H) ppm. $^{13}$C NMR (100.6 MHz, CDCl$_3$): δ=174.0, 165.2, 157.7, 156.2, 144.0, 141.4, 133.6, 132.1, 131.8, 130.6, 127.8, 127.3, 125.4, 125.1, 125.0, 122.6, 120.1, 113.9, 113.3, 67.4, 52.2, 47.2, 44.9, 36.8, 31.1 ppm. HRMS (ESI-TOF) (m/z): calcd. for $C_{33}H_{28}N_3O_6$ [M−H]$^−$ 562.1984. found 562.1984.

Scheme 12. Synthesis of (R)-4-(4'-N,N-dimethylamino-1,8-naphthalimido)-$N^2$-(9-fluorenylmethoxycarbonyl)-2-aminobutanoic acid (37)

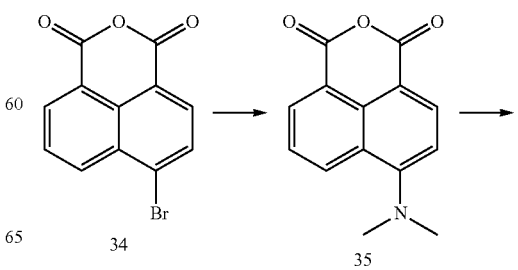

-continued

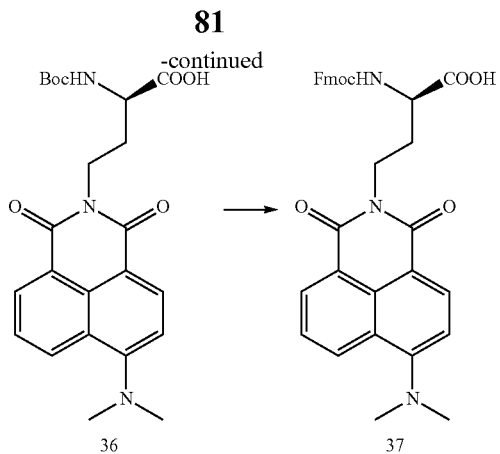

Example 13

Synthesis of the N³—(N-tert-butoxycarbonyl-2-aminoethyl)-N²,N³-dibenzyloxycarbonyl-(S)-2,3-diaminopropionic acid pentafluorophenyl ester (38) being a precursor for the amyloid-β peptide targeting ligands of the invention

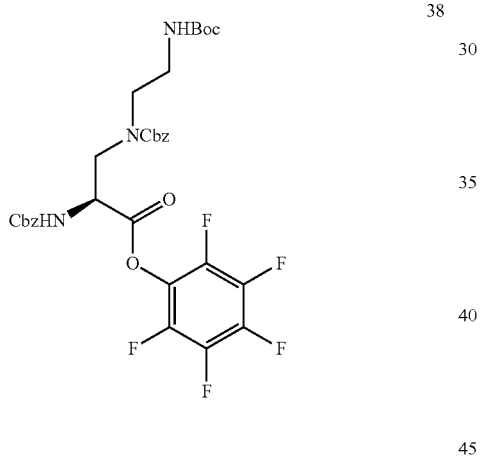

Synthesis of N³—(N-tert-butoxycarbonyl-2-aminoethyl)-N²,N³-dibenzyloxycarbonyl-(S)-2,3-diaminopropionic acid pentafluorophenyl ester (38)

AE-L-Dab building block (0.49 g, 0.95 mmol) was dissolved in anhydrous acetonitrile-pyridine (7:4 v/v) mixture (10 mL) under stirring and cooled in an ice-water bath. To the resulted solution pentafluorophenol (0.26 g, 1.42 mmol) was added under nitrogen atmosphere followed by the addition of N,N'-diisopropylcarbodiimide (0.44 mL, 2.85 mmol). The reaction mixture was allowed to warm to ambient temperature and was stirred for 20 h. Solvents were reduced in vacuo, the residue was acidified with 1% aqueous solution of citric acid and extracted with ethyl acetate. The organic phase was dried over $Na_2SO_4$, filtered and concentrated under reduced pressure. Product was purified by flash column chromatography using 0 to 30% EtOAc in cyclohexane as eluent to afford 38 (0.44 g, 68%). $^1$H NMR (400 MHz, $CDCl_3$): δ=7.32-7.21 (m, 10H), 5.11-4.99 (m, 4H), 4.88-4.78 (m, 1H), 3.96-3.85 (m, 1H), 3.81-3.61 (m, 1H), 3.41-3.09 (m, 4H), 1.40-1.29 (s, 9H) ppm. ESI-TOF MS m/z [M+Na]⁺ 703.8, calcd 704.2.

Scheme 13. Synthesis of the triamino acid building block 38.

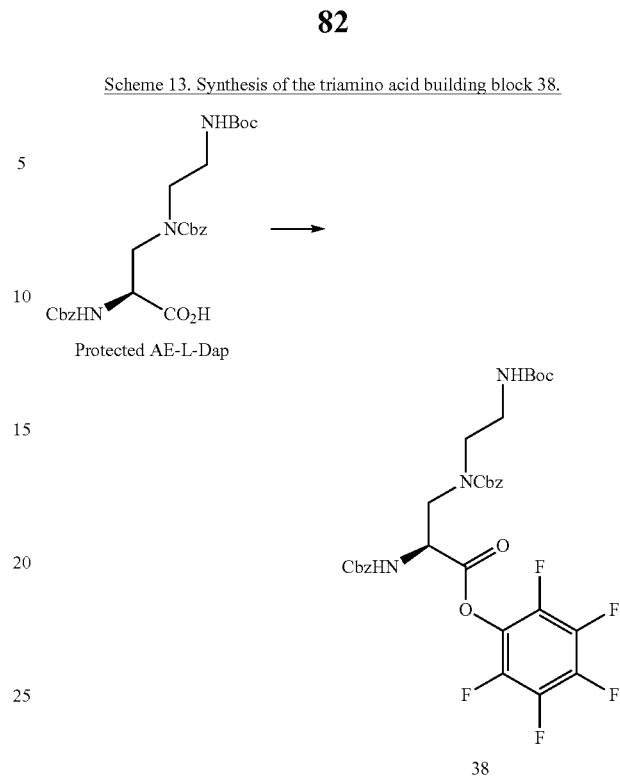

Example 14

Synthesis of the N³—(N-tert-butoxycarbonyl-2-aminoethyl)-N²,N³-dibenzyloxycarbonyl-(S)-2,3-diaminopropionic acid p-nitrophenyl ester (39) being a precursor for the amyloid-β peptide targeting ligands of the invention

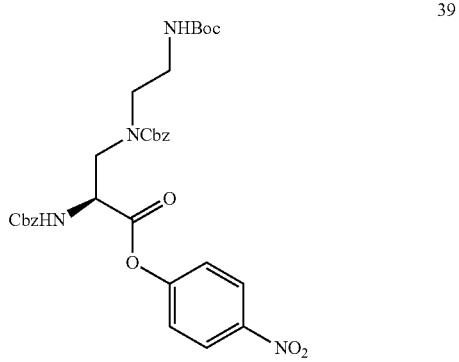 [SMILES: CC(C)(C)OC(=O)NCCN(C[C@H](NC(=O)OCc1ccccc1)C(=O)Oc1ccc([N+](=O)[O-])cc1)C(=O)OCc1ccccc1]

Synthesis of N³—(N-tert-butoxycarbonyl-2-aminoethyl)-N²,N³-dibenzyloxycarbonyl-(S)-2,3-diaminopropionic acid p-nitrophenyl ester (39)

AE-L-Dab (0.2 g, 0.39 mmol) and p-nitrophenol (0.16 g, 1.16 mmol) were dissolved in anhydrous pyridine (5 mL) and cooled in an ice-water bath. To the resulted solution N,N'-diisopropylcarbodiimide (0.3 mL, 1.95 mmol) was added dropwise under nitrogen atmosphere and the reaction mixture was allowed to warm to ambient temperature and was stirred for 28 h. Solvent was reduced in vacuo and co-evaporated with toluene. The reaction mixture was partitioned between dichloromethane and 1% aqueous solution of citric acid, the aqueous phase was washed with dichloromethane. The combined organic phase was dried over $Na_2SO_4$, filtered and concentrated under reduced pressure. Product was purified by flash column chromatography using 0 to 10% EtOAc in dichloromethane as eluent to give 39 (0.176 g, 71%). $^1$H NMR (400 MHz, $CDCl_3$): δ=8.21 (d, J=8.7 Hz, 1H), 7.39-7.21 (m, 12H), 6.24-6.12 (br. s, 1H), 5.19-5.02 (m, 4H), 4.80-4.64 (m, 1H), 3.97-3.75 (m, 2H), 3.52-3.13 (m, 4H), 1.48-1.34 (s, 9H) ppm. ESI-TOF MS m/z [M+Na]$^+$ 659.6, calcd 659.2.

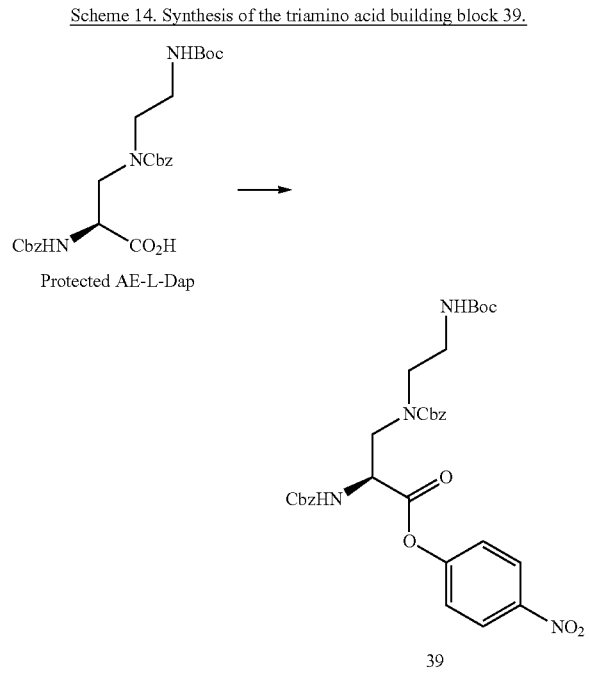

Scheme 14. Synthesis of the triamino acid building block 39.

39

Example 15

Synthesis of the 12-amino-12-oxododecanoic acid p-nitrophenyl ester (41) being a precursor for the amyloid-β peptide targeting ligands of the invention

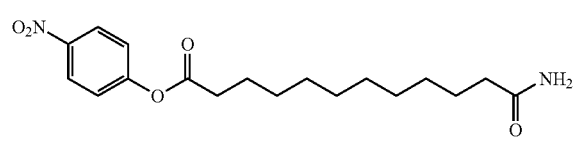

41

Synthesis of 12-amino-12-oxododecanoic acid (40)

Dodecanedioic acid monoethyl ester (0.52 g, 2.0 mmol) was treated with ammonia solution in methanol (25 mL) at room temperature for 24 h. Volatiles were removed in vacuo and the residue was subjected to flash column chromatography using EtOAc-toluene (1:1 v/v) mixture containing 10% of AcOH as eluent to give compound 40 (0.41 g, 89%). $^1$H NMR (400 MHz, DMSO-$d_6$): δ=7.20 (s, 1H), 6.64 (s, 1H), 2.16 (t, J=7.3 Hz, 2H), 2.01 (t, J=7.4 Hz, 2H), 1.52-1.41 (m, 4H), 1.24 (s, 12H) ppm; $^{13}$C NMR (100.6 MHz, DMSO-$d_6$): δ=174.5, 174.2, 35.0, 33.8, 28.79, 28.78, 28.7, 28.63, 28.61, 28.5, 25.0, 24.5 ppm. ESI-TOF MS m/z [M−H]$^-$ 228.0, calcd 228.2.

Synthesis of 12-amino-12-oxododecanoic acid p-nitrophenyl ester (41)

To the chilled solution (ice-water bath) of compound 40 (0.148 g, 0.645 mmol) and p-nitrophenol (0.269 g, 1.935 mmol) in anhydrous pyridine (10 mL) N,N'-diisopropylcarbodiimide (0.5 mL, 3.22 mmol) was added dropwise under nitrogen atmosphere. The reaction mixture was allowed to warm to ambient temperature and was stirred for 2 days. Solvent was reduced in vacuo and co-evaporated with toluene and EtOAc-toluene mixture. The residue was re-dissolved in EtOAc and filtered. The filtrate was concentrated under reduced pressure and the product was precipitated with cyclohexane, filtered, washed with cyclohexane and dried on pump to afford 41 (0.215 g, 95%). $^1$H NMR (400 MHz, DMSO-$d_6$): δ=8.30 (d, J=9.1 Hz, 2H), 7.43 (d, J=9.1 Hz, 2H), 7.20 (s, 1H), 6.65 (s, 1H), 2.63 (t, J=7.4 Hz, 2H), 2.01 (t, J=7.4 Hz, 2H), 1.70-1.59 (m, 2H), 1.51-1.41 (m, 2H), 1.40-1.19 (m, 12H) ppm; $^{13}$C NMR (100.6 MHz, DMSO-$d_6$): δ=174.2, 171.1, 155.3, 144.9, 125.1, 123.1, 35.0, 33.3, 28.8, 28.72, 28.68, 28.61, 28.5, 28.2, 25.0, 24.0 ppm. ESI-TOF MS m/z [M+Na]$^+$ 373.4, calcd 373.2.

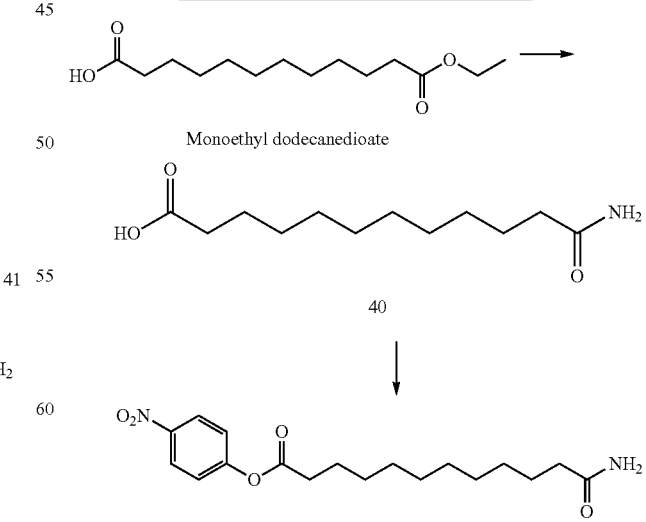

Scheme 15. Synthesis of the building block 41.

Monoethyl dodecanedioate

40

41

B) Synthesis Amyloid β-Peptide Targeting Ligands

Example 16

Synthesis of the (R)—N⁴—[N²—(N³—(N-decanoyl-2-aminoethyl)-(S)-2,3-diaminopropionyl)-D-tryptophanyl]-N²-glutanoyl-2,4-diaminobutanoic acid (49) being an amyloid-β peptide targeting ligands (DH18)

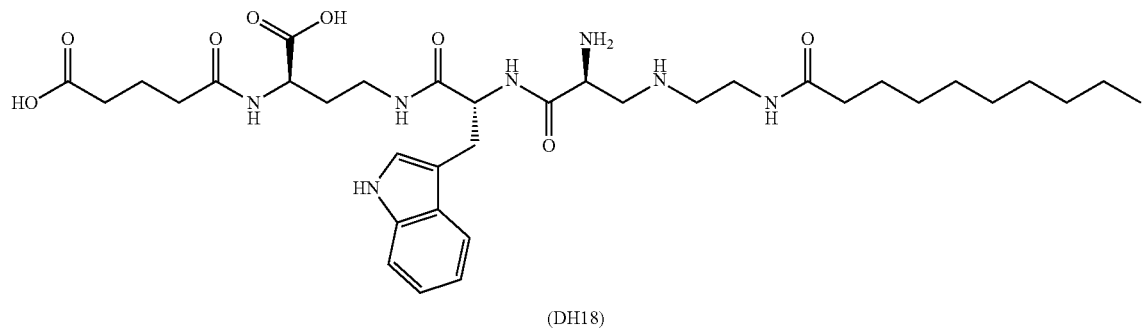

(DH18)

Synthesis of benzyl (R)—N⁴—[N²-(9-fluorenylmethoxycarbonyl)-D-tryptophanyl]-2,4-diaminobutyrate (43)

Compound 42 (0.13 g, 0.181 mmol) was treated with TFA-DCM (1:1 v/v) mixture (3 mL) containing 1% of 1,2-ethanedithiol and 1% of water for 2.5 h at room temperature. Solvents were partially evaporated in vacuo and residual volatiles were removed by co-evaporation with toluene. The residue was re-dissolved in ethyl acetate and washed with water. The organic phase was dried over Na$_2$SO$_4$, filtered and concentrated under reduced pressure. Product was purified by flash column chromatography using 0 to 5% MeOH in dichloromethane as eluent to afford 43 (0.105 g, 94%). $^1$H NMR (400 MHz, DMSO-d$_6$): δ=10.82 (s, 1H), 8.10 (t, J=5.5 Hz, 1H), 7.87 (d, J=7.5 Hz, 2H), 7.68-7.60 (m, 3H), 7.55 (d, J=8.3 Hz, 1H), 7.43-7.21 (m, 10H), 7.16 (d, J=1.9 Hz, 1H), 7.05 (t, J=7.5 Hz, 1H), 6.96 (t, J=7.4 Hz, 1H), 5.10 (s, 2H), 4.25-4.09 (m, 4H), 3.39-3.32 (m, 1H plus H$_2$O), 3.22-3.14 (m, 2H), 3.07 (dd, J=14.4, 4.6 Hz, 1H), 2.98-2.87 (m, 1H), 1.84-1.72 (m, 1H), 1.54-1.41 (m, 1H) ppm; $^{13}$C NMR (100.6 MHz, DMSO-d$_6$): δ=175.3, 171.7, 155.7, 143.74, 143.68, 140.6, 136.1, 136.0, 128.9, 128.3, 127.9, 127.8, 127.5, 127.23, 127.16, 127.0, 125.3, 125.2, 123.7, 121.3, 120.8, 120.0, 118.5, 118.1, 111.2, 110.2, 65.5, 55.5, 52.0, 46.5, 35.7, 33.9, 27.8 ppm. ESI-TOF MS m/z [M+H]$^+$ 617.6, calcd 617.3.

Synthesis of benzyl (R)—N⁴—[N²-(9-fluorenylmethoxycarbonyl)-D-tryptophanyl]-N²-glutanoyl-2,4-diaminobutyrate (44)

Glutaric anhydride (0.035 g, 0.308 mmol) was added to the solution of compound 43 (0.095 g, 0.154 mmol) in DCM-pyridine (4:1 v/v) mixture (5 mL) and the reaction mixture was stirred for 3 h at room temperature. Solvents were reduced in vacuo and the residual pyridine was removed by co-evaporation with toluene. The residue was subjected to flash column chromatography using 0 to 10% MeOH in dichloromethane as eluent to give 44 (0.108 g, 96%). $^1$H NMR (400 MHz, DMSO-d$_6$): δ=12.00 (br. s, 1H), 10.79 (s, 1H), 8.27 (d, J=7.3 Hz, 1H), 8.05 (t, J=5.4 Hz, 1H), 7.87 (d, J=7.5 Hz, 2H), 7.67-7.60 (m, 3H), 7.49 (d, J=8.3 Hz, 1H), 7.44-7.21 (m, 10H), 7.15 (d, J=1.9 Hz, 1H), 7.05 (t, J=7.4 Hz, 1H), 6.96 (t, J=7.4 Hz, 1H), 5.11 (s, 2H), 4.36-4.27 (m, 1H), 4.26-4.10 (m, 4H), 3.21-3.02 (m, 3H), 2.99-2.88 (m, 1H), 2.26-2.12 (m, 4H), 1.95-1.83 (m, 1H), 1.79-1.66 (m, 3H) ppm; $^{13}$C NMR (100.6 MHz, DMSO-d$_6$): δ=174.2, 174.1, 172.1, 171.8, 155.7, 143.75, 143.67, 140.6, 136.0, 135.9, 128.3, 127.9, 127.6, 127.5, 127.2, 127.0, 125.3, 125.2, 123.6, 121.3, 120.8, 120.0, 118.4, 118.1, 111.2, 110.2, 65.8, 65.6, 55.5, 50.1, 46.5, 35.6, 34.0, 32.7, 30.3, 27.9, 19.9 ppm. ESI-TOF MS m/z [M−H]$^-$ 729.1, calcd 729.3.

Synthesis of benzyl (R)—N⁴-D-tryptophanyl-N²-glutanoyl-2,4-diaminobutyrate (45)

Compound 44 (0.67 g, 0.92 mmol) was treated with 20% piperidine in DMF (5 mL) for 3 h at room temperature. Volatiles were evaporated in vacuo to dryness and co-evaporated with toluene. The crude product was triturated with diethyl ether (3 times). Solid residue was dissolved in small volume of methanol and product was precipitated with diethyl ether, filtered, washed with diethyl ether and dried on pump to afford 45 (0.45 g, 97%). $^1$H NMR (400 MHz, DMSO-d$_6$): δ=10.90 (s, 1H), 8.34 (d, J=7.4 Hz, 1H), 7.99 (t, J=5.4 Hz, 1H), 7.54 (d, J=7.9 Hz, 1H), 7.38-7.29 (m, 6H), 7.13 (d, J=1.9 Hz, 1H), 7.04 (t, J=7.5 Hz, 1H), 6.95 (t, J=7.4 Hz, 1H), 5.11 (s, 2H), 4.32-4.24 (m, 1H), 3.42 (dd, J=8.1, 4.9 Hz, 1H), 3.18-2.99 (m, 3H), 2.72 (dd, J=13.7, 8.6 Hz, 1H), 2.17-2.09 (m, 4H), 1.93-1.82 (m, 1H), 1.75-1.61 (m, 3H) ppm; $^{13}$C NMR (100.6 MHz, DMSO-d$_6$): δ=175.4, 174.5, 172.4, 171.9, 136.1, 135.9, 128.4, 127.9, 127.7, 127.3, 123.7, 120.8, 118.4, 118.1, 111.3, 110.5, 65.8, 55.2, 50.0, 35.0, 34.53, 34.46, 30.9, 30.5, 21.2 ppm. ESI-TOF MS m/z [M+H]$^+$ 509.1, calcd 509.2.

Synthesis of benzyl (R)—N⁴—[N²—(N³—(N-tert-butoxycarbonyl-2-aminoethyl)-N²,N³-dibenzyloxycarbonyl-(S)-2,3-diaminopropionyl)-D-tryptophanyl]-N²-glutanoyl-2,4-diaminobutyrate (46)

Method A.

Compound 38 (0.2 g, 0.293 mmol) was added to the solution of compound 45 (0.149 g, 0.293 mmol) in anhydrous DCM-pyridine (2:1 v/v) mixture (6 mL) under nitrogen atmosphere and the reaction mixture was stirred for 2 h at ambient temperature. Solvents were evaporated in vacuo and traces of pyridine were removed by co-evaporated with toluene. The residue was subjected to flash column chromatography using 0 to 12% MeOH in dichloromethane as eluent to give compound 46 (0.18 g, 62%).

Method B.

To the solution of 39 (0.04 g, 0.063 mmol) and 45 (0.032 g, 0.063 mmol) in anhydrous DCM-pyridine (2:1 v/v) mixture (0.9 mL) N,N'-diisopropylethylamine (0.016 mL, 0.0945 mmol) was added under nitrogen atmosphere and the reaction mixture was stirred overnight at ambient temperature. Solvents were reduced in vacuo and the residual pyridine was removed by co-evaporation with toluene. Product was purified by flash column chromatography using 0 to 12% MeOH in dichloromethane as eluent to give 46 (0.046 g, 73%). $^1$H NMR (400 MHz, DMSO-$d_6$): δ=10.77 (s, 1H), 8.34-8.18 (m, 2H), 8.06-7.94 (m, 1H), 7.54 (d, J=7.7 Hz, 1H), 7.37-7.25 (m, 17H), 7.12-6.99 (m, 2H), 6.93 (t, J=7.5 Hz, 1H), 6.88-6.74 (m, 1H), 5.10 (s, 2H), 5.06-4.91 (m, 4H), 4.51-4.41 (m, 1H), 4.38-4.21 (m, 2H), 3.50-3.23 (m, 2H plus H$_2$O), 3.22-2.87 (m, 8H), 2.23-2.10 (m, 4H), 1.91-1.77 (m, 1H), 1.75-1.63 (m, 3H), 1.34 (s, 9H) ppm; $^{13}$C NMR (100.6 MHz, DMSO-$d_6$): δ=174.2, 172.0, 171.5, 170.8, 170.6, 155.7, 135.9, 135.7, 128.15, 128.06, 127.7, 127.5, 127.4, 127.3, 127.1, 126.9, 123.3, 120.6, 118.1, 118.0, 111.0, 109.6, 66.0, 65.7, 65.4, 53.4, 53.3, 50.01, 49.96, 35.5, 34.0, 33.1, 30.2, 28.0, 20.5 ppm. ESI-TOF MS m/z [M–H]$^-$ 1004.5, calcd 1004.4.

Synthesis of benzyl (R)—N$^4$—[N$^2$—(N$^3$-(2-aminoethyl))-N$^2$,N$^3$-dibenzyloxycarbonyl-(S)-2,3-diaminopropionyl)-D-tryptophanyl]-N$^2$-glutanoyl-2,4-diaminobutyrate (47)

Compound 46 (47 mg, 47 μmol) was treated with TFA-DCM (1:4 v/v) mixture (2 mL) containing 2.5% of triisopropylsilane and 2.5% of water at room temperature for 1.5 h. Volatiles were removed in vacuo and co-evaporated with toluene. The residue was re-dissolved in small volume of methanol and product was precipitated with diethyl ether, filtered, washed with diethyl ether and dried on pump to afford 47 (40 mg, 95%). $^1$H NMR (400 MHz, DMSO-$d_6$): δ=10.78 (s, 1H), 8.32-8.17 (m, 2H), 8.09-7.90 (m, 1H), 7.55 (d, J=7.9 Hz, 1H), 7.49-7.24 (m, 17H), 7.14-7.00 (m, 2H), 6.98-6.90 (m, 1H), 5.10 (s, 2H), 5.08-4.93 (m, 4H), 4.53-4.43 (m, 1H), 4.41-4.22 (m, 2H), 3.55-2.75 (m, 10H plus H$_2$O), 2.23-2.11 (m, 4H), 1.92-1.77 (m, 1H), 1.75-1.63 (m, 3H) ppm; $^{13}$C NMR (100.6 MHz, DMSO-$d_6$): δ=174.2, 172.1, 171.7, 170.8, 169.4, 155.9, 136.0, 135.8, 128.3, 128.2, 127.9, 127.7, 127.6, 127.1, 123.4, 120.8, 118.2, 118.1, 111.2, 66.5, 65.8, 65.6, 53.5, 50.0, 49.9, 35.6, 34.0, 32.94, 32.90, 30.2, 20.5 ppm. ESI-TOF MS m/z [M–H]$^-$ 904.2, calcd 904.4.

Synthesis of benzyl (R)—N$^4$—[N$^2$—(N$^3$—(N-decanoyl-2-aminoethyl)-N$^2$,N$^3$-dibenzyloxycarbonyl-(S)-2,3-diaminopropionyl)-D-tryptophanyl]-N$^2$-glutanoyl-2,4-diaminobutyrate (48)

To the chilled solution of compound 47 (10 mg, 11 μmol) in anhydrous pyridine (1 mL) a decanoyl chloride (6.8 μL, 33 μmol) was added under nitrogen atmosphere and the reaction mixture was stirred at room temperature for 18 h. Excess of acyl chloride was quenched by the addition of methanol (50 μL). After the reaction mixture was stirred for 1 h volatiles were removed in vacuo, and co-evaporated with toluene and methanol. The residue was purified by flash column chromatography using 0 to 10% MeOH in dichloromethane as eluent to give compound 48 (9.7 mg, 83%). $^1$H NMR (400 MHz, CD$_3$OD): δ=7.56-7.50 (m, 1H), 7.37-7.18 (m, 16H), 7.06 (t, J=7.2 Hz, 1H), 7.02-6.94 (m, 2H), 5.12-4.88 (m, 6H), 4.62-4.52 (m, 1H), 4.42-4.27 (m, 2H), 3.53-2.95 (m, 10H plus CD$_3$OD residual peak), 2.31-2.17 (m, 4H), 2.10-1.75 (m, 5H), 1.72-1.57 (m, 1H), 1.55-1.43 (m, 2H), 1.33-1.15 (m, 12H), 0.84 (t, J=6.7 Hz, 3H) ppm. ESI-TOF MS m/z [M–H]$^-$ 1058.6, calcd 1058.5.

Synthesis of (R)—N$^4$—[N$^2$—(N$^3$—(N-decanoyl-2-aminoethyl)-(S)-2,3-diaminopropionyl)-D-tryptophanyl]-N$^2$-glutanoyl-2,4-diaminobutanoic acid (49)

Pd/C catalyst (0.04 g) was added to a solution of compound 48 (9 mg, 8.5 μmol) in AcOH-MeOH (1:1 v/v) mixture (2 mL) and stirred while H$_2$ gas was bubbled through the reaction mixture at ambient temperature for 2 h. The reaction mixture was filtered through a pad of Celite which was then washed with AcOH-MeOH (1:1 v/v) mixture. The filtrate was reduced in vacuo and acetic acid was partially removed by co-evaporated with toluene-methanol mixture. The residue was filtered through Millex-GV 0.22 μm filter unit, suspended in H$_2$O—CH$_3$CN (9:1 v/v) mixture and lyophilized. Crude product was purified by RP-HPLC with a gradient elution 20%-60% of solvent B in 40 min (solvent A=0.1% TFA in water; solvent B=0.1% TFA in 90% aqueous acetonitrile), $t_R$ 34.0 min. Solvents were partially evaporated in vacuo and the residue was lyophilized to afford compound 49 (2.1 mg, 35%). $^1$H NMR (400 MHz, CD$_3$OD): δ=7.62 (d, J=7.9 Hz, 1H), 7.35 (d, J=8.0 Hz, 1H), 7.16-7.07 (m, 2H), 7.03 (t, J=7.5 Hz, 1H), 4.71 (t, J=7.2 Hz, 1H), 4.41 (dd, J=10.6, 3.8 Hz, 1H), 3.93 (t, J=5.6 Hz, 1H), 3.37-3.10 (m, 6H plus CD$_3$OD residual peak), 2.98-2.83 (m, 2H), 2.72 (t, J=5.3 Hz, 2H), 2.40-2.28 (m, 4H), 2.19 (t, J=7.3 Hz, 2H), 2.10-2.00 (m, 1H), 1.96-1.86 (m, 2H), 1.79-1.66 (m, 1H), 1.65-1.53 (m, 2H), 1.36-1.23 (m, 12H), 0.90 (t, J=6.4 Hz, 3H) ppm. ESI-TOF MS m/z [M–H]$^-$ 700.2, calcd 700.4.

Scheme 16. Synthesis of ligand 49 (DH18).

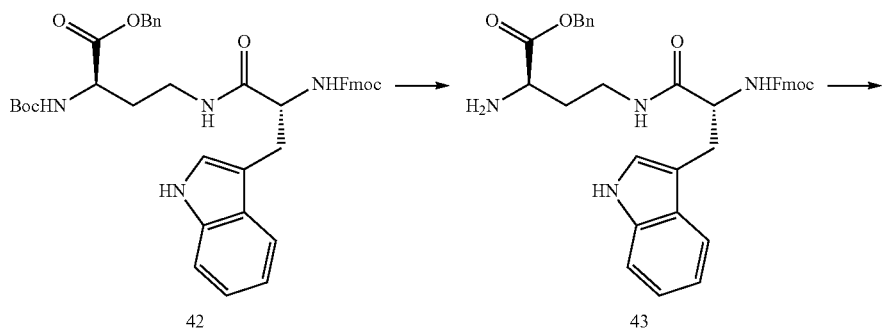

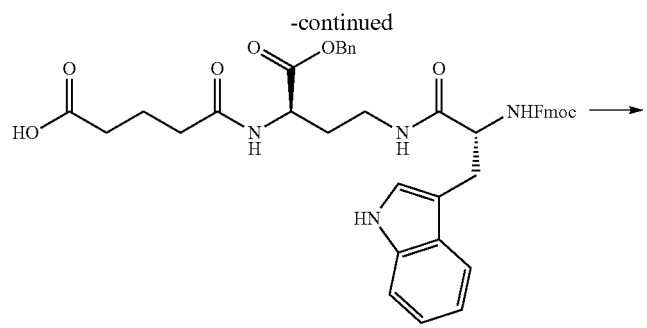
44
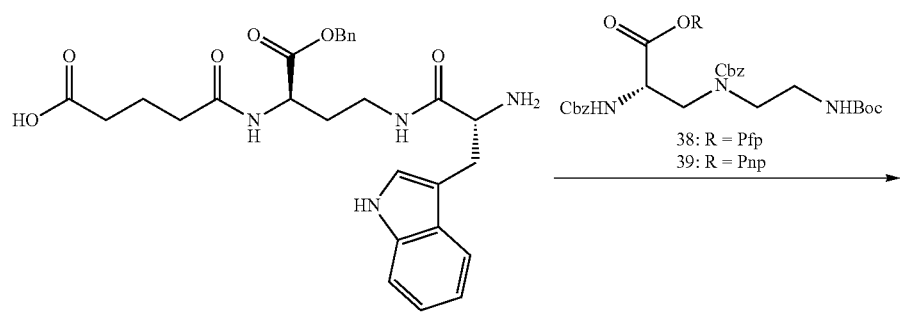
45
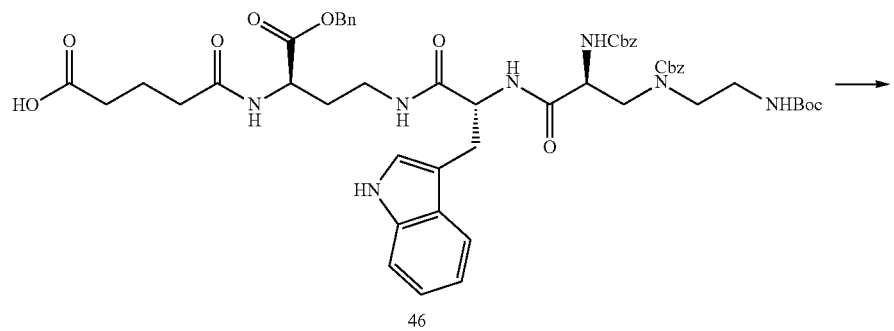
46
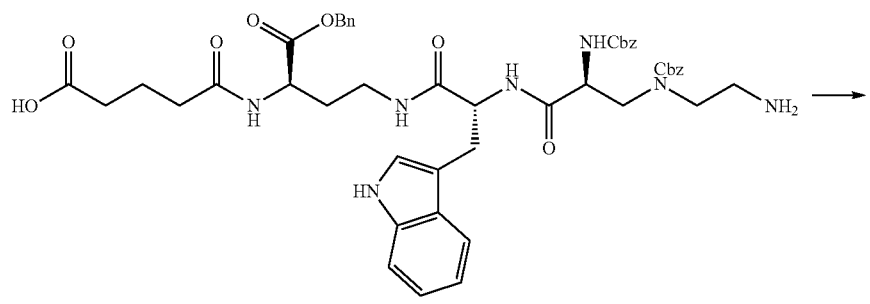
47
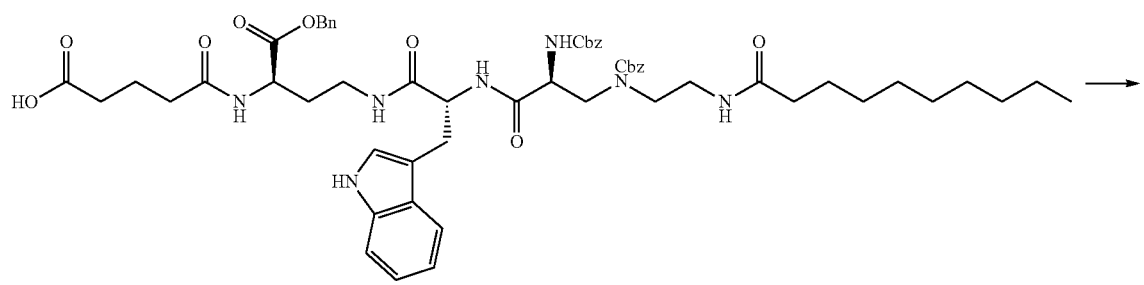
48

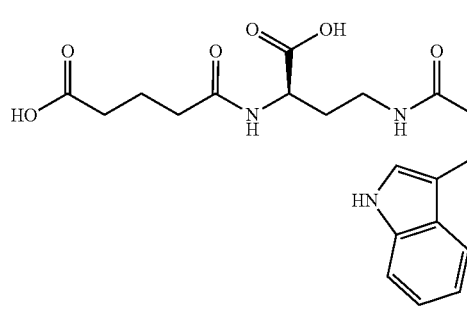

49

Example 17

Synthesis of the (R)—$N_4$—[$N^2$—($N^3$—(N-(12-amino-12-oxododecanoyl)-2-aminoethyl)-(S)-2,3-diaminopropionyl)-D-tryptophanyl]-$N^2$-glutanoyl-2,4-diaminobutanoic acid (51) being an amyloid-β peptide targeting ligand (DH20)

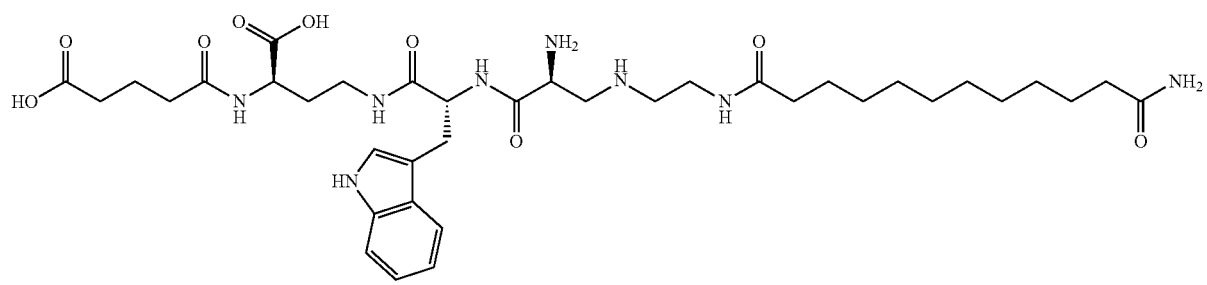

(DH20)

Synthesis of benzyl (R)—$N^4$—[$N^2$—($N^3$—(N-(12-amino-12-oxododecanoyl)-2-aminoethyl)-$N^2$,$N^3$-dibenzyloxycarbonyl-(S)-2,3-diaminopropionyl)-D-tryptophanyl]-$N^2$-glutanoyl-2,4-diaminobutyrate (50)

To the solution of compound 47 (10 mg, 11 µmol) and compound 41 (11.5 mg, 33 µmol) in anhydrous pyridine (1 mL) a N,N'-diisopropylethylamine (3 µL, 16.5 µmol) was added under nitrogen atmosphere and the reaction mixture was stirred at room temperature for 20 h. Solvent was reduced in vacuo and the residual pyridine was removed by co-evaporation with toluene and toluene-MeOH. The residue was purified by flash column chromatography using 0 to 20% MeOH in dichloromethane as eluent to give compound 50 (11.3 mg, 92%). $^1$H NMR (400 MHz, CD$_3$OD): δ=7.59-7.53 (m, 1H), 7.37-7.22 (m, 16H), 7.09-7.02 (m, 2H), 7.01-6.96 (t, J=7.4 Hz, 1H), 5.15-4.93 (m, 6H), 4.65-4.55 (m, 1H), 4.46-4.32 (m, 2H), 3.59-3.38 (m, 2H), 3.33-3.03 (m, 8H plus CD$_3$OD residual peak), 2.33-2.21 (m, 4H), 2.20-2.15 (t, J=7.5 Hz, 2H), 2.11-1.94 (m, 3H), 1.92-1.81 (m, 2H), 1.79-1.65 (m, 1H), 1.63-1.45 (m, 4H), 1.34-1.20 (m, 12H) ppm; $^{13}$C NMR (100.6 MHz, CD$_3$OD): δ=176.5, 176.1, 173.8, 173.1, 172.3, 138.1, 137.9, 137.2, 129.63, 129.56, 129.4, 129.2, 129.1, 128.9, 128.7, 124.7, 122.6, 120.0, 119.4, 112.5, 101.4, 68.7, 68.1, 56.0, 55.9, 51.7, 51.6, 43.9, 37.2, 37.1, 36.6, 36.1, 31.8, 30.52, 30.49, 30.4, 30.34, 30.3 26.9, 22.8 ppm. ESI-TOF MS m/z [M−H]$^-$ 1116.0, calcd 1115.5.

Synthesis of (R)—$N^4$—[$N^2$—($N^3$—(N-(12-amino-12-oxododecanoyl)-2-aminoethyl)-(S)-2,3-diaminopropionyl)-D-tryptophanyl]-$N^2$-glutanoyl-2,4-diaminobutanoic acid (51)

Pd/C catalyst (0.04 g) was added to a solution of compound 50 (11 mg, 9.8 µmol) in acetic acid (2 mL) and stirred while H$_2$ gas was bubbled through the reaction mixture at ambient temperature for 2 h. The reaction mixture was filtered through a pad of Celite which was then washed with AcOH-MeOH (1:1 v/v) mixture. The filtrate was reduced in vacuo and acetic acid was partially removed by co-evaporated with toluene-methanol mixture. The residue was filtered through Millex-GV 0.22 µm filter unit, suspended in H$_2$O—CH$_3$CN (9:1 v/v) mixture and lyophilized. Crude product was purified by RP-HPLC with a gradient elution 20%-60% of solvent B in 40 min (solvent A=0.1% TFA in water; solvent B=0.1% TFA in 90% aqueous acetonitrile), $t_R$ 22.5 min. Solvents were partially evaporated in vacuo and the residue was lyophilized to afford compound 51 (3.1 mg, 41%). $^1$H NMR (400 MHz, CD$_3$OD): δ=7.63 (d, J=8.3 Hz, 1H), 7.35 (d, J=8.1 Hz, 1H), 7.17-7.08 (m, 2H), 7.03 (t, J=7.4 Hz, 1H), 4.71 (t, J=7.3 Hz, 1H), 4.40 (dd, J=10.7, 3.9 Hz, 1H), 4.22 (t, J=5.7 Hz, 1H), 3.61-3.40 (m, 2H), 3.37-3.06 (m, 6H plus CD$_3$OD residual peak), 2.99-2.86 (m, 2H), 2.40-2.29 (m, 4H), 2.27-2.14 (m, 4H), 2.11-1.98 (m, 1H), 1.96-1.85 (m, 2H), 1.78-1.66 (m, 1H), 1.65-1.52 (m, 4H), 1.37-1.23 (m, 12H) ppm. ESI-TOF MS m/z [M−H]$^-$ 757.2, calcd 757.4.

Scheme 17. Synthesis of ligand 51 (DH20).
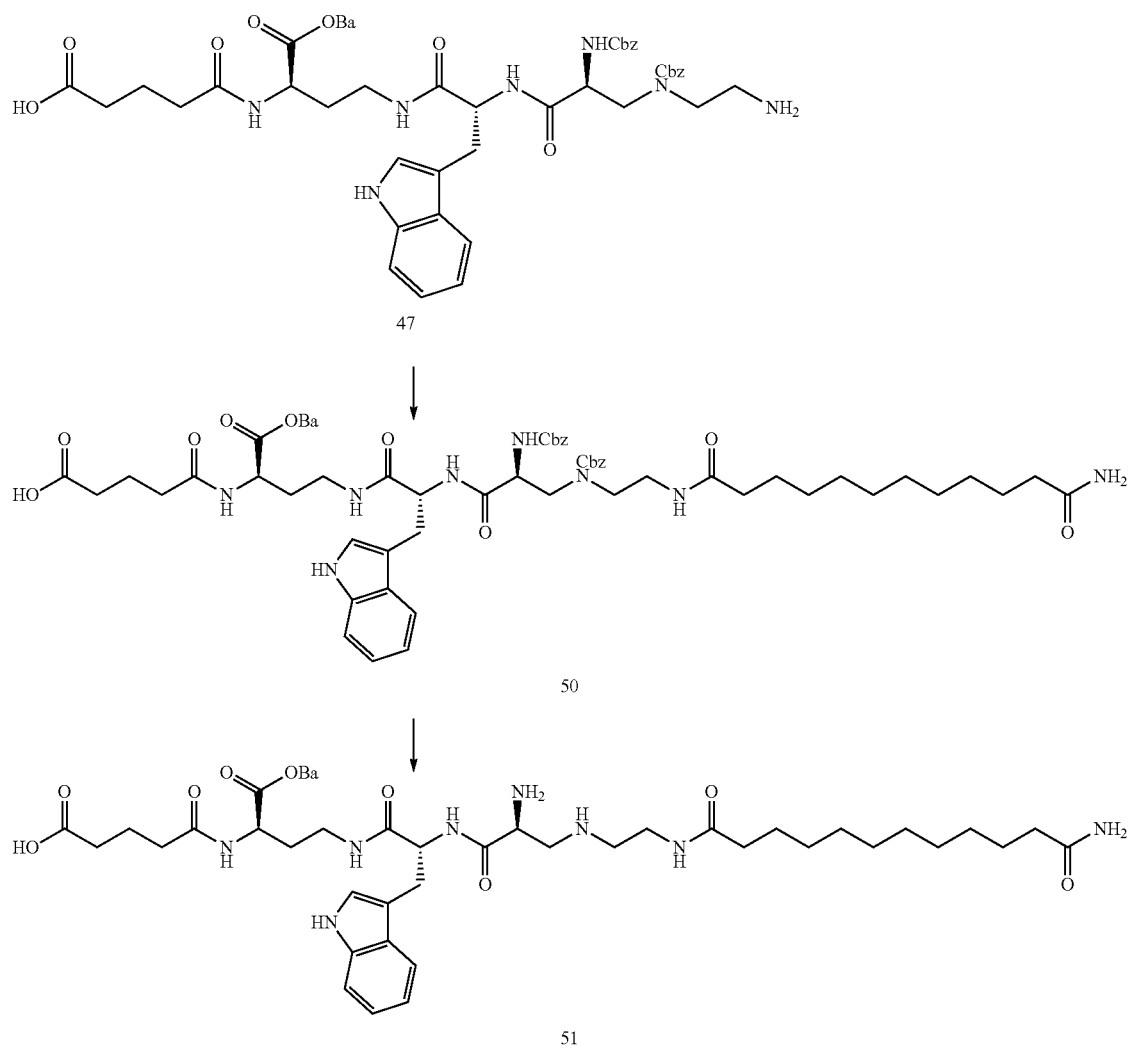
Example 18
Synthesis of HO-Gla-D-Dab-(COOH)-D-DMNA-L-Dap-(NH₂)-AE-decanoyl (54) being an amyloid-β peptide targeting ligand (DH18 Dmn)
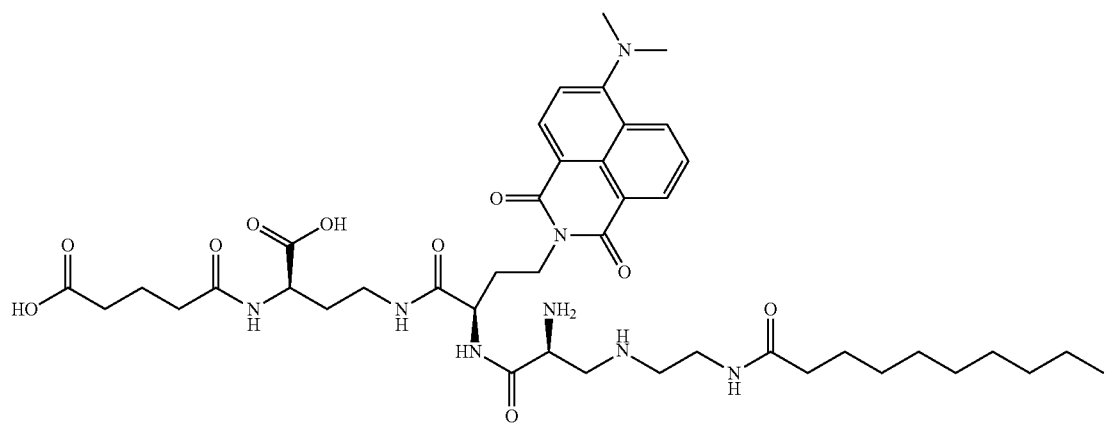

Wang resin (0.5 g, loading 0.9 mmol/g) was taken into a 5 mL syringe (pit fitted), with a stop at the outlet. Resin was swelled for 0.5 h with 4 mL of dry DMF. Glutaric anhydride (0.257 g, 2.25 mmol) and 4-DMAP (0.055 g, 0.45 mmol) were dissolved in DMF (3 mL). The resin was treated with this solution for 66 h at room temperature under moderate shaking condition, followed by washing with DMF (5 mL×3). A part of this resin (0.1 g) was taken into a similar syringe and treated with DMF solution (2 mL) containing HOAt (0.037 g, 0.27 mmol), DIC (0.042 mL, 0.27 mmol) and DIPEA (0.047 mL, 0.27 mmol) and shaken for 0.25 h. Next, compound 30 (0.038 g, 0.108 mmol) was dissolved in DMF (2 mL) and added into the same reaction mixture. It was shaken for 18 h at room temperature, followed by washing with DMF (3 mL×3). It was treated with 40% piperidine in DMF containing 0.1 M HOBt (2 mL×3, 10 min each time), followed by washing with DMF (3 mL×6). Compound 37 (0.056 g, 0.099 mmol), DIC (0.031 mL) and HOBt (0.027 g, 0.198 mmol) was dissolved in DMF (2 mL) and shaken well for 0.25 h. Resin was treated with this solution for 3 h at room temperature, followed by washing of the resin by DMF (3 mL×3). Next, it was treated with 40% piperidine in DMF containing 0.1 M HOBt (2 mL×3, 10 min each time), followed by washing with DMF (3 mL×6). A part of this resin (0.02 g) was taken in a similar syringe. Compound 8 (0.0128 g, 0.0225 mmol), DIC (0.007 mL, 0.045 mmol) and HOBt (0.006 g, 0.045 mmol) was dissolved in DMF (2 mL) and shaken well for 0.25 h. Next, the resin was treated with the above mentioned solution at room temperature (3 h×2), followed by washing with DMF (3 mL×3). Next, it was treated with 40% piperidine in DMF containing 0.1 M HOBt (2 mL×3, 10 min each time), followed by washing with DMF (3 mL×6). Decanoic acid (0.008 g, 0.045 mmol), DIC (0.014 mL, 0.09 mmol) and HOBt (0.012 g, 0.09 mmol) was dissolved in DMF (2 mL) and shaken at room temperature for 0.25 h. Resin was reacted with above mentioned solution (1 h×2), washed with DMF (3 mL×3), methanol (3 mL×3) and DCM (3 mL×3). Next, resin was treated with a cocktail of TFA (1.9 mL), water (0.05 mL) and TRIS (0.05 mL) for 4 h at room temperature. Resulting solution was collected in a plastic tube and TFA was removed from the solution by blowing it with nitrogen gas. Excess amount of cold diethylether was added into it and it was kept at −20° C. for overnight. Next, the tube was centrifuged (6000 rpm, 6 min) when the solid peptide precipitates. Upper solution was decanted and remaining solid was dissolved in water (2 mL). It was treated with 0.05 M aqueous methanolic LiOH solution (1 mL, MeOH:water 1:1) for 1 h at room temperature. After completion of the reaction, reaction mixture was evaporated to dryness and purified by high performance liquid chromatography (HPLC) using buffer solution (A: 0.1% trifluoroacetic acid in water; B: 0.1% trifluoroacetic acid in acetonitrile). Fractions containing pure peptide were pooled together and solvent was removed in a lyophilizer to obtain the desired peptide 54 (1.4 mg yield). ESI-TOF MS (m/z): calcd. for $C_{42}H_{63}N_8O_{10}$ [M+H]+ 839.5. found 838.7.

Scheme 18. Synthesis of HO-Gla-D-Dab-(COOH)-D-DMNA-L-Dap-(NH$_2$)-AE- decanoyl or DH18 Dmn (54).

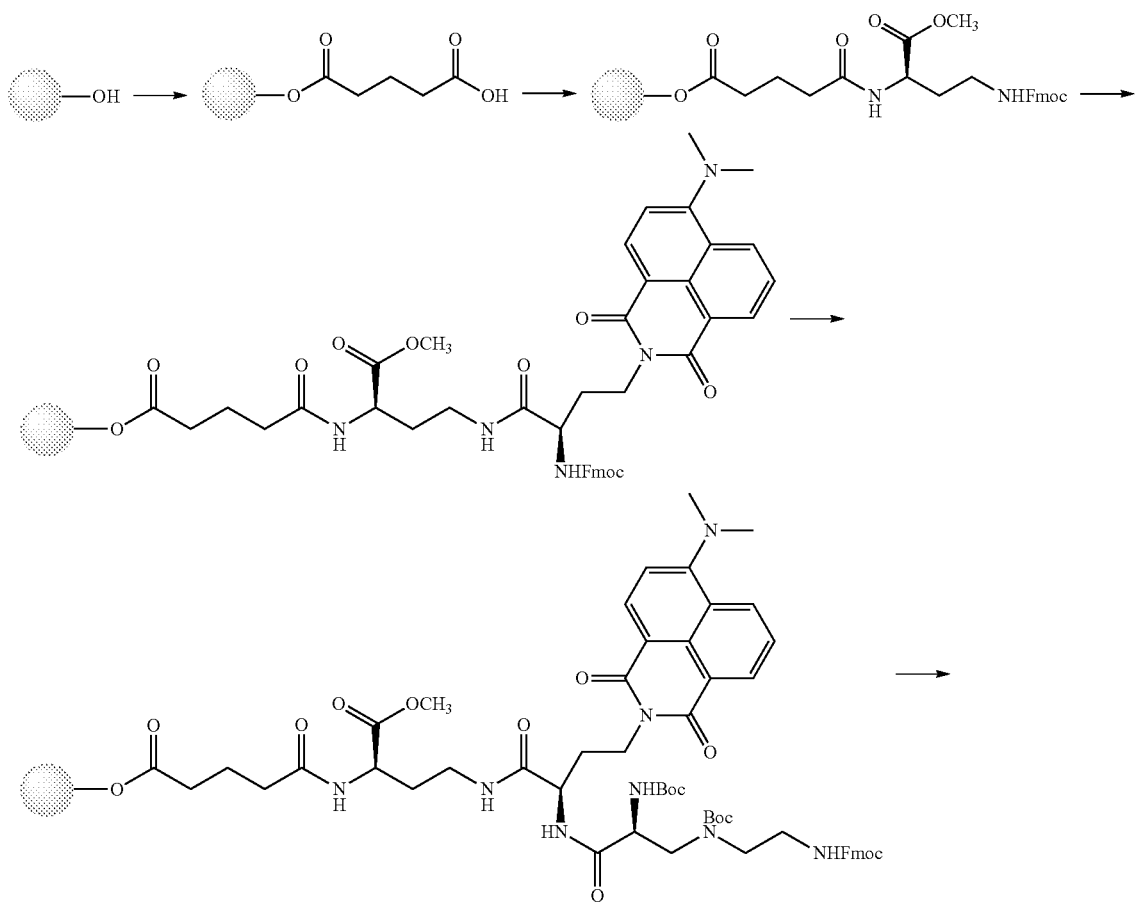

-continued
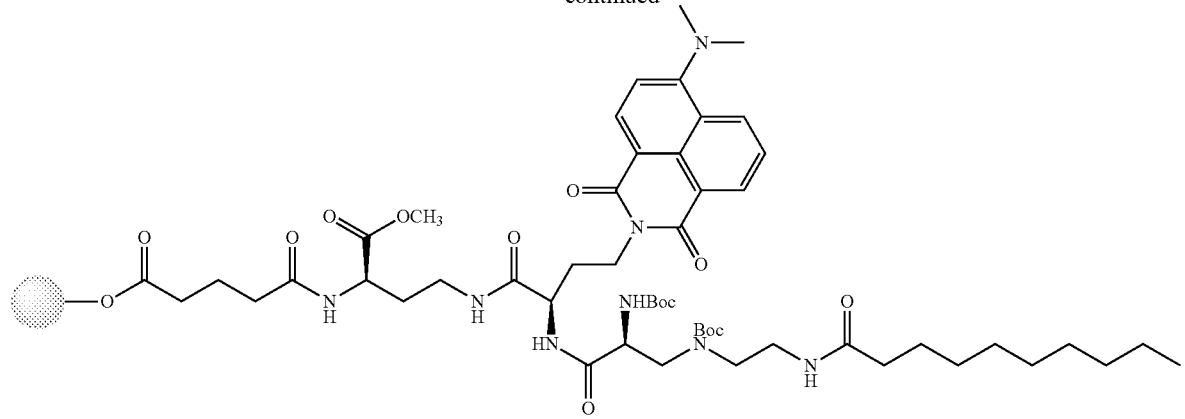
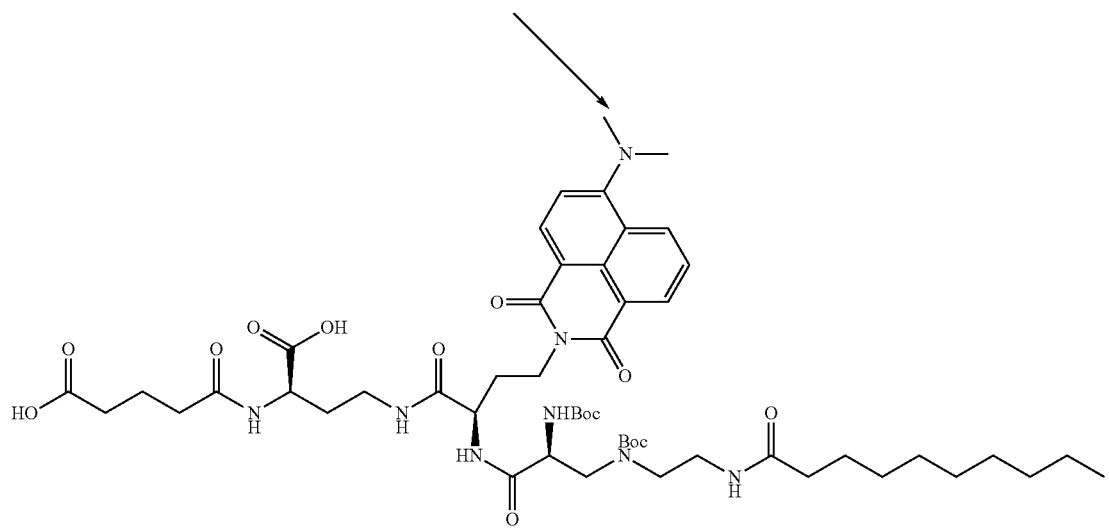
54
Example 19
Synthesis of HO-Gla-D-Dab-(COOH)-D-DMNA-L-Dap-(NH₂)—CH₂CH(NH₂)—C6 (55) being an amyloid-β peptide targeting ligand (6AEDabD-mnDabGla)
55
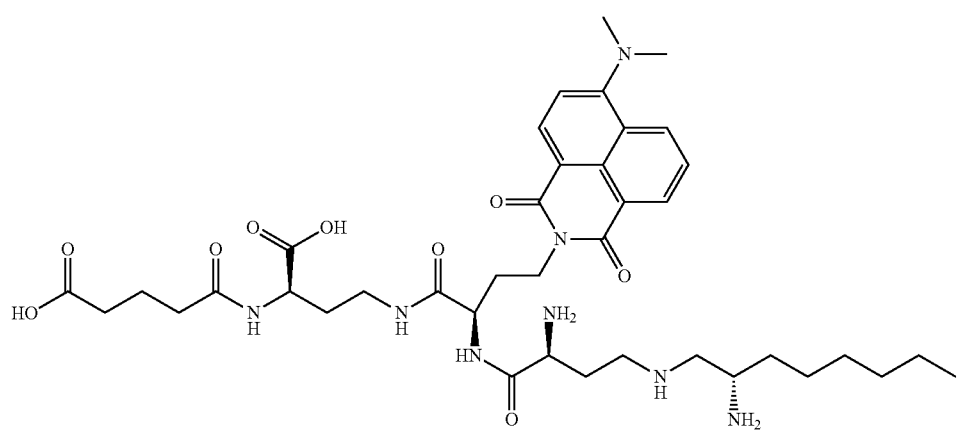

Wang resin (0.5 g, loading 0.9 mmol/g) was taken into a 5 mL syringe (pit fitted), with a stop at the outlet. Resin was swelled for 0.5 h with 4 mL of dry DMF. Glutaric anhydride (0.257 g, 2.25 mmol) and 4-DMAP (0.055 g, 0.45 mmol) were dissolved in DMF (3 mL). The resin was treated with this solution for 66 h at room temperature under moderate shaking condition, followed by washing with DMF (5 mL×3). A part of this resin (0.1 g) was taken into a similar syringe and treated with DMF solution (2 mL) containing HOAt (0.037 g, 0.27 mmol), DIC (0.042 mL, 0.27 mmol) and DIPEA (0.047 mL, 0.27 mmol) and shaken for 0.25 h. Next, compound 30 (0.038 g, 0.108 mmol) was dissolved in DMF (2 mL) and added into the same reaction mixture. It was shaken for 18 h at room temperature, followed by washing with DMF (3 mL×3). It was treated with 40% piperidine in DMF containing 0.1 M HOBt (2 mL×3, 10 min each time), followed by washing with DMF (3 mL×6). Compound 37 (0.056 g, 0.099 mmol), DIC (0.031 mL) and HOBt (0.027 g, 0.198 mmol) was dissolved in DMF (2 mL) and shaken well for 0.25 h. Resin was treated with this solution for 3 h at room temperature, followed by washing of the resin by DMF (3 mL×3). Next, it was treated with 40% piperidine in DMF containing 0.1 M HOBt (2 mL×3, 10 min each time), followed by washing with DMF (3 mL×6). A part of this resin (0.02 g) was taken in a similar syringe. Compound 22 (0.015 g, 0.0225 mmol), DIC (0.007 mL, 0.045 mmol) and HOBt (0.006 g, 0.045 mmol) was dissolved in DMF (2 mL) and shaken well for 0.25 h. Next, the resin was treated with the above mentioned solution at room temperature (3 h×2), followed by washing with DMF (3 mL×3). Next, it was treated with 40% piperidine in DMF containing 0.1 M HOBt (2 mL×3, 10 min each time), followed by washing with DMF (3 mL×6). Next, resin was treated with a cocktail of TFA (1.9 mL), water (0.05 mL) and TRIS (0.05 mL) for 4 h at room temperature. Resulting solution was collected in a plastic tube and TFA was removed from the solution by blowing it with nitrogen gas. Excess amount of cold diethylether was added into it and it was kept at −20° C. for overnight. Next, the tube was centrifuged (6000 rpm, 6 min) when the solid peptide precipitates. Upper solution was decanted and remaining solid was dissolved in water (2 mL). It was treated with 0.05 M aqueous methanolic LiOH solution (1 mL, MeOH:water 1:1) for 1 h at room temperature. After completion of the reaction, reaction mixture was evaporated to dryness and purified by high performance liquid chromatography (HPLC) using buffer solution (A: 0.1% trifluoroacetic acid in water; B: 0.1% trifluoroacetic acid in acetonitrile). Fractions containing pure peptides were pooled together and solvent was removed in a lyophilizer to obtain the desired peptide 55 (1.6 mg). ESI-TOF MS (m/z): calcd. for $C_{39}H_{59}N_8O_9$ $[M+H]^+$ 783.4. found 783.0.

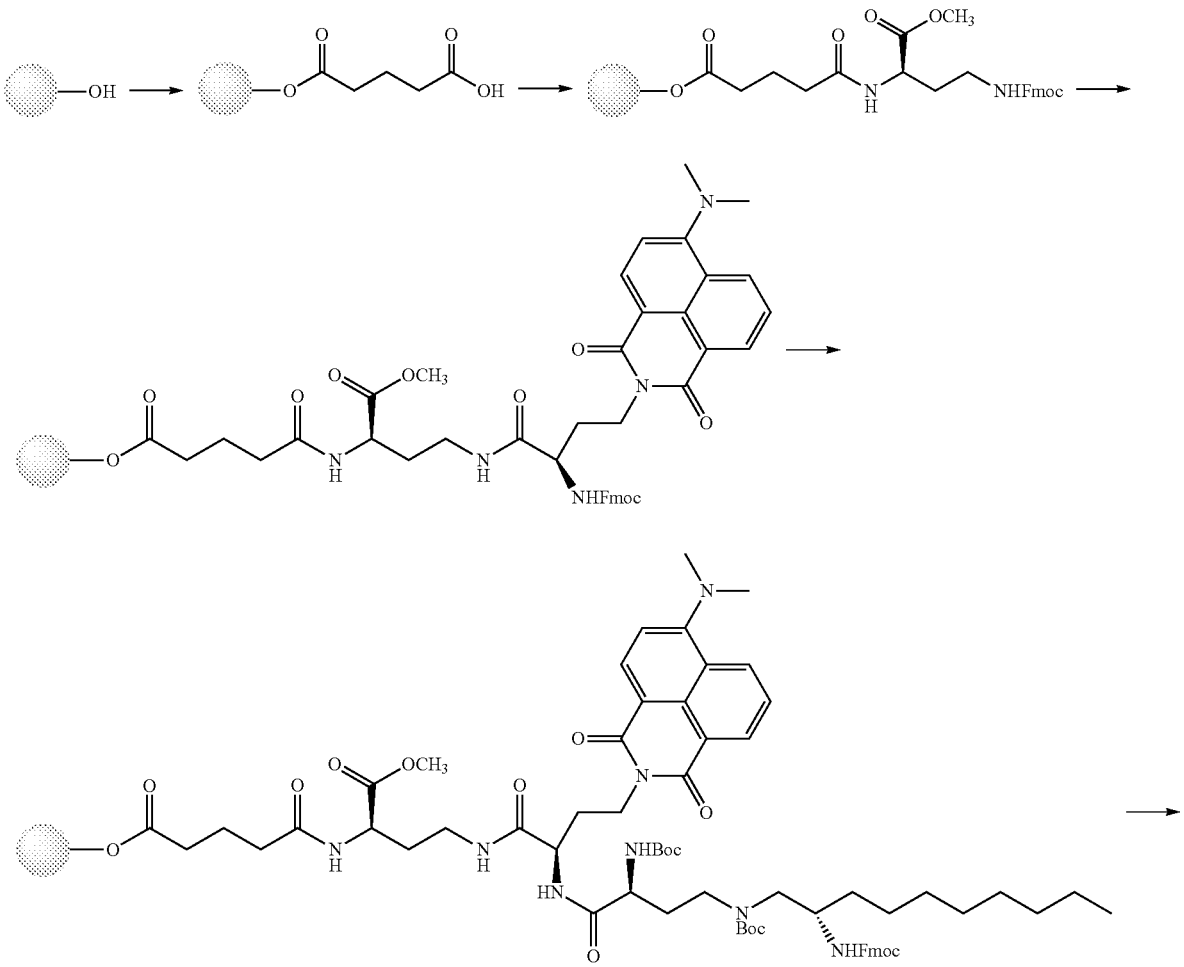

Scheme 19. Synthesis of HO-Gla-D-Dab-(COOH)-D-DMNA-L-Dap-(NH$_2$)-CH$_2$CH(NH$_2$)-C6 or 6AEDabDmnDabGla (55).

-continued
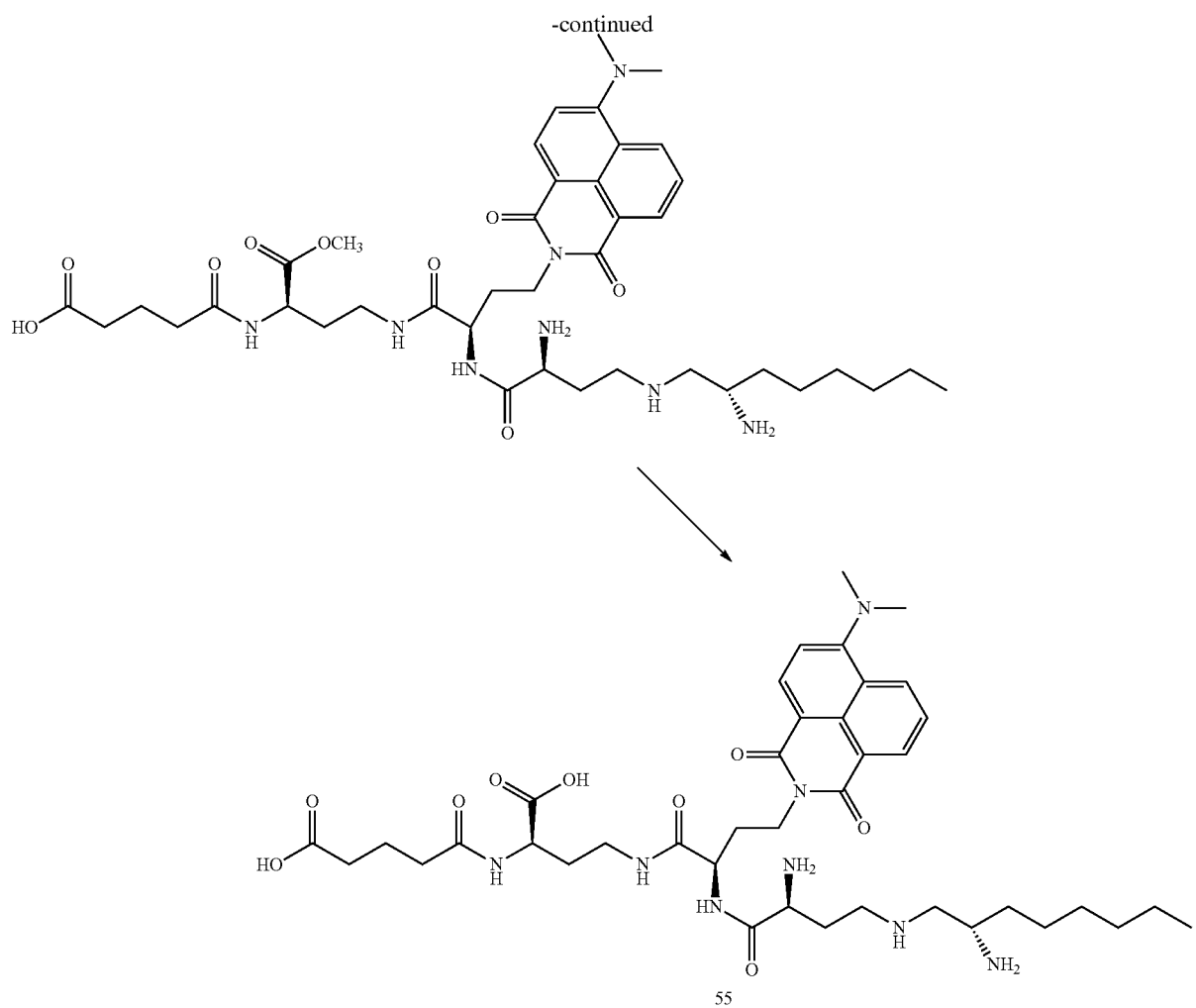
55
Example 20
Synthesis of HO-Gla-D-Dab-(COOH)-D-DMNA-L-Dap-(NH₂)—CH₂CH(NH₂)—C8 (56) being an amyloid-β peptide targeting ligand (8AEDabD-mnDabGla)
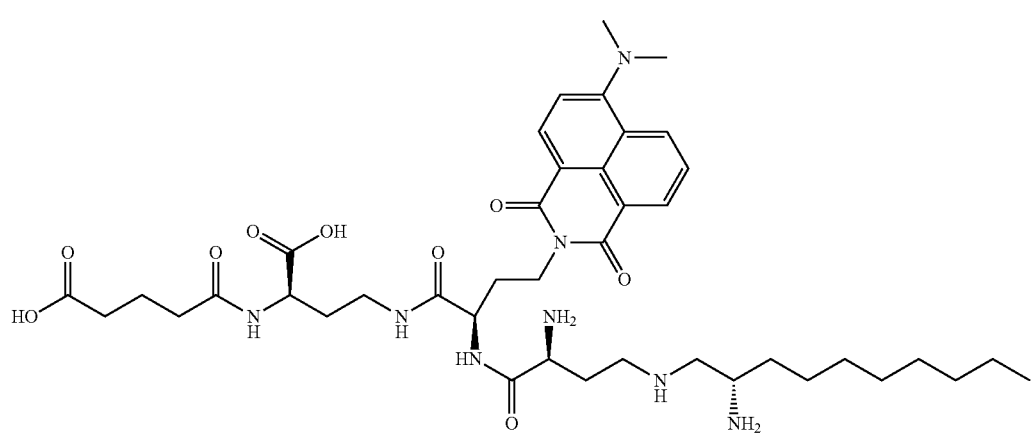
56

Wang resin (0.5 g, loading 0.9 mmol/g) was taken into a 5 mL syringe (pit fitted), with a stop at the outlet. Resin was swelled for 0.5 h with 4 mL of dry DMF. Glutaric anhydride (0.257 g, 2.25 mmol) and 4-DMAP (0.055 g, 0.45 mmol) were dissolved in DMF (3 mL). The resin was treated with this solution for 66 h at room temperature under moderate shaking condition, followed by washing with DMF (5 mL×3). A part of this resin (0.1 g) was taken into a similar syringe and treated with DMF solution (2 mL) containing HOAt (0.037 g, 0.27 mmol), DIC (0.042 mL, 0.27 mmol) and DIPEA (0.047 mL, 0.27 mmol) and shaken for 0.25 h. Next, compound 30 (0.038 g, 0.108 mmol) was dissolved in DMF (2 mL) and added into the same reaction mixture. It was shaken for 18 h at room temperature, followed by washing with DMF (3 mL×3). It was treated with 40% piperidine in DMF containing 0.1 M HOBt (2 mL×3, 10 min each time), followed by washing with DMF (3 mL×6). Compound 37 (0.056 g, 0.099 mmol), DIC (0.031 mL) and HOBt (0.027 g, 0.198 mmol) was dissolved in DMF (2 mL) and shaken well for 0.25 h. Resin was treated with this solution for 3 h at room temperature, followed by washing of the resin by DMF (3 mL×3). Next, it was treated with 40% piperidine in DMF containing 0.1 M HOBt (2 mL×3, 10 min each time), followed by washing with DMF (3 mL×6). A part of this resin (0.02 g) was taken in a similar syringe. Compound 27 (0.0156 g, 0.0225 mmol), DIC (0.007 mL, 0.045 mmol) and HOBt (0.006 g, 0.045 mmol) was dissolved in DMF (2 mL) and shaken well for 0.25 h. Next, the resin was treated with the above mentioned solution at room temperature (3 h×2), followed by washing with DMF (3 mL×3). Next, it was treated with 40% piperidine in DMF containing 0.1 M HOBt (2 mL×3, 10 min each time), followed by washing with DMF (3 mL×6). Next, resin was treated with a cocktail of TFA (1.9 mL), water (0.05 mL) and TRIS (0.05 mL) for 4 h at room temperature. Resulting solution was collected in a plastic tube and TFA was removed from the solution by blowing it with nitrogen. Excess amount of cold diethylether was added into it and it was kept at −20° C. for overnight. Next, the tube was centrifuged (6000 rpm, 6 min) when the solid peptide precipitates. Upper solution was decanted and remaining solid was dissolved in water (2 mL). It was treated with 0.05 M aqueous methanolic LiOH solution (1 mL, MeOH:water 1:1) for 1 h at room temperature. After completion of the reaction, reaction mixture was evaporated to dryness and purified by high performance liquid chromatography (HPLC) using buffer solution (A: 0.1% trifluoroacetic acid in water; B: 0.1% trifluoroacetic acid in acetonitrile). Fractions containing pure peptides were pooled together and solvent was removed in a lyophilizer to obtain the desired peptide 56 (1.3 mg). ESI-TOF MS (m/z): calcd. for $C_{41}H_{63}N_8O_9$ [M+H]$^+$ 811.5. found 810.9.

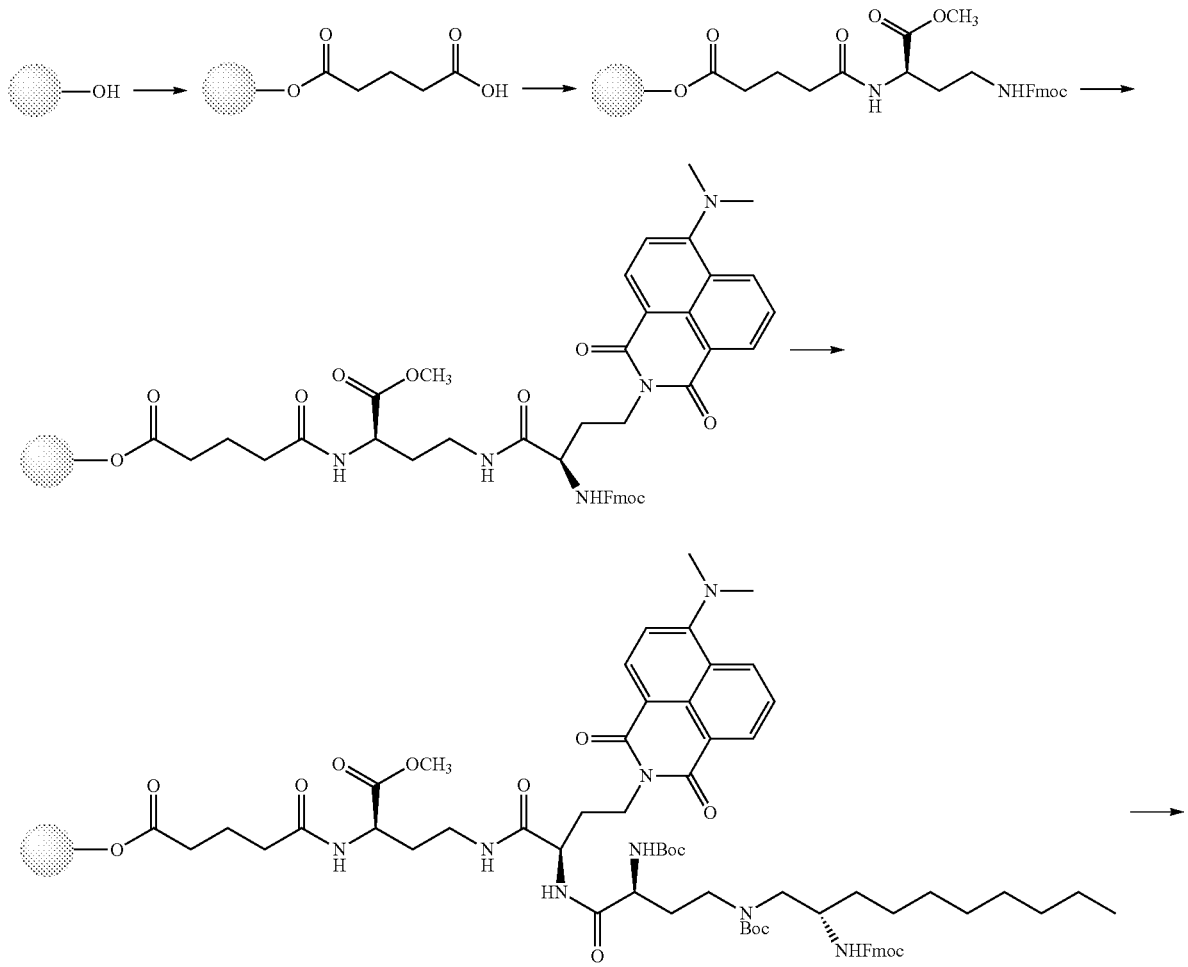

Scheme 20. Synthesis of HO-Gla-D-Dab-(COOH)-D-DMNA-L-Dap-(NH$_2$)-CH$_2$CH(NH$_2$)-C8 or 8AEDabDmnDabGla (56).

-continued

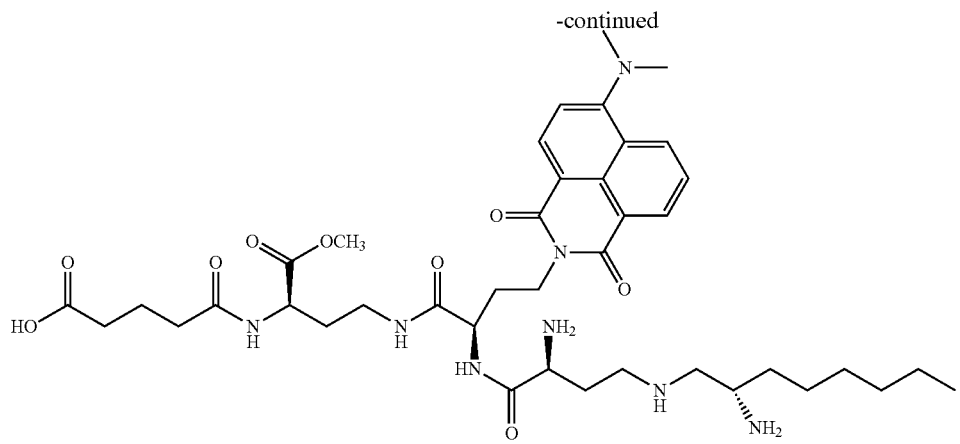

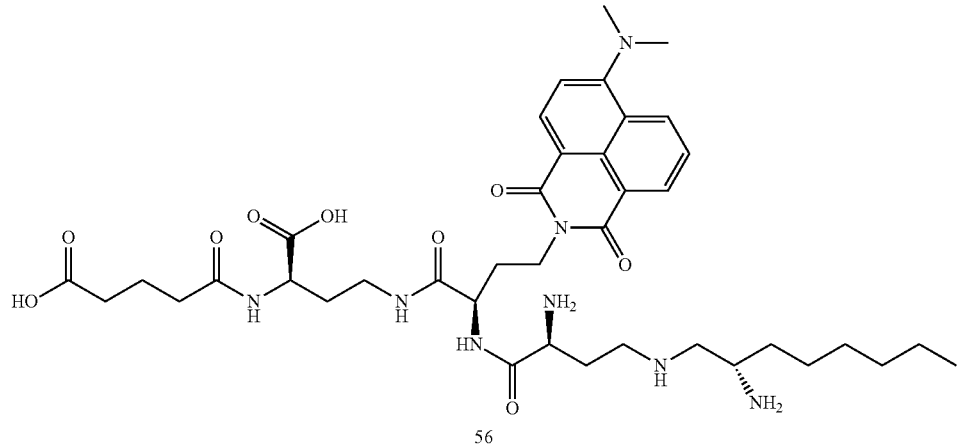 [SMILES: CCCCCC[C@H](N)CNCC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
56

Example 21

Synthesis of HO-Gla-D-Dab-(COOH)-D-(p-acet-amido-biphenyl)-L-Dap-(NH₂)— CH₂CH(NH₂)— C4 (1) being an amyloid β-peptide targeting ligand (4AEDabpBpGla)

Wang resin (0.5 g, loading 0.9 mmol/g) was taken into a 5 mL syringe (pit fitted), with a stop at the outlet. Resin was swelled for 0.5 h with 4 mL of dry DMF. Glutaric anhydride (0.257 g, 2.25 mmol) and 4-DMAP (0.055 g, 0.45 mmol) were dissolved in DMF (3 mL). The resin was treated with this solution for 66 h at room temperature under moderate

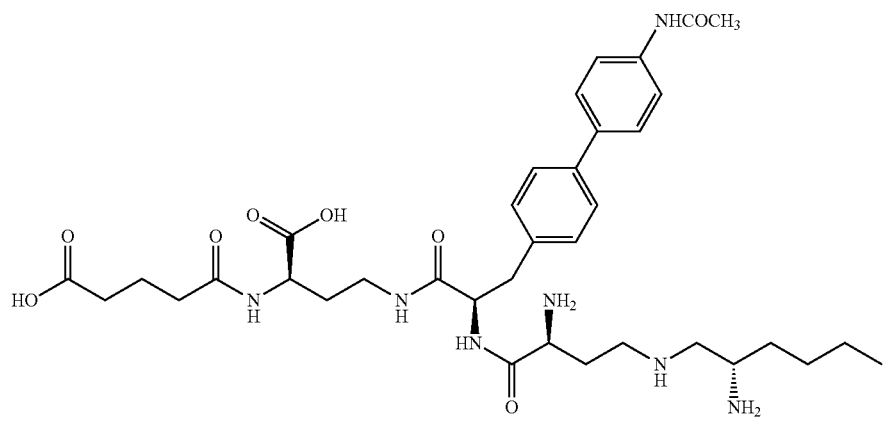

shaking condition, followed by washing with DMF (5 mL×3). A part of this resin (0.1 g) was taken into a similar syringe and treated with DMF solution (2 mL) containing HOAt (0.037 g, 0.27 mmol), DIC (0.042 mL, 0.27 mmol) and DIPEA (0.047 mL, 0.27 mmol) and shaken for 0.25 h. Next, compound 30 (0.038 g, 0.108 mmol) was dissolved in DMF (2 mL) and added into the same reaction mixture. It was shaken for 18 h at room temperature, followed by washing with DMF (3 mL×3). It was treated with 40% piperidine in DMF containing 0.1 M HOBt (2 mL×3, 10 min each time), followed by washing with DMF (3 mL×6). Compound 33 (0.062 g, 0.119 mmol), DIC (0.037 mL, 0.238 mmol) and HOBt (0.032 g, 0.238 mmol) was dissolved in DMF (2 mL) and shaken well for 0.25 h. Resin was treated with this solution for 3 h at room temperature, followed by washing of the resin by DMF (3 mL×3, 2 min each time). Next, it was treated with 40% piperidine in DMF containing 0.1 M HOBt (2 mL×3, 10 min each time), followed by washing with DMF (3 mL×6, 2 min each time). A part of this resin (0.02 g) was taken in a similar syringe. Compound 17 (0.021 g, 0.034 mmol), DIC (0.008 mL, 0.068 mmol) and HOBt (0.009 g, 0.068 mmol) was dissolved in DMF (2 mL) and shaken well for 0.25 h. Next, the resin was treated with the above mentioned solution at room temperature (3 h×2), followed by washing with DMF (3 mL×3, 2 min each time). Next, it was treated with 40% piperidine in DMF containing 0.1 M HOBt (2 mL×3, 10 min each time), followed by washing with DMF (3 mL×6, 2 min each time). Next, resin was treated with a cocktail of TFA (1.9 mL), water (0.05 mL) and TRIS (0.05 mL) for 4 h at room temperature. Resulting solution was collected in a plastic tube and TFA was removed from the solution by blowing it with nitrogen gas. Excess amount of cold diethylether was added into it and it was kept at −20° C. for overnight. Next, the tube was centrifuged (6000 rpm, 6 min) when the solid peptide precipitates. Upper solution was decanted and remaining solid was dissolved in water (2 mL). It was treated with 0.05 M aqueous methanolic LiOH solution (1 mL, MeOH:water 1:1) for 1 h at room temperature. After completion of the reaction, reaction mixture was evaporated to dryness and purified by high performance liquid chromatography (HPLC) using buffer solution (A: 0.1% trifluoroacetic acid in water; B: 0.1% trifluoroacetic acid in acetonitrile). Fractions containing pure peptide were pooled together and solvent was removed in a lyophilizer to obtain the desired peptide 1 (1.1 mg yield). ESI-TOF MS (m/z): calcd. for $C_{36}H_{53}N_7O_8$ [M+H]$^+$ 711.4. found 711.8.

Scheme 21. Synthesis of HO-Gla-D-Dab-(COOH)-D-(p-acetamido-biphenyl)-L-Dap-(NH$_2$)-CH$_2$CH(NH$_2$)-C4 or 4AEDabpBpGla (1).

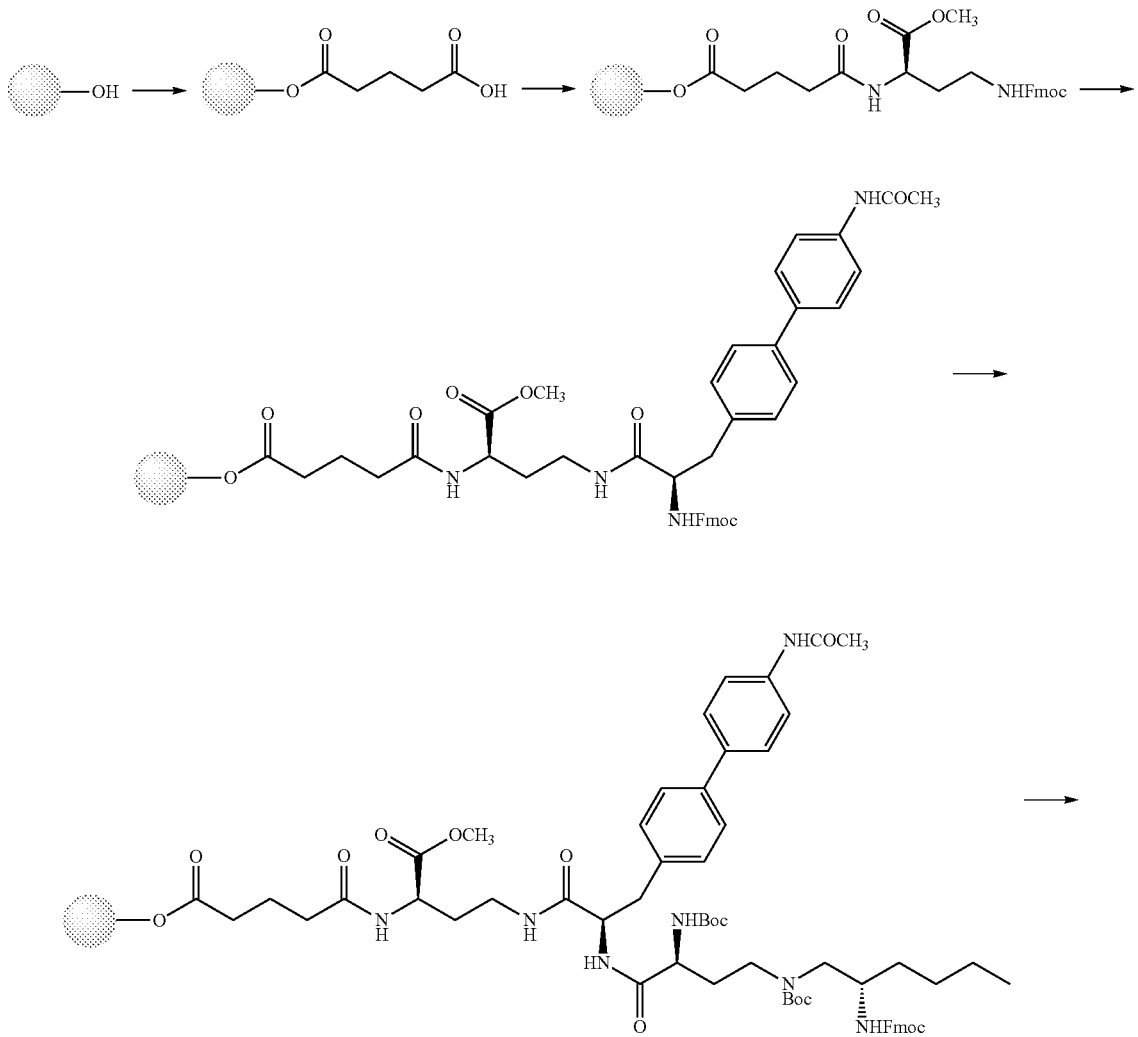

-continued

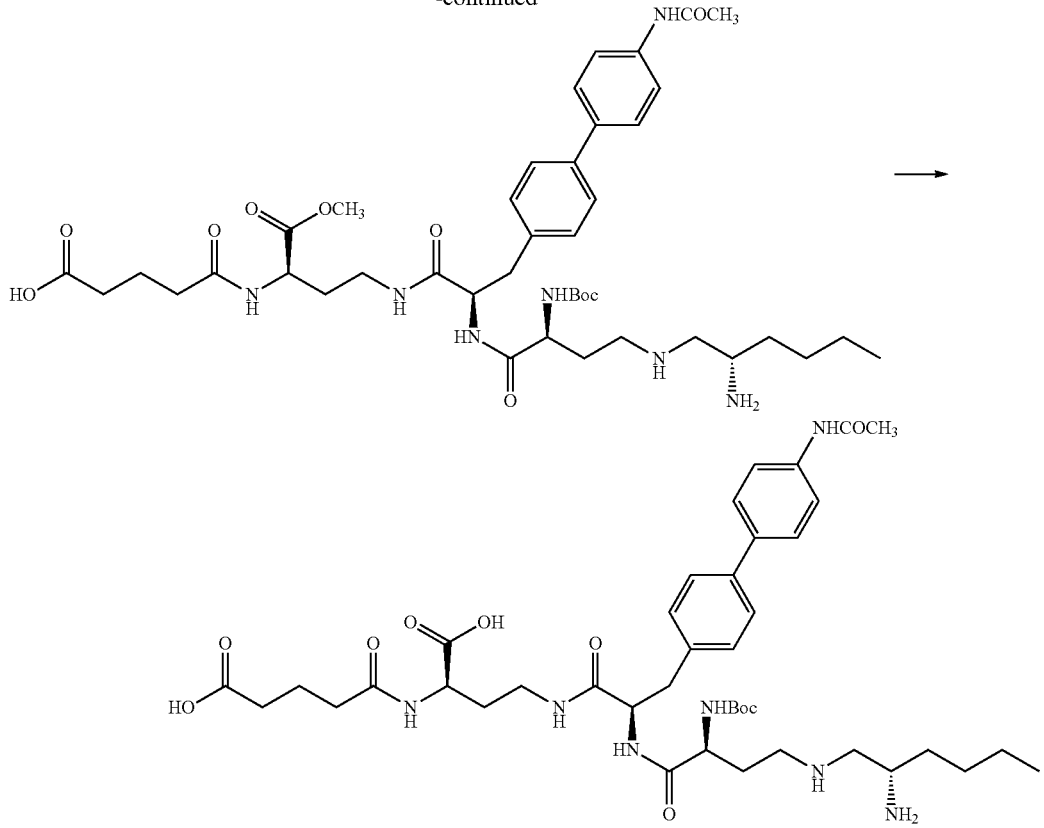

Example 22

Synthesis of HO-Gla-D-Dab-(COOH)-D-(p-acet-amido-biphenyl)-L-Dap-(NH₂)—CH₂CH(NH₂)—C8 (2) being an amyloid β-peptide targeting ligand (8AEDabpBpDabGla)

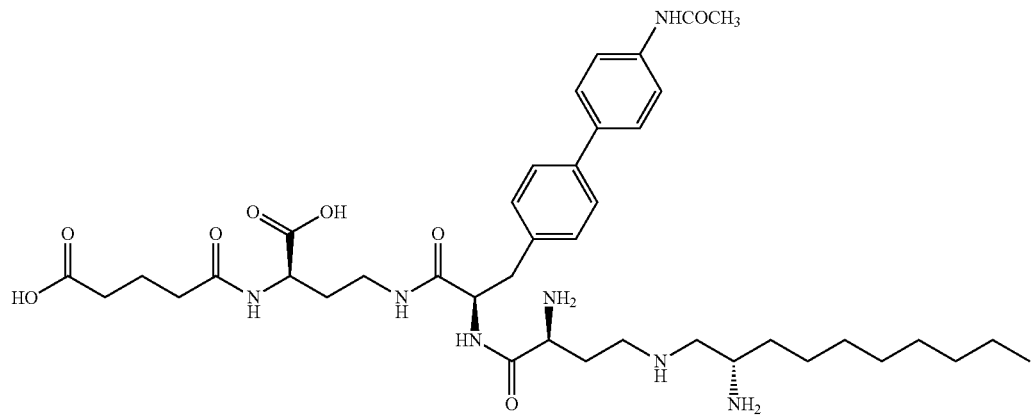

Wang resin (0.5 g, loading 0.9 mmol/g) was taken into a 5 mL syringe (pit fitted), with a stop at the outlet. Resin was swelled for 0.5 h with 4 mL of dry DMF. Glutaric anhydride (0.257 g, 2.25 mmol) and 4-DMAP (0.055 g, 0.45 mmol) were dissolved in DMF (3 mL). The resin was treated with this solution for 66 h at room temperature under moderate shaking condition, followed by washing with DMF (5 mL×3). A part of this resin (0.1 g) was taken into a similar syringe and treated with DMF solution (2 mL) containing HOAt (0.037 g, 0.27 mmol), DIC (0.042 mL, 0.27 mmol) and DIPEA (0.047 mL, 0.27 mmol) and shaken for 0.25 h. Next, compound 30 (0.038 g, 0.108 mmol) was dissolved in DMF (2 mL) and added into the same reaction mixture. It was shaken for 18 h at room temperature, followed by washing with DMF (3 mL×3). It was treated with 40% piperidine in DMF containing 0.1 M HOBt (2 mL×3, 10 min each time), followed by washing with DMF (3 mL×6). Compound 33 (0.062 g, 0.119 mmol), DIC (0.037 mL, 0.238 mmol) and HOBt (0.032 g, 0.238 mmol) was dissolved in DMF (2 mL) and shaken well for 0.25 h. Resin was treated with this solution for 3 h at room temperature, followed by washing of the resin by DMF (3 mL×3, 2 min each time). Next, it was treated with 40% piperidine in DMF containing 0.1 M HOBt (2 mL×3, 10 min each time), followed by washing with DMF (3 mL×6, 2 min each time). A part of this resin (0.02 g) was taken in a similar syringe. Compound 27 (0.024 g, 0.034 mmol), DIC (0.011 mL, 0.068 mmol) and HOBt (0.009 g, 0.068 mmol) was dissolved in DMF (2 mL) and shaken well for 0.25 h. Next, the resin was treated with the above mentioned solution at room temperature (3 h×2), followed by washing with DMF (3 mL×3, 2 min each time). Next, it was treated with 40% piperidine in DMF containing 0.1 M HOBt (2 mL×3, 10 min each time), followed by washing with DMF (3 mL×6, 2 min each time). Next, resin was treated with a cocktail of TFA (1.9 mL), water (0.05 mL) and TRIS (0.05 mL) for 4 h at room temperature. Resulting solution was collected in a plastic tube and TFA was removed from the solution by blowing it with nitrogen gas. Excess amount of cold diethylether was added into it and it was kept at −20° C. for overnight. Next, the tube was centrifuged (6000 rpm, 6 min) when the solid peptide precipitates. Upper solution was decanted and remaining solid was dissolved in water (2 mL). It was treated with 0.05 M aqueous methanolic LiOH solution (1 mL, MeOH:water 1:1) for 1 h at room temperature. After completion of the reaction, reaction mixture was evaporated to dryness and purified by high performance liquid chromatography (HPLC) using buffer solution (A: 0.1% trifluoroacetic acid in water; B: 0.1% trifluoroacetic acid in acetonitrile). Fractions containing pure peptides were pooled together and solvent was removed in a lyophilizer to obtain the desired peptide 2 (1.2 mg). ESI-TOF MS (m/z): calcd. for $C_{40}H_{61}N_7O_8$ [M+H]$^+$ 767.5. found 767.9.

Scheme 22. Synthesis of HO-Gla-D-Dab-(COOH)-D-(p-acetamido-biphenyl)-L-Dap-(NH$_2$)-CH$_2$CH(NH$_2$)-C8 or 8AEDapbpBpDabGla (2).

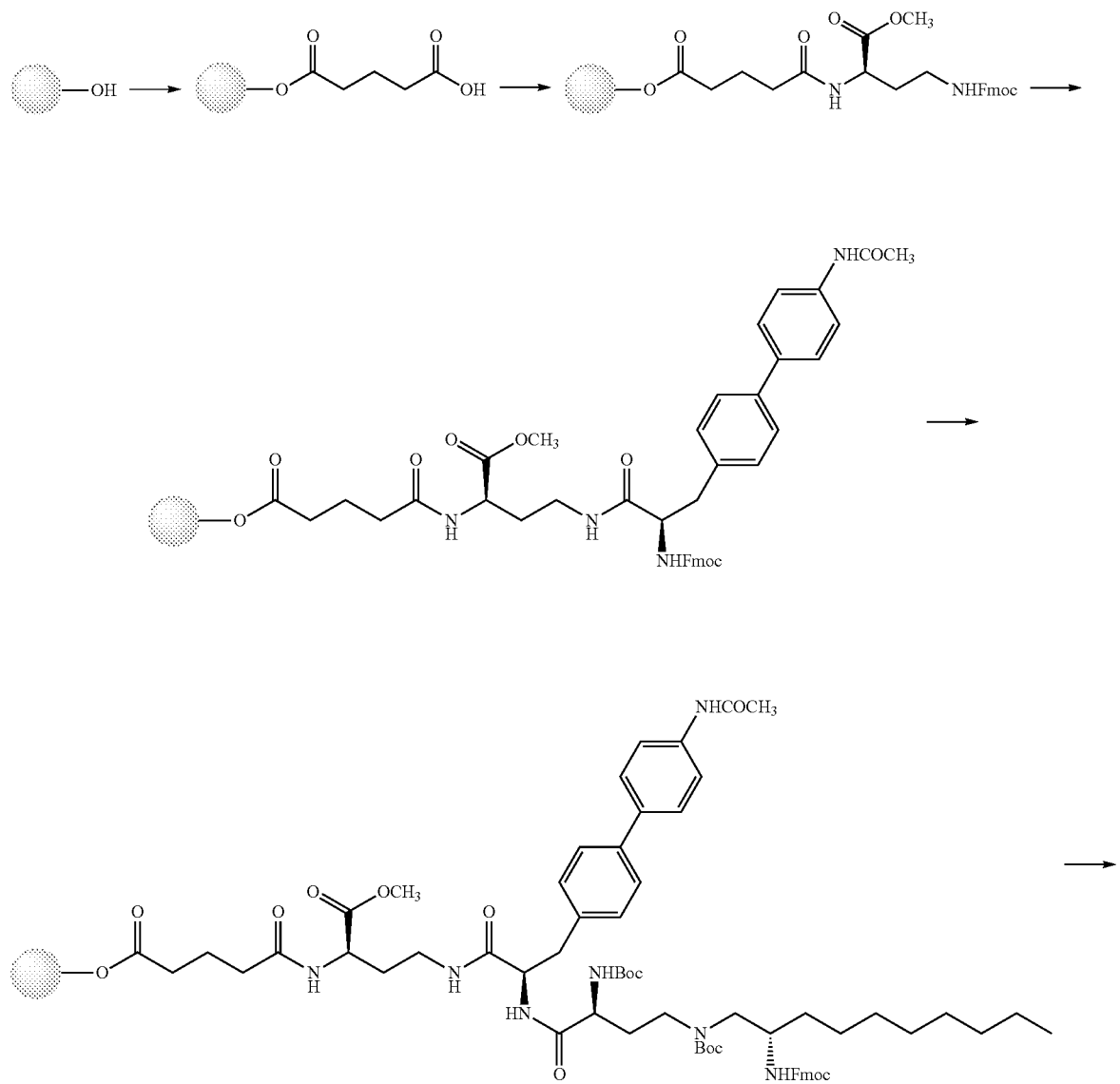

-continued

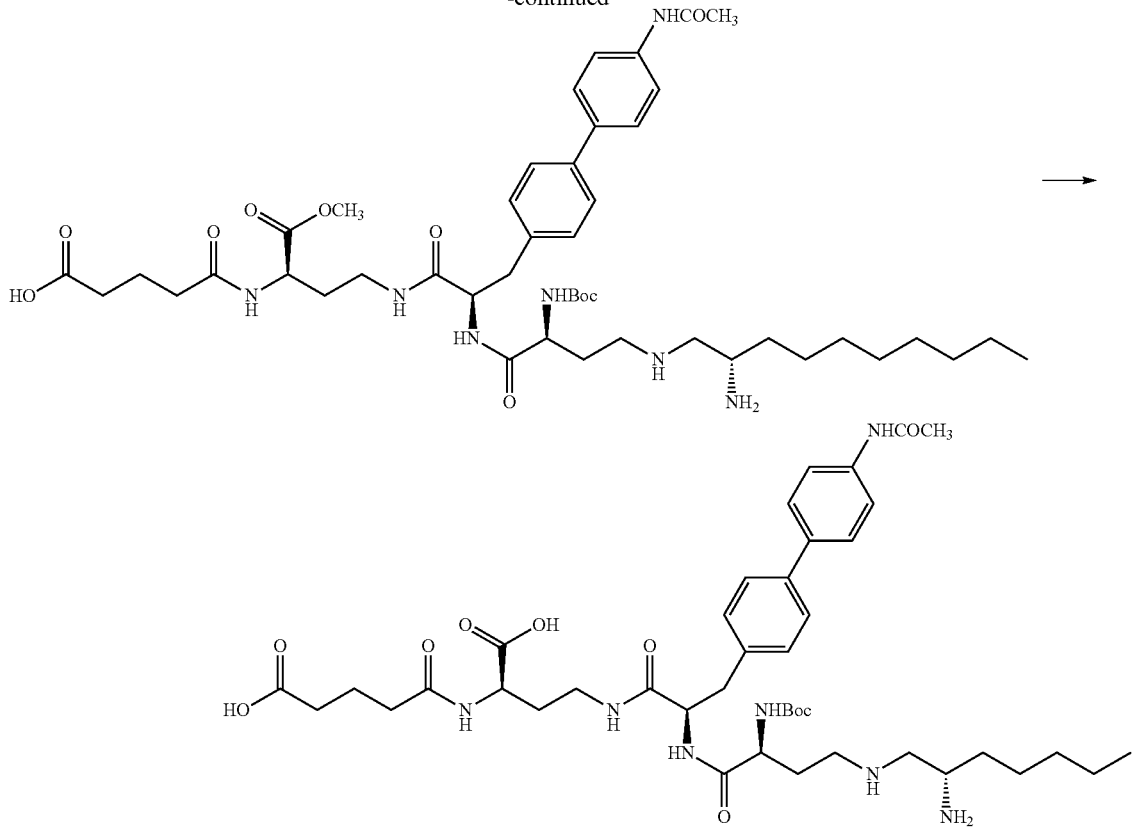

Example 23

Molecular Dynamics Studies on AR

Preparation of Aβ and Ligands $A\beta_{13-26}$ adopts an α-helical conformation in the membrane environment,[18] therefore the initial model structure of $A\beta_{13-26}$ was built in an α-helical conformation as in our previous simulation studies (Juneja, A. et al. *J. Chem. Theory Comput.* 2013, 9, 834-846; Ito, M. et al. *PLoS One* 2012, 7, e30510). Since $A\beta_{13-26}$ (HHQKLVFFAEDVGS) is a fragment of the full peptide, the N- and C-termini are made neutral by capping with N-terminal acetyl and C-terminal amide groups respectively, mimicking the uncharged amide linkage on both ends of $A\beta_{13-26}$ in the full length peptide. The peptides were built with the ionizable residues in their charged states, where basic residues (H13, H14 and K16) are protonated and acidic residues (E22 and D23) are deprotonated. Ionizable functional groups of ligands are prepared in their charged states.

Molecular Dynamics Simulation

Simulations are performed at 360 K for $A\beta_{13-26}$ alone and with ligands. The temperature in each simulation was maintained by coupling all atoms to a Langevin heat bath with frictional coefficient $\beta=2$ ps$^{-1}$. (Loncharich, R. J. et al. *Biopolymers* 1992, 32, 523-535). All simulations and analyses were carried out using CHARMM (Brooks, B. R. et al. *Journal of Computational Chemistry* 1983, 4, 187-217; Brooks, B. R. et al. *Journal of Computational Chemistry* 2009, 30, 1545-1614) version c36a6 with the CHARMM22/ CMAP all-hydrogen force field (MacKerell, A. D. et al. *Journal of Physical Chemistry B* 1998, 102, 3586-3616; MacKerell, A. D. et al. *Journal of the American Chemical Society* 2004, 126, 698-699) using either an implicit solvent model GBMV II (Lee, M. S. et al. *J Comput Chem* 2003, 24, 1348-1356) or in explicit solvent. The ligands are peptidomimetic and are designed using amino acid moieties, and therefore ligands can be used without any problem in simulations. The SHAKE algorithm (Ryckaert, J. P. et al. *Journal of Computational Physics* 1977, 23, 327-341) was used to fix the length of the covalent bonds involving hydrogen atoms, allowing an integration time step of 2 fs to be used in the integration of Newton's equations. The simulation parameters specific to implicit solvent model GBMV II and explicit solvent are similar to the ones used in earlier simulation studies (Ito, M. et al. *PLoS One* 2012, 7, e30510; Juneja, A. et al. *J. Chem. Theory Comput.* 2013, 9, 834-846). All calculations were performed on a GNU/Linux PC cluster with 64 bit Intel Xeon and AMD processors.

Before simulating $A\beta_{13-26}$ with or without ligands using implicit solvent model GBMV II, the structures of respective models were optimized by 2000 steps of steepest descent followed by 4000 steps of adopted basis Newton-Raphson. The system was heated up to the target temperature of 360 K gradually for 20 ps employing velocity rescaling. The system was then shifted to Langevin heat bath at respective temperature by coupling all atoms with frictional coefficient of $\beta=2$ ps$^{-1}$ and equilibrated for 30 ps. After equilibration, production run of 100 ns were carried out with coordinates saved every 1 ps.

Before simulating $A\beta_{13-26}$ with or without ligands in explicit solvent, structures of the solvated systems were optimized by 500 steps of steepest descent energy minimization with a harmonic restraint of 20 kcal/mol/Å$^2$ on Aβ$_{13-26}$ and ligand followed by 1500 steps of adopted basis Newton-Raphson energy minimization without any harmonic restraint. After the systems were heated up to 360 K gradually for 50 ps, 20 ns long production run at 360 K was carried out. The simulations were performed for the optimized systems under periodic boundary conditions at a constant pressure (1 atm) using the Langevin piston method (Feller, S. et al. *The Journal of Chemical Physics* 1995, 103, 4613-4621) with piston mass 400 amu, collision frequency 20 ps$^{-1}$ and bath temperature (360 K). The average temperature was checked every 4 ps, and was found to remain within 5 K of the target temperature after the heating MD run. During the MD simulations, no harmonic restraints were imposed on any molecule in the systems, and coordinates were saved every 1 ps.

Analysis

Every snapshot (1 ps) of the production run (100 ns) was analyzed. To examine the effect of ligands on the structural changes in Aβ$_{13-26}$, the root-mean-square deviation (RMSD) and the number of α-helical backbone hydrogen bonds (aHBs) of the residues 15-24 of Aβ$_{13-26}$ were calculated in presence of ligands employing similar criteria from our previous studies (Ito, M. et al. *PLoS One* 2012, 7, e30510; Juneja, A. et al. *J. Chem. Theory Comput.* 2013, 9, 834-846). The root-mean-square deviation (RMSD) was computed for the middle region (15-24) of Aβ$_{13-26}$ and thus avoiding large fluctuations originating from mobile the N- and C-termini. The reported backbone heavy atoms RMSD was calculated against the initial energy-minimized coordinates along the MD simulation. The α-helical backbone hydrogen bonds (aHBs) were defined using the criterion acceptor-hydrogen distance <2.4 Å (Deloof, H. et al. *Journal of the American Chemical Society* 1992, 114, 4028-4035). The helicity is based on backbone torsion angles (φ, ψ) and on the Kabsch-Sander DSSP algorithm (Kabsch, W.; Sander, C. *Biopolymers* 1983, 22, 2577-2637). For torsion angle based helicity analysis, the results are reported as the fraction of the 10 torsion angle (φ, ψ) pairs in the middle region (15-24) of Aβ$_{13-26}$ that are in the α-helical region ($-89 \leq \phi \leq -39$ and $-66 \leq \psi \leq -16$) (Hovmoller, S. et al. *Acta Crystallographica Section D* 2002, 58, 768-776).

Example 24

Electrophysiology for Aβ Peptide Targeting Ligands (Gamma Oscillations in C57BL/6 Mice Hippocampal Slices)

Aβ peptide targeting ligands were tested and compared with first-generation ligands (Pep1 b and Dec-DETA) for the effect on pharmacologically induced (100 nM kainate) rhythmic network activity in the gamma-frequency range (3-80 Hz, gamma oscillations (Fisahn, A. *J Physiol* 2005, 562, 65-72; Fisahn, A. et al. *Nature* 1998, 394, 186-189) in hippocampal slice preparations. Gamma oscillations play an important role in higher processes in the brain, such as learning, memory and cognition, and are markedly reduced in patients diagnosed with Alzheimer's disease who exhibit cognitive deficits (Ribary, U. et al. *Proc Natl Acad Sci USA* 1991, 88, 11037-11041).

Animals

Experiments were carried out in accordance with ethical permit granted by Norra Stockholms Djurförsöksetiska Nämnd to AF (N45/13). C57BL/6 mice of either sex (postnatal days 14-23, supplied from Charles River, Germany) were used in all experiments. The animals were deeply anaesthetized using isofluorane before being sacrificed by decapitation.

Tissue Preparation

The brain was dissected out and placed in ice-cold ACSF (artificial cerebrospinal fluid) modified for dissection. This solution contained (in mM); 80 NaCl, 24 NaHCO$_3$, 25 Glucose, 1.25 NaH$_2$PO$_4$, 1 Ascorbic acid, 3 NaPyruvate, 2.5 KCl, 4 MgCl$_2$, 0.5 CaCl$_2$, 75 Sucrose. Horizontal sections (350 µm thick) of the ventral hippocampi of both hemispheres were prepared with a Leica VT1200S vibratome (Microsystems, Stockholm, Sweden). Immediately after slicing sections were transferred to a submerged incubation chamber containing standard ACSF (in mM): 124 NaCl, 30 NaHCO$_3$, 10 Glucose, 1.25 NaH$_2$PO$_4$, 3.5 KCl, 1.5 MgCl$_2$, 1.5 CaCl$_2$. The chamber was held at 34° C. for at least 20 minutes after dissection. It was subsequently allowed to cool to ambient room temperature (19-22° C.) for a minimum of 40 minutes. Peptides were added to the incubation solution 15 minutes before transferring slices to the interface-style recording chamber. While incubating slices were continuously supplied with carbogen gas (5% CO$_2$, 95% O$_2$) bubbled into the ACSF. Chemical compounds used in intracellular and extracellular solutions were obtained from Sigma-Aldrich Sweden AB (Stockholm, Sweden). The Kainic acid was obtained from Tocris.

Electrophysiology

Recordings were carried out in hippocampal area CA3 with borosilicate glass microelectrodes, pulled to a resistance of 3-7 MO. Local field potentials (LFP) were recorded at 34° C. using microelectrodes filled with ACSF placed in stratum pyramidale. LFP oscillations were elicited by applying kainic acid (100 nM) to the extracellular bath. The oscillations were allowed to stabilize for 20 minutes before any recordings were carried out. LFP recordings were performed with a 4 channel amplifier/signal conditioner M102-amplifier (Electronics lab, Faculty of Mathematics and Natural Sciences, University of Cologne, Cologne, Germany). The signals were sampled at 10 kHz, conditioned using a Hum Bug 50 Hz noise eliminator (Quest Scientific, North Vancouver, BC, Canada), software low-pass filtered at 1 kHz, digitized and stored using a Digidata 1322A and Clampex 9.6 software (Molecular devices, CA, USA).

Analysis

Power spectral density plots (from 60 s long LFP recordings) were calculated in averaged Fourier-segments of 8192 points using Axograph X (Kagi, Berkeley, Calif., USA). Oscillation power was calculated by integrating the power spectral density between 20 and 80 Hz. Data is reported as means±standard errors of the means in the text and as median and upper/lower quartile in the figure box plots. For statistical analysis the Mann-Whitney U-test was used.

Effect of the Ligands on Gamma Oscillations in Hippocampal Slice Preparations

LFP recordings in area CA3 revealed control gamma oscillations of $5.58 \cdot 10^{-09} \pm 3.98 \cdot 10^{-10}$ V$^2$ power (n=16). Incubation of slices for 15 min with 50 nM Aβ1-42 prior to kainate superfusion significantly decreased gamma oscillation power ($1.97 \cdot 10^{-09} \pm 2.98 \cdot 10^{-10}$ V$^2$; n=12; U=188.0, n1=16, n2=12, p<0.0001 two-tailed).

Addition of the ligands Pep1 b (250 nM) and Dec-DETA (250 nM) to the 15 min incubation with 50 nM Aβ resulted in partial prevention of the Aβ-induced decrease of kainate-induced gamma oscillations for Pep1 b ($3.44 \cdot 10^{-09} \pm 3.15 \cdot 10^{-10}$ V$^2$; n=11; Pep1b vs control kainate: U=153.0, n1=16, n2=13, p=0.0008 two-tailed; Pep1 b vs Aβ: U=110.0, n1=12, n2=13, p=0.0056 two-tailed) and higher prevention for Dec-DETA (4.94 $10^{-09}$±4.08 $10^{-10}$ $V^2$; n=14; Dec-DETA vs control kainate: U=134.0, n1=16, n2=14, p=0.376 two-tailed). Addition of the ligands DH18 (250 nM) and DH20 (250 nM) to the 15 min incubation with 50 nM Aβ resulted in complete prevention of the Aβ-induced decrease of kainate-induced gamma oscillations (7.59 $10^{-09}$±6.31 $10^{-10}$ $V^2$; n=13; DH18 vs control kainate: U=161.0, n1=16, n2=13, p=0.012 two-tailed); (7.59 $10^{-09}$±6.31 $10^{-10}$ $V^2$; n=16; DH20 vs control kainate: U=164.0, n1=16, n2=16, p=0.184 two-tailed).

Similar experiments with addition of the ligands DH18 (50 nM), DH20 (50 nM) as well as DH18_Dmn (50 nM), i.e. only equvimolar amounts, to the 15 min incubation with 50 nM Aβ also resulted in complete prevention of the Aβ-induced decrease of kainate-induced gamma oscillations.

Control experiments for the first-generation (Pep1 b and Dec-DETA) and second-generation peptide ligands (DH18, DH20 and DH18_Dmn) showed that neither of these ligands had an effect on kainate-induced gamma oscillations in the absence of Aβ.

Our data shows that the new ligands DH18, DH20 and DH18_Dmn are more effective than first generation ligands in preventing Aβ-induced degradation of network gamma oscillations.

Example 25

Electron Microscopy of Fibrils Formation from $Aβ_{1-42}$ in the Presence of Aβ Peptide Targeting Ligands Electron Microscopy Samples of $Aβ_{1-42}$ peptide (5 μM) alone or mixed with 5 or 25 μM of each ligand in a volume of 100 μl, were incubated at 37° C. for 9 hours. Aliquotes of 2 μl were taken from the different samples, adsorbed on copper grids and negatively stained with 2.5% uranyl acetate in 50% ethanol. The samples were examined and photographed using a Hitachi H7100 microscope operated at 75 kV.

Results

The first generation of ligands (Nerelius, et. al., *Proc. Natl. Acad. Sci. USA*, 2009, 106, 9191) were designed to interact with two polar regions and one hydrophobic region (e.g. Pep 1 b) or with one polar region and another hydrophobic region (e.g., Dec-DETA). A number of different new ligands were designed for stabilization of the helical conformation of the central portion of the Aβ peptide. The novel ligands are designed to more or less act as a "clamp" for the Aβ peptide by interaction with more regions, i.e., to interact with two hydrophobic regions as well as two or three polar areas. Examples of such ligands together with Pep 1 b, Dec-DETA and some other new ligands are shown below.

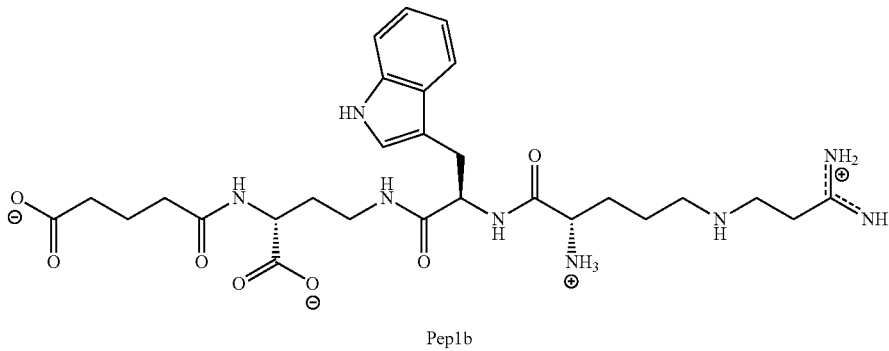

Pep1b

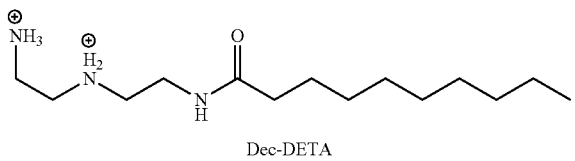

Dec-DETA

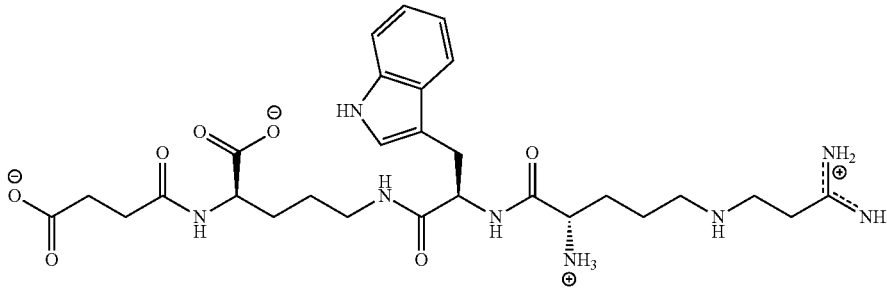

RO9_Pep2

-continued
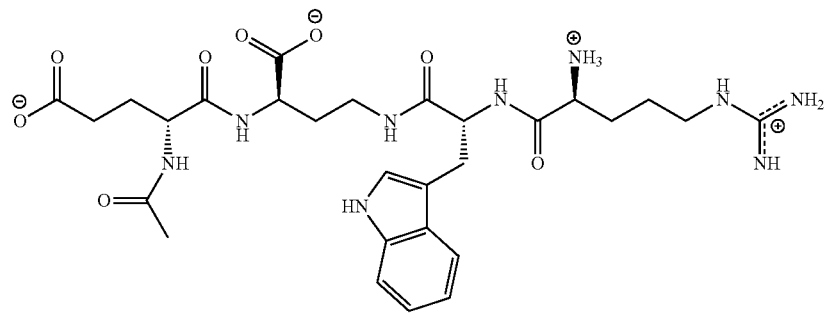
RdWDabdE
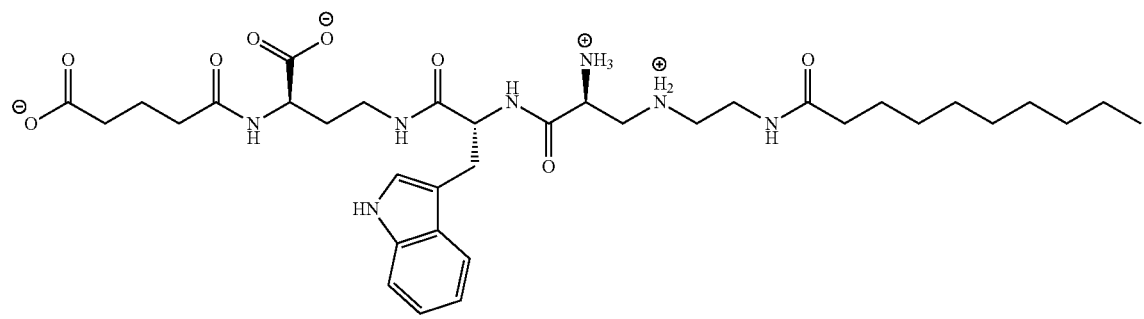
DH18
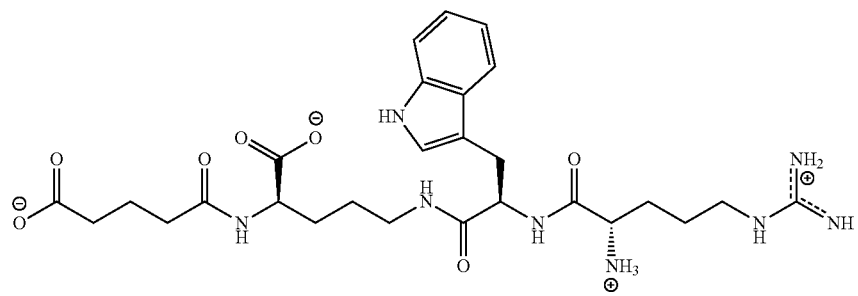
RO13_Pep3
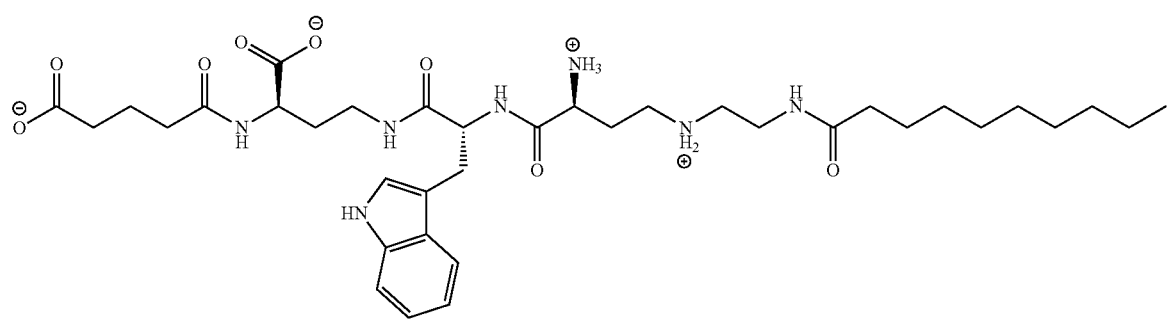
DecAEDab -continued
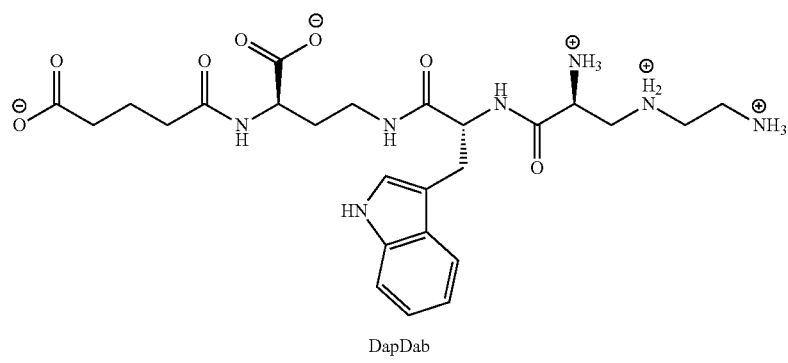
DapDab
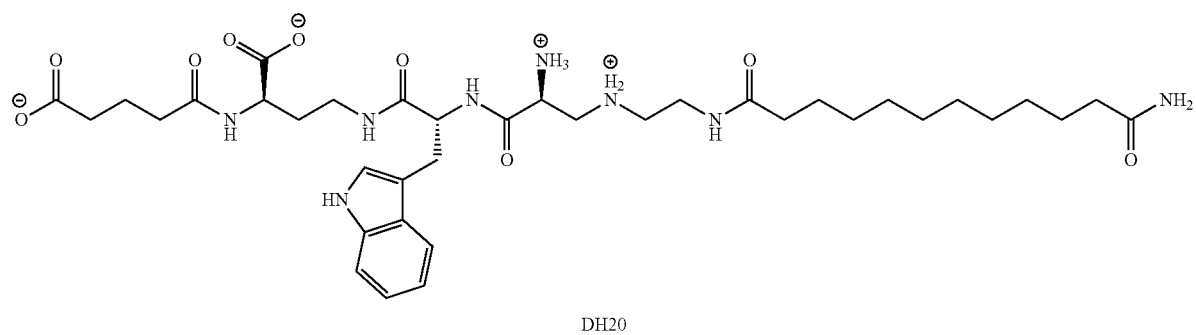
DH20
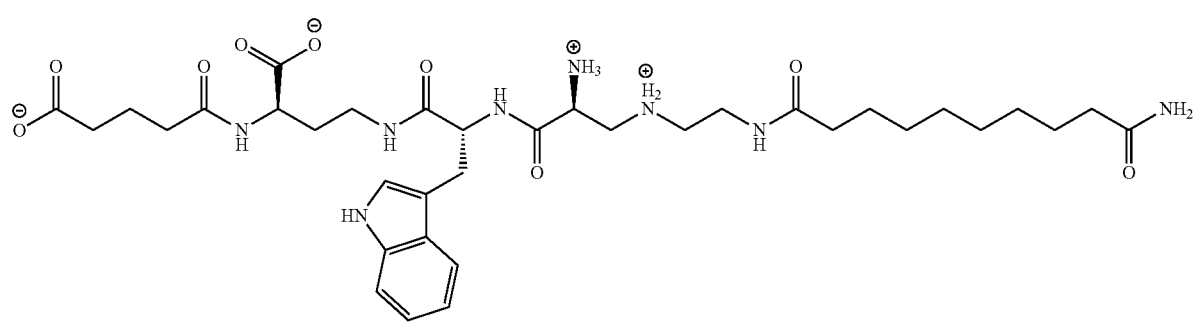
ADecAEDap
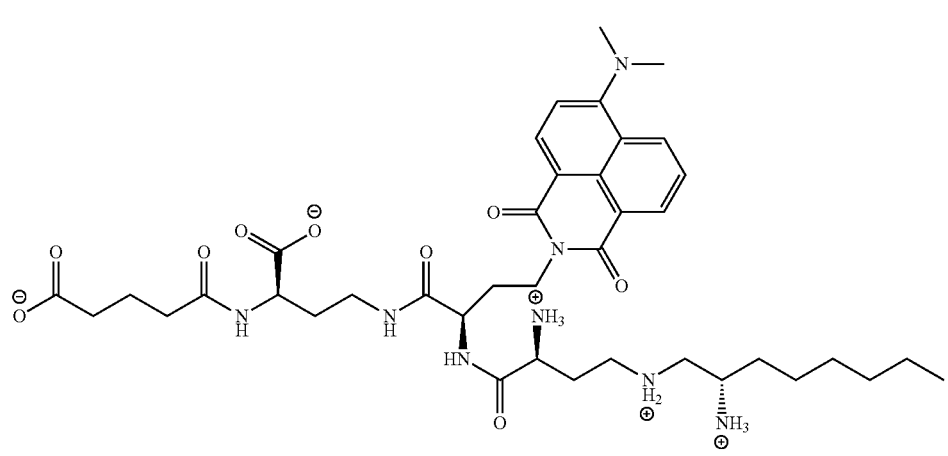
8AEDabDmnDabGla

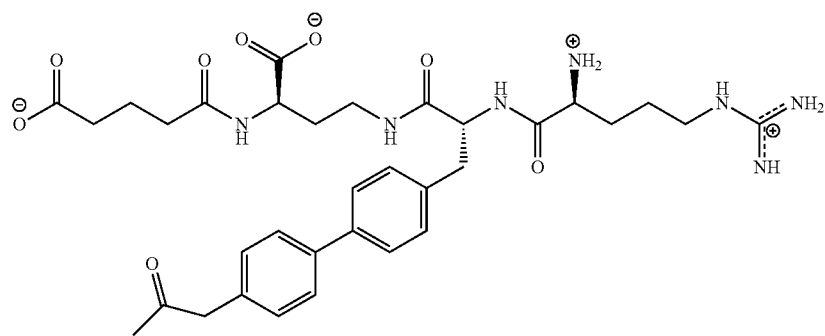
pBpDab
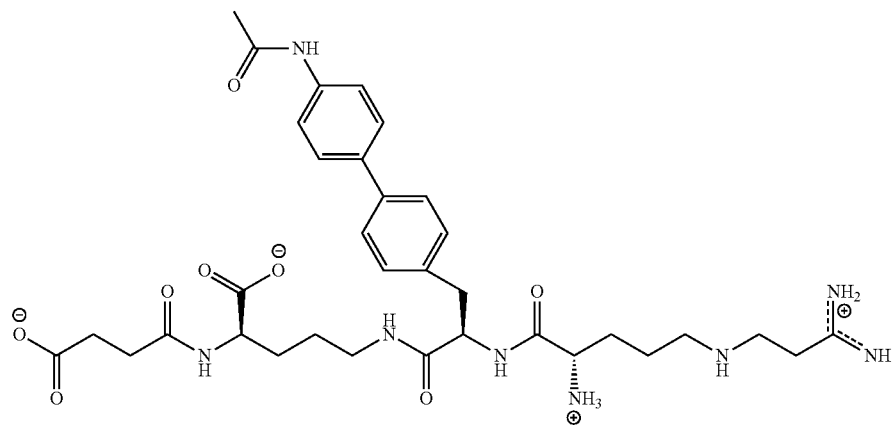
pBpOrn
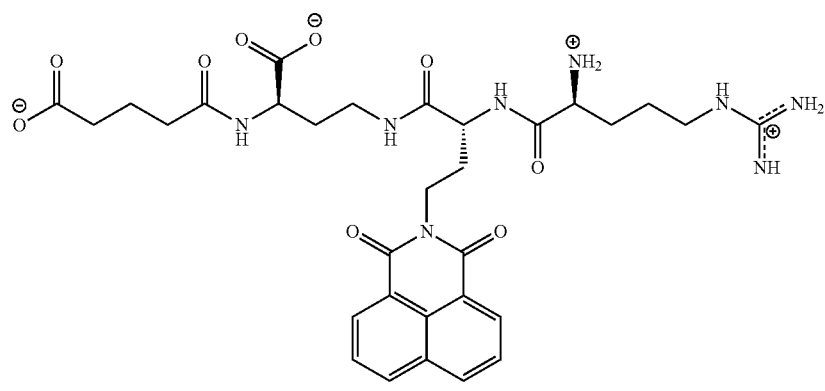
DmnDab
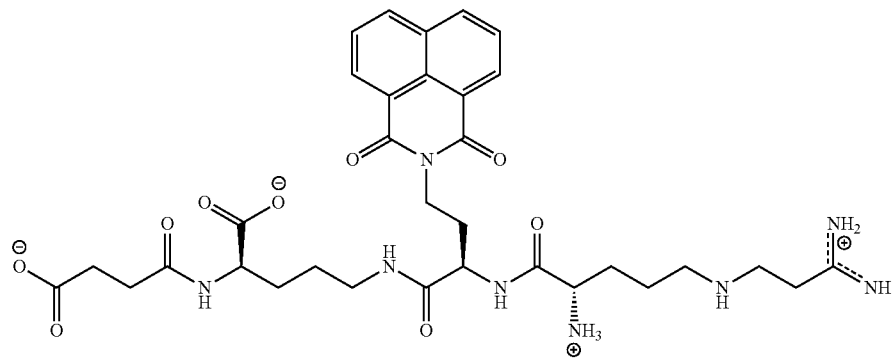
DmnOrn

-continued
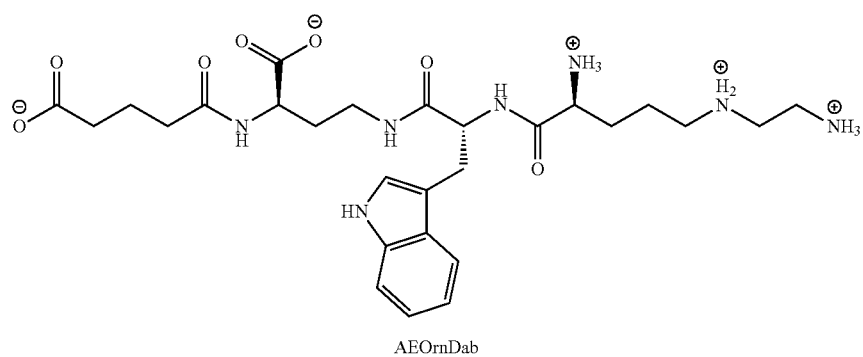
AEOrnDab
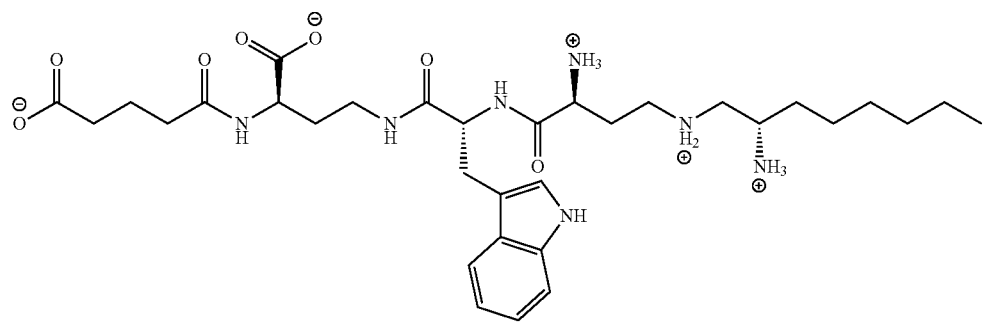
6NAEDab
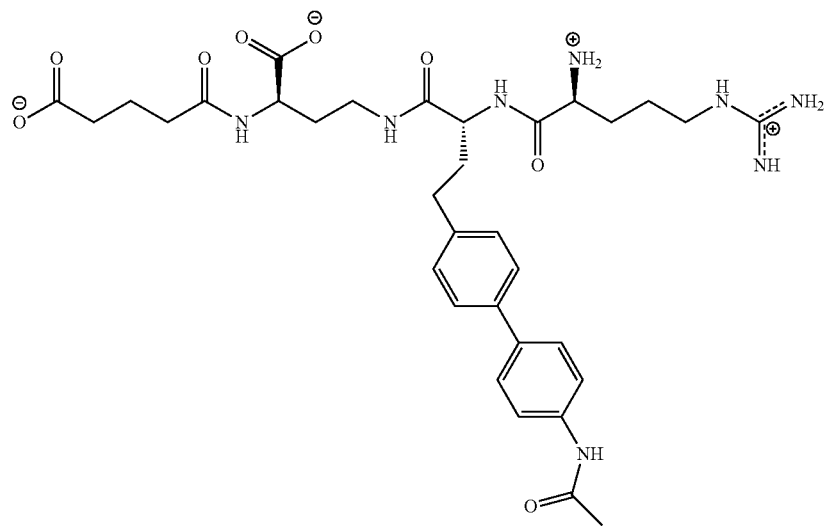
hBpDab

-continued
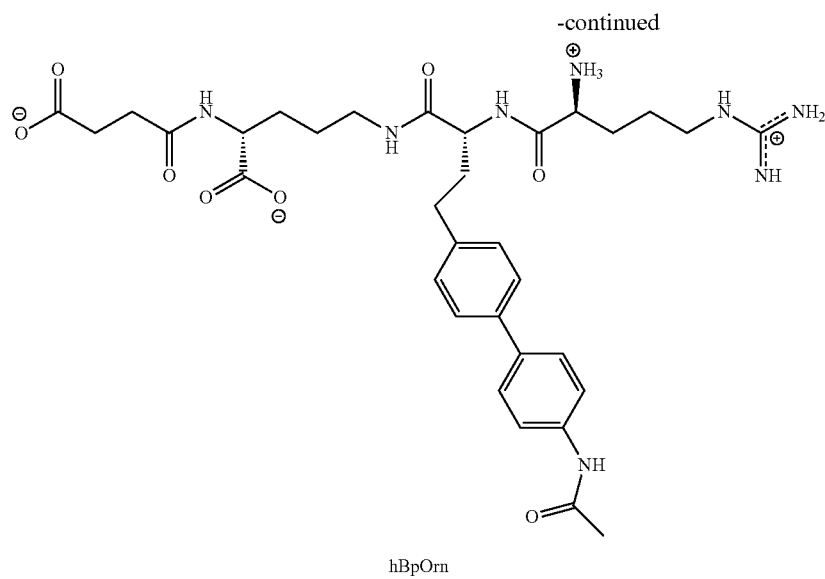
hBpOrn
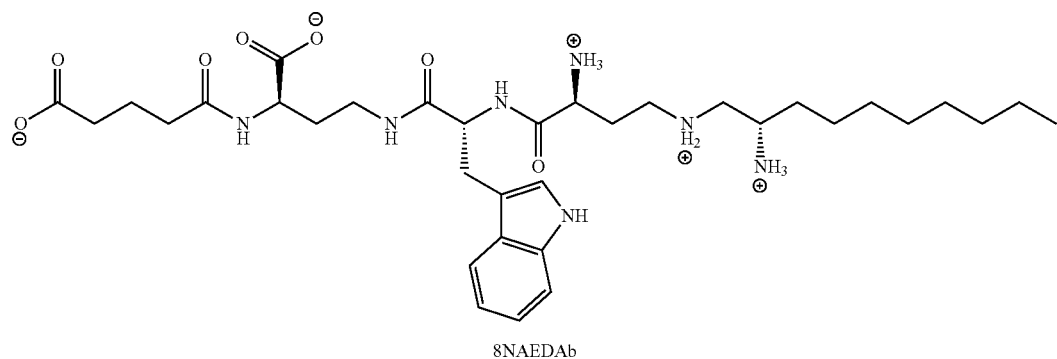
8NAEDAb
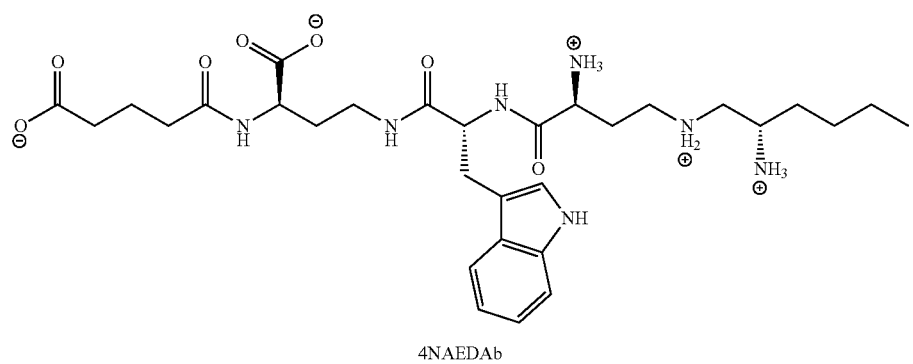
4NAEDAb
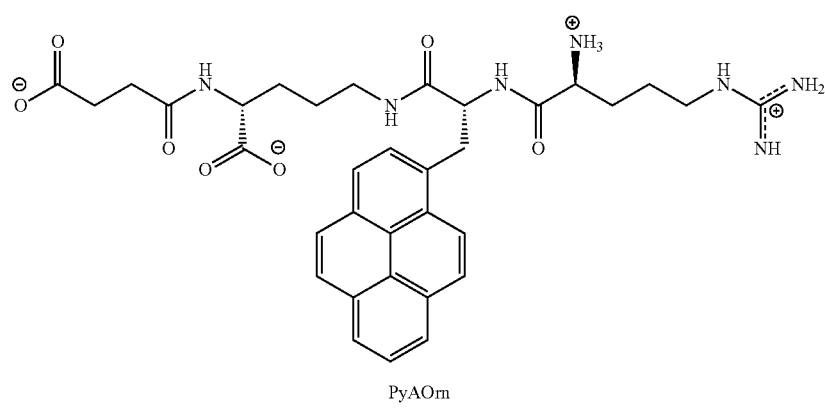
PyAOrn -continued
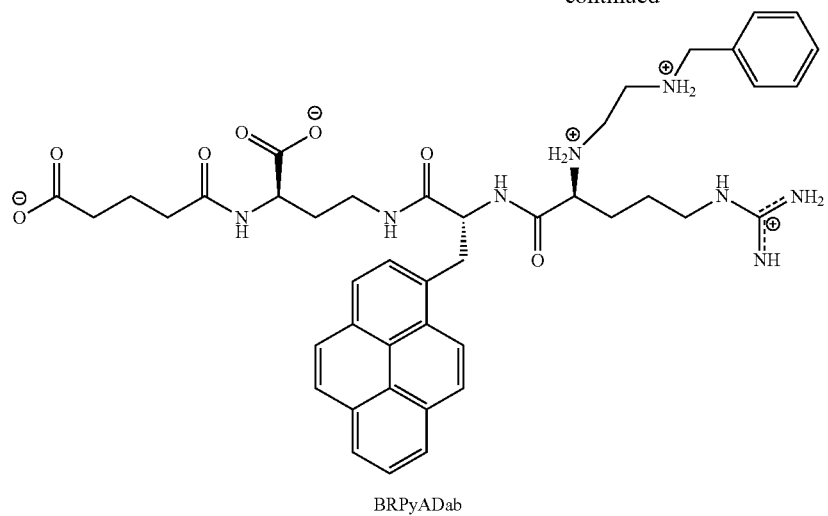
BRPyADab
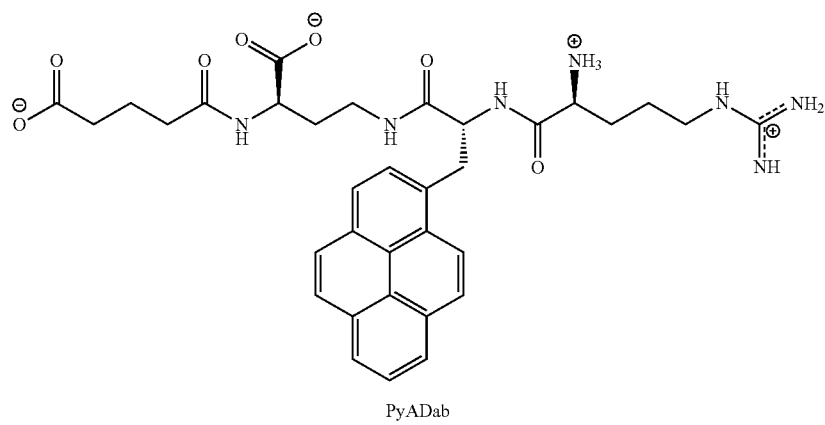
PyADab
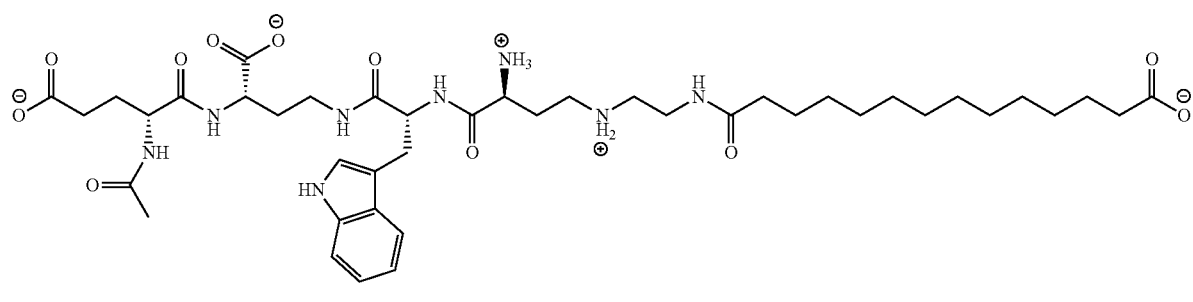
MDAEDabWLDabdE
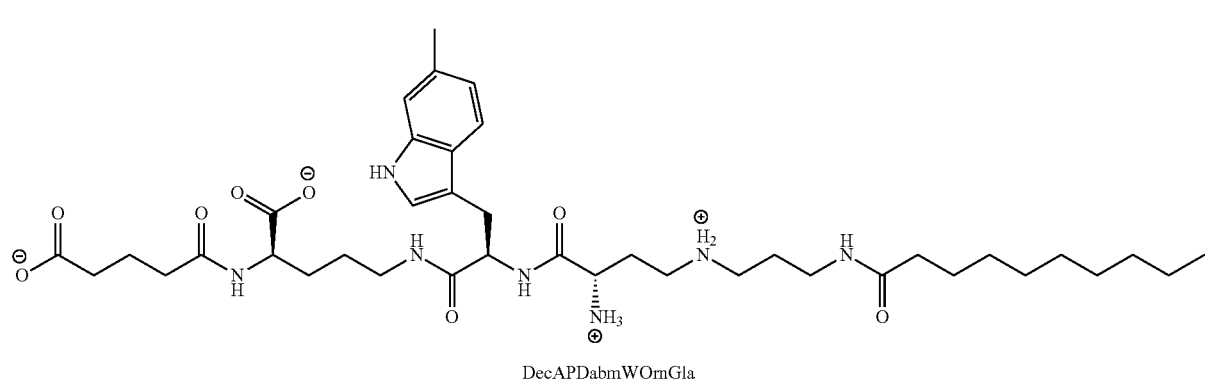
DecAPDabmWOrnGla

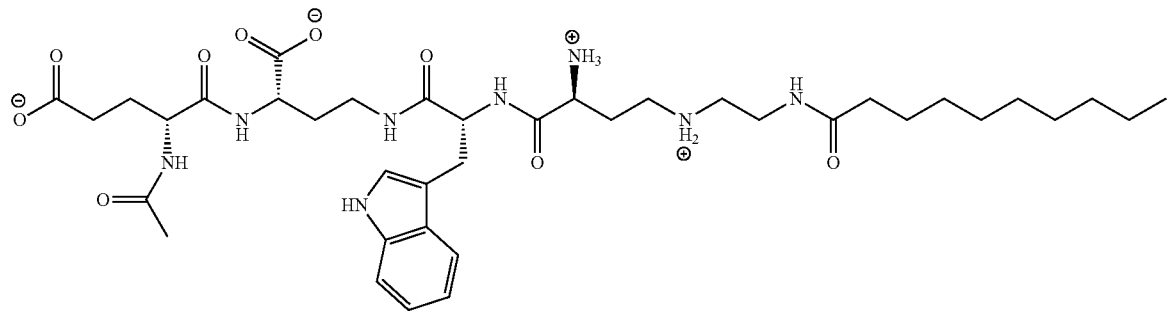
DecAEDabWDabdE
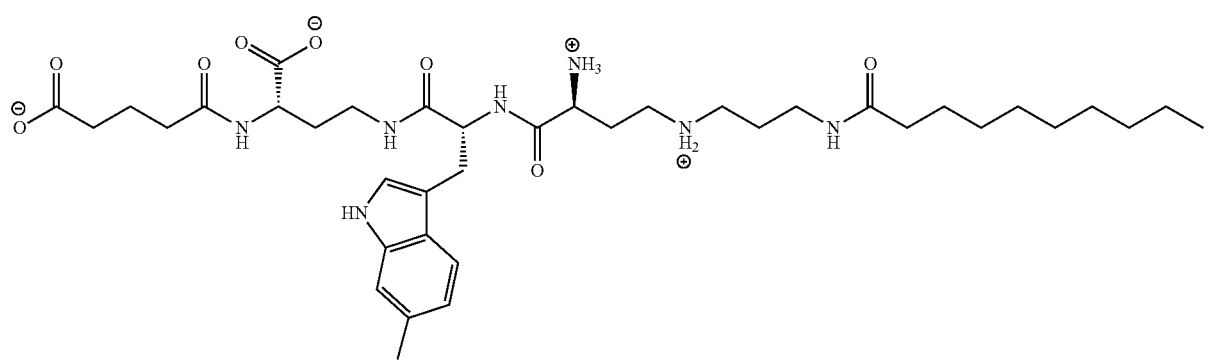
DecAPDabmW
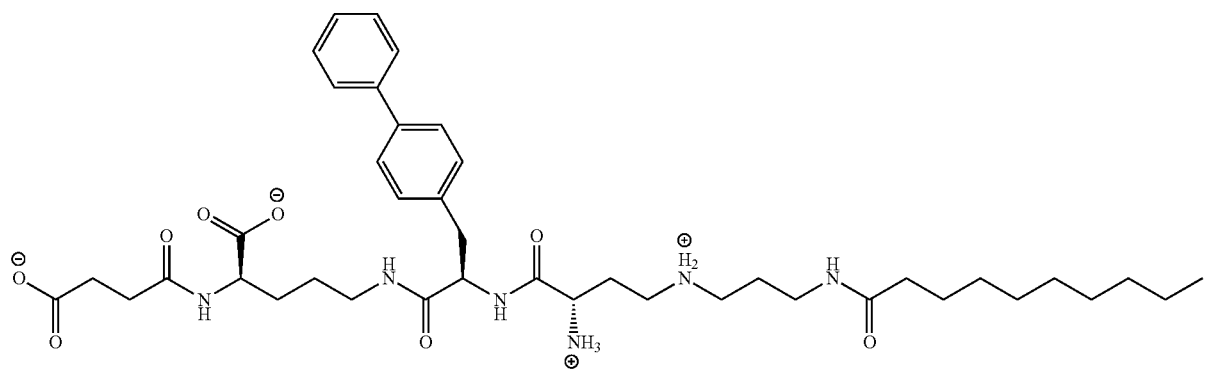
DecAPDabpBpOrnSu
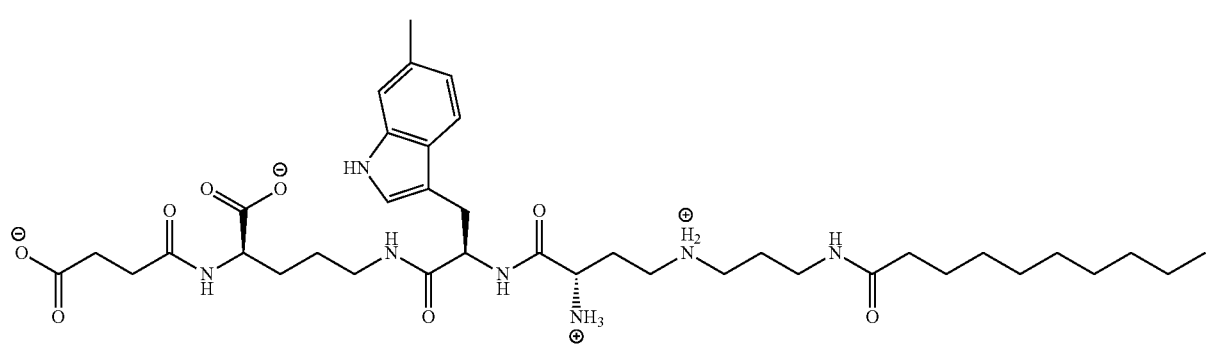
DecAPDabmWOrnSu -continued
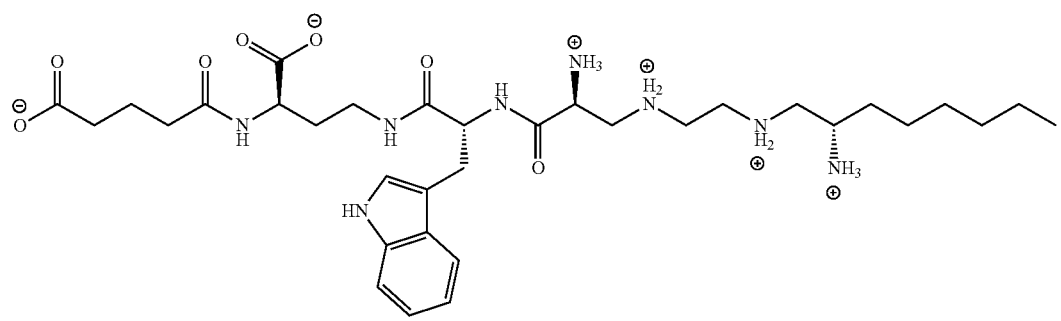
6NAEAEDap
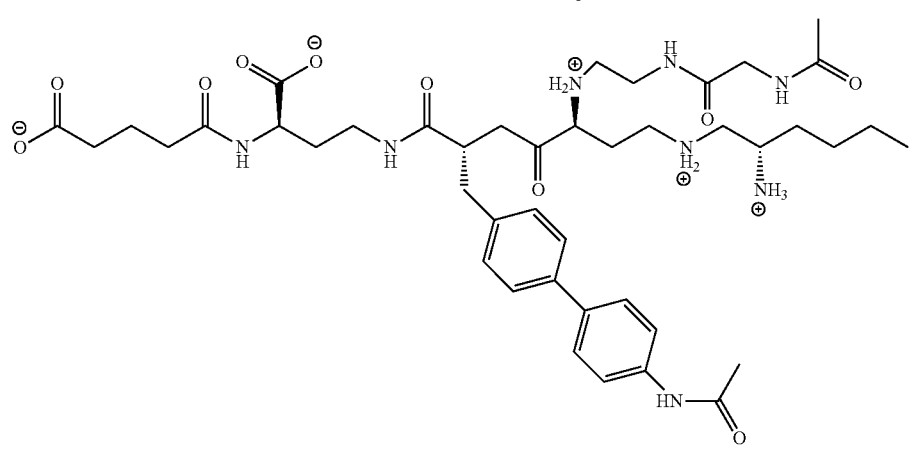
Ac4NdiAEDabpBp
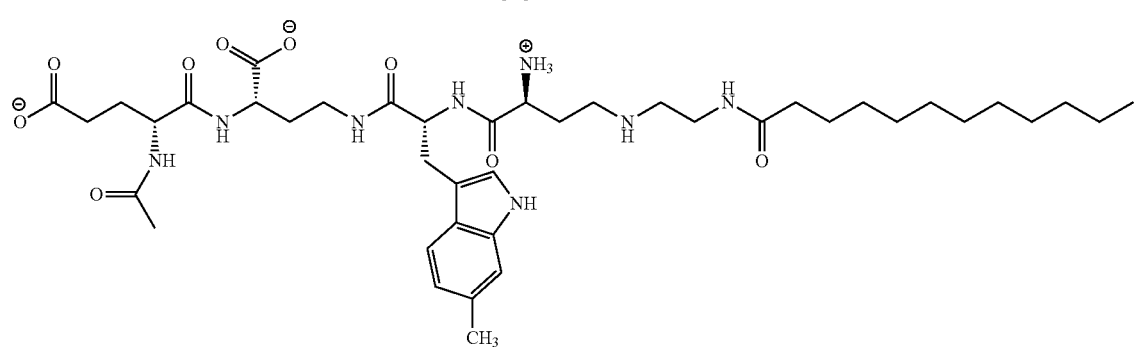
DodecAEDabWDabdE
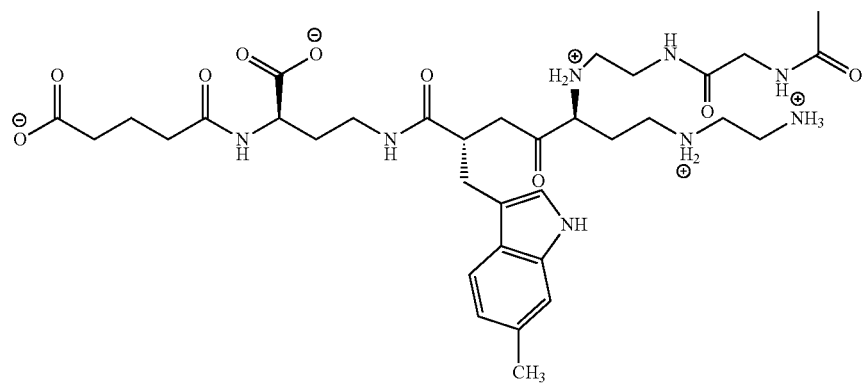
AcGdiAEDab

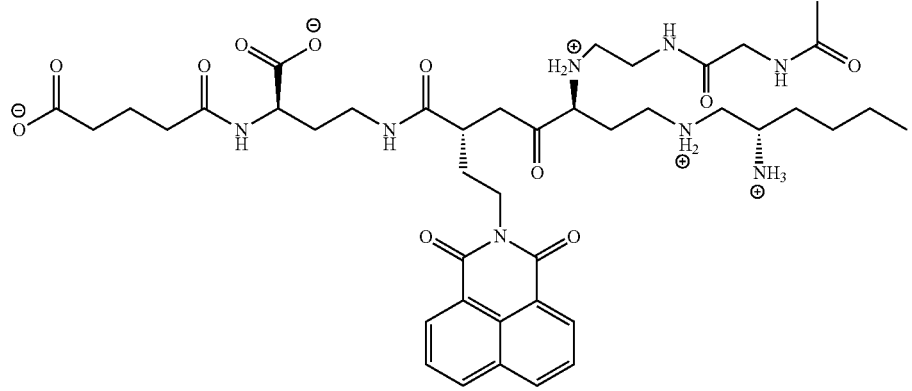
AcG4NdiAEDabDmn
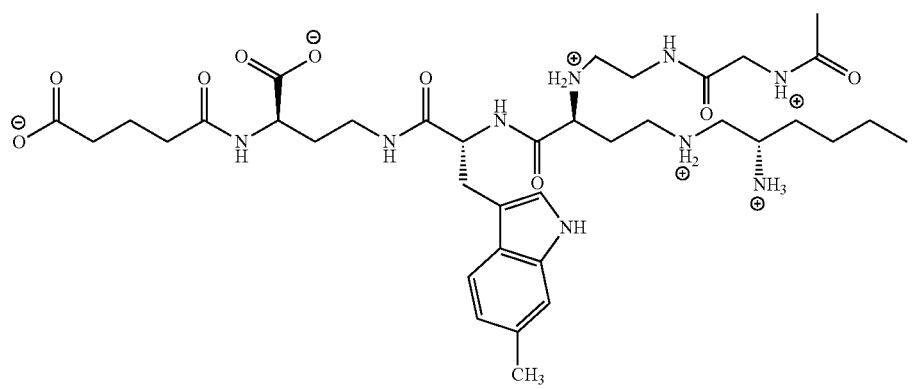
AcG6NdiAEDabmW
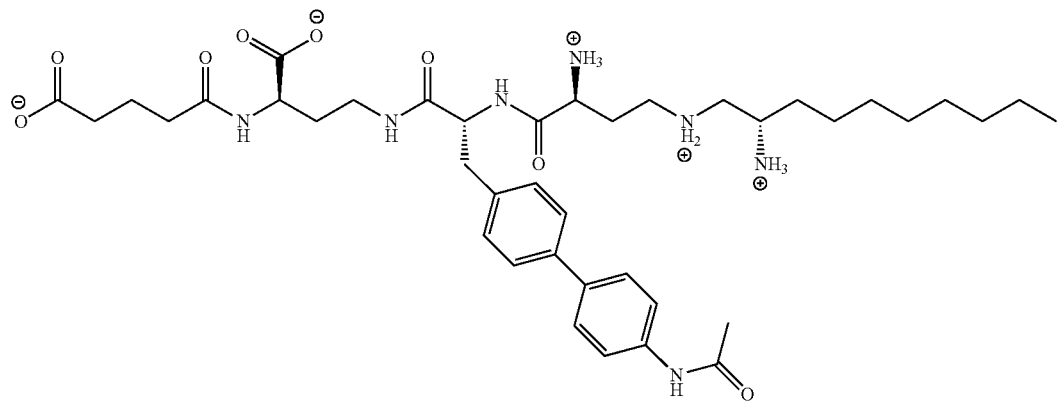
8AEDabpBp

-continued
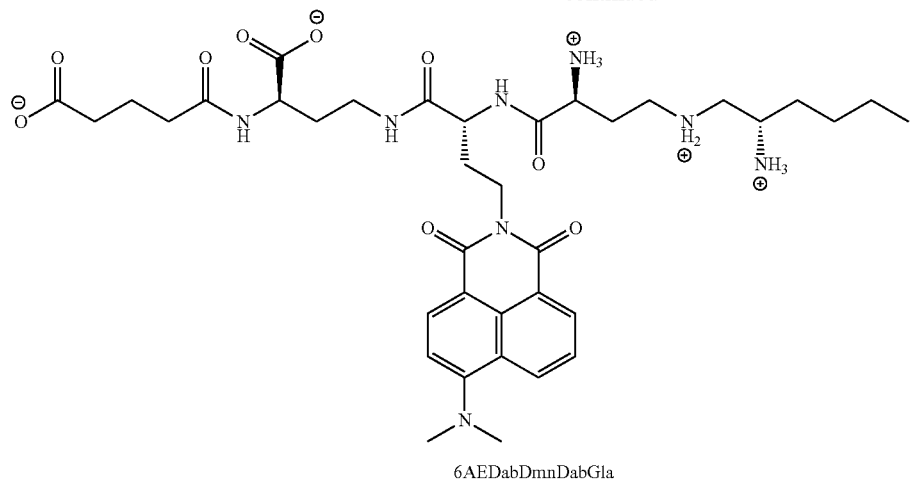
6AEDabDmnDabGla
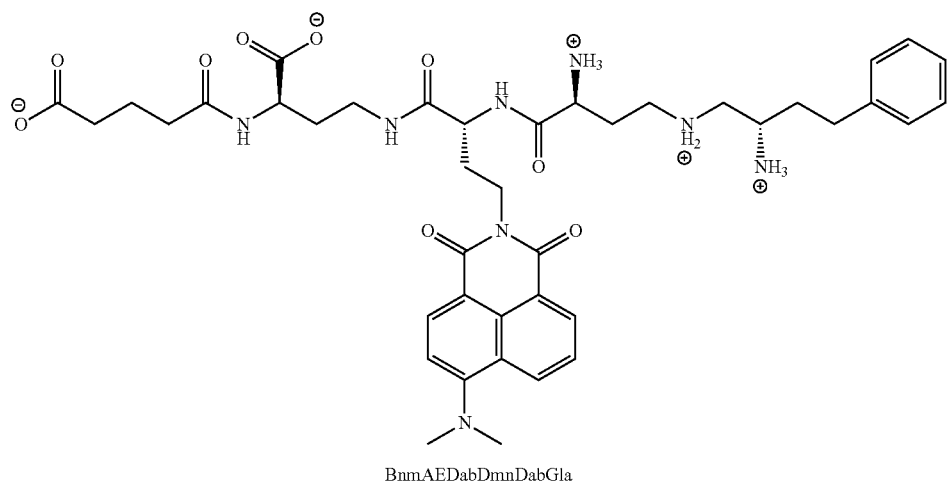
BnmAEDabDmnDabGla
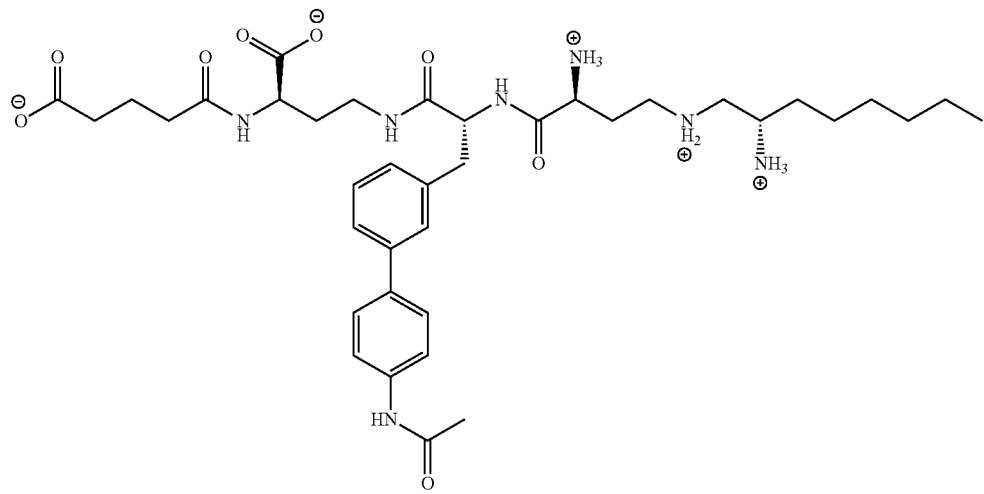
6AEDabBpDabGla

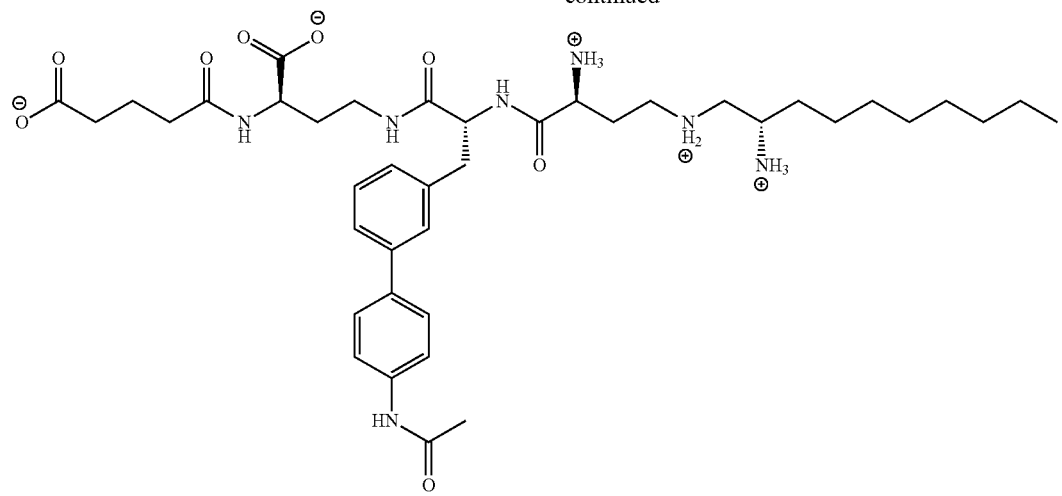
8AEDabBpDabGla
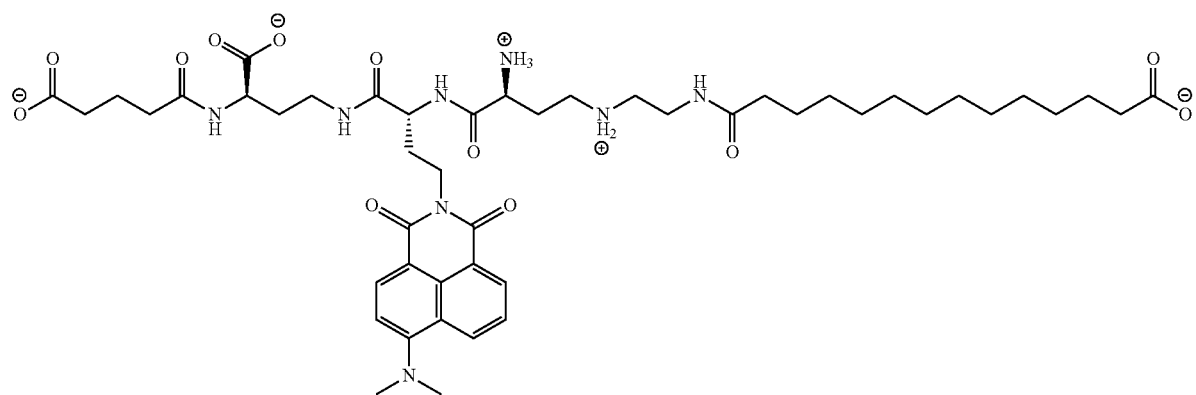
MDAEDabDmnLDabGla
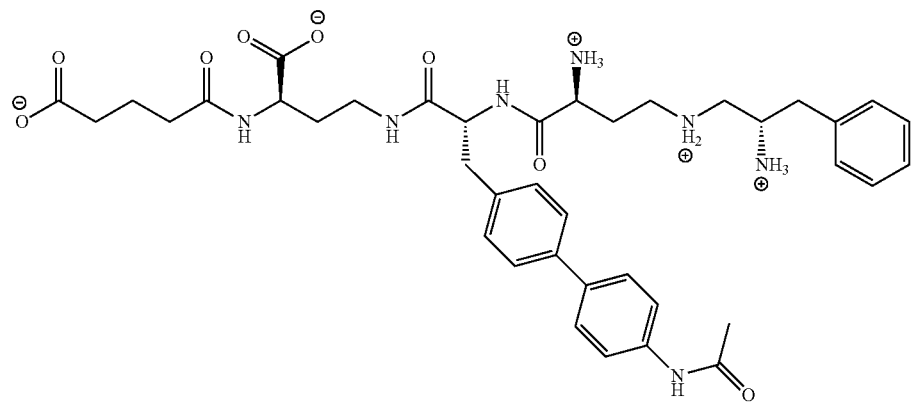
BnAEDabpBp

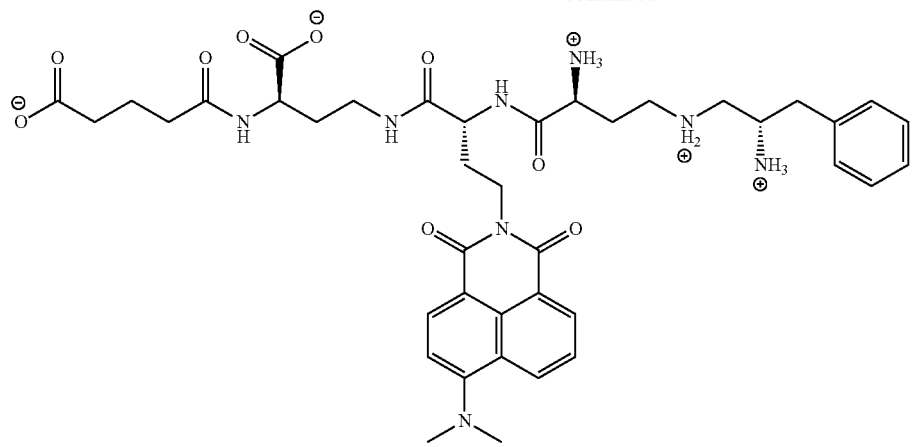
BnAEDabDmnDabGla
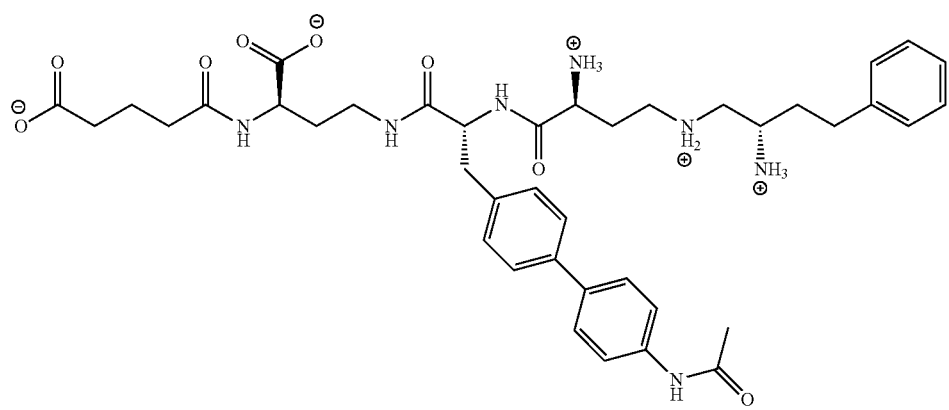
BnmAEDabpBp
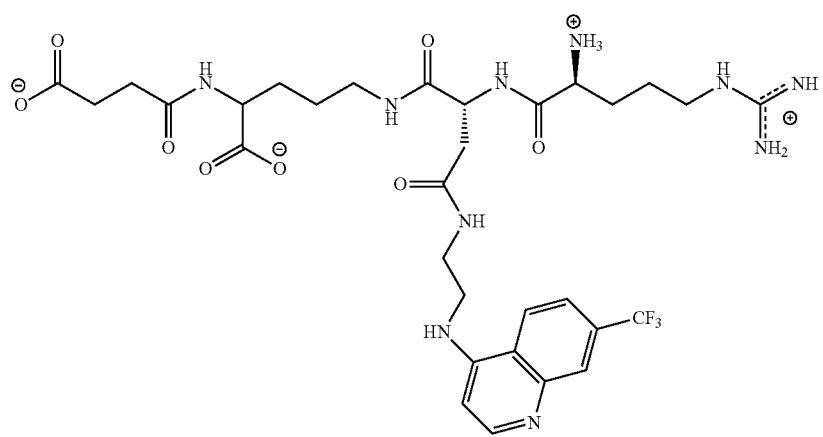
RfqOrnSu

-continued
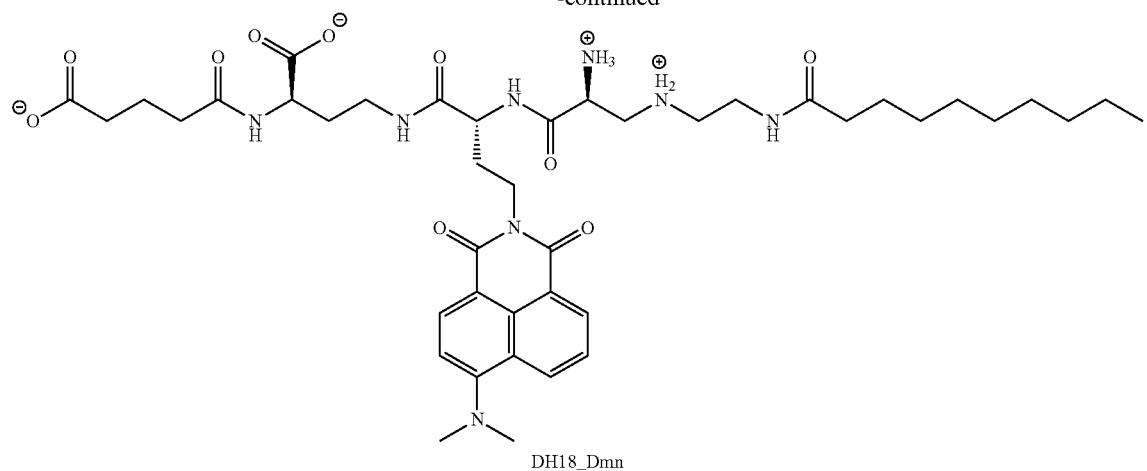
DH18_Dmn
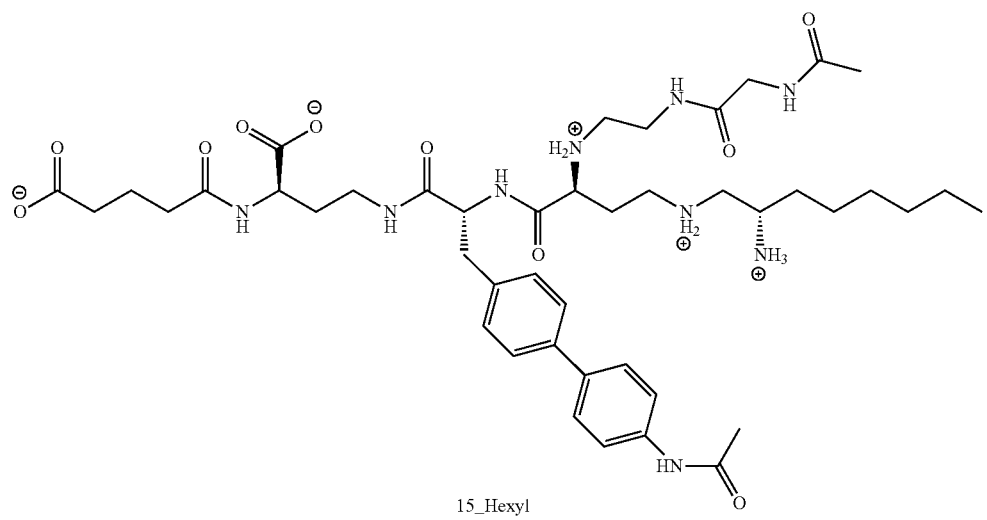
15_Hexyl
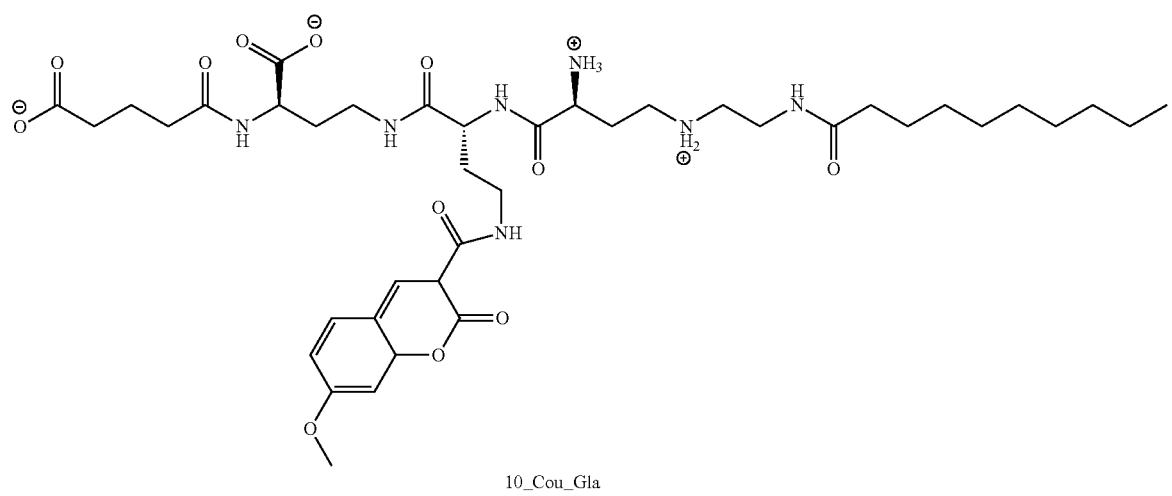
10_Cou_Gla

-continued
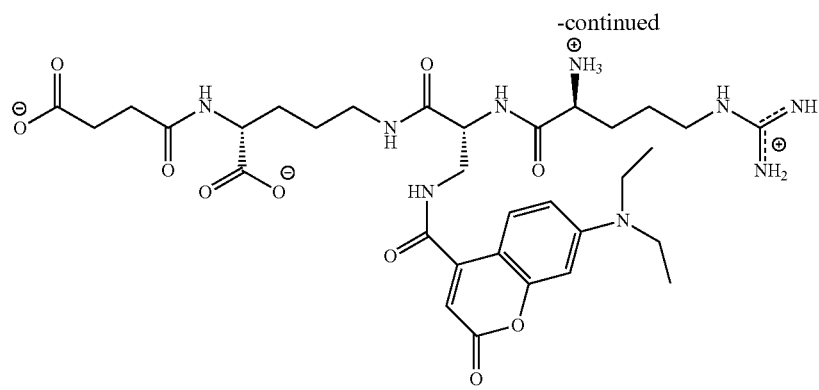
RaxDOrnSuc
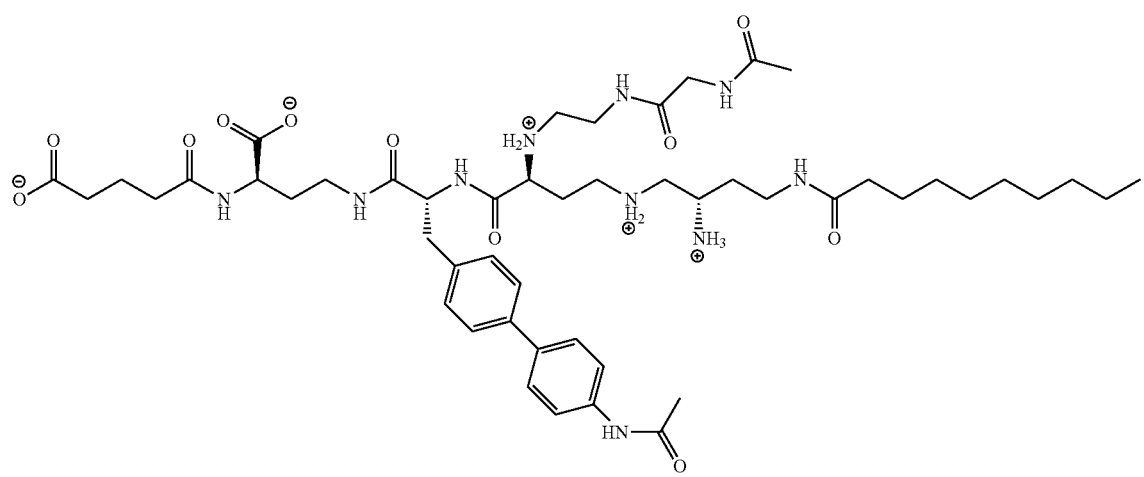
8AEXDabpBp
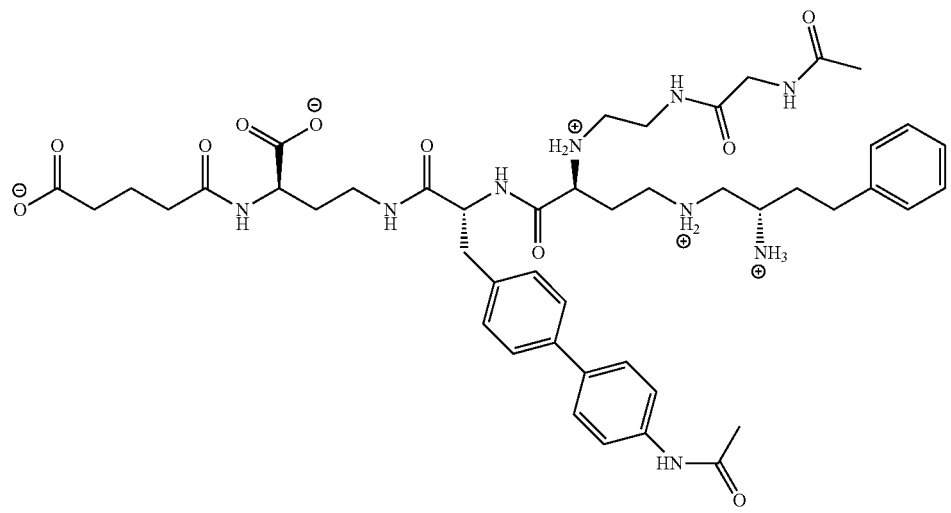
BnmAEXDabpBp

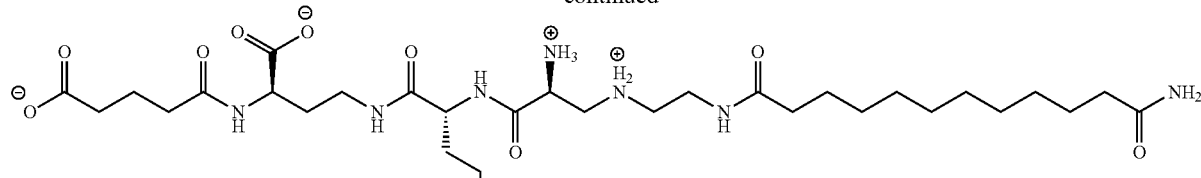

DH20_Dmn

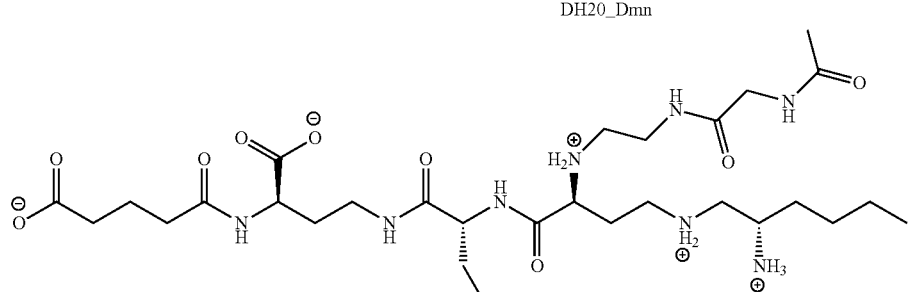

AcG4NdiAEDabNap

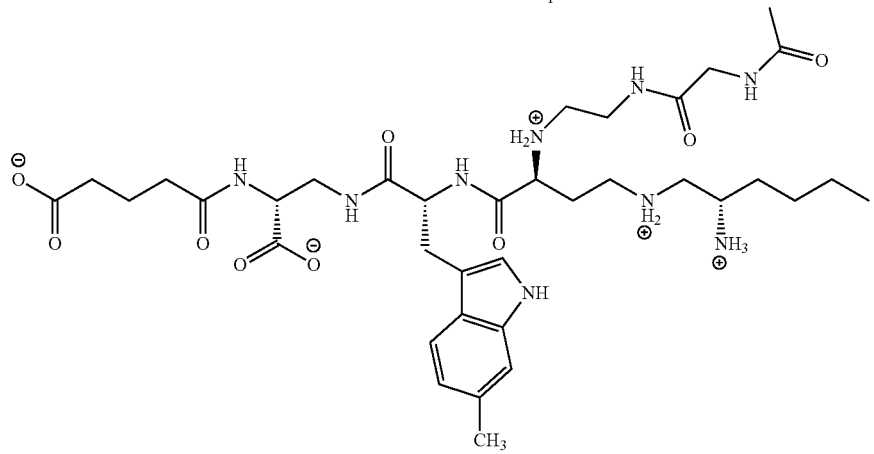

AcG4NdiAEDabmW

The different novel designs were first evaluated for their ability to stabilize the central helix of the Aβ peptide using molecular dynamics and compared to the published Pep 1 b and Dec-DETA ligands. A number of novel amino acid building blocks were synthesized in order to allow synthesis of the different designed ligands as exemplified in examples 1-22. Several examples of multistep synthesis both in solution and on solid phase ligands is also presented. A large number of potential ligands were subjected to molecular dynamics simulation (see below) and some of the synthesized ligands were also investigated with respect to ability to reduce fibril formation and especially the ability to reverse the toxic reduction of electrophysiological gamma-oscillation by the Aβ-peptide.

Effects of Ligands on the Stability of $A\beta_{13-26}$

During the implicit solvent simulations using GBMV II, Aβ13-26 is found unfolded in absence of ligands as backbone heavy atoms average RMSD is ~4 Å and αHBs<2

(Table 1). On the other hand Aβ$_{13-26}$ with most of the ligands is still in a helical state with average RMSD<2 Å and aHBs 3-6 (Table 1). A number of the novel "straddling/clamping" ligands designed to cover several surfaces of the Aβ-peptide stabilizes Aβ$_{13-26}$ substantially better than the first generation ligand Pep1b as is seen in average values of aHBs count and backbone RMSD (Table 1).

Explicit solvent simulations of Aβ$_{13-26}$ with selected designed ligands display consistency with the result from the simulations using implicit solvent on the corresponding ligands. The ligands that give highly retained helicity with the implicit solvent model GBMV II do so in explicit solvent as well (Table 2).

TABLE 1

Parameters from complexes of Aβ$_{13-26}$ with different designed ligands after 100 ns molecular dynamics simulations at 360 K (using an implicit solvent (GBMVII) model) displaying that complexes with the new "straddling" ligands retain the α-helical structure of the Aβ-peptide to a higher degree than the first generation of ligands (Dec-DETA and Pep1b).

| ligand name | Average αHBs | Average RMSD Backbone heavy atoms (Å) | Average helicity (torsion angle) | Average helicity (DSSP) |
|---|---|---|---|---|
| Aβ13-26 (alone) | 1.62 | 3.88 | 0.53 | 0.33 |
| Dec-DETA | 4.41 | 0.84 | 0.90 | 0.73 |
| pep1b | 4.56 | 0.75 | 0.87 | 0.73 |
| RO9_pep2 | 3.73 | 1.21 | 0.74 | 0.55 |
| pBpDab | 4.34 | 0.91 | 0.84 | 0.71 |
| pBpOrn | 3.87 | 0.88 | 0.79 | 0.61 |
| DmnDab | 4.86 | 0.83 | 0.89 | 0.81 |
| DmnOrn | 4.91 | 0.97 | 0.89 | 0.82 |
| MDAEDabWLDabdE | 5.55 | 0.72 | 0.98 | 0.93 |
| RdWDabdE | 3.47 | 1.35 | 0.78 | 0.57 |
| DecAEDabWDabdE | 5.46 | 0.81 | 0.96 | 0.90 |
| DodecAEDabWDabdE | 5.49 | 0.83 | 0.96 | 0.90 |
| AcGdiAEDab | 4.33 | 1.68 | 0.78 | 0.73 |
| 6NAEDab | 5.16 | 0.77 | 0.91 | 0.85 |
| AcG6NdiAEDabmW | 5.06 | 0.87 | 0.92 | 0.85 |
| Ac4NdiAEDabpBp | 5.26 | 0.76 | 0.94 | 0.88 |
| AcG4NdiAEDabDmn | 4.90 | 1.02 | 0.92 | 0.84 |
| AcG4NdiAEDabNap | 4.22 | 1.55 | 0.76 | 0.69 |
| AcG4NdiAEDabmW | 3.99 | 1.59 | 0.71 | 0.66 |
| DH18 | 5.20 | 0.70 | 0.94 | 0.86 |
| DecAPDabpBpOrnSu | 4.79 | 0.86 | 0.82 | 0.75 |
| DecAEDab | 5.12 | 0.78 | 0.93 | 0.86 |
| DecAPDabmW | 3.81 | 1.61 | 0.71 | 0.61 |
| DecAPDabmWOrnGla | 5.18 | 0.77 | 0.94 | 0.87 |
| DecAPDabmWOrnSu | 3.40 | 2.21 | 0.67 | 0.53 |
| RO13_Pep3 | 4.06 | 1.91 | 0.76 | 0.68 |
| AEOrnDab | 4.44 | 1.14 | 0.86 | 0.74 |
| DapDab | 4.92 | 0.82 | 0.89 | 0.81 |
| 6NAEAEDap | 3.55 | 1.70 | 0.67 | 0.55 |
| DH20 | 5.02 | 0.75 | 0.91 | 0.83 |
| ADecAEDap | 3.78 | 1.56 | 0.68 | 0.58 |
| 8NAEDab | 4.48 | 1.01 | 0.84 | 0.73 |
| 4NAEDab | 4.72 | 1.19 | 0.86 | 0.79 |
| RfqOrnSu | 3.41 | 1.67 | 0.71 | 0.54 |
| RaxDOrnSuc | 4.86 | 0.82 | 0.86 | 0.80 |
| hBpDab | 4.35 | 1.06 | 0.85 | 0.72 |
| hBpOrn | 4.65 | 0.92 | 0.87 | 0.77 |
| PyAOrn | 2.68 | 1.65 | 0.65 | 0.38 |
| PyADab | 4.49 | 0.98 | 0.84 | 0.74 |
| BRPyADab | 5.12 | 0.87 | 0.92 | 0.86 |
| 8AEDabpBp | 4.27 | 1.12 | 0.78 | 0.67 |
| 8AEDabDmnDabGla | 5.30 | 1.21 | 0.92 | 0.88 |
| BnmAEDabDmnDabGla | 5.21 | 0.98 | 0.93 | 0.87 |
| 6AEDabDmnDabGla | 5.05 | 1.30 | 0.90 | 0.84 |
| BnAEDabDmnDabGla | 5.04 | 1.17 | 0.88 | 0.83 |
| 8AEDabBpDabGla | 4.51 | 0.98 | 0.83 | 0.72 |
| 6AEDabBpDabGla | 4.93 | 0.95 | 0.90 | 0.82 |
| BnmAEdabpBp | 5.09 | 0.81 | 0.89 | 0.82 |
| BnAEdabpBp | 5.11 | 0.92 | 0.93 | 0.85 |
| MDAEDabmDmnLDabGla | 3.79 | 1.24 | 0.73 | 0.58 |
| DH18_Dmn | 5.26 | 0.76 | 0.95 | 0.89 |
| DH20_Dmn | 5.41 | 0.61 | 0.95 | 0.90 |
| 15_Hexyl | 5.34 | 0.75 | 0.96 | 0.90 |
| BnmAEXDabpBp | 4.94 | 0.88 | 0.93 | 0.83 |
| 8AEXDabpBp | 4.10 | 1.23 | 0.82 | 0.69 |

TABLE 2

Parameters from complexes of Aβ$_{13-26}$ with selected designed ligands after 100 ns molecular dynamics simulations at 360 K (using an explicit solvent model) displays a consistency in that ligands that give a highly retained helicity with the GBMVII model do so also with explicit water present.

| ligand name | Average αHBs | Average RMSD Backbone heavy atoms (Å) | Average helicity (torsion angle) | Average helicity (DSSP) |
|---|---|---|---|---|
| Dec-DETA | 3.88 | 0.89 | 0.89 | 0.64 |
| Pep1b | 4.07 | 0.87 | 0.90 | 0.68 |
| pBpDab | 3.83 | 1.39 | 0.82 | 0.66 |
| DmnDab | 4.47 | 0.91 | 0.93 | 0.78 |
| MDAEDabWLDabdE | 5.05 | 0.88 | 0.95 | 0.86 |
| DecAEDabWDabdE | 4.76 | 0.99 | 0.95 | 0.82 |
| 6NAEDab | 3.36 | 1.87 | 0.75 | 0.59 |
| Ac4NdiAEDabpBp | 5.14 | 0.86 | 0.97 | 0.88 |
| AcG4NdiAEDabDmn | 4.52 | 0.86 | 0.91 | 0.79 |
| DH18 | 5.03 | 0.86 | 0.97 | 0.87 |
| RO13_Pep3 | 3.93 | 1.36 | 0.85 | 0.68 |
| DH20 | 4.49 | 0.87 | 0.93 | 0.79 |
| 8NAEDab | 4.59 | 0.90 | 0.95 | 0.82 |
| 4NAEDab | 4.38 | 0.95 | 0.90 | 0.74 |
| RdWDabdE | 4.30 | 1.13 | 0.85 | 0.70 |
| 8AEDabpBp | 4.39 | 0.82 | 0.93 | 0.78 |
| BnmAEDabDmnDabGla | 3.24 | 1.40 | 0.66 | 0.48 |
| 6AEDabDmnDabGla | 3.22 | 1.33 | 0.69 | 0.63 |
| BnAEDabDmnDabGla | 3.73 | 1.81 | 0.69 | 0.49 |
| 8AEDabBpDabGla_2 | 4.63 | 1.03 | 0.85 | 0.75 |
| 6AEDabBpDabGla | 3.97 | 1.00 | 0.90 | 0.64 |
| DH18_Dmn | 4.92 | 0.86 | 0.81 | 0.78 |
| 15_Hexyl | 4.86 | 0.80 | 0.80 | 0.73 |
| 8AEXDabpBp | 4.16 | 1.21 | 0.78 | 0.61 |

The "straddling" or "clamping" of the central helix of the Aβ-peptide by the designed ligands can be visualized in FIG. 1. That the designed ligands forces Aβ retain a higher number of alfa-hydrogen bonds (aHBs) is clearly seens in the histograms showing the relative frequencies of the appearance of the Aβ structures sorted out by the number of n aHBs of the Aβ middle region (FIG. 2).

The contact maps of interactions (FIG. 3) show that the designed ligands give contacts essentially with all heavy atoms of the ligands and that contact is achieved with all the targeted regions in Aβ for hydrophobic and polar contacts.

Effect of the Ligands on Gamma Oscillations in Hippocampal Slice Preparations

LFP recordings in area CA3 revealed control gamma oscillations of $5.58 \cdot 10^{-09} \pm 3.98 \cdot 10^{-10}$ V$^2$ power (n=16). Incubation of slices for 15 min with 50 nM Aβ1-42 prior to kainate superfusion significantly decreased gamma oscillation power ($1.97 \cdot 10^{-09} \pm 2.98 \cdot 10^{-10}$ V$^2$; n=12; U=188.0, n1=16, n2=12, p<0.0001 two-tailed). Addition of the ligands DH18 (250 nM), and DH20 (250 nM) to the 15 min incubation with 50 nM Aβ resulted in complete prevention of the Aβ-induced decrease of kainate-induced gamma oscillations ($7.59 \cdot 10^{-09} \pm 6.31 \cdot 10^{-10}$ V$^2$; n=13; DH18 vs control kainate: U=161.0, n1=16, n2=13, p=0.012 two-tailed; FIG. 4); ($7.59 \cdot 10^{-09} \pm 6.31 \cdot 10^{-10}$ V$^2$; n=16; DH20 vs control kainate: U=164.0, n1=16, n2=16, p=0.184 two-tailed; FIG. 5).

Control experiments for the ligands, DH18 and DH20 showed that neither of these ligands had an effect on kainate-induced gamma oscillations in the absence of Aβ (Pep1 b: 4.38 $10^{-09} \pm 2.65 \ 10^{-10}$ V$^2$; n=8; Dec-DETA: 5.55 $10^{-09} \pm 5.23 \ 10^{-10}$ V$^2$; n=8; FIG. 9; AEDabDab: 5.39 $10^{-09} \pm 3.49 \ 10^{-10}$ V$^2$; n=8; DH18: 6.22 $10^{-09} \pm 4.57 \ 10^{-10}$ V$^2$; n=8; DH20: 4.98 $10^{-09} \pm 3.66 \ 10^{-10}$ V$^2$; n=8; FIG. 6). With the previously reported ligand Pep1 b (250 nM) only partial prevention of the Aβ-induced decrease of kainate-induced gamma oscillations is obtained while DH18 and DH20 give complete prevention (FIG. 7). Thus, our data shows that novel ligands of the invention are more effective in preventing Aβ-induced degradation of network gamma oscillations.

Further experiments on gamma-oscillation in hippocampus slices show that that ligands DH-18, DH-20 and DH18_Dmn reverse Aβ-induced toxicity due to reduction of gamma oscillation and that these ligands are effective also at only a 1:1 ratio to Aβ1-42. (FIGS. 8 and 9).

Effect of Ligands on Fibril Formation by Aβ$_{1-42}$

Some amount of amorphous aggregates was found in all samples. Fibrils were formed by Aβ$_{1-42}$ when incubated alone. Aβ$_{1-42}$ incubated with Pep1 b fibrils were formed but to somewhat lesser extent. Incubations of Aβ$_{1-42}$ with novel ligands of the invention, DH18, DH20, DH18_Dmn and 8AEDabDmnDabGla all gave rise to less fibrils than with Aβ$_{1-42}$ alone as well as when compared to Aβ$_{1-42}$ together with Pep1 b.

The invention claimed is:

1. A compound selected from the group consisting of:

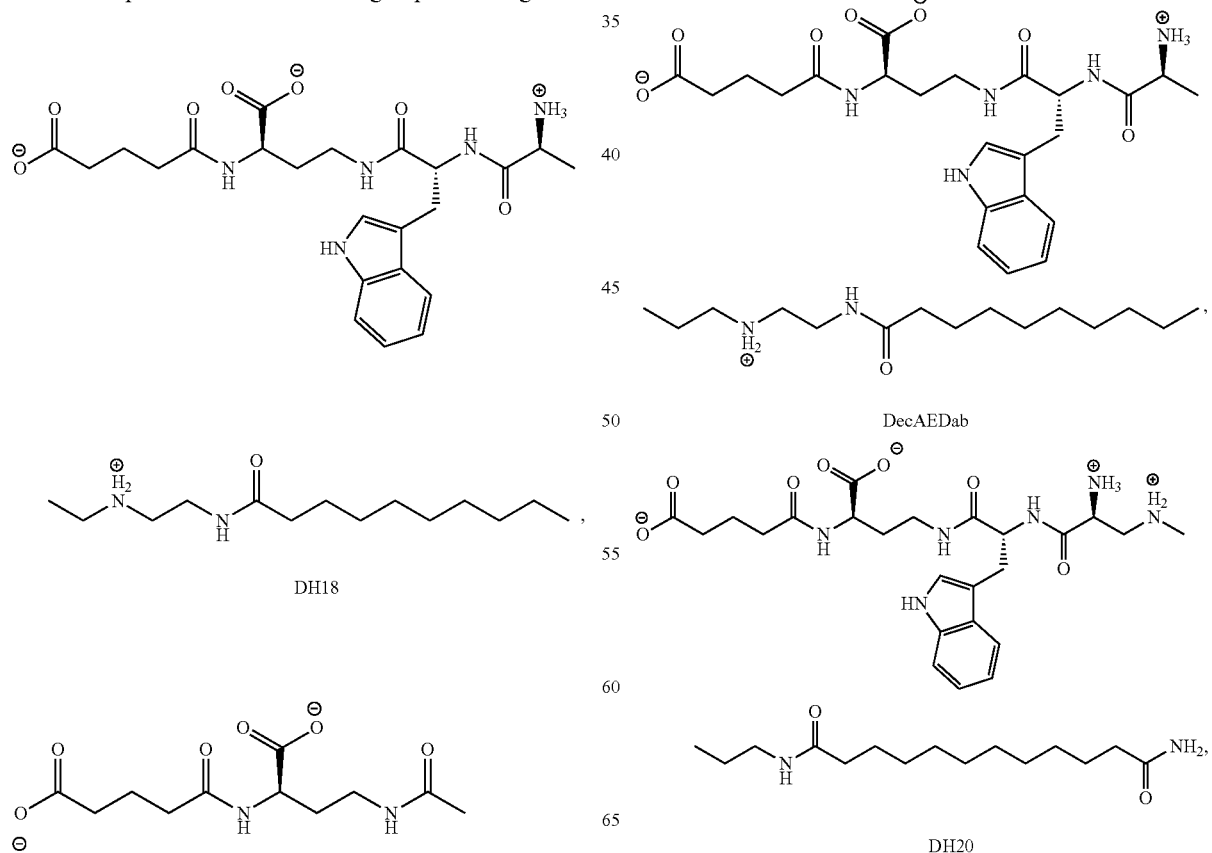

153
-continued
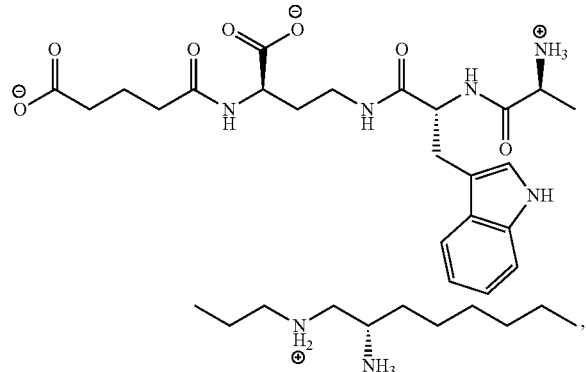
6NAEDab
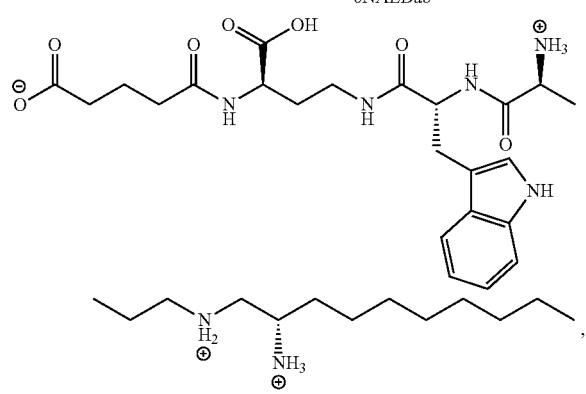
8NAEDAb
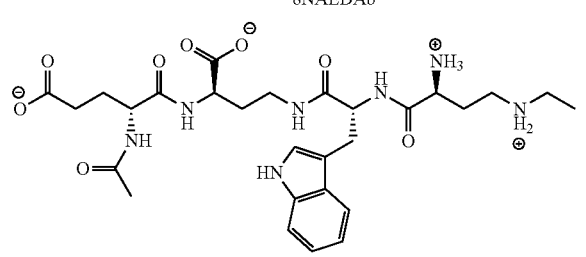
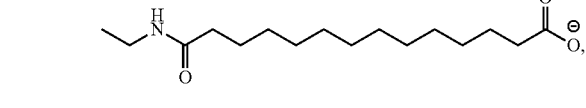
MDAEDabWLDabdE
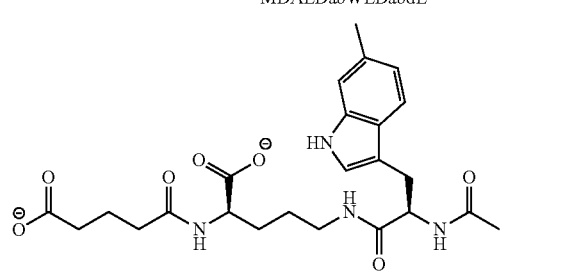
DecAPDabmWOrnGla
154
-continued
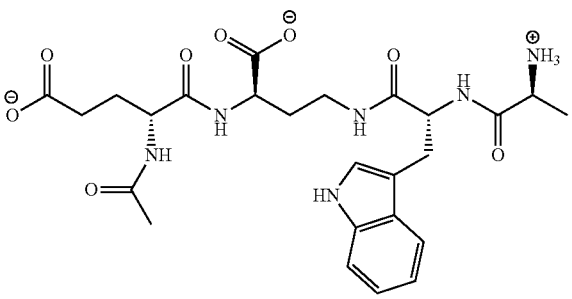
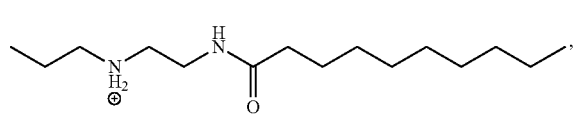
DecAEDabWDabdE
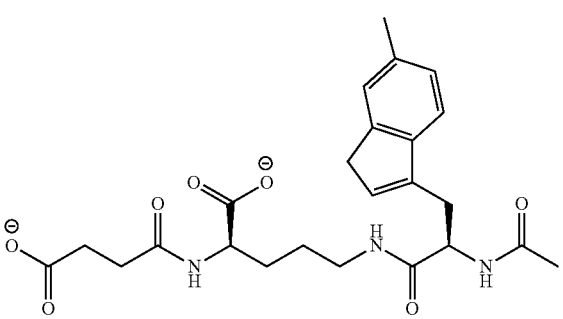
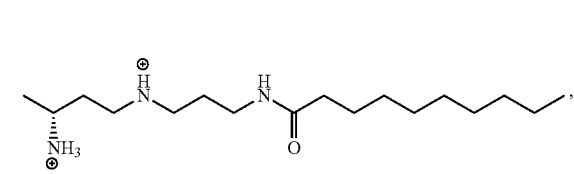
DecAPDabmWOrnSu
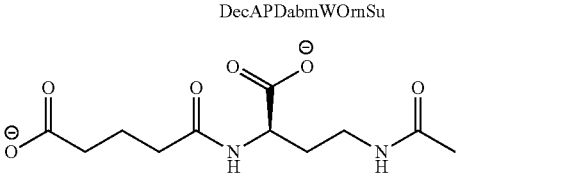
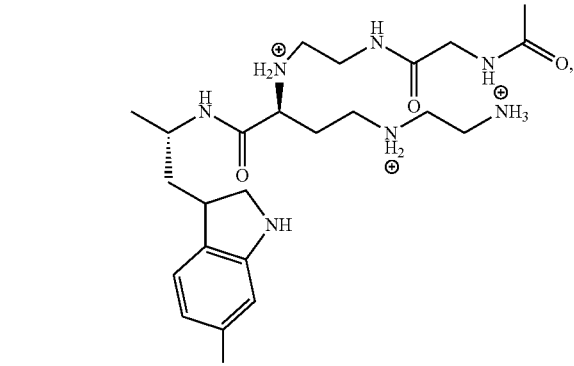
AcGdiAEDab

155
-continued
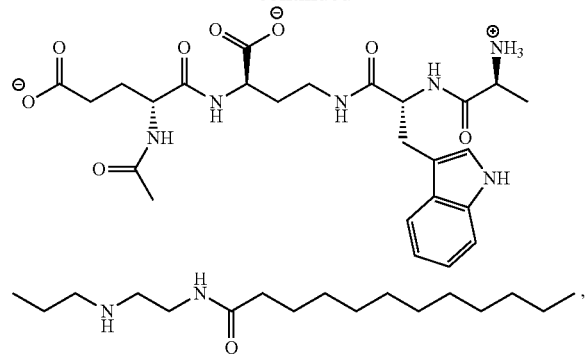
DodecAEDabWDabdE
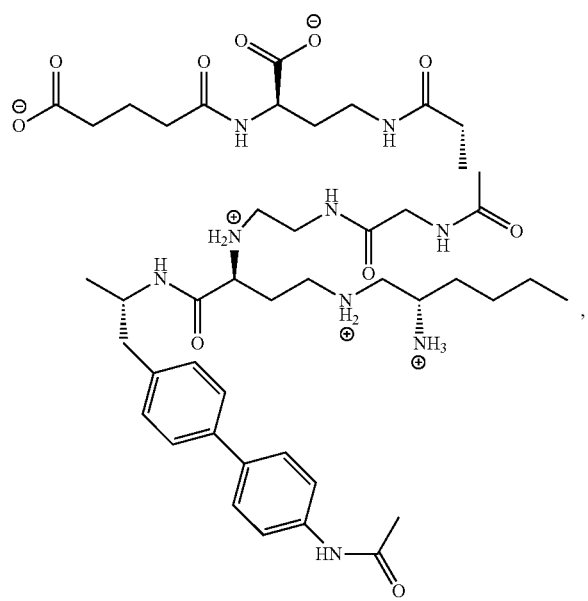
Ac4NdiAEDabpBp
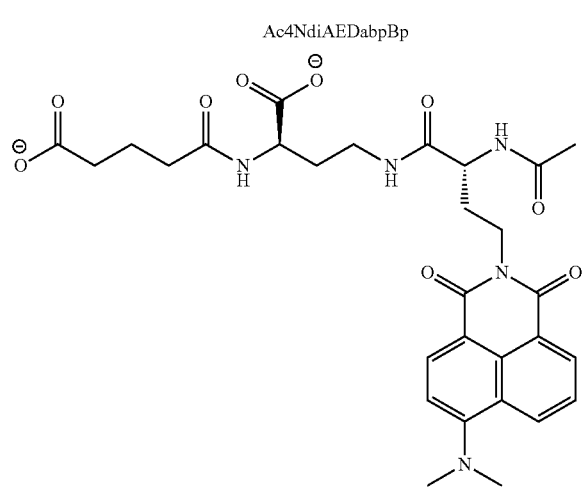
BnmAEDabDmnDabGla
156
-continued
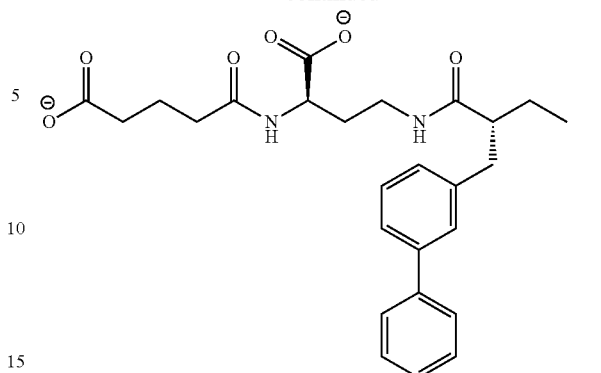
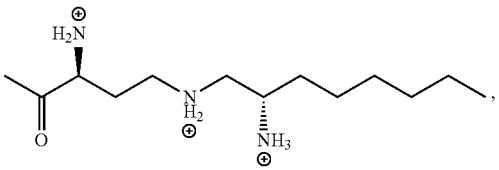
6AEDabBpDabGla
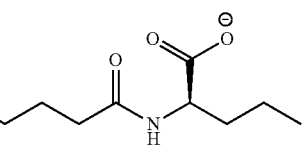
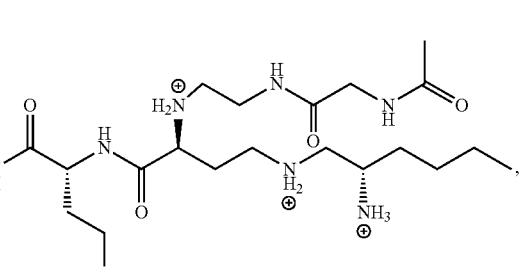
AcG4NdiAEDabDmn
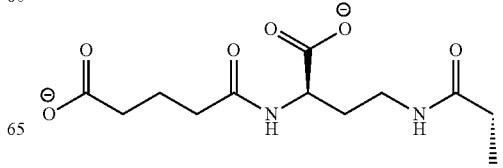

157
-continued
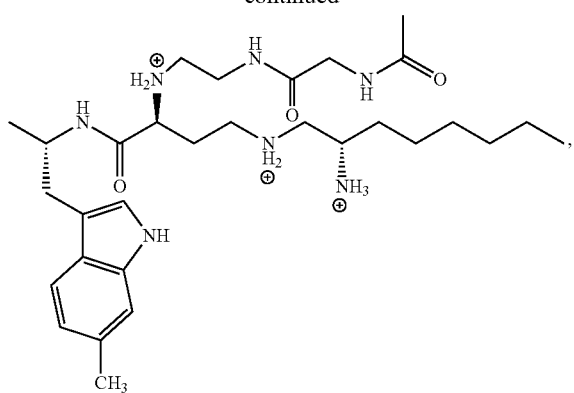
AcG6NdiAEDabmW
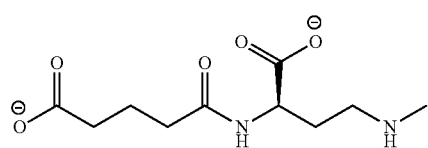
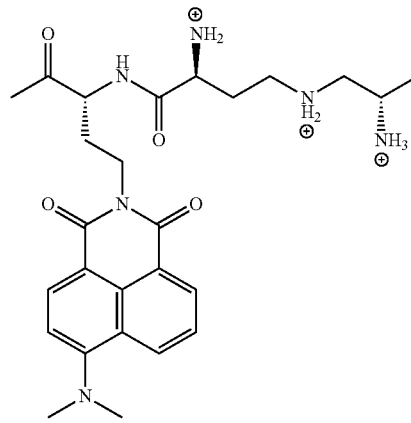
6AEDabDmnDabGla
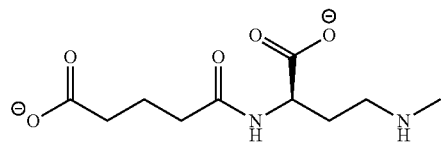
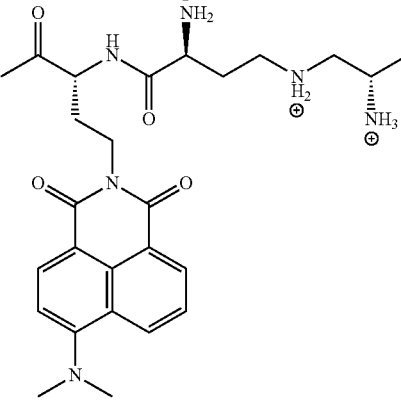
BnAEDabDmnDabGla
158
-continued
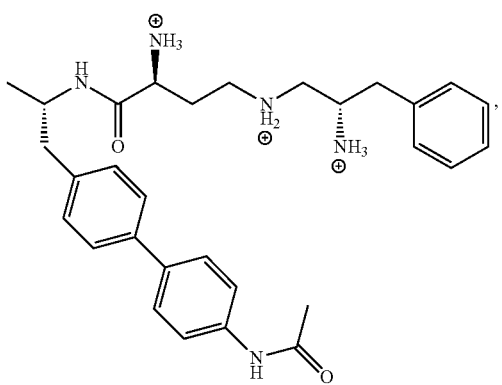
BnAEDabpBp
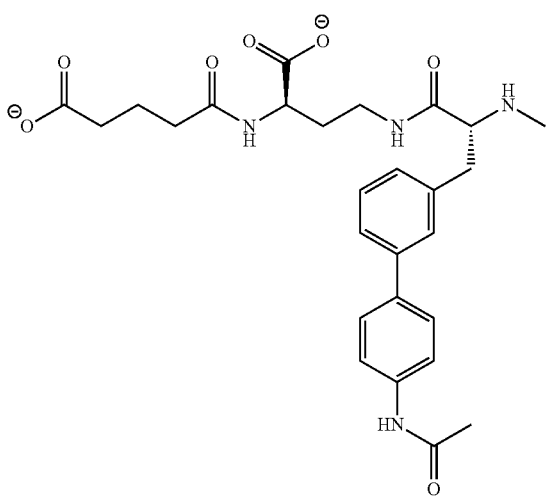
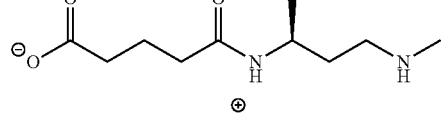
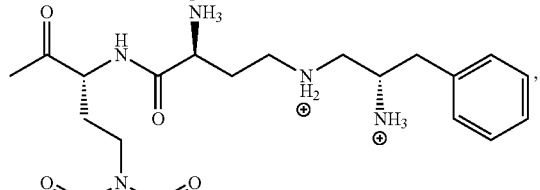
8AEDabBpDabGla
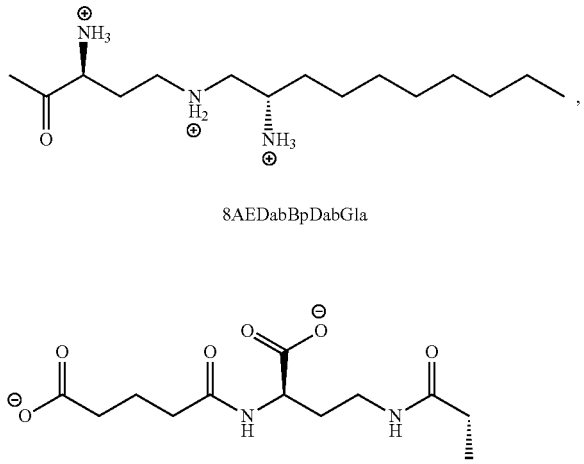
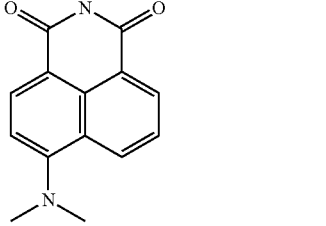

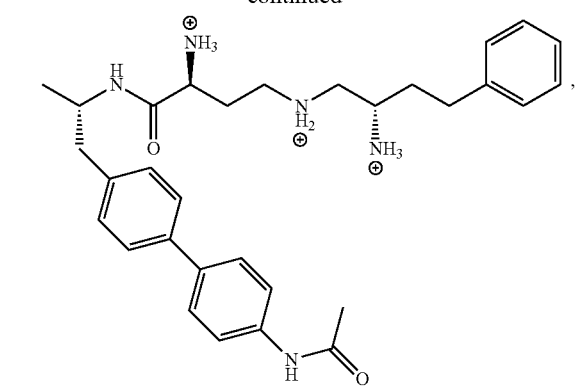
BnmAEDabpBp
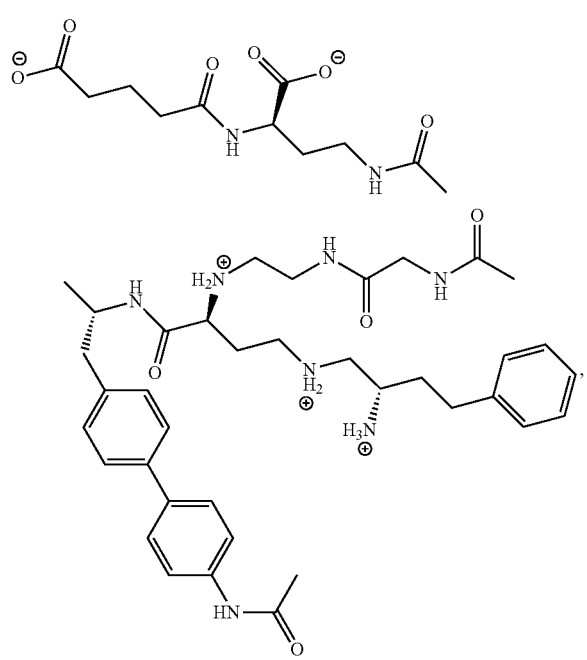
BnmAEXDabpBp
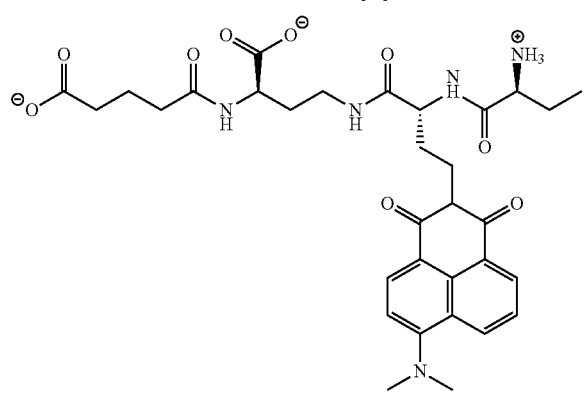
DH18_Dmn
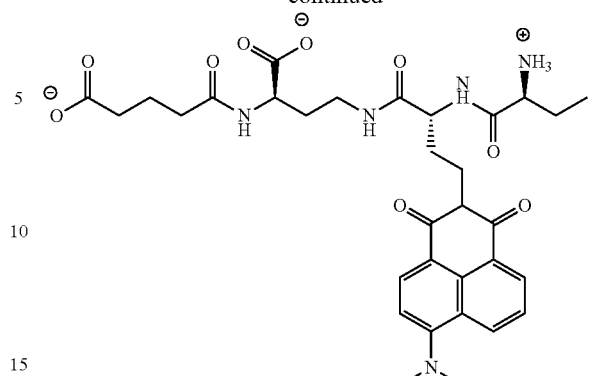
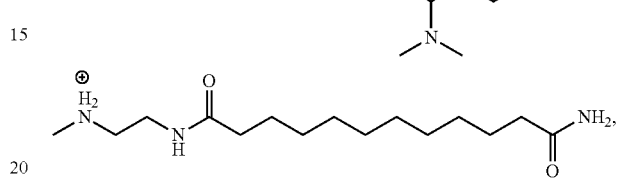
DH20_Dmn
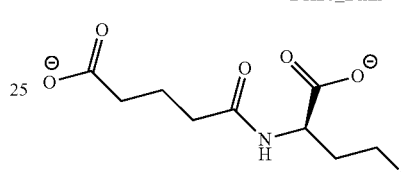
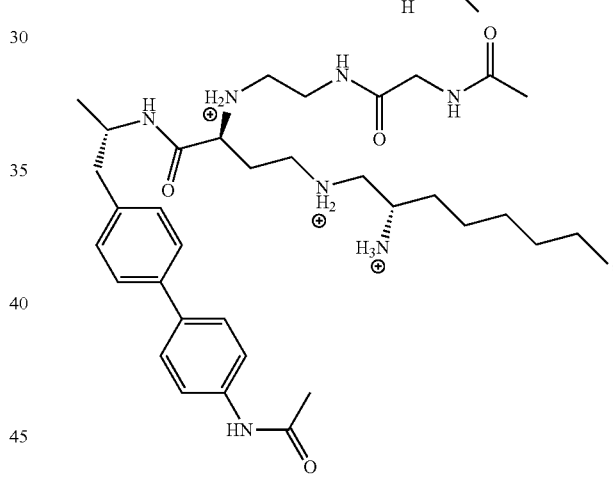
15_Hexyl
and
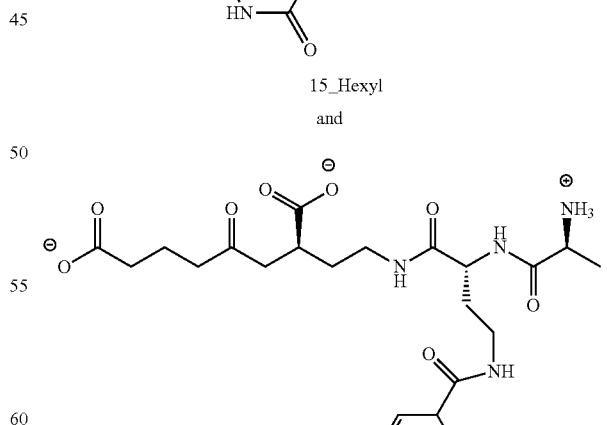

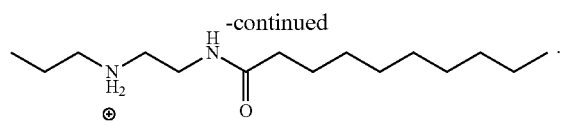
2. The compound according to claim 1, selected from the group consisting of:
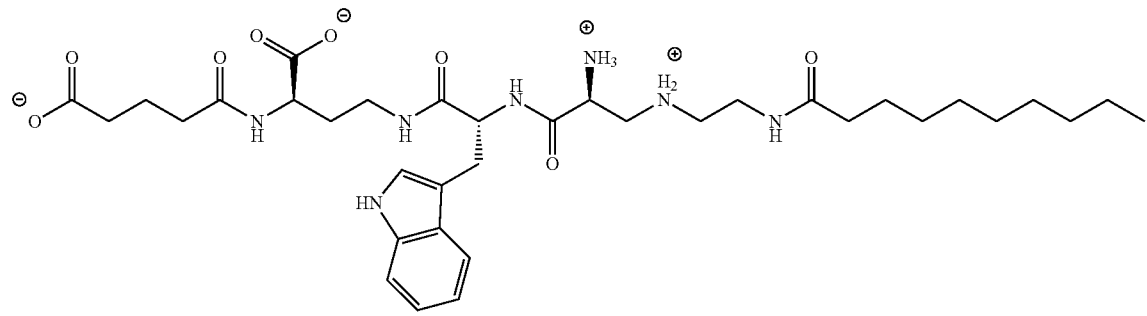
DH18
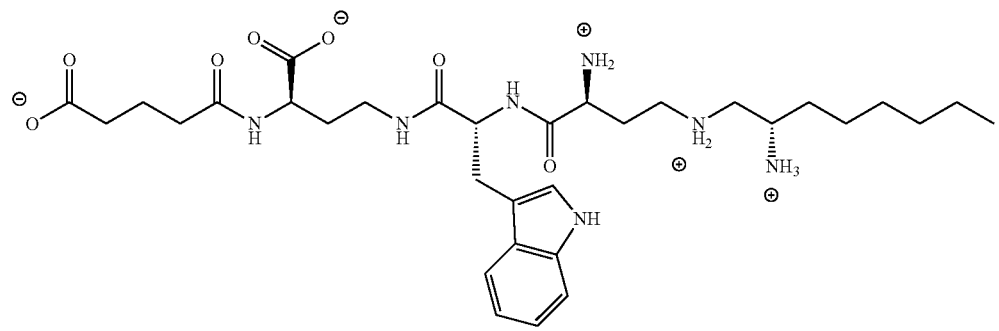
6NAEDab
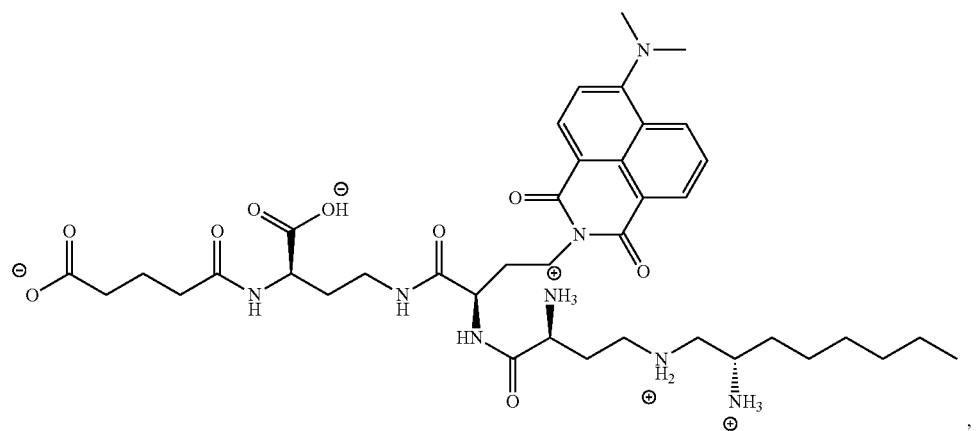
8AEDabDmnDabGla -continued
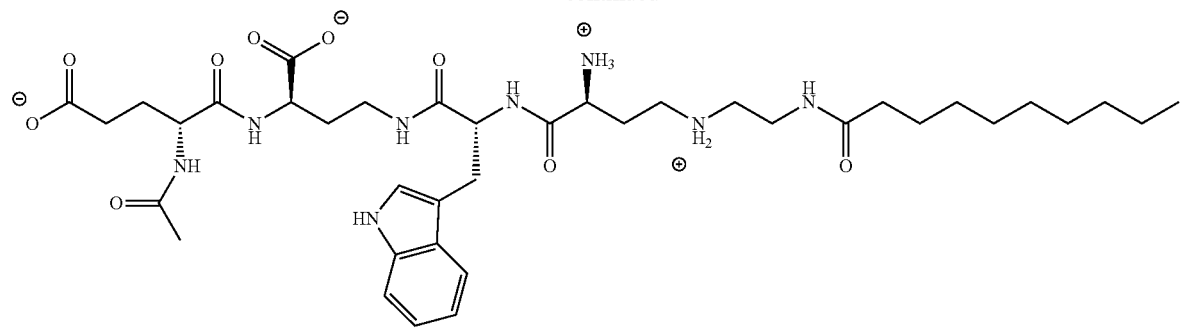
DecAEDabWDabdE
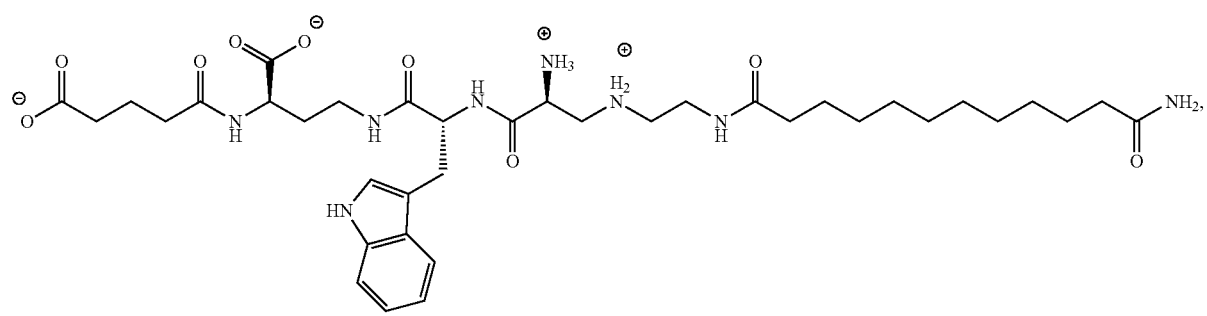
DH20
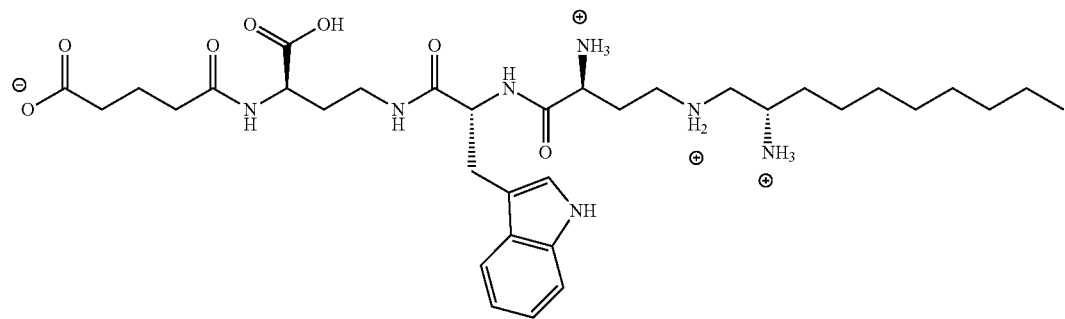
8NAEDAb
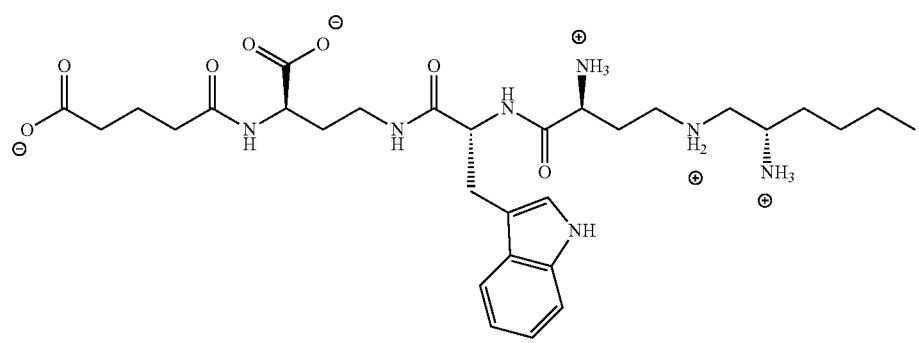
4NAEDAb

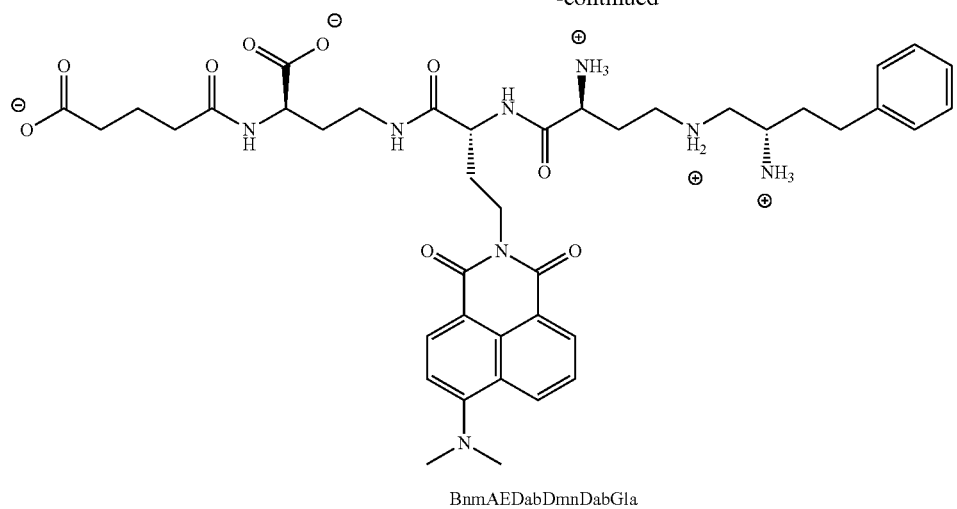
BnmAEDabDmnDabGla
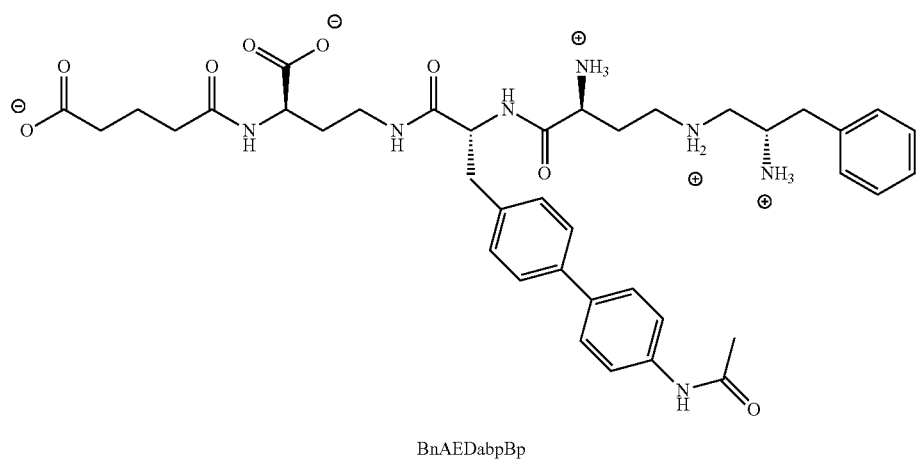
BnAEDabpBp
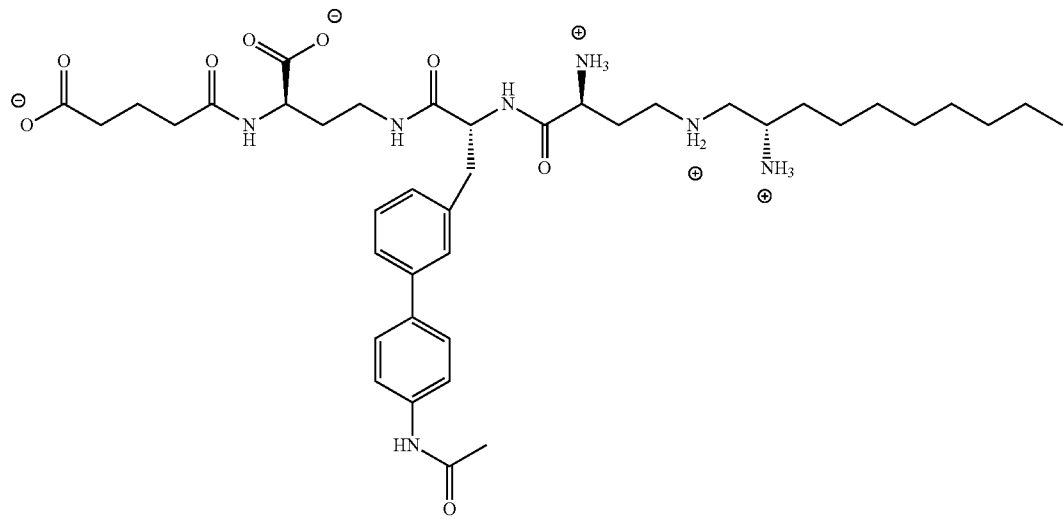
8AEDabBpDabGla

-continued
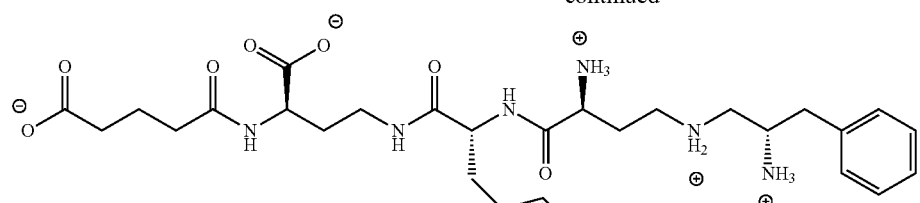
BnAEDabpBp
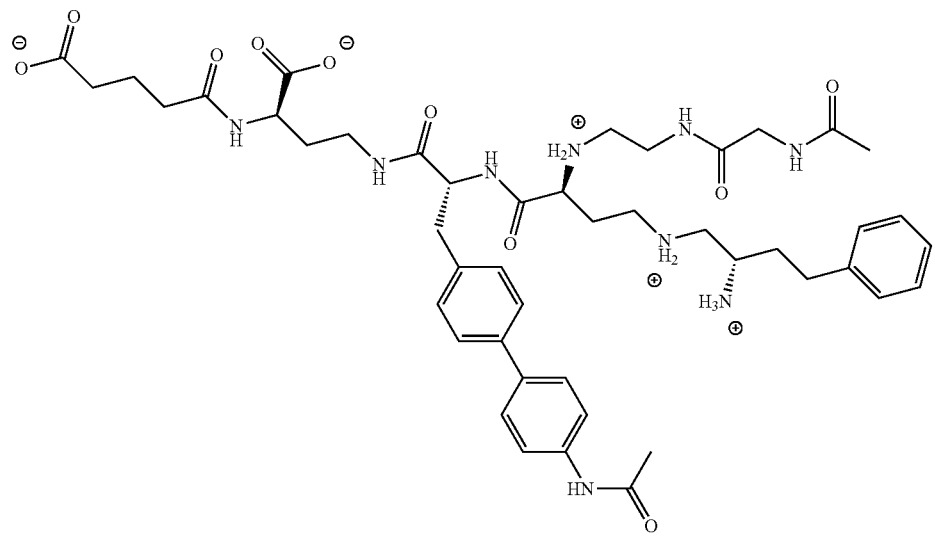
BnmAEXDabpBp
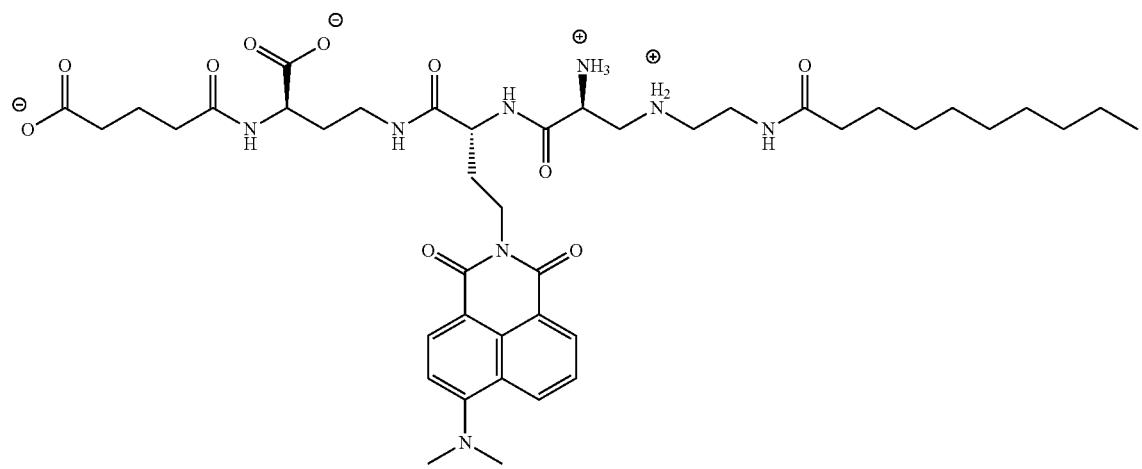
DH18_Dmn

-continued
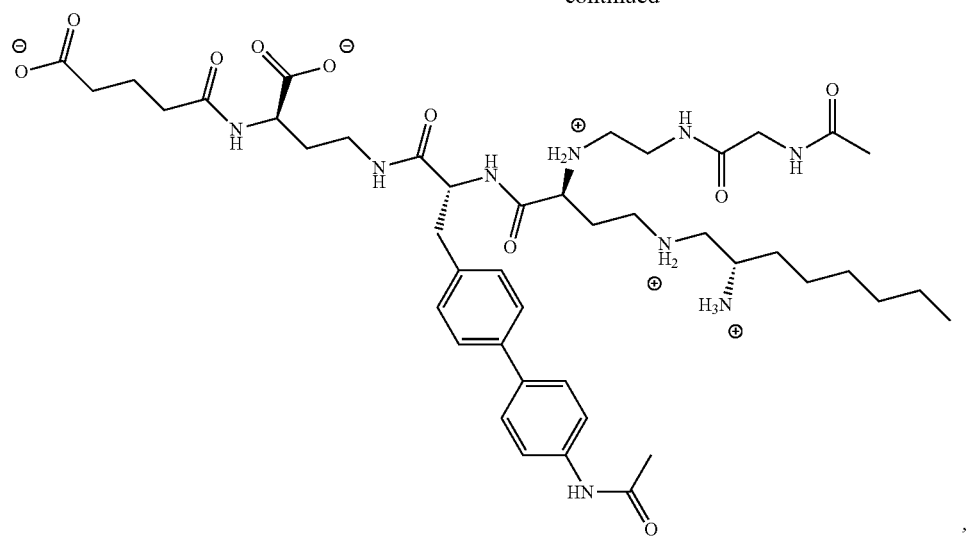
15_Hexyl
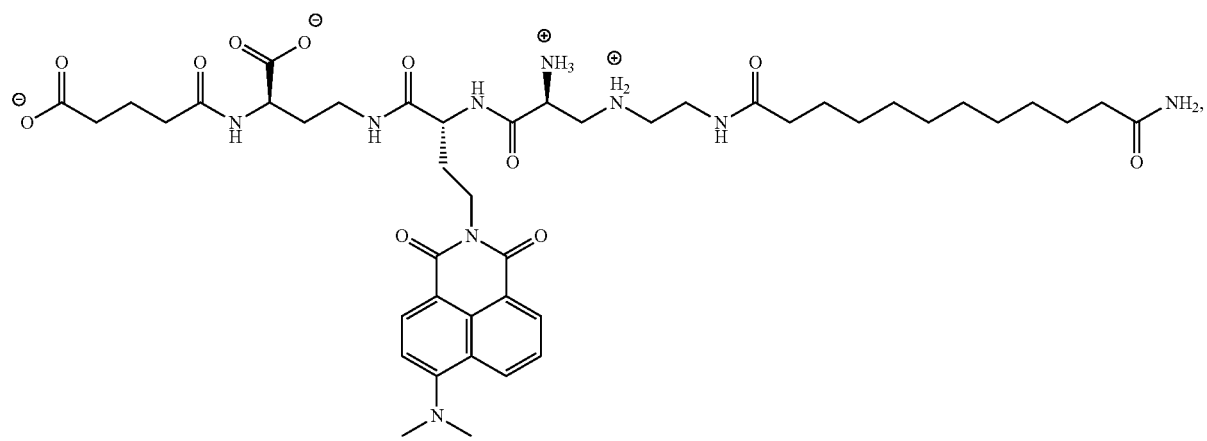
DH20_Dmn
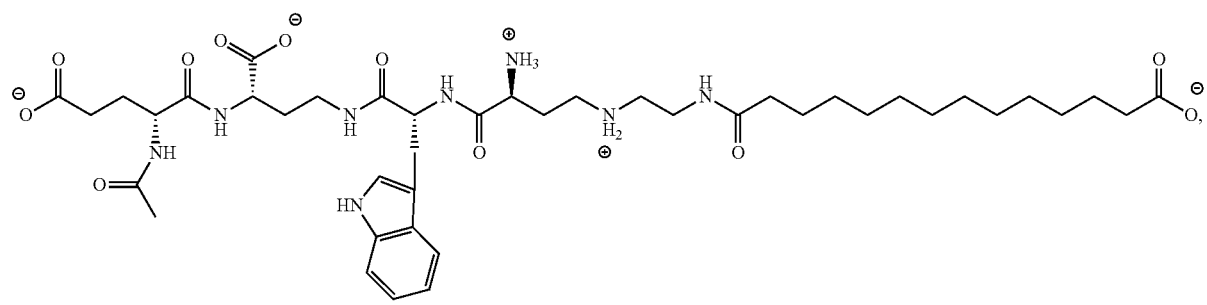
MDAEDabWLDabdE

-continued
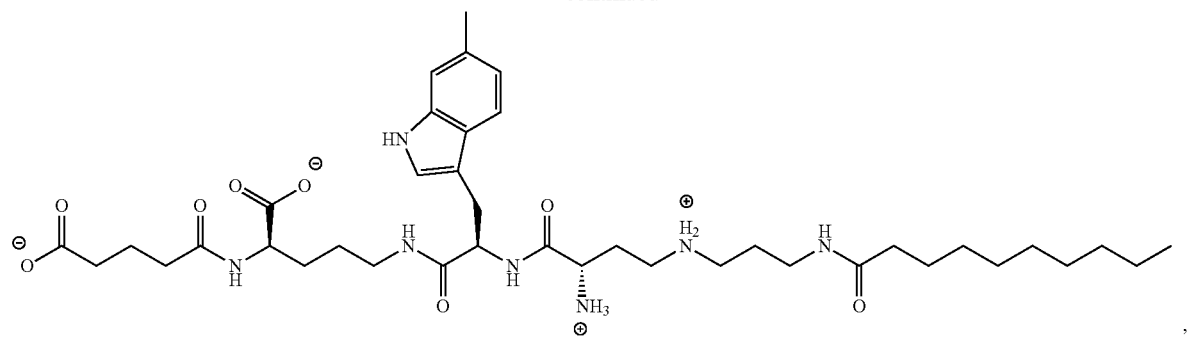
DecAPDabmWOrnGla
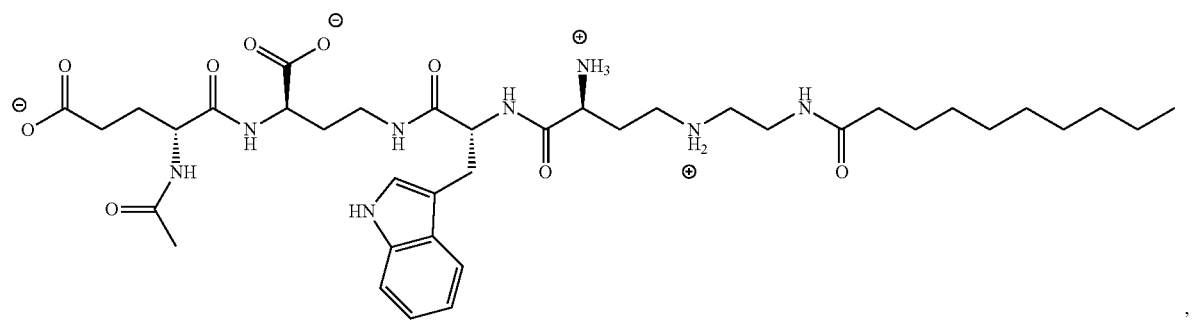
DecAEDabWDabdE
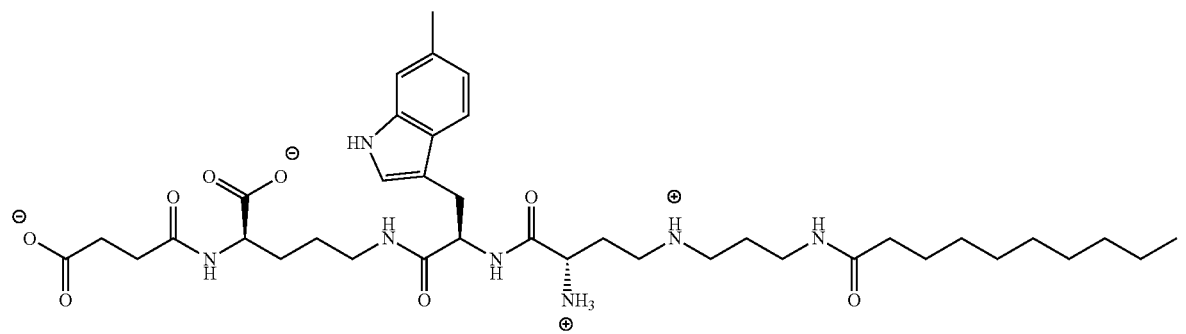
DecAPDabmWOrnSu
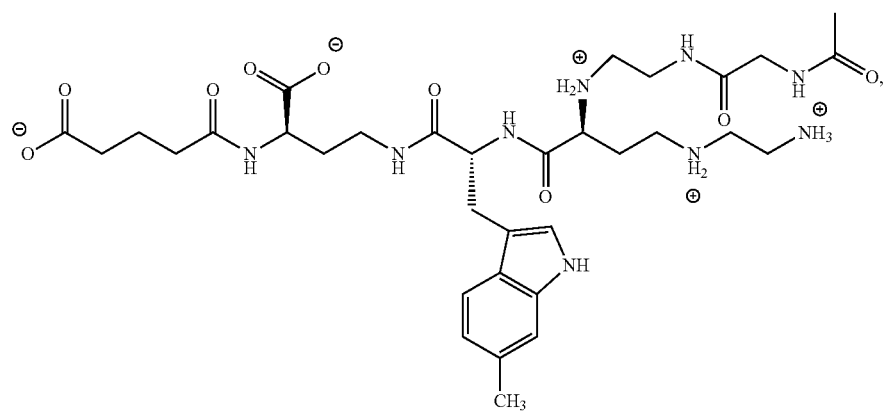
AcGdiAEDab -continued
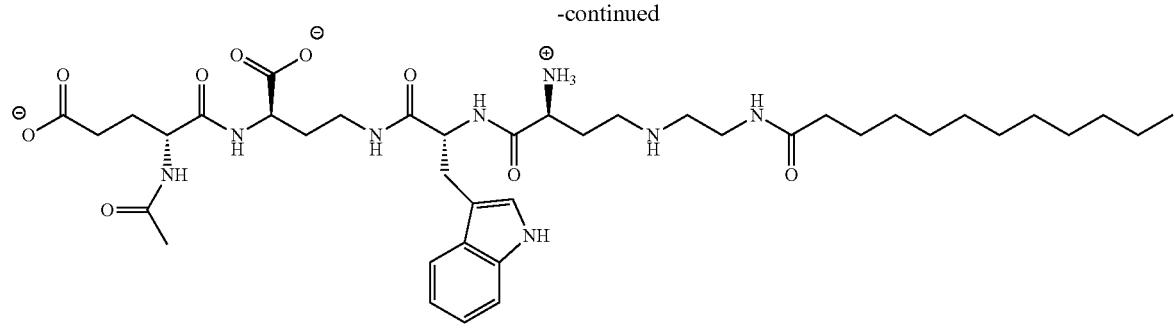
DodecAEDabWDabdE
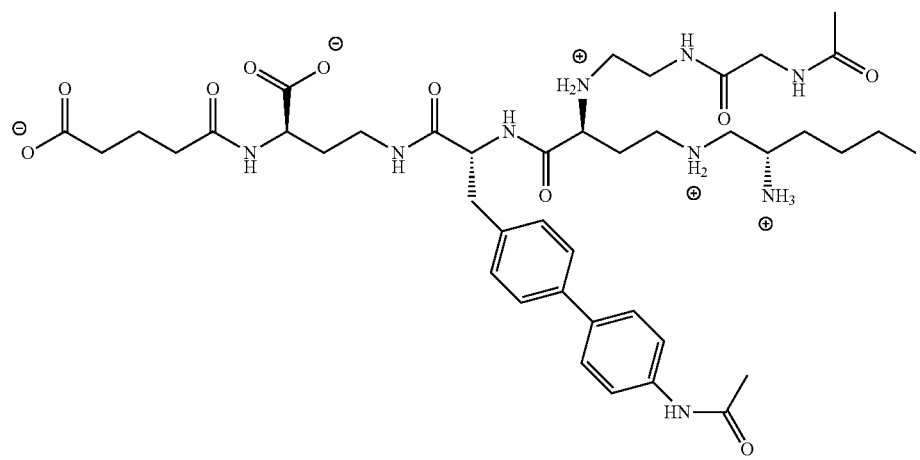
Ac4NdiAEDabpBp
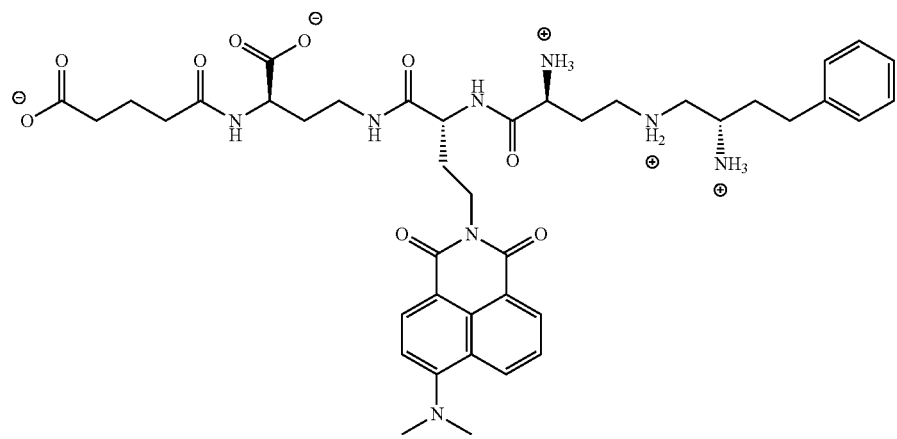
BnmAEDabDmnDabGla -continued
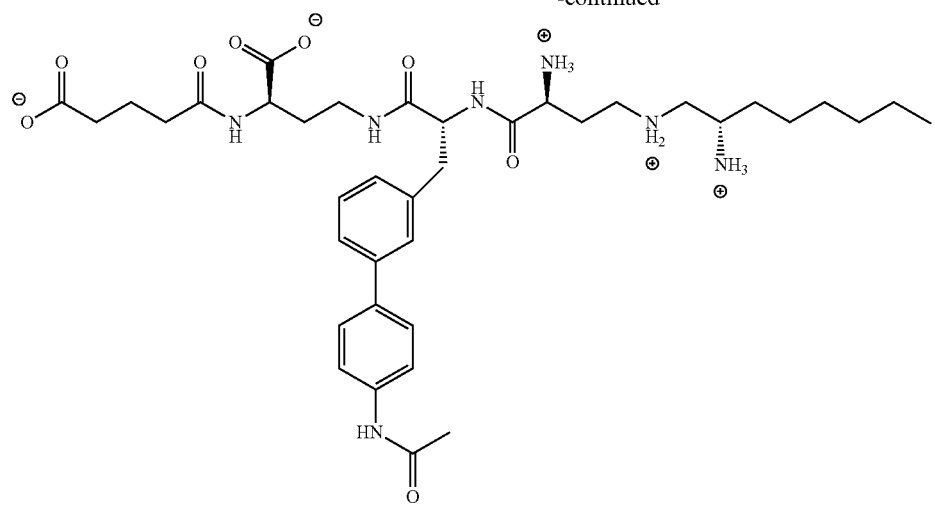
6AEDabBpDabGla
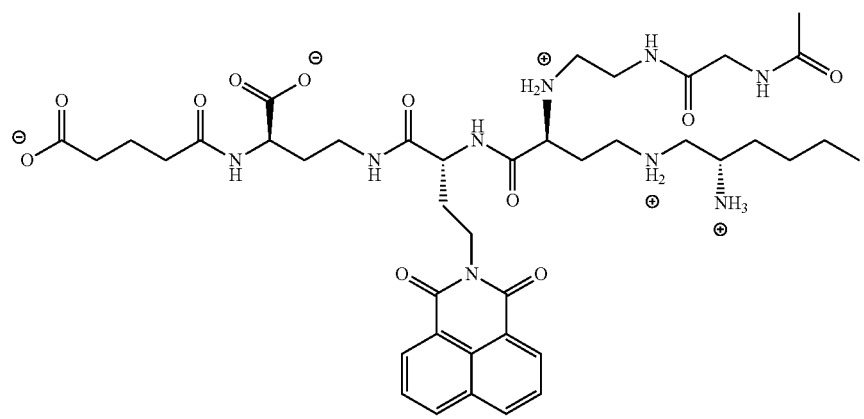
AcG4NdiAEDabDmn
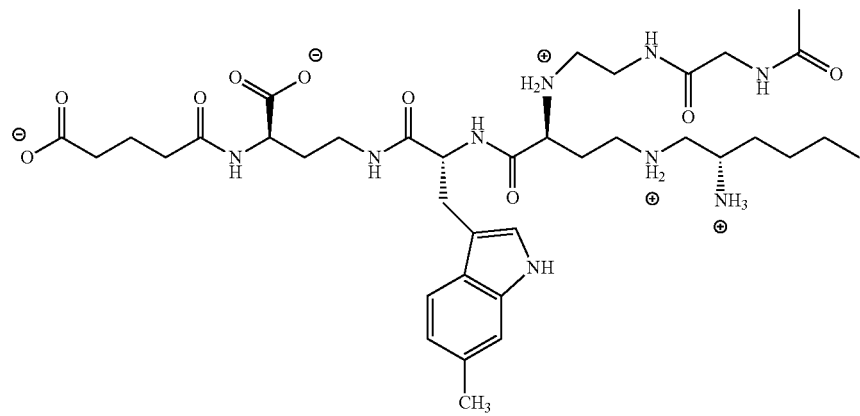
AcG6NdiAEDabmW
, and -continued
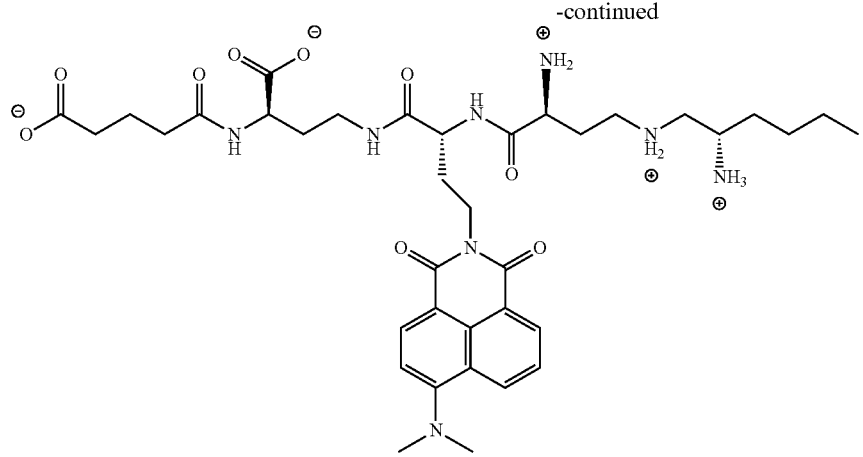
6AEDabDmnDabGla
25
3. A compound selected from the group consisting of:
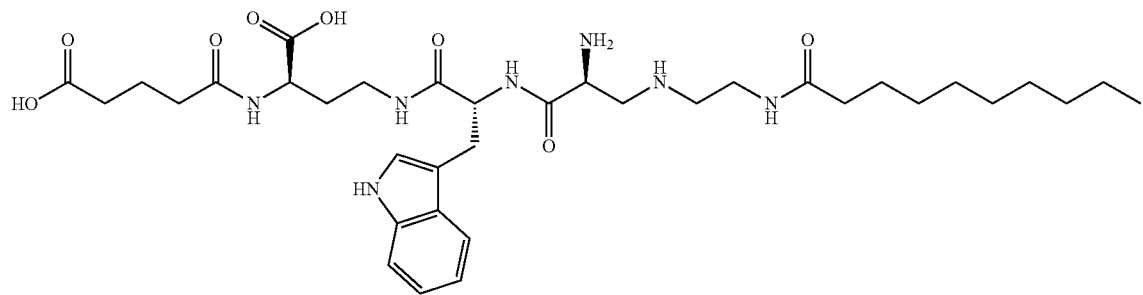 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]
(R)—N⁴—[N²—(N³—(N-decanoyl-2-aminoethyl)-(S)-2,
3-diaminopropionyl)-D-tryptophanyl]-N²-glutanoyl-2,
4-diaminobutanoic acid;
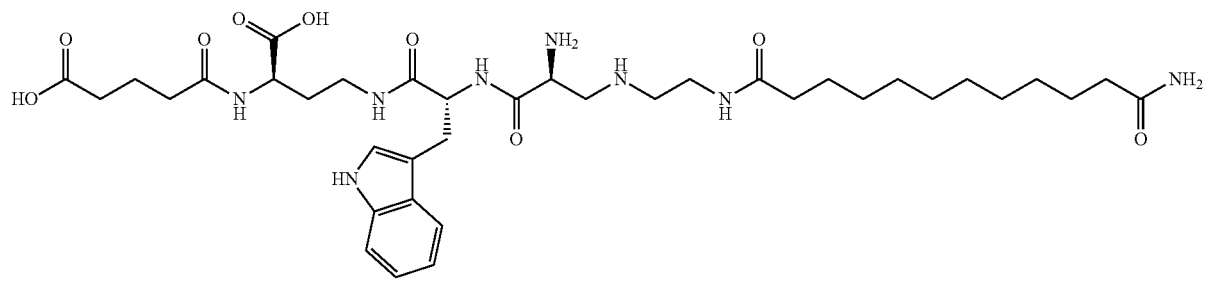 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid;
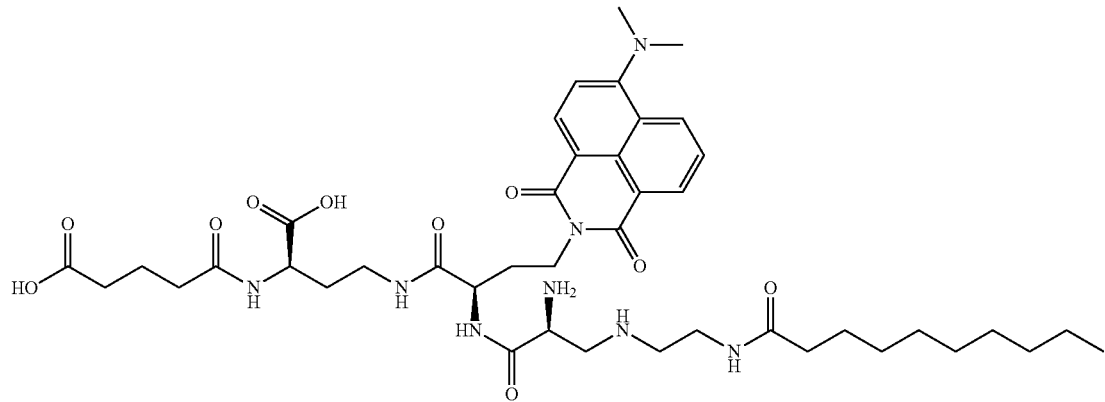 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)-AE-decanoyl;
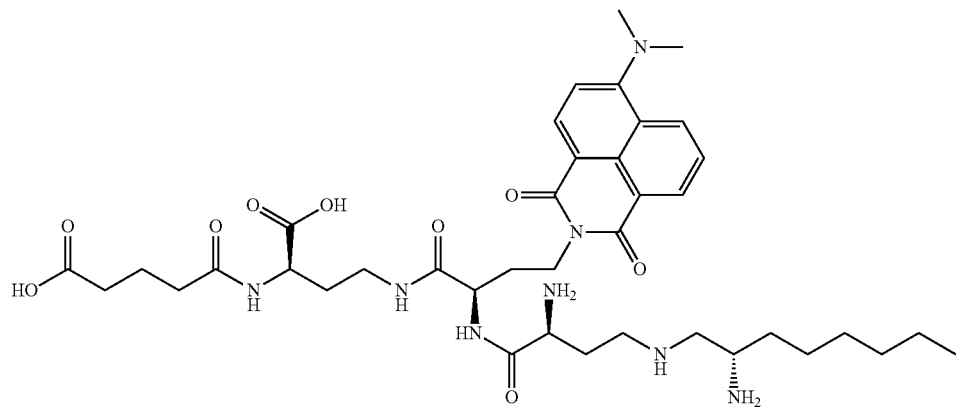 [SMILES: CCCCCC[C@H](N)CNCC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)—CH₂CH(NH₂)—C6; and
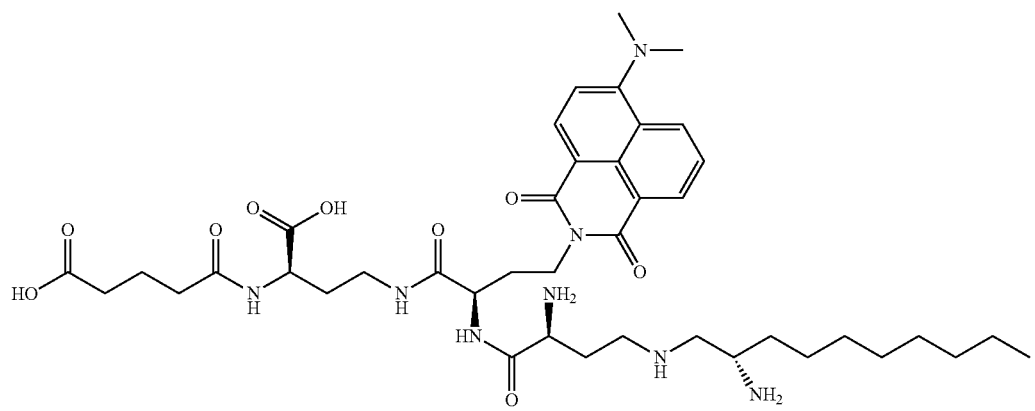 [SMILES: CCCCCCCC[C@H](N)CNCC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)—CH₂CH(NH₂)—C8.
4. The compound according to claim 3, selected from the group consisting of:

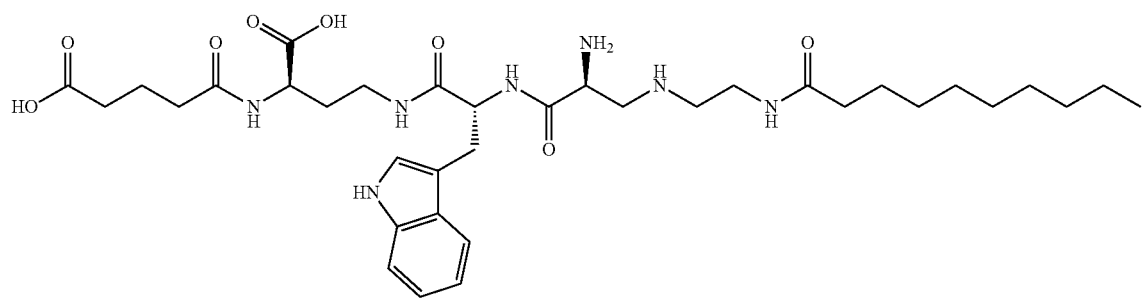 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]
(R)—N⁴—[N²—(N³—(N-decanoyl-2-aminoethyl)-(S)-2,
3-diaminopropionyl)-D-tryptophanyl]-N²-glutanoyl-2,
4-diaminobutanoic acid;
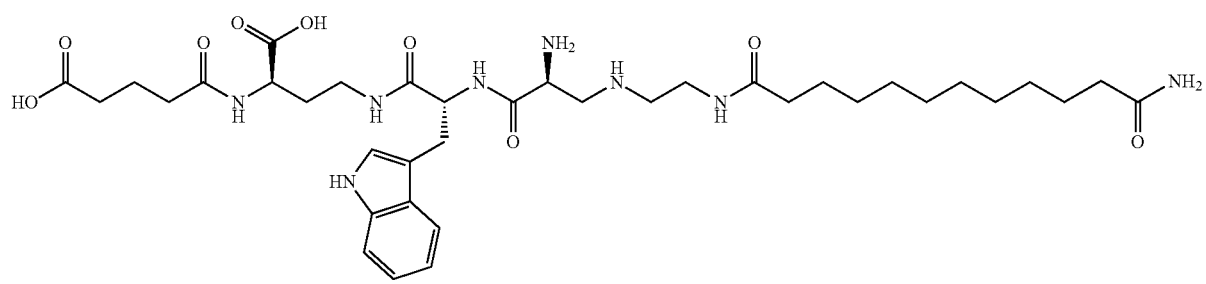 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]
(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid; and
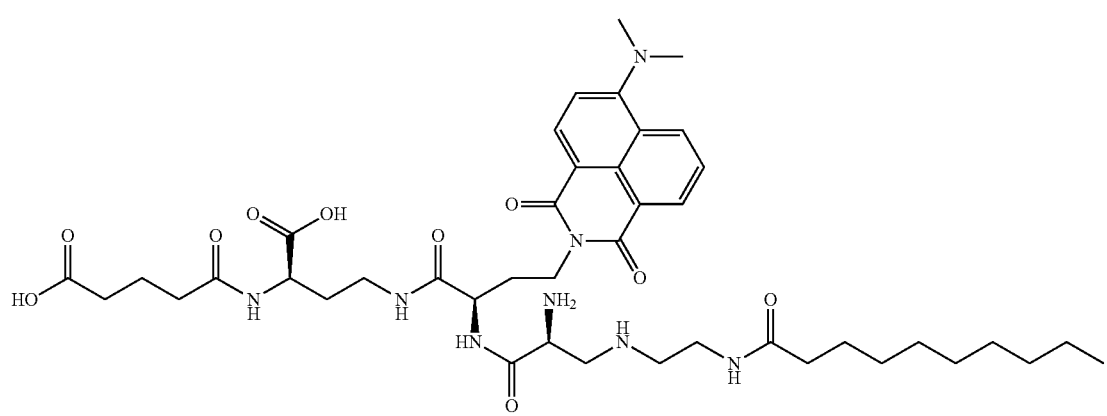 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]
HO-Gla-D-Dab-(COOH)-D-DMNA-L-Dap-(NH₂)-AE-decanoyl.
5. The compound according to claim 4, wherein said compound is

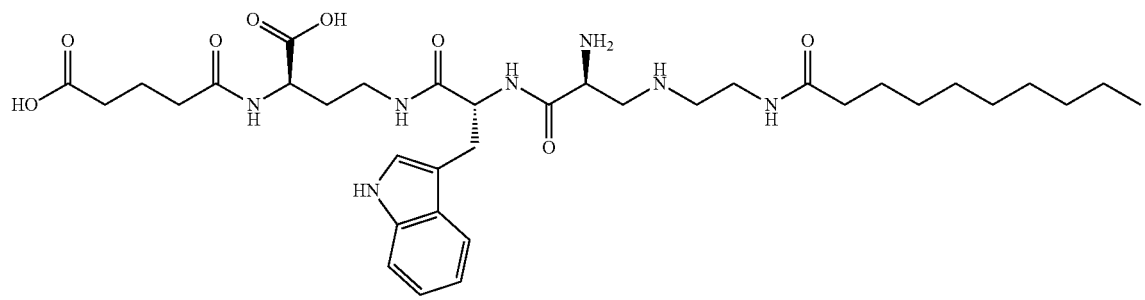 [SMILES: CCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-decanoyl-2-aminoethyl)-(S)-2,3-diaminopropionyl]-D-tryptophanyl]-N²-glutanoyl-2,4-diaminobutanoic acid.

6. The compound according to claim 4, wherein said compound is

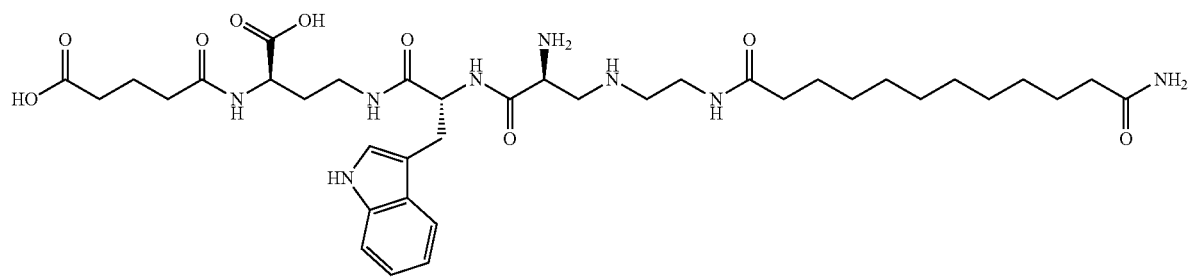 [SMILES: NC(=O)CCCCCCCCCCC(=O)NCCNC[C@H](N)C(=O)N[C@H](Cc1c[nH]c2ccccc12)C(=O)NCC[C@@H](NC(=O)CCCC(=O)O)C(=O)O]

(R)—N⁴—[N²—(N³—(N-(12-amino-12-oxododecanoyl)-2-aminoethyl)-(S)-2,3-diaminopropionyl)-D-tryptophanyl]-N²-glutanoyl-2,4-diaminobutanoic acid.

7. The compound according to claim 4, wherein said compound is

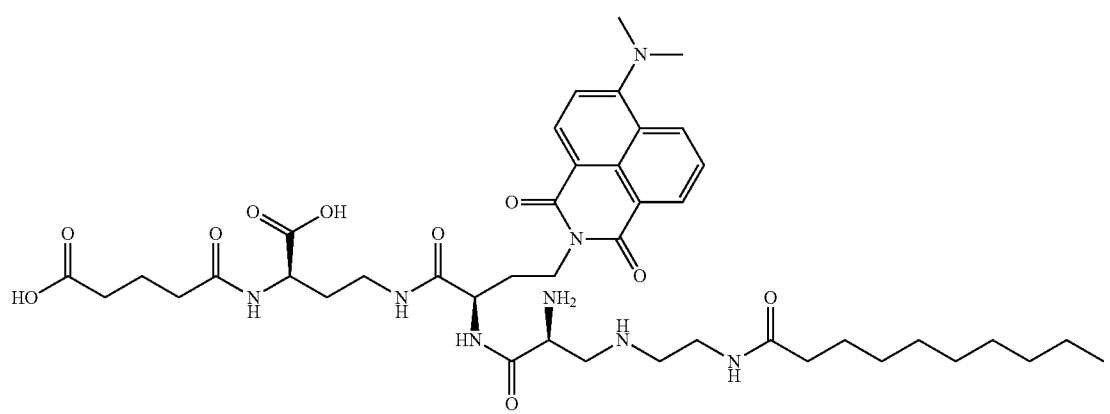 [SMILES: CCCCCCCCCC(=O)NCCNC[C@H](N)C(=O)N[C@H](CCN1C(=O)c2cccc3c(N(C)C)ccc(c23)C1=O)C(=O)NCC[C@@H](NC(=O)CCCC(=O)O)C(=O)O]

HO-Gla-D-Dab-(COOH)-D-DMNA-L-Dap-(NH₂)-AE-decanoyl.

8. A compound selected from the group consisting of:

N³—(N-tert-butoxycarbonyl-2-aminoethyl)-N²,N³-dibenzyloxycarbonyl-(S)-2,3-diaminopropionic acid;

N⁴—(N-tert-butoxycarbonyl-2-aminoethyl)-N²,N⁴-dibenzyloxycarbonyl-(S)-2,4-diaminobutanoic acid;

N²,N⁴-dibenzyloxycarbonyl-N⁴—[N-(9-fluorenylmethoxycarbonyl)-2-aminoethyl]-(S)-2,4-diaminobutanoic acid;

N²,N³-bis-tert-butoxycarbonyl-N³—[N-(9-fluorenylmethoxycarbonyl)-2-aminoethyl]-(S)-2,3-diaminopropionic acid;

N²,N⁴-bis-tert-butoxycarbonyl-N⁴—[N-(9-fluorenylmethoxycarbonyl)-2-aminoethyl]-(S)-2,4-diaminobutanoic acid;

N²,N⁵-bis-tert-butoxycarbonyl-N⁵—[N-(9-fluorenylmethoxycarbonyl)-2-aminoethyl]-(S)-2,5-diaminopentanoic acid;

(2S,7S)—N²-(tert-butoxycarbonyl)-N⁷-(9-fluorenylmethoxycarbonyl)-5-tert-butoxycarbonyl-5-aza-2,7-diaminoundecanoic acid;

(2S,7S)—N²-(tert-butoxycarbonyl)-N⁷-(9-fluorenylmethoxycarbonyl)-5-(tert-butoxycarbonyl)-5-aza-2,7-diaminotridecanoic acid;

(2S,7S)—N²-(tert-butoxycarbonyl)-N⁷-(9-fluorenylmethoxycarbonyl)-5-(tert-butoxycarbonyl)-5-aza-2,7-diaminopentdecanoic acid;

(R)-methyl-N⁴-(9-fluorenylmethoxycarbonyl)-2,4-diaminobutanoate;
4-(4'-acetamidophenyl)-N²-(9-fluorenylmethoxycarbonyl)-D-phenylalanine;
(R)-2-(9-fluorenylmethoxycarbonyl)amino-3-(4'-acetamido-[1,1'-biphenyl]-4-yl)propanoic acid;
(R)-4-(4'-N,N-dimethylamino-1,8-naphthalimido)-N²-(9-fluorenylmethoxycarbonyl)-2-aminobutanoic acid;
N³—(N-tert-butoxycarbonyl-2-aminoethyl)-N²,N³-dibenzyloxycarbonyl-(S)-2,3-diaminopropionic acid pentafluorophenyl ester;
N³—(N-tert-butoxycarbonyl-2-aminoethyl)-N²,N³-dibenzyloxycarbonyl-(S)-2,3-diaminopropionic acid p-nitrophenyl ester; and
12-amino-12-oxododecanoic acid p-nitrophenyl ester.

\* \* \* \* \*